United States Patent
Kato et al.

(10) Patent No.: US 12,187,803 B2
(45) Date of Patent: Jan. 7, 2025

(54) BISPECIFIC ANTIBODY THAT BINDS TO CD116 AND CD131

(71) Applicant: KYOWA KIRIN CO., LTD., Tokyo (JP)

(72) Inventors: Akifumi Kato, Tokyo (JP); Harue Nishiya, Tokyo (JP); Ryosuke Nakano, Tokyo (JP); Toshimasa Harumoto, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 0 days.

(21) Appl. No.: 18/587,502

(22) Filed: Feb. 26, 2024

(65) Prior Publication Data

US 2024/0190980 A1    Jun. 13, 2024

Related U.S. Application Data

(63) Continuation of application No. PCT/JP2022/032233, filed on Aug. 26, 2022.

(30) Foreign Application Priority Data

Aug. 26, 2021 (JP) ................................. 2021-138181

(51) Int. Cl.
| | | |
|---|---|---|
| C07K 16/28 | (2006.01) | |
| C12N 5/10 | (2006.01) | |
| C12N 15/62 | (2006.01) | |
| C12N 15/63 | (2006.01) | |
| A61K 39/395 | (2006.01) | |
| C07K 14/705 | (2006.01) | |
| C07K 14/71 | (2006.01) | |
| C07K 14/715 | (2006.01) | |

(52) U.S. Cl.
CPC ...... C07K 16/2866 (2013.01); C07K 16/2863 (2013.01); C07K 16/2896 (2013.01); C12N 5/10 (2013.01); C12N 15/62 (2013.01); C12N 15/63 (2013.01); C07K 2317/31 (2013.01); C07K 2317/51 (2013.01); C07K 2317/515 (2013.01)

(58) Field of Classification Search
CPC ........ A61K 2039/505; A61K 39/39558; A61K 39/3955; C07K 16/2866; C07K 16/2863; C07K 16/2896; C07K 2317/31
See application file for complete search history.

(56) References Cited

U.S. PATENT DOCUMENTS

| 2019/0062438 A1 | 2/2019 | Owczarek et al. |
| 2019/0256587 A1 | 8/2019 | Becher et al. |
| 2021/0070851 A1 | 3/2021 | Tugues et al. |
| 2021/0324091 A1 | 10/2021 | Owczarek et al. |
| 2023/0340100 A1 | 10/2023 | Becher et al. |

FOREIGN PATENT DOCUMENTS

| JP | 2019-500859 | 1/2019 | |
| JP | 2021-514368 | 6/2021 | |
| WO | WO-2006017759 A2 * | 2/2006 | ......... C07K 16/2851 |
| WO | 2017/021540 | 2/2017 | |
| WO | 2018/227142 | 12/2018 | |

OTHER PUBLICATIONS

International Search Report issued Nov. 1, 2022 in International (PCT) Application No. PCT/JP2022/032233.
Stanley, Edouard et al., "Granulocyte/macrophage colony-stimulating factor-deficient mice show no major perturbation of hematopoiesis but develop a characteristic pulmonary pathology", Proc. Natl. Acad. Sci. USA, Jun. 1994, vol. 91, pp. 5592-5596.
Hansen, Guido et al., "The Structure of the GM-CSF Receptor Complex Reveals a Distinct Mode of Cytokine Receptor Activation", Cell, Aug. 2008, vol. 134, pp. 496-507.
Broughton, Sophie E. et al., "The βc receptor family—Structural insights and their functional implications", Cytokine, 2015, vol. 74, pp. 247-258.
Kitamura, Takayuki et al., "Idiopathic Alveolar Proteinosis as an Autoimmune Disease with Neutralizing Antibody against Granulocyte/Macrophage Colony-Stimulating Factor", J. Exp. Med., Sep. 1999, vol. 190, No. 6, pp. 875-880.
Han, Xiaonan et al., "Granulocyte-Macrophage Colony-Stimulating Factor Autoantibodies in Murine Ileitis and Progressive Ileal Crohn's Disease", Gastroenterology, 2009, vol. 136, pp. 1261-1271.
Gathungu, Grace et al., "Granulocyte-Macrophage Colony-Stimulating Factor Autoantibodies: A Marker of Aggressive Crohn's Disease", Inflamm Bowel Dis, Jul. 2013, vol. 19, pp. 1671-1680.
Hussein, AM et al., "Effects of granulocyte-macrophage colony stimulating factor produced in Chinese hamster ovary cells (regramostim), *Escherichia coli* (molgramaostim) and yeast (sargramostim) in priming peripheral blood progenitor cells for use with autologous bone marrow after high-dose chemotherapy", Eur J Hematol, 1995, vol. 54, pp. 281-287.
Tazawa, R. et al., "Inhaled GM-CSF for Pulmonary Alveolar Proteinosis", N Engl J Med, Sep. 2019, vol. 381, No. 10, pp. 923-932.
Korzenik, Joshua R. et al., "Sargramostim for Active Crohn's Disease", N Engl J Med, May 2005, vol. 352, No. 21, pp. 2193-2201.
Heinzelman, Pete et al., "Cytokine refacing effect reduces granulocyte macrophage colony-stimulating factor susceptibility to antibody neutralization", Protein Engineering, Design & Selection, 2015, vol. 28, No. 10, pp. 461-466.

(Continued)

Primary Examiner — Bridget E Bunner
(74) Attorney, Agent, or Firm — Wenderoth, Lind & Ponack, L.L.P.

(57) ABSTRACT

An object of the present invention is to provide a bispecific antibody having an agonist activity to a GM-CSF receptor, and a bispecific antibody fragment thereof. The present invention relates to a bispecific antibody or a bispecific antibody fragment thereof containing: a first antigen-binding domain; and a second antigen-binding domain, in which one of the first antigen-binding domain and the second antigen-binding domain is an antigen-binding domain binding to CD116, and the other one is an antigen-binding domain binding to CD131.

14 Claims, 19 Drawing Sheets

Specification includes a Sequence Listing.

(56) References Cited

OTHER PUBLICATIONS

Uchida, Kanji et al., "High-affinity autoantibodies specifically eliminate granulocyte-macrophage colony-stimulating factor activity in the lungs of patients with idiopathic pulmonary alveolar proteinosis", Blood, Feb. 2004, vol. 103, No. 3, pp. 1089-1098.
Kolumam, Ganesh et al., "Sustained Brown Fat Stimulation and Insulin Sensitization by a Humanized Bispecific Antibody Agonist for Fibroblast Growth Factor Receptor 1/βKlotho Complex", EbioMedicine, 2015, vol. 2, pp. 730-743.
Hasegawa, Aiko et al., "Mutated GM-CSF-based CAR-T cells targeting CD116/CD131 complexes exhibit enhanced anti-tumor effects against acute myeloid leukaemia", Clinical & Translational Immunology, 2021, vol. 10, e1282, 16 pages.
Heinzelman, Pete et al., "Engineering Superactive Granulocyte Macrophage Colony-Stimulating Factor Transferrin Fusion Proteins as Orally-Delivered Candidate Agents for Treating Neurodegenerative Disease", Biotechnol. Prog., 2015, vol. 31. No. 3, pp. 668-677.
Uchida, Kanji et al., "Granulocyte/macrophage-colony-stimulating factor autoantibodies and myeloid cell immune functions in healthy subjects", Blood, Mar. 2009, vol. 113, No. 11, pp. 2547-2556.

\* cited by examiner

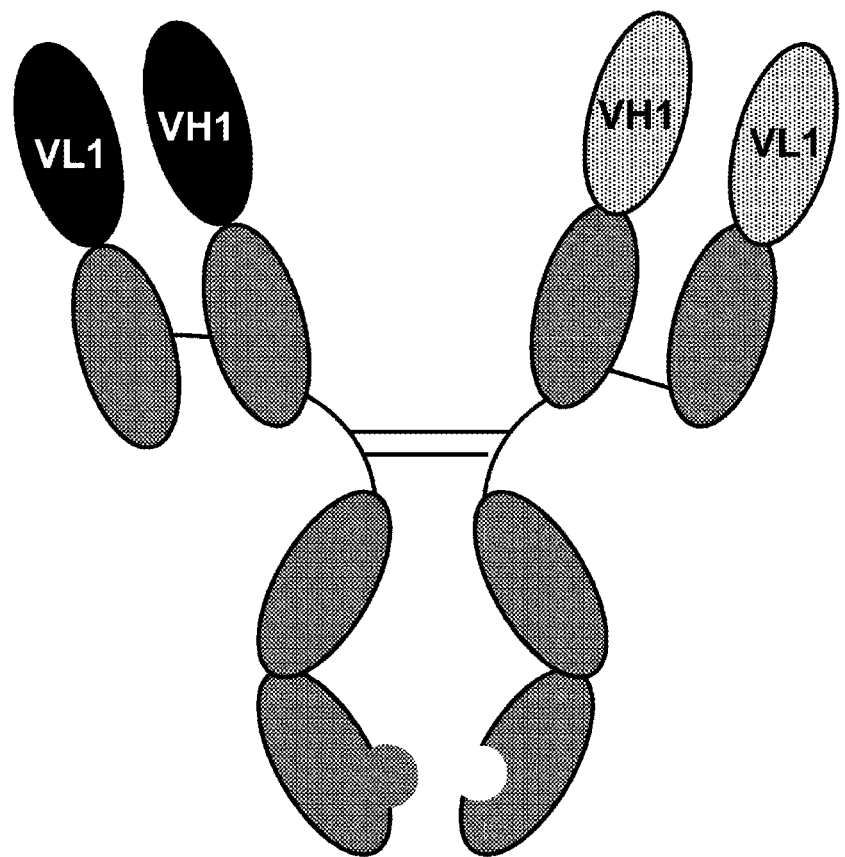

BISPECIFIC ANTIBODY THAT BINDS TO CD116 AND CD131

SEQUENCE LISTING

A sequence listing in electronic (XML file) format is filed with this application and incorporated herein by reference. The name of the XML file is "Sequence_Listing.xml"; the file was created on Feb. 23, 2024; the size of the file is 219,752 bytes.

TECHNICAL FIELD

The present invention relates to a bispecific antibody containing antigen-binding domains binding to CD116 and CD131, a bispecific antibody fragment thereof, a DNA encoding the bispecific antibody or the bispecific antibody fragment thereof, a vector containing the DNA, a hybridoma and transformant producing the bispecific antibody or the bispecific antibody fragment thereof, a method for producing the bispecific antibody or the bispecific antibody fragment thereof, a therapeutic and diagnostic agent containing the bispecific antibody and the bispecific antibody fragment thereof, a therapeutic and diagnostic method using the bispecific antibody and the bispecific antibody fragment thereof, and a detection or measurement reagent containing the bispecific antibody and the bispecific antibody fragment thereof.

BACKGROUND ART

A granulocyte macrophage colony-stimulating factor (GM-CSF) is an approximately 22 kDa glycoprotein consisting of 127 amino acid residues, and is a factor that acts on myeloid progenitor cells to promote differentiation and proliferation. Although the GM-CSF is not necessary for homeostatic hematopoiesis, the GM-CSF is essential for differentiation of alveolar macrophages.

It is reported that, in fact, in analysis using a GM-CSF knockout animal, blood cells such as neutrophils, monocytes, and eosinophils are normal, but impaired maturation of alveolar macrophages is observed, leading to an abnormality in pulmonary surfactant processing (NPL1).

The GM-CSF exerts a physiological effect thereof by specifically binding to a GM-CSF receptor expressed on a cell membrane. The GM-CSF receptor is expressed on neutrophils, eosinophils, monocytes, macrophages, and progenitor cells thereof. The GM-CSF receptor is a heteropolymer composed of two types of subunits, i.e., an α-chain (CD116) and a βc chain (common β-chain, CD131).

Both CD116 and CD131 are single-pass transmembrane proteins and belong to a cytokine receptor superfamily. CD116 is responsible for specific binding to the GM-CSF, and CD131 is a constituent molecule common to both IL-3 receptor and IL-5 receptor, and is mainly responsible for signal transduction.

A signal transduction molecule JAK2 binds to an intracellular region of CD131, and phosphorylation of the JAK2 and tyrosine residues in the intracellular region of CD131 activates a JAK2/STAT5 pathway, an Ras/MAP kinase pathway, and a PI-3 kinase pathway, which act on cell survival, proliferation, differentiation, and activation.

In a steady state, CD116 and CD131 exist separately on a cell membrane. When CD116 and CD131 act as the GM-CSF receptor, the GM-CSF first specifically binds to CD116. It is revealed that CD116 alone has low affinity for a GM-CSF, but when CD131 is added, the GM-CSF binds to CD116 with high affinity, a complex is formed, and signals are transduced by a special activation mechanism. FIG. 1 schematically shows the mechanism.

As shown in FIG. 1, CD131 forms a dimer in a steady state, and a hexamer is formed through binding of each CD131 molecule with a GM-CSF and CD116. However, in the hexamer state, a distance between transmembrane regions of CD131 is about 120 Å, and a distance between JAK2s increases and no signal flows. Further, when the two hexamers combine to form a dodecamer, a distance between transmembrane regions of CD131 in the dodecamer is about 10 Å, and a distance between JAK2s is close to about 10 Å, allowing mutual phosphorylation, and phosphorylation of the JAK2 and tyrosine residues in intracellular regions CD131 occurs, thereby transducing signals (NPL2 and NPL3).

So far, a disease is reported that occurs due to production of excessive autoantibodies to a GM-CSF within a body of a patient and neutralization of the GM-CSF. For example, in acquired pulmonary alveolar proteinosis, anti-GM-CSF autoantibodies are frequently observed at high concentrations (NPL4 and NPL5). The pulmonary alveolar proteinosis is a disease in which pulmonary surfactants accumulate abnormally in alveolar spaces, making breathing difficult, and it is thought that autoantibodies neutralize GM-CSFs and inhibit alveolar macrophage differentiation, resulting in an abnormality in pulmonary surfactant processing. It is reported that anti-GM-CSF autoantibodies are observed even in Crohn's diseases and are implicated in pathogenesis (NPL6 and NPL7).

A recombinant GM-CSF preparation was approved and sold as a pharmaceutical product in Europe, North America, Australia, etc. in the 1990s, and is used as a subcutaneous injection for myelosuppression after cancer chemotherapy, myelodysplastic syndrome, aplastic anemia, and colonization promotion after bone marrow transplantation. There are two types of preparations, i.e., molgramostim derived from *Escherichia coli* and sargramostim derived from yeast, and no significant difference in activity is observed between the two (NPL8). Treatment of pulmonary alveolar proteinosis and Crohn's disease is attempted using the preparations, and a therapeutic effect is reported, particularly for pulmonary alveolar proteinosis (NPL9 and NPL10).

Although it is reported that neutralization by autoantibodies is reduced by amino acid modification of the GM-CSF molecule, the effect remains slight (NPL11). Research is reported in which a receptor-binding peptide is connected with a linker as a GM-CSF mimetic, which has a property of transmitting signals through a GM-CSF receptor, like the GM-CSF, but is completely different from the GM-CSF as a molecule (PTL1).

CITATION LIST

Patent Literature

PTL1: WO2018/227142
PTL2: WO2017/021540

Non-Patent Literature

NPL1: Proc. Natl. Acad. Sci. USA, 91, 5592-5596 (1994)
NPL2: Cell, 134, 496-507 (2008)
NPL3: Cytokine, 74, 247-258 (2015)
NPL4: J. Exp. Med., 190, 875-880 (1999)
NPL5: Blood, 113, 2547-2556 (2009)
NPL6: Gastroenterology, 136, 1261-1271 (2009)

NPL7: Inflamm. Bowel Dis., 19, 1671-1680 (2013)
NPL8: Eur J Haematol., 55, 348-356 (1995)
NPL9: N Engl J Med., 381, 923-932 (2019)
NPL10: N Engl J Med., 352, 2193-2201 (2005)
NPL11: Protein Eng Des Sel., 28, 461-466 (2015)
NPL12: Blood, 103, 1089-1098 (2004)
NPL13: EbioMedicine, 30, 730-743 (2015)

SUMMARY OF INVENTION

Technical Problem

A previously studied GM-CSF receptor-binding peptide has a problem of insufficient efficacy, and a possible reason for this is that the GM-CSF receptor-binding peptide is derived from a GM-CSF sequence and is therefore neutralized by a patient autoantibody. Considering that autoantibodies to the GM-CSF are produced for various epitopes of the GM-CSF (NPL12), it is considered difficult to solve the neutralization of the GM-CSF receptor peptide by patient autoantibodies by molecular modification of an administered peptide.

On the other hand, it is shown that agonists can be obtained by using a bispecific antibody not only for a receptor consisting of homodimers, such as an erythropoietin receptor or a growth hormone receptor, but also for a receptor consisting of heterodimers (multimers), such as an interleukin 2 (IL-2) receptor or a fibroblast growth factor (FGF) receptor and a β-Klotho protein complex (NPL13 and NPL2). However, a GM-CSF receptor agonist is not reported so far. As described above, an activation mechanism of the GM-CSF receptor is very complex, and therefore it is not considered easy to prepare a substance having an agonist activity. In order to exert the agonist activity on the GM-CSF receptor, it is considered that it is necessary to mimic changes in distance and angle between CD116 and CD131 caused by binding with a GM-CSF and formation of a complex.

The present invention is made in view of such circumstances, and an object thereof is to provide a bispecific antibody having an agonist activity to a GM-CSF receptor, a bispecific antibody fragment thereof, a DNA encoding the bispecific antibody or the bispecific antibody fragment thereof, a vector containing the DNA, a hybridoma and transformant producing the bispecific antibody or the bispecific antibody fragment thereof, a method for producing the bispecific antibody or the bispecific antibody fragment thereof, a therapeutic and diagnostic agent containing the bispecific antibody or the bispecific antibody fragment thereof, a therapeutic and diagnostic method using the bispecific antibody or the bispecific antibody fragment thereof, and a detection or measurement reagent containing the bispecific antibody or the bispecific antibody fragment thereof.

Solution to Problem

The present inventors have found that, since a GM-CSF receptor is composed of CD116 and CD131, a bispecific antibody having an agonist activity to the GM-CSF receptor can be prepared by preparing a bispecific antibody containing antigen-binding domains binding to CD116 and CD131, which are constituent molecules of the GM-CSF receptor, thereby completing the present invention.

That is, the present invention relates to the following.

1. A bispecific antibody or a bispecific antibody fragment thereof containing:
 a first antigen-binding domain; and
 a second antigen-binding domain, in which
 one of the first antigen-binding domain and the second antigen-binding domain is an antigen-binding domain binding to CD116, and the other one is an antigen-binding domain binding to CD131.

2. The bispecific antibody or the bispecific antibody fragment thereof according to above 1, which has an agonist activity to a granulocyte macrophage-colony stimulating factor (hereinafter abbreviated as GM-CSF) receptor.

3. The bispecific antibody or the bispecific antibody fragment thereof according to above 1 or 2, in which the first antigen-binding domain and the second antigen-binding domain each contain a heavy chain variable region (hereinafter abbreviated as VH) and a light chain variable region (hereinafter abbreviated as VL).

4. The bispecific antibody or the bispecific antibody fragment thereof according to any one of above 1 to 3, which binds to CD116 and CD131 in a monovalent or divalent manner, separately.

5. The bispecific antibody or the bispecific antibody fragment thereof according to any one of above 1 to 4, in which the antigen-binding domain binding to CD131 is any one selected from the following (1a) to (1e):
 (1a) an antigen-binding domain containing a VH containing complementarity determining regions (hereinafter abbreviated as CDRs) 1 to 3 containing the amino acid sequences represented by SEQ ID NOs: 61 to 63, respectively, and a VL containing CDRs 1 to 3 containing the amino acid sequences represented by SEQ ID NOs: 64 to 66, respectively,
 (1b) an antigen-binding domain containing a VH containing CDRs 1 to 3 containing the amino acid sequences represented by SEQ ID NOs: 67 to 69, respectively, and a VL containing CDRs 1 to 3 containing the amino acid sequences represented by SEQ ID NOs: 70 to 72, respectively,
 (1c) an antigen-binding domain containing a VH containing CDRs 1 to 3 containing the amino acid sequences represented by SEQ ID NOs: 73 to 75, respectively, and a VL containing CDRs 1 to 3 containing the amino acid sequences represented by SEQ ID NOs: 76 to 78, respectively,
 (1d) an antigen-binding domain containing a VH containing CDRs 1 to 3 containing the amino acid sequences represented by SEQ ID NOs: 79 to 81, respectively, and a VL containing CDRs 1 to 3 containing the amino acid sequences represented by SEQ ID NOs: 82 to 84, respectively, and
 (1e) an antigen-binding domain containing a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively.

6. The bispecific antibody or the bispecific antibody fragment thereof according to any one of above 1 to 5, in which the antigen-binding domain binding to CD131 is any one selected from the following (1A) to (1E):
 (1A) an antigen-binding domain containing a VH containing the amino acid sequence represented by SEQ ID NO: 21 and a VL containing the amino acid sequence represented by SEQ ID NO: 22, (1B) an antigen-binding domain containing a VH containing the amino acid sequence represented by SEQ ID NO: 23 and a VL containing the amino acid sequence represented by SEQ ID NO: 24,
(1C) an antigen-binding domain containing a VH containing the amino acid sequence represented by SEQ ID NO: 25 and a VL containing the amino acid sequence represented by SEQ ID NO: 26,
(1D) an antigen-binding domain containing a VH containing the amino acid sequence represented by SEQ ID NO: 27 and a VL containing the amino acid sequence represented by SEQ ID NO: 28, and
(1E) an antigen-binding domain containing a VH containing the amino acid sequence represented by SEQ ID NO: 29 and a VL containing the amino acid sequence represented by SEQ ID NO: 30.

7. The bispecific antibody or the bispecific antibody fragment thereof according to any one of above 1 to 6, in which the antigen-binding domain binding to CD116 is any one selected from the following (2a) to (2q) and (2r-1) to (2r-12):
(2a) an antigen-binding domain containing a VH containing CDRs 1 to 3 containing the amino acid sequences represented by SEQ ID NOs: 31 to 33, respectively, and a VL containing CDRs 1 to 3 containing the amino acid sequences represented by SEQ ID NOs: 34 to 36, respectively,
(2b) an antigen-binding domain containing a VH containing CDRs 1 to 3 containing the amino acid sequences represented by SEQ ID NOs: 37 to 39, respectively, and a VL containing CDRs 1 to 3 containing the amino acid sequences represented by SEQ ID NOs: 40 to 42, respectively,
(2c) an antigen-binding domain containing a VH containing CDRs 1 to 3 containing the amino acid sequences represented by SEQ ID NO: 43 to 45, respectively, and a VL containing CDRs 1 to 3 containing the amino acid sequences represented by SEQ ID NO: 46 to 48, respectively,
(2d) an antigen-binding domain containing a VH containing CDRs 1 to 3 containing the amino acid sequences represented by SEQ ID NOs: 49 to 51, respectively, and a VL containing CDRs 1 to 3 containing the amino acid sequences represented by SEQ ID NOs: 52 to 54, respectively,
(2e) an antigen-binding domain containing a VH containing CDRs 1 to 3 containing the amino acid sequences represented by SEQ ID NOs: 55 to 57, respectively, and a VL containing CDRs 1 to 3 containing the amino acid sequences represented by SEQ ID NOs: 58 to 60, respectively,
(2f) an antigen-binding domain containing a VH containing CDRs 1 to 3 containing the amino acid sequences represented by SEQ ID NOs: 104 to 106, respectively, and a VL containing CDRs 1 to 3 containing the amino acid sequences represented by SEQ ID NOs: 88 to 90, respectively,
(2g) an antigen-binding domain containing a VH containing CDRs 1 to 3 containing the amino acid sequences represented by SEQ ID NOs: 107 to 109, respectively, and a VL containing CDRs 1 to 3 containing the amino acid sequences represented by SEQ ID NOs: 88 to 90, respectively,
(2h) an antigen-binding domain containing a VH containing CDRs 1 to 3 containing the amino acid sequences represented by SEQ ID NOs: 110 to 112, respectively, and a VL containing CDRs 1 to 3 containing the amino acid sequences represented by SEQ ID NOs: 88 to 90, respectively,
(2i) an antigen-binding domain containing a VH containing CDRs 1 to 3 containing the amino acid sequences represented by SEQ ID NOs: 113 to 115, respectively, and a VL containing CDRs 1 to 3 containing the amino acid sequences represented by SEQ ID NOs: 88 to 90, respectively,
(2j) an antigen-binding domain containing a VH containing CDRs 1 to 3 containing the amino acid sequences represented by SEQ ID NOs: 116 to 118, respectively, and a VL containing CDRs 1 to 3 containing the amino acid sequences represented by SEQ ID NOs: 88 to 90, respectively,
(2k) an antigen-binding domain containing a VH containing CDRs 1 to 3 containing the amino acid sequences represented by SEQ ID NOs: 119 to 121, respectively, and a VL containing CDRs 1 to 3 containing the amino acid sequences represented by SEQ ID NOs: 88 to 90, respectively,
(2l) an antigen-binding domain containing a VH containing CDRs 1 to 3 containing the amino acid sequences represented by SEQ ID NOs: 122 to 124, respectively, and a VL containing CDRs 1 to 3 containing the amino acid sequences represented by SEQ ID NOs: 88 to 90, respectively,
(2m) an antigen-binding domain containing a VH containing CDRs 1 to 3 containing the amino acid sequences represented by SEQ ID NOs: 125 to 127, respectively, and a VL containing CDRs 1 to 3 containing the amino acid sequences represented by SEQ ID NOs: 88 to 90, respectively,
(2n) an antigen-binding domain containing a VH containing CDRs 1 to 3 containing the amino acid sequences represented by SEQ ID NOs: 128 to 130, respectively, and a VL containing CDRs 1 to 3 containing the amino acid sequences represented by SEQ ID NOs: 88 to 90, respectively,
(2o) an antigen-binding domain containing a VH containing CDRs 1 to 3 containing the amino acid sequences represented by SEQ ID NOs: 131 to 133, respectively, and a VL containing CDRs 1 to 3 containing the amino acid sequences represented by SEQ ID NOs: 88 to 90, respectively,
(2p) an antigen-binding domain containing a VH containing CDRs 1 to 3 containing the amino acid sequences represented by SEQ ID NOs: 134 to 136, respectively, and a VL containing CDRs 1 to 3 containing the amino acid sequences represented by SEQ ID NOs: 88 to 90, respectively,
(2q) an antigen-binding domain containing a VH containing CDRs 1 to 3 containing the amino acid sequences represented by SEQ ID NOs: 137 to 139, respectively, and a VL containing CDRs 1 to 3 containing the amino acid sequences represented by SEQ ID NOs: 88 to 90, respectively,
(2r-1) an antigen-binding domain containing a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with lysine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-2) an antigen-binding domain containing a VH containing CDR1 containing the amino acid sequence represented by SEQ ID NO: 137, CDR2 containing an amino acid sequence in which a modification to substitute glycine at position 17 in the amino acid sequence represented by SEQ ID NO: 138 with aspartic acid is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-3) an antigen-binding domain containing a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-4) an antigen-binding domain containing a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with leucine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-5) an antigen-binding domain containing a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with serine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-6) an antigen-binding domain containing a VH containing CDR1 containing an amino acid sequence in which a modification to substitute leucine at position 2 in the amino acid sequence represented by SEQ ID NO: 137 with valine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-7) an antigen-binding domain containing a VH containing CDR1 containing an amino acid sequence in which a modification to substitute leucine at position 2 in the amino acid sequence represented by SEQ ID NO: 137 with phenylalanine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-8) an antigen-binding domain containing a VH containing CDR1 containing an amino acid sequence in which a modification to substitute serine at position 3 in the amino acid sequence represented by SEQ ID NO: 137 with alanine and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-9) an antigen-binding domain containing a VH containing CDR1 containing an amino acid sequence in which a modification to substitute leucine at position 2 in the amino acid sequence represented by SEQ ID NO: 137 with tyrosine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-10) an antigen-binding domain containing a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid is introduced, and a VL containing CDRs 1 to 3 containing the amino acid sequences represented by SEQ ID NOs: 88 to 90, respectively, (2r-11) an antigen-binding domain containing a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid, tyrosine at position 5 with tryptophan, and tyrosine at position 6 with methionine is introduced, and a VL containing CDRs 1 to 3 containing the amino acid sequences represented by SEQ ID NOs: 88 to 90, respectively, and (2r-12) an antigen-binding domain containing a VH containing CDR1 containing an amino acid sequence in which a modification to substitute leucine at position 2 in the amino acid sequence represented by SEQ ID NO: 137 with phenylalanine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively.

8. The bispecific antibody or the bispecific antibody fragment thereof according to any one of above 1 to 7, in which the antigen-binding domain binding to CD116 is any one selected from the following (2A) to (2Y) and (2Z-1) to (2Z-20):

(2A) an antigen-binding domain containing a VH containing the amino acid sequence represented by SEQ ID NO: 11 and a VL containing the amino acid sequence represented by SEQ ID NO: 12, (2B) an antigen-binding domain containing a VH containing the amino acid sequence represented by SEQ ID NO: 13 and a VL containing the amino acid sequence represented by SEQ ID NO: 14,
(2C) an antigen-binding domain containing a VH containing the amino acid sequence represented by SEQ ID NO: 15 and a VL containing the amino acid sequence represented by SEQ ID NO: 16,
(2D) an antigen-binding domain containing a VH containing the amino acid sequence represented by SEQ ID NO: 17 and a VL containing the amino acid sequence represented by SEQ ID NO: 18,
(2E) an antigen-binding domain containing a VH containing the amino acid sequence represented by SEQ ID NO: 19 and a VL containing the amino acid sequence represented by SEQ ID NO: 20,
(2F) an antigen-binding domain containing a VH containing the amino acid sequence represented by SEQ ID NO: 92 and a VL containing the amino acid sequence represented by SEQ ID NO: 30,
(2G) an antigen-binding domain containing a VH containing the amino acid sequence represented by SEQ ID NO: 93 and a VL containing the amino acid sequence represented by SEQ ID NO: 30,
(2H) an antigen-binding domain containing a VH containing the amino acid sequence represented by SEQ ID NO: 94 and a VL containing the amino acid sequence represented by SEQ ID NO: 30,
(2I) an antigen-binding domain containing a VH containing the amino acid sequence represented by SEQ ID NO: 95 and a VL containing the amino acid sequence represented by SEQ ID NO: 30,
(2J) an antigen-binding domain containing a VH containing the amino acid sequence represented by SEQ ID NO: 96 and a VL containing the amino acid sequence represented by SEQ ID NO: 30,
(2K) an antigen-binding domain containing a VH containing the amino acid sequence represented by SEQ ID NO: 97 and a VL containing the amino acid sequence represented by SEQ ID NO: 30,
(2L) an antigen-binding domain containing a VH containing the amino acid sequence represented by SEQ ID NO: 98 and a VL containing the amino acid sequence represented by SEQ ID NO: 30,
(2M) an antigen-binding domain containing a VH containing the amino acid sequence represented by SEQ ID NO: 99 and a VL containing the amino acid sequence represented by SEQ ID NO: 30,
(2N) an antigen-binding domain containing a VH containing the amino acid sequence represented by SEQ ID NO: 100 and a VL containing the amino acid sequence represented by SEQ ID NO: 30,
(2O) an antigen-binding domain containing a VH containing the amino acid sequence represented by SEQ ID NO: 101 and a VL containing the amino acid sequence represented by SEQ ID NO: 30,
(2P) an antigen-binding domain containing a VH containing the amino acid sequence represented by SEQ ID NO: 102 and a VL containing the amino acid sequence represented by SEQ ID NO: 30,
(2Q) an antigen-binding domain containing a VH containing the amino acid sequence represented by SEQ ID NO: 103 and a VL containing the amino acid sequence represented by SEQ ID NO: 30,
(2R) an antigen-binding domain containing a VH containing the amino acid sequence represented by SEQ ID NO: 176 and a VL containing the amino acid sequence represented by SEQ ID NO: 30,
(2S) an antigen-binding domain containing a VH containing the amino acid sequence represented by SEQ ID NO: 177 and a VL containing the amino acid sequence represented by SEQ ID NO: 30,
(2T) an antigen-binding domain containing a VH containing the amino acid sequence represented by SEQ ID NO: 178 and a VL containing the amino acid sequence represented by SEQ ID NO: 30,
(2U) an antigen-binding domain containing a VH containing the amino acid sequence represented by SEQ ID NO: 179 and a VL containing the amino acid sequence represented by SEQ ID NO: 30,
(2V) an antigen-binding domain containing a VH containing the amino acid sequence represented by SEQ ID NO: 182 and a VL containing the amino acid sequence represented by SEQ ID NO: 30,
(2W) an antigen-binding domain containing a VH containing the amino acid sequence represented by SEQ ID NO: 183 and a VL containing the amino acid sequence represented by SEQ ID NO: 30,
(2X) an antigen-binding domain containing a VH containing the amino acid sequence represented by SEQ ID NO: 184 and a VL containing the amino acid sequence represented by SEQ ID NO: 30,
(2Y) an antigen-binding domain containing a VH containing the amino acid sequence represented by SEQ ID NO: 185 and a VL containing the amino acid sequence represented by SEQ ID NO: 30,
(2Z-1) an antigen-binding domain containing a VH containing the amino acid sequence represented by SEQ ID NO: 190 and a VL containing the amino acid sequence represented by SEQ ID NO: 30,
(2Z-2) an antigen-binding domain containing a VH containing the amino acid sequence represented by SEQ ID NO: 191 and a VL containing the amino acid sequence represented by SEQ ID NO: 30,
(2Z-3) an antigen-binding domain containing a VH containing the amino acid sequence represented by SEQ ID NO: 192 and a VL containing the amino acid sequence represented by SEQ ID NO: 30,
(2Z-4) an antigen-binding domain containing a VH containing the amino acid sequence represented by SEQ ID NO: 193 and a VL containing the amino acid sequence represented by SEQ ID NO: 30,
(2Z-5) an antigen-binding domain containing a VH containing the amino acid sequence represented by SEQ ID NO: 194 and a VL containing the amino acid sequence represented by SEQ ID NO: 30,
(2Z-6) an antigen-binding domain containing a VH containing the amino acid sequence represented by SEQ ID NO: 195 and a VL containing the amino acid sequence represented by SEQ ID NO: 30,
(2Z-7) an antigen-binding domain containing a VH containing the amino acid sequence represented by SEQ ID NO: 196 and a VL containing the amino acid sequence represented by SEQ ID NO: 30,
(2Z-8) an antigen-binding domain containing a VH containing the amino acid sequence represented by SEQ ID NO: 197 and a VL containing the amino acid sequence represented by SEQ ID NO: 30,
(2Z-9) an antigen-binding domain containing a VH containing the amino acid sequence represented by SEQ ID NO: 198 and a VL containing the amino acid sequence represented by SEQ ID NO: 30,
(2Z-10) an antigen-binding domain containing a VH containing the amino acid sequence represented by SEQ ID NO: 199 and a VL containing the amino acid sequence represented by SEQ ID NO: 30, (2Z-11) an antigen-binding domain containing a VH containing the amino acid sequence represented by SEQ ID NO: 200 and a VL containing the amino acid sequence represented by SEQ ID NO: 30, (2Z-12) an antigen-binding domain containing a VH containing the amino acid sequence represented by SEQ ID NO: 201 and a VL containing the amino acid sequence represented by SEQ ID NO: 30, (2Z-13) an antigen-binding domain containing a VH containing the amino acid sequence represented by SEQ ID NO: 202 and a VL containing the amino acid sequence represented by SEQ ID NO: 30, (2Z-14) an antigen-binding domain containing a VH containing the amino acid sequence represented by SEQ ID NO: 203 and a VL containing the amino acid sequence represented by SEQ ID NO: 30, (2Z-15) an antigen-binding domain containing a VH containing the amino acid sequence represented by SEQ ID NO: 204 and a VL containing the amino acid sequence represented by SEQ ID NO: 30, (2Z-16) an antigen-binding domain containing a VH containing the amino acid sequence represented by SEQ ID NO: 205 and a VL containing the amino acid sequence represented by SEQ ID NO: 30, (2Z-17) an antigen-binding domain containing a VH containing the amino acid sequence represented by SEQ ID NO: 206 and a VL containing the amino acid sequence represented by SEQ ID NO: 30, (2Z-18) an antigen-binding domain containing a VH containing the amino acid sequence represented by SEQ ID NO: 207 and a VL containing the amino acid sequence represented by SEQ ID NO: 30, (2Z-19) an antigen-binding domain containing a VH containing the amino acid sequence represented by SEQ ID NO: 208 and a VL containing the amino acid sequence represented by SEQ ID NO: 30, and (2Z-20) an antigen-binding domain containing a VH containing the amino acid sequence represented by SEQ ID NO: 209 and a VL containing the amino acid sequence represented by SEQ ID NO: 30.

9. The bispecific antibody or the bispecific antibody fragment thereof according to any one of above 1 to 8, in which the first antigen-binding domain is the antigen-binding domain binding to CD131, and the second antigen-binding domain is the antigen-binding domain binding to CD116.

10. The bispecific antibody or the bispecific antibody fragment thereof according to any one of above 1 to 9, in which
the first antigen-binding domain and the second antigen-binding domain are each Fab (hereinafter abbreviated as a first Fab and a second Fab, respectively),
the first Fab contains a heavy chain ($VH_1$-CH1) containing a VH and CH1 domain, and a light chain (VL-CL), and
the second Fab contains a heavy chain ($VH_2$-CH1') containing a VH and CH1 domain, and a light chain (VL-CL).

11. The bispecific antibody or the bispecific antibody fragment thereof according to above 10, containing:
one first Fab;
one second Fab; and
hinge regions, in which
a C-terminus of the heavy chain in the first Fab and a C-terminus of the heavy chain in the second Fab bind to N-termini of the hinge regions, respectively.

12. The bispecific antibody or the bispecific antibody fragment thereof according to above 10, containing:
a following first polypeptide;
a following second polypeptide; and
hinge regions, in which
a C-terminus of the first polypeptide and a C-terminus of the second polypeptide bind to N-termini of the hinge regions, respectively,
the first polypeptide: a polypeptide containing at least the first Fab ($VH_1$-CH1, VL-CL) at an N-terminus, and
the second polypeptide: a polypeptide containing at least the second Fab ($VH_2$-CH1', VL-CL) at a C-terminus.

13. The bispecific antibody or the bispecific antibody fragment thereof according to above 10, containing:
two polypeptide chains ($VH_1$-CH1-$VH_2$-CH1') in which a C-terminus of the heavy chain in the first Fab and an N-terminus of the heavy chain in the second Fab bind to each other directly or via a linker; and
hinge regions, in which
C-termini of the two polypeptide chains bind to N-termini of the hinge regions, respectively.

14. The bispecific antibody or the bispecific antibody fragment thereof according to any one of above 11 to 13, further containing:
Fc regions, in which
N-termini of the Fc regions bind to C-termini of the hinge regions.

15. The bispecific antibody or the bispecific antibody fragment thereof according to any one of above 1 to 14, in which the bispecific antibody is any one selected from the following (x1) to (x12) and (x13-1) to (x13-12):

(x1) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 104 to 106, respectively, and a VL containing CDRs 1 to 3 containing the amino acid sequences represented by SEQ ID NOs: 88 to 90, respectively, (x2) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 107 to 109, respectively, and a VL containing CDRs 1 to 3 containing the amino acid sequences represented by SEQ ID NOs: 88 to 90, respectively, (x3) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 110 to 112, respectively, and a VL containing CDRs 1 to 3 containing the amino acid sequences represented by SEQ ID NOs: 88 to 90, respectively, (x4) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 113 to 115, respectively, and a VL containing CDRs 1 to 3 containing the amino acid sequences represented by SEQ ID NOs: 88 to 90, respectively, (x5) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 116 to 118, respectively, and a VL containing CDRs 1 to 3 containing the amino acid sequences represented by SEQ ID NOs: 88 to 90, respectively, (x6) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 119 to 121, respectively, and a VL containing CDRs 1 to 3 containing the amino acid sequences represented by SEQ ID NOs: 88 to 90, respectively, (x7) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 122 to 124, respectively, and a VL containing CDRs 1 to 3 containing the amino acid sequences represented by SEQ ID NOs: 88 to 90, respectively, (x8) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 125 to 127, respectively, and a VL containing CDRs 1 to 3 containing the amino acid sequences represented by SEQ ID NOs: 88 to 90, respectively, (x9) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 128 to 130, respectively, and a VL containing CDRs 1 to 3 containing the amino acid sequences represented by SEQ ID NOs: 88 to 90, respectively, (x10) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 131 to 133, respectively, and a VL containing CDRs 1 to 3 containing the amino acid sequences represented by SEQ ID NOs: 88 to 90, respectively, (x11) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 134 to 136, respectively, and a VL containing CDRs 1 to 3 containing the amino acid sequences represented by SEQ ID NOs: 88 to 90, respectively, (x12) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 137 to 139, respectively, and a VL containing CDRs 1 to 3 containing the amino acid sequences represented by SEQ ID NOs: 88 to 90, respectively, (x13-1) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with lysine is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-2) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute glycine at position 17 in the amino acid sequence represented by SEQ ID NO: 138 with aspartic acid is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-3) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-4) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with leucine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-5) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with serine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-6) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute leucine at position 2 in the amino acid sequence represented by SEQ ID NO: 137 with valine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (x13-7) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute leucine at position 2 in the amino acid sequence represented by SEQ ID NO: 137 with phenylalanine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (x13-8) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute serine at position 3 in the amino acid sequence represented by SEQ ID NO: 137 with alanine and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (x13-9) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute leucine at position 2 in the amino acid sequence represented by SEQ ID NO: 137 with tyrosine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively,
- (x13-10) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid is introduced, and a VL containing CDRs 1 to 3 containing the amino acid sequences represented by SEQ ID NOs: 88 to 90, respectively,
- (x13-11) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid, tyrosine at position 5 with tryptophan, and tyrosine at position 6 with methionine is introduced, and a VL containing CDRs 1 to 3 containing the amino acid sequences represented by SEQ ID NOs: 88 to 90, respectively, and
- (x13-12) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute leucine at position 2 in the amino acid sequence represented by SEQ ID NO: 137 with phenylalanine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively.

16. The bispecific antibody or the bispecific antibody fragment thereof according to any one of above 1 to 15, in which the bispecific antibody is any one selected from the following (y1) to (y12) and (y13-1) to (y13-20):
- (y1) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 175, and a VL containing the amino acid sequence represented by SEQ ID NO: 30,
- (y2) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 176, and a VL containing the amino acid sequence represented by SEQ ID NO: 30,
- (y3) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 177, and a VL containing the amino acid sequence represented by SEQ ID NO: 30,
- (y4) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 178, and a VL containing the amino acid sequence represented by SEQ ID NO: 30,
- (y5) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 179, and a VL containing the amino acid sequence represented by SEQ ID NO: 30,
- (y6) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 180, and a VL containing the amino acid sequence represented by SEQ ID NO: 30,
- (y7) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 181, and a VL containing the amino acid sequence represented by SEQ ID NO: 30,
- (y8) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 182, and a VL containing the amino acid sequence represented by SEQ ID NO: 30, (y9) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 183, and a VL containing the amino acid sequence represented by SEQ ID NO: 30, (y10) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 184, and a VL containing the amino acid sequence represented by SEQ ID NO: 30, (y11) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 185, and a VL containing the amino acid sequence represented by SEQ ID NO: 30, (y12) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 186, and a VL containing the amino acid sequence represented by SEQ ID NO: 30, (y13-1) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 190, and a VL containing the amino acid sequence represented by SEQ ID NO: 30, (y13-2) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 191, and a VL containing the amino acid sequence represented by SEQ ID NO: 30, (y13-3) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 192, and a VL containing the amino acid sequence represented by SEQ ID NO: 30, (y13-4) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 193, and a VL containing the amino acid sequence represented by SEQ ID NO: 30, (y13-5) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 194, and a VL containing the amino acid sequence represented by SEQ ID NO: 30, (y13-6) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 195, and a VL containing the amino acid sequence represented by SEQ ID NO: 30, (y13-7) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 196, and a VL containing the amino acid sequence represented by SEQ ID NO: 30, (y13-8) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 197, and a VL containing the amino acid sequence represented by SEQ ID NO: 30, (y13-9) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 198, and a VL containing the amino acid sequence represented by SEQ ID NO: 30, (y13-10) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 199, and a VL containing the amino acid sequence represented by SEQ ID NO: 30, (y13-11) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 200, and a VL containing the amino acid sequence represented by SEQ ID NO: 30, (y13-12) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 201, and a VL containing the amino acid sequence represented by SEQ ID NO: 30, (y13-13) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 202, and a VL containing the amino acid sequence represented by SEQ ID NO: 30, (y13-14) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 203, and a VL containing the amino acid sequence represented by SEQ ID NO: 30, (y13-15) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 204, and a VL containing the amino acid sequence represented by SEQ ID NO: 30, (y13-16) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 205, and a VL containing the amino acid sequence represented by SEQ ID NO: 30, (y13-17) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 206, and a VL containing the amino acid sequence represented by SEQ ID NO: 30, (y13-18) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 207, and a VL containing the amino acid sequence represented by SEQ ID NO: 30, and (y13-19) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 208, and a VL containing the amino acid sequence represented by SEQ ID NO: 30, (y13-20) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 209, and a VL containing the amino acid sequence represented by SEQ ID NO: 30.

17. The bispecific antibody or the bispecific antibody fragment thereof according to above 13 or 14, in which the polypeptide chain is the polypeptide chain in which the C-terminus of the heavy chain ($VH_1$-CH1) in the first Fab and the N-terminus of the heavy chain ($VH_2$-CH1') in the second Fab bind to each other directly or via a linker, and ($VH_1$-CH1-$VH_2$) in the polypeptide chain is any one selected from the following (v1) to (v12) and (v13-1) to (v13-20):

(v1) ($VH_1$-CH1-$VH_2$) containing a $VH_1$ containing the amino acid sequence represented by SEQ ID NO: 29, a CH1 containing the amino acid sequence represented by SEQ ID NO: 144, and a $VH_2$ containing the amino acid sequence represented by SEQ ID NO: 175 in order from an N-terminus, (v2) ($VH_1$-CH1-$VH_2$) containing a $VH_1$ containing the amino acid sequence represented by SEQ ID NO: 29, a CH1 containing the amino acid sequence represented by SEQ ID NO: 144, and a $VH_2$ containing the amino acid sequence represented by SEQ ID NO: 176 in order from an N-terminus, (v3) ($VH_1$-CH1-$VH_2$) containing a $VH_1$ containing the amino acid sequence represented by SEQ ID NO: 29, a CH1 containing the amino acid sequence represented by SEQ ID NO: 144, and a $VH_2$ containing the amino acid sequence represented by SEQ ID NO: 177 in order from an N-terminus, (v4) ($VH_1$-CH1-$VH_2$) containing a $VH_1$ containing the amino acid sequence represented by SEQ ID NO: 29, a CH1 containing the amino acid sequence represented by SEQ ID NO: 144, and a $VH_2$ containing the amino acid sequence represented by SEQ ID NO: 178 in order from an N-terminus, (v5) ($VH_1$-CH1-$VH_2$) containing a $VH_1$ containing the amino acid sequence represented by SEQ ID NO: 29, a CH1 containing the amino acid sequence represented by SEQ ID NO: 144, and a $VH_2$ containing the amino acid sequence represented by SEQ ID NO: 179 in order from an N-terminus, (v6) ($VH_1$-CH1-$VH_2$) containing a $VH_1$ containing the amino acid sequence represented by SEQ ID NO: 29, a CH1 containing the amino acid sequence represented by SEQ ID NO: 144, and a $VH_2$ containing the amino acid sequence represented by SEQ ID NO: 180 in order from an N-terminus, (v7) ($VH_1$-CH1-$VH_2$) containing a $VH_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 181 in order from an N-terminus, (v8) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 182 in order from an N-terminus, (v9) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 183 in order from an N-terminus, (v10) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 184 in order from an N-terminus, (v11) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 185 in order from an N-terminus, (v12) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 186 in order from an N-terminus, (v13-1) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 190 in order from an N-terminus, (v13-2) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 191 in order from an N-terminus, (v13-3) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 192 in order from an N-terminus, (v13-4) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 193 in order from an N-terminus, (v13-5) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 194 in order from an N-terminus, (v13-6) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 195 in order from an N-terminus, (v13-7) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 196 in order from an N-terminus, (v13-8) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 197 in order from an N-terminus, (v13-9) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 198 in order from an N-terminus, (v13-10) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 199 in order from an N-terminus, (v13-11) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 200 in order from an N-terminus, (v13-12) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 201 in order from an N-terminus, (v13-13) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 202 in order from an N-terminus, (v13-14) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 203 in order from an N-terminus, (v13-15) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 204 in order from an N-terminus, (v13-16) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 205 in order from an N-terminus, (v13-17) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 206 in order from an N-terminus, (v13-18) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 207 in order from an N-terminus, (v13-19) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 208 in order from an N-terminus, and (v13-20) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 209 in order from an N-terminus.

18. The bispecific antibody or the bispecific antibody fragment thereof according to above 17 containing:

two heavy chains each containing the polypeptide chain in which the C-terminus of the heavy chain (VH$_1$-CH1) in the first Fab and the N-terminus of the heavy chain (VH$_2$-CH1') in the second Fab bind to each other directly or via a linker, a hinge region whose N-terminus binds to a C-terminus of the polypeptide chain, and an Fc region (CH2-CH3) whose N-terminus binds to the C-terminus of the hinge region; and four light chains (VL-CL), in which the CH1' and the Fc region (CH2-CH3) contain the amino acid sequence represented by any one of SEQ ID NOs: 145 to 172, and the light chain contains a VL containing the amino acid sequence represented by SEQ ID NO: 30.

A1. The bispecific antibody or the bispecific antibody fragment thereof according to any one of above 1 to 18, which binds to CD116 and CD131 in a divalent manner, separately.

A2. The bispecific antibody or the bispecific antibody fragment thereof according to any one of above 10, 15, 16, and A1, containing:

two first Fabs;
two second Fabs;
hinge regions; and
Fc regions, in which
the C-termini of the heavy chains of the first antigen-binding domains in the two first Fabs bind to the N-termini of the hinge regions, respectively,
the C-terminus of the hinge region binds to the N-terminus of the Fc region, and
the N-termini of the heavy chains of the second antigen-binding domains in the two second Fabs bind to the C-termini of the Fc regions, respectively.

A3. The bispecific antibody or the bispecific antibody fragment thereof according to any one of above 13 to 17, A1, and A2, in which the Fc region is of IgG1 or IgG4 subclass.

A4. The bispecific antibody or the bispecific antibody fragment thereof according to any one of above 14 to 18 and A1 to A3, in which the Fc region is of the IgG1 subclass and contains amino acid residue substitutions of L234A, L235A, and G237A as represented by an EU index, or the Fc region is of the IgG4 subclass and contains amino acid residue substitutions of S228P, L235E and R409K as represented by the EU index.

A5. The bispecific antibody or the bispecific antibody fragment thereof according to any one of above 14 to 18 and A1 to A4, in which the Fc region further contains an amino acid residue substitution of H435F as represented by the EU index.

19. A DNA encoding the bispecific antibody or the bispecific antibody fragment thereof according to any one of above 1 to 18 and A1 to A5.

20. A recombinant vector containing the DNA according to above 19.

21. A transformant obtained by introducing the recombinant vector according to above 20 into a host cell.

22. A therapeutic and/or diagnostic agent for a disease associated with a GM-CSF, containing: the bispecific antibody or the bispecific antibody fragment thereof according to any one of above 1 to 18 and A1 to A5 as an active ingredient.

A6. A method for producing the bispecific antibody or the bispecific antibody fragment thereof according to any one of above 1 to 17, and A1 to A5, the method including: culturing the transformant according to above 21 in a medium; producing and accumulating the bispecific antibody or the bispecific antibody fragment thereof according to any one of above 1 to 18 and A1 to A5 in a culture; and collecting the bispecific antibody or the bispecific antibody fragment thereof from the culture.

A7. The therapeutic agent and/or diagnostic agent according to above 22, in which the disease associated with a GM-CSF is a disease associated with an autoantibody to a GM-CSF.

A8. A therapeutic and/or diagnostic method for a disease associated with a GM-CSF, including using the bispecific antibody or the bispecific antibody fragment thereof according to any one of above 1 to 18 and A1 to A5.

A9. The therapeutic and/or diagnostic method according to above A8, in which the disease associated with a GM-CSF is a disease associated with an autoantibody to a GM-CSF.

A10. The bispecific antibody or the bispecific antibody fragment thereof according to any one of above 1 to 18 and A1 to A5, for use in treatment and/or diagnosis of a disease associated with a GM-CSF.

A11. The bispecific antibody or the bispecific antibody fragment thereof according to above A10, in which the disease associated with a GM-CSF is a disease associated with an autoantibody to a GM-CSF.

A12. Use of the bispecific antibody or the bispecific antibody fragment thereof according to any one of above 1 to 18 and A1 to A5 for the manufacture of a therapeutic and/or diagnostic agent for a diseases associated with a GM-CSF.

A13. The use according to above A12, in which the disease associated with a GM-CSF is a disease associated with an autoantibody to a GM-CSF.

A14. A reagent for detecting or measuring at least one of CD116 and CD131, containing the bispecific antibody or the bispecific antibody fragment thereof according to any one of above 1 to 18 and A1 to A5.

23. A method for purifying a composition containing an antibody, the method including: purifying an antibody containing an Fc region by Protein A column chromatography, in which the antibody is an antibody with an H435F mutation introduced in the Fc region.

24. The bispecific antibody or the bispecific antibody fragment thereof according to any one of above 1 to 18, which binds to an epitope containing W at position 163 and R at position 221 in CD131 (SEQ ID NO: 211) and an epitope containing N at position 156, K at position 158, and T at position 187 in CD116 (SEQ ID NO: 210).

Advantageous Effects of Invention

According to the present invention, there is provided a novel bispecific antibody binding to CD116 and CD131, a novel bispecific antibody having an agonist activity to a GM-CSF receptor, a bispecific antibody fragment thereof, a DNA encoding the bispecific antibody or the bispecific antibody fragment thereof, a vector containing the DNA, a hybridoma or transformant producing the bispecific antibody or the bispecific antibody fragment thereof, a method for producing the bispecific antibody or the bispecific antibody fragment thereof, a therapeutic and diagnostic agent containing the bispecific antibody or the bispecific antibody fragment thereof, a therapeutic and diagnostic method using the bispecific antibody or the bispecific antibody fragment thereof, and a detection or measurement reagent containing the bispecific antibody or the bispecific antibody fragment thereof.

BRIEF DESCRIPTION OF DRAWINGS

FIG. 2 shows a schematic diagram of an IgG-type CD131-CD116 bispecific antibody.

FIG. 3A shows the agonist activity of the IgG-type CD131-CD116 bispecific antibody using CD131-16 as an anti-CD131 antibody. FIG. 3B shows the agonist activity of the IgG-type CD131-CD116 bispecific antibody using CD131-B2 as the anti-CD131 antibody (an average value of 2 wells), and a horizontal axis represents a concentration of the antibody.

FIG. 4A shows a structure of an N-terminus type CD131-CD116 bispecific antibody or an N-terminus type CD116-CD131 bispecific antibody. FIG. 4B shows a structure of a C-terminus type CD131-CD116 bispecific antibody and a C-terminus type CD116-CD131 bispecific antibody.

FIGS. 9A, 9B and 9C show the agonist activity of the CD131-CD116 bispecific antibody to GM-CSF receptor-expressing Ba/F3 cells, IL-3 receptor-expressing Ba/F3 cells, and IL-5 receptor-expressing Ba/F3 cells (mean value±standard deviation of n=3), respectively. IgG4PE R409K is used for all constant regions, and a horizontal axis represents a concentration of the antibody.

FIG. 18A shows a sensorgram showing binding to human FcRn when an IgG4PE R409K wild type (WT) is used as the Fc region. FIG. 18B shows a sensorgram when an IgG4PE R409 I253A mutant is used as the Fc region. FIG. 18C shows a sensorgram when IgG4PE R409 H435F is used as the Fc region, in which when I253A and H435F mutants are used, no binding to human FcRn is observed, and a vertical axis shows a resonance unit (RU), and a horizontal axis shows a time (sec).

DESCRIPTION OF EMBODIMENTS

Figure 1:
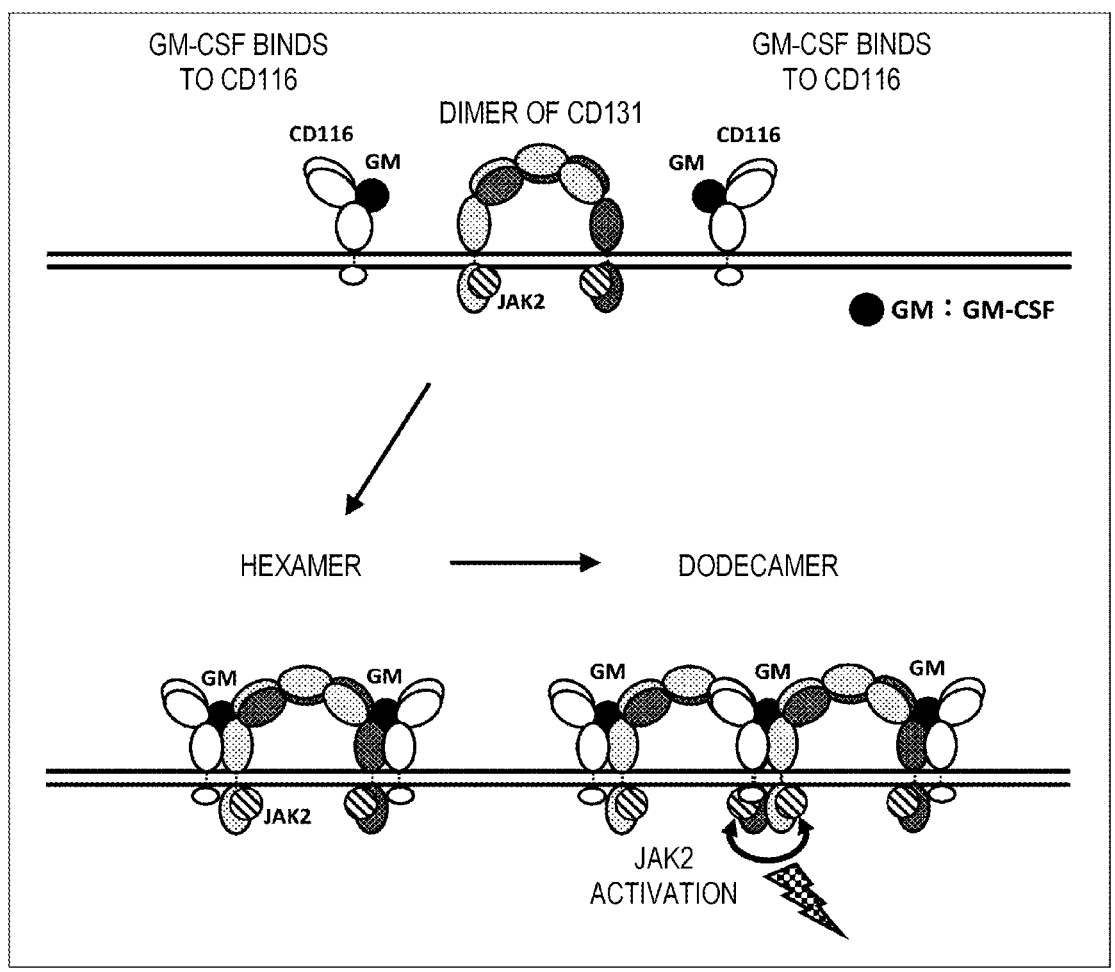
FIG. 1 shows a schematic diagram of a GM-CSF receptor.

The present invention relates to a novel bispecific antibody binding to CD116 and CD131, or a novel bispecific antibody having an agonist activity to a GM-CSF receptor, and a bispecific antibody fragment thereof.

CD116 in the present invention is used in the same meaning as CSF2RA, GM-CSFRα, GM-CSF-R-alpha, CDw116, CSF2RAX, CSF2RAY, CSF2RX, CSF2RY, GMCSFR, GMR, MGC3848, and MGC4838.

Examples of CD116 include monkey CD116 containing an amino acid sequence shown in human CD116 containing the amino acid sequence shown in GenBank accession No. P15509 in NCBI (ncbi.nlm.nih.gov). Examples of CD116 include a polypeptide consisting of an amino acid sequence obtained by deleting, substituting, or adding one or more amino acids in the amino acid sequence shown in GenBank accession No. P15509, and having a function of CD116.

CD116 of the present invention also includes a polypeptide containing an amino acid sequence having a homology of generally 70% or more, preferably 80% or more, and further preferably 90% or more with the amino acid sequence shown in GenBank accession No. P15509, and a polypeptide consisting of an amino acid sequence having a homology of most preferably 95% or more, 96% or more, 97% or more, 98% or more, and 99% or more therewith, and having the function of CD116.

The polypeptide containing an amino acid sequence obtained by deleting, substituting, or adding one or more amino acid residues in the amino acid sequence shown in GenBank accession No. P15509 can be obtained by introducing a mutation in a site-directed manner into a DNA encoding the amino acid sequence shown in GenBank accession No. P15509, for example, by using a site-directed mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proceeding of the National Academy of Sciences in USA, 82, 488 (1985)]. The number of amino acids to be deleted, substituted, or added is not particularly limited, and is preferably 1 to several tens of amino acids, for example 1 to 20 amino acids, and more preferably 1 to several amino acids, for example 1 to 5 amino acids.

Examples of the gene encoding CD116 include the nucleotide sequence of human CD116 shown in SEQ ID NO: 6 or GenBank accession No. X17648, and the nucleotide sequence of monkey CD116 shown in SEQ ID NO: 7.

For example, the gene encoding CD116 of the present invention also includes a gene containing a DNA that consists of a nucleotide sequence obtained by deleting, substituting, or adding one or more bases in the nucleotide sequence shown in SEQ ID NO: 6, GenBank accession No. X17648, or SEQ ID NO: 7 and encodes a polypeptide having the function of CD116, a gene containing a DNA that consists of a nucleotide sequence having a homology of preferably 60% or more with the nucleotide sequence shown in SEQ ID NO: 6, GenBank accession No. X17648, or SEQ ID NO: 7, a nucleotide sequence having a homology of more preferably 80% or more therewith, or a nucleotide sequence having a homology of further preferably 95% or more therewith and encodes a polypeptide having the function of CD116, and a gene containing a DNA that consists of a DNA that hybridizes under stringent conditions with a DNA consisting of the nucleotide sequence shown in SEQ ID NO: 6, GenBank accession No. X17648, or SEQ ID NO: 7 and encodes a polypeptide having the function of CD116.

The DNA that hybridizes under stringent conditions means, for example, a hybridizable DNA obtained by a colony hybridization method, plaque hybridization method, Southern blot hybridization method, or DNA microarray method using, as a probe, a DNA having the nucleotide sequence shown in SEQ ID NO: 6, GenBank accession No. X17648, or SEQ ID NO: 7.

Specific examples thereof include a DNA that can be identified by performing hybridization [Molecular Cloning, A Laboratory Manual, Second Edition, Cold Spring Harbor Laboratory Press (1989), Current Protocols in Molecular Biology, John Wiley & Sons (1987-1997), DNA Cloning 1: Core Techniques, A Practical Approach, Second Edition, Oxford University (1995)] at 65° C. in the presence of 0.7 mol/L to 1.0 mol/L sodium chloride using a filter or a slide glass on which a DNA derived from a hybridized colony or plaque, or a PCR product or an oligo DNA having the sequence is immobilized, and then washing the filter or the slide glass under a condition of 65° C. using a 0.1× to 2×SSC solution (a composition of the 1×SSC solution consists of 150 mmol/L sodium chloride and 15 mmol/L sodium citrate). Examples of the hybridizable DNA include a DNA having a homology of preferably 60% or more with the nucleotide sequence shown in SEQ ID NO: 6, GenBank accession No. X17648, or SEQ ID NO: 7, a DNA having a homology of more preferably 80% or more therewith, and a DNA having a homology of further preferably 95% or more therewith.

Genetic polymorphisms are often observed in the nucleotide sequences of genes encoding eukaryotic proteins. The gene encoding CD116 in the present invention also includes genes used in the present invention that have small-scale mutations in nucleotide sequences thereof due to such polymorphisms.

Unless otherwise specified, a numerical value of homology in the present invention may be a numerical value calculated using a homology search program known to those skilled in the art. Examples of the numerical value of homology for the nucleotide sequence include numerical values calculated using default parameters in BLAST [J. Mol. Biol., 215, 403 (1990)], and examples of the numerical value of homology for the amino acid sequence include numerical values calculated using default parameters in BLAST2 [Nucleic Acids Research, 25, 3389 (1997); Genome Research, 7, 649 (1997)].

The polypeptide consisting of a partial sequence of the amino acid sequence of CD116 can be prepared by a method known to those skilled in the art, and for example, the polypeptide consisting of the partial sequence of CD116 can be prepared by deleting a part of a DNA encoding the amino acid sequence shown in GenBank accession No. P15509, and culturing a transformant introduced with an expression vector containing the partial DNA.

Based on the polypeptide or DNA prepared by the above method, for example, a polypeptide having an amino acid sequence obtained by deleting, substituting, or adding one or more amino acids in a partial sequence of the amino acid sequence shown in GenBank accession No. P15509 can be obtained by the same method as above.

Further, the polypeptide consisting of the partial sequence of the amino acid sequence of CD116, or the polypeptide having the amino acid sequence obtained by deleting, substituting, or adding one or more amino acids in the partial sequence of the amino acid sequence of CD116 can be produced by chemical synthesis methods such as a fluorenylmethyloxycarbonyl (Fmoc) method and a t-butyloxycarbonyl (tBoc) method.

Examples of an extracellular region of CD116 in the present invention include a region predicted from the amino acid sequence of human CD116 shown in GenBank accession No. P15509 using a known transmembrane region prediction program SOSUI, TMHMM ver.2 (https://services.healthtech.dtu.dk/service.php?TMHMM-2.0) or an ExPASy Proteomics Server (http://Ca.expasy.org/). Specifically, examples of the extracellular region of CD116 include amino acid sequences shown at positions 23 to 320 in GenBank accession No. P15509.

Examples of the function of CD116 include binding of a ligand GM-CSF [Cytokine Growth Factor Rev., 12, 19 (2001)]. Examples of cells expressing CD116 include monocytes, granulocytes, and progenitor cells thereof, endothelial cells, fibroblasts, and Langerhans cells.

CD131 in the present invention is used in the same meaning as CSF2RB, IL3RB, IL5RB, SMDP5, a common β receptor, and βc. Examples of CD131 include human CD131 containing the amino acid sequence shown in UniProt Entry No. P32927, and monkey CD131 containing the amino acid sequence shown in GenBank accession No. XP_015312724_1. In addition, examples thereof include a polypeptide consisting of an amino acid sequence obtained by deleting, substituting, or adding one or more amino acids in the amino acid sequence shown in UniProt Entry No. P32927 or GenBank accession No. XP 015312724_1, and having a function of CD131.

CD131 in the present invention also includes a polypeptide containing an amino acid sequence having a homology of generally 70% or more, preferably 80% or more, and further preferably 90% or more with the amino acid sequence shown in UniProt Entry No. P32927 or GenBank accession No. XP_015312724_1, and a polypeptide consisting of an amino acid sequence having a homology of most preferably 95% or more, 96% or more, 97% or more, 98% or more, and 99% or more therewith, and having the function of CD131.

The polypeptide having an amino acid sequence obtained by deleting, substituting, or adding one or more amino acid residues in UniProt Entry No. P32927 or GenBank accession No. XP_015312724_1 can be obtained, for example, by introducing a mutation in a site-directed manner into a DNA encoding the amino acid sequence shown in UniProt Entry No. P32927 or GenBank accession No. XP_015312724_1 using the above-described site-directed mutagenesis method. The number of amino acids to be deleted, substituted, or added is not particularly limited, and is preferably 1 to several tens of amino acids, for example 1 to 20 amino acids, and more preferably 1 to several amino acids, for example 1 to 5 amino acids.

Examples of the gene encoding CD131 include the nucleotide sequence of human CD131 shown in SEQ ID NO: 1 or GenBank accession No. M59941, and the nucleotide sequence of monkey CD131 shown in SEQ ID NO: 2.

For example, the gene encoding CD131 in the present invention also includes a gene containing a DNA that consists of a nucleotide sequence obtained by deleting, substituting, or adding one or more bases in the nucleotide sequence shown in SEQ ID NO: 1, GenBank accession No. M59941, or SEQ ID NO: 2 and encodes a polypeptide having the function of CD131, a gene containing a DNA that consists of a nucleotide sequence having a homology of preferably 60% or more with the nucleotide sequence shown in SEQ ID NO: 1, GenBank accession No. M59941, or SEQ ID NO: 2, a nucleotide sequence having a homology of more preferably 80% or more therewith, or a nucleotide sequence having a homology of further preferably 95% or more therewith and encodes a polypeptide having the function of CD131, and a gene containing a DNA that consists of a DNA that hybridizes under stringent conditions with a DNA consisting of the nucleotide sequence shown in SEQ ID NO: 1, GenBank accession No. M59941, or SEQ ID NO: 2 and encodes a polypeptide having the function of CD131.

As described above, the DNA that hybridizes under stringent conditions means, for example, a hybridizable DNA obtained by a colony hybridization method, plaque hybridization method, Southern blot hybridization method, or DNA microarray method using, as a probe, a DNA having the nucleotide sequence shown in SEQ ID NO: 1, GenBank accession No. M59941, or SEQ ID NO: 2. Examples of the hybridizable DNA include a DNA having a homology of preferably 60% or more with the nucleotide sequence shown in SEQ ID NO: 1, GenBank accession No. M59941, or SEQ ID NO: 2, a DNA having a homology of more preferably 80% or more therewith, and a DNA having a homology of further preferably 95% or more therewith.

Genetic polymorphisms are often observed in the nucleotide sequences of genes encoding eukaryotic proteins. The gene encoding CD131 in the present invention also includes genes used in the present invention that have small-scale mutations in nucleotide sequences thereof due to such polymorphisms.

The polypeptide consisting of a partial sequence of an amino acid sequence of CD131 can be prepared using a DNA encoding the amino acid sequence shown in UniProt Entry No. P32927 or GenBank accession No. XP_015312724_1 by a method known to those skilled in the art in the same manner as described above.

Examples of an extracellular region of CD131 in the present invention include a region predicted from the amino acid sequence of human CD131 shown in UniProt Entry No. P32927 by the same method as described above. Specifically, examples of the extracellular region of CD131 include amino acid sequences shown at positions 17 to 443 in UniProt Entry No. P32927.

Examples of the function of CD131 include association with CD116 (GM-CSFRα), CD123 (IL-3Rα), and CD125 (IL-5Rα), and transduction of GM-CSF, IL-3, and IL-5 signals into cells, respectively [Cytokine Growth Factor Rev., 12, 19 (2001)].

Examples of cells expressing CD131 include monocytes, granulocytes, and initial B cells.

An antibody is a protein derived from a gene (referred to as an "antibody gene") that encodes all or a part of a variable region of a heavy chain and a constant region of the heavy chain, and a variable region of a light chain and a constant region of the light chain, which constitute an immunoglobulin. The antibody of the present invention also includes antibodies or antibody fragments of any immunoglobulin class and subclass.

The heavy chain (H chain) indicates a polypeptide having a larger molecular weight among two types of polypeptides constituting an immunoglobulin molecule. The heavy chain determines a class and a subclass of the antibody. IgA, IgD, IgE, IgG, and IgM have an α-chain, a δ-chain, an ε-chain, a γ-chain, and a μ-chain, respectively, as heavy chains, and constant regions of the heavy chains are characterized by different amino acid sequences. The light chain (L chain) indicates a polypeptide having a smaller molecular weight among two types of polypeptides constituting an immunoglobulin molecule. In the case of a human antibody, there are two types of light chains, i.e., a κ chain and a λ chain.

The variable region (V region) generally indicates a region rich in diversity that exists within an amino acid sequence on an N-terminus side of an immunoglobulin. A region other than the variable region is called a constant region (C region) because it has a structure with little diversity. The variable regions of the heavy chain and the light chain associate to form an antigen-binding site and determine a binding property of the antibody to an antigen.

In a heavy chain of a human antibody, a variable region corresponds to the amino acid sequence at positions 1 to 117 in the EU index (Kabat et al., Sequences of proteins of immunological interest, 1991 Fifth edition) of Kabat et al., and a constant region corresponds to the amino acid sequence at position 118 and subsequent positions. In a light chain of a human antibody, the amino acid sequence at positions 1 to 107 in Kabat numbering by Kabat et al. corresponds to a variable region, and the amino acid sequence at position 108 and subsequent positions corresponds to a constant region. Hereinafter, the heavy chain variable region and the light chain variable region are abbreviated as VH and VL, respectively.

The antigen-binding site is a site in an antibody that recognizes and binds to an antigen, and indicates a site that forms a three-dimensional structure complementary to an antigenic determinant (epitope). The antigen-binding site generates a strong intermolecular interaction with the antigenic determinant. The antigen-binding site is composed of a VH and a VL each containing at least three complementarity determining regions (CDRs). In the case of a human antibody, a VH and a VL each have three CDRs. The CDRs are referred to as CDR1, CDR2, and CDR3 in order from an N-terminus side.

Among a constant region, a heavy chain constant region and a light chain constant region are denoted by CH and CL, respectively. The CH is classified according to an α chain, a δ chain, a ε chain, a γ chain, and a μ chain, which are subclasses of a heavy chain. The CH is composed of a CH1 domain, a hinge domain, a CH2 domain, and a CH3 domain aligned in order from an N-terminus side, and the CH2 domain and the CH3 domain are collectively called an Fc region. On the other hand, the CL is classified into two subclasses called a Cλ chain and a Cκ chain.

A monoclonal antibody is an antibody secreted by an antibody-producing cell retaining monoclonality, and recognizes a single epitope (also referred to as antigenic determinant). Monoclonal antibody molecules have the same amino acid sequence (primary structure) and have a single structure. A polyclonal antibody refers to a population of antibody molecules secreted by antibody-producing cells of different clones. An oligoclonal antibody refers to a population of antibody molecules that is a mixture of a plurality of different monoclonal antibodies.

The epitope refers to a structural site on an antigen that an antibody recognizes and binds to. Examples of the epitope include a single amino acid that a monoclonal antibody recognizes and binds to, a three-dimensional structure consisting of an amino acid sequence, an amino acid sequence to which a sugar chain binds, and a three-dimensional structure consisting of an amino acid sequence to which a sugar chain binds.

The monoclonal antibody in the present invention may include an antibody produced by hybridomas and a recombinant antibody produced by a transformant transformed with an expression vector containing an antibody gene.

The hybridomas can be prepared, for example, by preparing antigens, obtaining antibody-producing cells having antigenic specificity from an animal immunized with the antigens, and fusing the antibody-producing cells and myeloma cells. A desired monoclonal antibody can be obtained by culturing the hybridomas or administering the hybridomas to an animal to induce ascites carcinoma of the hybridomas, and then separating and purifying the culture medium or ascites fluid. As the animal to be immunized with the antigen, any animals can be used as long as hybridomas can be prepared, and mice, rats, hamsters, rabbits, and the like are preferably used. In addition, the hybridomas can be prepared by obtaining antibody-producing cells from such an immune animal, immunizing the cells in vitro, and then fusing the cells with myeloma cells.

Examples of the recombinant antibody in the present invention include an antibody produced by a gene recombination technique, such as a recombinant mouse antibody, a recombinant rat antibody, a recombinant hamster antibody, a recombinant rabbit antibody, a humanized chimeric antibody (also referred to as chimeric antibody), a humanized antibody (also referred to as CDR-grafted antibody), and a human antibody. In the recombinant antibody, depending on the target animal species and purpose, it can be determined which animal species the heavy chain and light chain variable regions and constant regions are to be used. For example, when the target animal species is human, the variable regions can be derived from a human or a non-human animal such as mice, and the constant regions and linkers can be derived from a human.

The chimeric antibody indicates an antibody consisting of a VH and a VL of an antibody from an animal other than human (non-human animal) and a CH and a CL of a human antibody. Any non-human animals can be used as long as hybridomas can be prepared, such as mice, rats, hamsters, and rabbits. The chimeric antibody can be produced by obtaining a cDNA encoding a VH and a VL from monoclonal antibody-producing hybridomas derived from a non-human animal, inserting the cDNA into an animal cell expression vector having a DNA encoding a CH and a CL of a human antibody, constructing a chimeric antibody expression vector, and introducing chimeric antibody expression vector into an animal cell to express the chimeric antibody.

The humanized antibody indicates an antibody obtained by grafting CDRs of a VH and a VL of a non-human animal antibody onto corresponding CDRs of a VH and a VL of a human antibody. A region other than the CDRs of the VH and the VL is referred to as a framework region (hereinafter referred to as FR). The humanized antibody can be produced by constructing a cDNA encoding an amino acid sequence of a VH consisting of an amino acid sequence of CDRs of a VH of a non-human animal antibody and an amino acid sequence of an FR of a VH of any human antibody, and a cDNA encoding an amino acid sequence of a VL consisting of an amino acid sequence of CDRs of a VL of a non-human animal antibody and an amino acid sequence of an FR of a VH of any human antibody, inserting the cDNAs into an animal cell expression vector having a DNA encoding a CH and a CL of a human antibody, constructing a humanized antibody expression vector, and introducing the humanized antibody expression vector into an animal cell to express the humanized antibody.

The human antibody originally refers to an antibody naturally occurring in the human body, and also includes an antibody obtained from a human antibody phage library prepared by recent advances in genetic engineering, cellular engineering, and developmental engineering technologies and human antibody-producing transgenic animals.

The antibody naturally occurring in the human body can be obtained, for example, by immortalizing human peripheral lymphocytes by infection with EB virus, cloning the human peripheral lymphocytes, culturing the lymphocytes that produce the antibody, and purifying the antibody from the culture supernatant.

The human antibody phage library is a library in which an antibody fragment such as Fab or a single-chain Fv (scFv) is expressed on a phage surface by inserting an antibody gene prepared from a human B cell into a phage gene. From the library, a phage expressing an antibody fragment having a desired antigen-binding activity on the surface can be collected by using the binding activity to a substrate immobilized with the antigen as an indicator. The antibody fragment can be further converted into a human antibody molecule consisting of two complete H chains and two complete L chains by a genetic engineering technique.

The human antibody-producing transgenic animal means an animal with a human antibody gene incorporated into a cell thereof. Specifically, for example, a human antibody-producing transgenic mouse can be prepared by introducing a human antibody gene into a mouse ES cell and grafting the ES cell into a mouse initial embryo to produce an individual. The human antibody derived from the human antibody-producing transgenic animal can be prepared by obtaining hybridomas using a hybridoma preparing method used in a general non-human animal, and culturing the hybridomas to produce and accumulate the antibody in the culture supernatant.

The CH of the recombinant antibody may be any one belonging to human immunoglobulin, and those of the human immunoglobulin G (hIgG) class are preferred. Further, any of the subclasses of the hIgG class, such as hIgG1, hIgG2, hIgG3, and hIgG4, can be used. The CL of the recombinant antibody may be any one belonging to human immunoglobulin, and those of a κ class or a λ class can be used.

In the present invention, the bispecific antibody refers to a polypeptide or a protein having antigen-binding domains that specifically bind to two different epitopes, respectively. The bispecific antibody may bind to different epitopes of a single antigen or may bind to different antigens. When binding to different antigens, those antigens may be present in the same cell or in different cells.

The bispecific antibody of the present invention includes a first antigen-binding domain and a second antigen-binding domain that specifically bind to CD131 and CD116, respectively, as two different kinds of epitopes. One of the first antigen-binding domain and the second antigen-binding domain is an antigen-binding domain binding to CD116, and the other one is an antigen-binding domain binding to CD131.

Examples of the epitope of the bispecific antibody of the present invention include an epitope containing tryptophan (W) at position 163 and arginine (R) at position 221 in CD131 (SEQ ID NO: 211), and an epitope containing asparagine (N) at position 156, lysine (K) at position 158, and threonine (T) at position 187 in CD116 (SEQ ID NO: 210). The epitope containing tryptophan (W) at position 163 and arginine (R) at position 221 in CD131 (SEQ ID NO: 211), and the epitope containing asparagine (N) at position 156, lysine (K) at position 158, and threonine (T) at position 187 in CD116 (SEQ ID NO: 210) are both three-dimensional structural epitopes.

In the present invention, binding of the polypeptide, the antibody or the antibody fragment thereof, or the bispecific antibody or the bispecific antibody fragment thereof to CD116 and/or CD131 can be confirmed by a method of confirming a binding property between an antibody and a cell expressing CD131 or CD116 to be evaluated using, for example, a known immunological detection method, and preferably a fluorescent cell staining method. A known immunological detection method [Monoclonal Antibodies-Principles and Practice, Third Edition, Academic Press (1996), Antibodies-A Laboratory Manual, Cold Spring Harbor Laboratory (1988), Monoclonal Antibody Laboratory Manual, Kodansha Scientific (1987)], and the like can be used in combination.

The bispecific antibody or the antibody fragment thereof of the present invention also includes an antibody obtained by deleting, adding, substituting, or inserting one or more amino acid residues in the amino acid sequence constituting the bispecific antibody or the antibody fragment thereof of the present invention and having the same activity as that of the antibody or the antibody fragment thereof described above, or an antibody fragment thereof.

The number of amino acids to be deleted, substituted, inserted and/or added is one or more, and the number thereof is not particularly limited, and is a number capable of performing deletion, substitution, insertion or addition by a well-known technique such as a site-directed mutagenesis method described in Molecular Cloning, The Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci USA, 82, 488 (1985). For example, the number thereof is generally 1 to several tens, preferably 1 to 20, more preferably 1 to 10, and further preferably 1 to 5.

The deletion, substitution, insertion, or addition of one or more amino acid residues in the above amino acid sequence of the bispecific antibody of the present invention indicates the following. It means deletion, substitution, insertion, or addition of one or more amino acid residues in any one or a plurality of amino acid sequences within the same sequence. The deletion, substitution, insertion, or addition may occur simultaneously, and the amino acid residue to be substituted, inserted, or added may be either a natural type or a non-natural type.

Examples of the natural amino acid residue include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, and L-cysteine.

Preferred examples of mutually substitutable amino acid residues are shown below. Amino acid residues included in the same group can be substituted for each other.

Group A: leucine, isoleucine, norleucine, valine, norvaline, alanine, 2-aminobutanoic acid, methionine, O-methylserine, t-butylglycine, t-butylalanine, and cyclohexylalanine Group B: aspartic acid, glutamic acid, isoaspartic acid, isoglutamic acid, 2-aminoadipic acid, and 2-aminosuberic acid Group C: asparagine and glutamine Group D: lysine, arginine, ornithine, 2,4-diaminobutanoic acid, and 2,3-diaminopropionic acid Group E: proline, 3-hydroxyproline, and 4-hydroxyproline Group F: serine, threonine, and homoserine Group G: phenylalanine and tyrosine The bispecific antibody or the antibody fragment thereof of the present invention may contain a non-natural amino acid, and examples of the non-natural amino acid include a Z lysine derivative (N6-((benzyloxy) carbonyl)-L-lysine derivative) disclosed in WO2017/030156, a TCO*-Lys (N6-(((trans-cyclooct-2-ene-1-yl)oxy)carbonyl)-L-lysine), or a BCN-Lys (N6-((bicyclo[6.1.0]non-4-yn-9-ylmethoxy) carbonyl)-L-lysine).

The bispecific antibody or the bispecific antibody fragment thereof of the present invention also includes an antibody containing any post-translationally modified amino acid residues. Examples of the post-translational modification include deletion of a lysine residue at a C-terminus of an H chain (lysine clipping) and substitution of a glutamine residue at an N-terminus of the polypeptide with pyroglutamine (pyroGlu) [Beck et al, Analytical Chemistry, 85, 715-736 (2013)].

Examples of the bispecific antibody or the bispecific antibody fragment thereof of the present invention include a bispecific antibody having a GM-CSF receptor agonist activity or a bispecific antibody fragment thereof.

The bispecific antibody or the bispecific antibody fragment thereof of the present invention is preferably a bispecific antibody that does not exhibit a GM-CSF receptor agonist activity in cells that do not express CD116 and CD131, but exhibits a GM-CSF receptor agonist activity only in cells that express CD116 and CD131, or a bispecific antibody fragment thereof.

The bispecific antibody or the bispecific antibody fragment thereof of the present invention is preferably one that does not transmit a signal to an IL-3 receptor or IL-5 receptor, which has CD131 as a common constituent molecule with the GM-CSF receptor.

The bispecific antibody or the bispecific antibody fragment thereof of the present invention may bind to CD116 and CD131 expressed on the same cell, or may bind to CD116 and CD131 expressed on different cells, and preferably binds to CD116 and CD131 expressed on the same cell.

The agonist activity refers to an activity of binding to a receptor and transducing intracellular information similar to that of an original ligand of the receptor.

The bispecific antibody of the present invention preferably has an agonist activity to a GM-CSF receptor. The bispecific antibody of the present invention binds to both CD116 and CD131 to act on the GM-CSF receptor in the same manner as a GM-CSF to exhibit the agonist activity.

In the present invention, the agonist activity to the GM-CSF receptor refers to an activity in which, for example, when a GM-CSF binds to both CD116 and CD131 on a cell, a signal is transduced from a GM-CSF receptor into the cell, resulting in activation of the cell, promotion of cell proliferation, and increase in cell viability, induction of differentiation, and the like. Specifically, the agonist activity to the GM-CSF receptor refers to an activity in which when a GM-CSF or the bispecific antibody of the present invention binds to both CD116 and CD131 on a monocyte, a signal is transduced from a GM-CSF receptor, and differentiation into macrophages is induced.

The bispecific antibody or the bispecific antibody fragment thereof of the present invention is preferably one that has an agonist activity to a GM-CSF receptor and transduces a signal to the cell after binding to a GM-CSF receptor. The bispecific antibody or the bispecific antibody fragment thereof of the present invention is preferably one that binds to a GM-CSF receptor on a monocyte and has an ability to induce differentiation into macrophage.

The bispecific antibody or the bispecific antibody fragment thereof of the present invention is preferably one that binds to CD116 and CD131 expressed on the same cell, induces formation of a GM-CSF receptor complex, and transduces a signal into the cell. The bispecific antibody or the bispecific antibody fragment thereof of the present invention is preferably one that binds to CD116 and CD131 on a monocyte and has an ability to induce differentiation into macrophage.

The agonist activity to the GM-CSF receptor can be confirmed, for example, by expressing a GM-CSF receptor of a human red spore cell line TF-1 (CRL-2003) or the like, and evaluating a cell proliferation ratio, a survival rate, the number of living cells, and the like by using cells that proliferate in a GM-CSF-dependent manner.

The ability to induce differentiation into macrophage can be confirmed, for example, by evaluating a change in expression levels of CD14 and CD206, which are marker molecules for monocytes and macrophages, the number of cells, morphology of cells, and the like by using human peripheral blood mononuclear cell (PBMC)-derived monocytes.

That is, specific examples of the bispecific antibody and the bispecific antibody fragment thereof of the present invention include one which acts as a GM-CSF receptor agonist when binds to both CD116 and CD131, and/or a bispecific antibody having an ability to induce differentiation of macrophages to monocytes or a bispecific antibody fragment thereof.

The number of antigen-binding domains that one molecule of the bispecific antibody has for an antigen is called a binding valency. For example, in the present invention, when one molecule of bispecific antibody has one antigen-binding domain binding to CD116 and one antigen-binding domain binding to CD131, such a bispecific antibody binds to CD116 and CD131 in a monovalent manner.

The bispecific antibody of the present invention preferably binds to CD116 and CD131 in a monovalent or divalent manner, separately, and more preferably binds to CD116 and CD131 in a divalent manner from the viewpoint of improving agonist activity.

In the present invention, the first antigen-binding domain and the second antigen-binding domain may be any domains that specifically recognize and bind to CD131 and CD116, respectively. For example, any form such as a polypeptide which can be prepared by a gene recombination technique, such as an antibody, a ligand, a receptor, and a naturally occurring interaction molecule, a protein molecule, and a fragment thereof, and a conjugate of the protein molecule with a low molecule or a natural product may be used.

The first antigen-binding domain and the second antigen-binding domain may be recombinant binding proteins using binding domains of known binding molecules such as an antibody (hereinafter also referred to as an immunoglobulin), a ligand, and a receptor, and examples thereof include a recombinant protein containing antibody CDRs binding to each antigen, and a recombinant protein containing antibody variable regions (VH and VL) containing CDRs, an antibody fragment of an antibody variable region, or binding domains of ligands binding to each antigen.

In the present invention, an immunoglobulin domain has an amino acid sequence similar to an immunoglobulin, and a minimum unit of the immunoglobulin domain is a peptide consisting of about 100 amino acid residues in which at least two cysteine residues are present. In the present invention, the immunoglobulin domain includes polypeptides containing a plurality of the above-described minimum unit immunoglobulin domains. Examples of the immunoglobulin domain include a VH, a CH1, a CH2, and a CH3 of an immunoglobulin heavy chain, and a VL and a CL of an immunoglobulin light chain.

The animal species of the immunoglobulin is not particularly limited, and humans are preferred. A subclass of a constant region of the immunoglobulin heavy chain may be any of IgD, IgM, IgG1, IgG2, IgG3, IgG4, IgA1, IgA2, and IgE, and preferred examples thereof include IgG-derived and IgM-derived. A subclass of a constant region of the immunoglobulin light chain may be either κ or λ.

The immunoglobulin domain also presents in proteins other than an immunoglobulin, and examples thereof include immunoglobulin domains contained in proteins belonging to the immunoglobulin superfamily, such as a major histocompatibility antigen (MHC), a CD1, a B7, and a T cell receptor (TCR). Any immunoglobulin domain can be used as the immunoglobulin domain for use in the bispecific antibody of the present invention.

In the case of human IgG, the CH1 refers to a region having an amino acid sequence at positions 118 to 215 as indicated by the EU index. Similarly, the CH2 indicates a region having an amino acid sequence at positions 231 to 340 as indicated by the EU index of Kabat et al, and the CH3 refers to a region having an amino acid sequence at positions 341 to 447 as indicated by the EU index of Kabat et al. Between the CH1 and the CH2, there is a highly flexible amino acid region called a hinge region (hereinafter sometimes referred to as hinge). The hinge region refers to a region having an amino acid sequence at positions 216 to 230 as indicated by the EU index of Kabat et al.

The CL refers to a region having an amino acid sequence at positions 108 to 214 as indicated by Kabat numbering in the case of a K chain of a human antibody, and the CL refers to a region having an amino acid sequence at positions 108 to 215 in the case of a λ chain.

The antigen-binding domain binding to CD131 in the bispecific antibody of the present invention refers to an antigen-binding domain having a function of specifically recognizing and binding to an extracellular region of CD131.

The antigen-binding domain binding to CD116 in the bispecific antibody of the present invention refers to an antigen-binding domain having a function of specifically recognizing and binding to an extracellular region of CD116.

The bispecific antibody of the present invention may have an Fc region of an antibody in addition to the antigen-binding domain binding to CD116 and the antigen-binding domain binding to CD131. From the viewpoint of stability and ease of preparation, the Fc region is preferably of the IgG1 or IgG4 subclass, each more preferably containing the amino acid residue substitutions shown below.

(1) When the Fc region is of the IgG1 subclass, the Fc region preferably contains the amino acid residue substitutions of L234A, L235A, and G237A as represented by the EU index, and more preferably contains the amino acid residue substitution of H435F as represented by the EU index in addition to the above amino acid residue substitutions.

(2) When the Fc region is of the IgG4 subclass, the Fc region preferably contains the amino acid residue substitutions of S228P, L235E and R409K as represented by the EU index, and more preferably contains the amino acid residue substitution of H435F as represented by the EU index in addition to the above amino acid residue substitutions.

The antigen-binding domain in the present invention may be a single chain or a multimer consisting of a plurality of polypeptide chains as long as it has an antigen-binding ability to CD131 or CD116. Examples of the antigen-binding domain include an antibody, an antibody fragment, or a partial fragment of a GM-CSF that binds to CD131 or CD116.

The antigen-binding domain in the present invention preferably contains a VH and a VL each containing antibody CDRs binding to each antigen (CD131 or CD116).

Examples of the antigen-binding domain binding to CD131 in the present invention include an antigen-binding domain selected from the following (1a) to (1e):

(1a) an antigen-binding domain containing a VH containing CDRs 1 to 3 containing the amino acid sequences represented by SEQ ID NOs: 61 to 63, respectively, and a VL containing CDRs 1 to 3 containing the amino acid sequences represented by SEQ ID NOs: 64 to 66, respectively, (1b) an antigen-binding domain containing a VH containing CDRs 1 to 3 containing the amino acid sequences represented by SEQ ID NOs: 67 to 69, respectively, and a VL containing CDRs 1 to 3 containing the amino acid sequences represented by SEQ ID NOs: 70 to 72, respectively, (1c) an antigen-binding domain containing a VH containing CDRs 1 to 3 containing the amino acid sequences represented by SEQ ID NOs: 73 to 75, respectively, and a VL containing CDRs 1 to 3 containing the amino acid sequences represented by SEQ ID NOs: 76 to 78, respectively, (1d) an antigen-binding domain containing a VH containing CDRs 1 to 3 containing the amino acid sequences represented by SEQ ID NOs: 79 to 81, respectively, and a VL containing CDRs 1 to 3 containing the amino acid sequences represented by SEQ ID NOs: 82 to 84, respectively, and (1e) an antigen-binding domain containing a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively.

More specific examples of the antigen-binding domain binding to the CD131 in the present invention include any one selected from the following (1A) to (1E):

(1A) an antigen-binding domain containing a VH containing the amino acid sequence represented by SEQ ID NO: 21 and a VL containing the amino acid sequence represented by SEQ ID NO: 22, (1B) an antigen-binding domain containing a VH containing the amino acid sequence represented by SEQ ID NO: 23 and a VL containing the amino acid sequence represented by SEQ ID NO: 24, (1C) an antigen-binding domain containing a VH containing the amino acid sequence represented by SEQ ID NO: 25 and a VL containing the amino acid sequence represented by SEQ ID NO: 26, (1D) an antigen-binding domain containing a VH containing the amino acid sequence represented by SEQ ID NO: 27 and a VL containing the amino acid sequence represented by SEQ ID NO: 28, and (1E) an antigen-binding domain containing a VH containing the amino acid sequence represented by SEQ ID NO: 29 and a VL containing the amino acid sequence represented by SEQ ID NO: 30.

Specific examples of the antigen-binding domain binding to CD116 in the present invention include any one selected from the following (2a) to (2q) and (2r-1) to (2r-12):

(2a) an antigen-binding domain containing a VH containing CDRs 1 to 3 containing the amino acid sequences represented by SEQ ID NOs: 31 to 33, respectively, and a VL containing CDRs 1 to 3 containing the amino acid sequences represented by SEQ ID NOs: 34 to 36, respectively, (2b) an antigen-binding domain containing a VH containing CDRs 1 to 3 containing the amino acid sequences represented by SEQ ID NOs: 37 to 39, respectively, and a VL containing CDRs 1 to 3 containing the amino acid sequences represented by SEQ ID NOs: 40 to 42, respectively, (2c) an antigen-binding domain containing a VH containing CDRs 1 to 3 containing the amino acid sequences represented by SEQ ID NO: 43 to 45, respectively, and a VL containing CDRs 1 to 3 containing the amino acid sequences represented by SEQ ID NO: 46 to 48, respectively, (2d) an antigen-binding domain containing a VH containing CDRs 1 to 3 containing the amino acid sequences represented by SEQ ID NOs: 49 to 51, respectively, and a VL containing CDRs 1 to 3 containing the amino acid sequences represented by SEQ ID NOs: 52 to 54, respectively, (2e) an antigen-binding domain containing a VH containing CDRs 1 to 3 containing the amino acid sequences represented by SEQ ID NOs: 55 to 57, respectively, and a VL containing CDRs 1 to 3 containing the amino acid sequences represented by SEQ ID NOs: 58 to 60, respectively, (2f) an antigen-binding domain containing a VH containing CDRs 1 to 3 containing the amino acid sequences represented by SEQ ID NOs: 104 to 106, respectively, and a VL containing CDRs 1 to 3 containing the amino acid sequences represented by SEQ ID NOs: 88 to 90, respectively, (2g) an antigen-binding domain containing a VH containing CDRs 1 to 3 containing the amino acid sequences represented by SEQ ID NOs: 107 to 109, respectively, and a VL containing CDRs 1 to 3 containing the amino acid sequences represented by SEQ ID NOs: 88 to 90, respectively, (2h) an antigen-binding domain containing a VH containing CDRs 1 to 3 containing the amino acid sequences represented by SEQ ID NOs: 110 to 112, respectively, and a VL containing CDRs 1 to 3 containing the amino acid sequences represented by SEQ ID NOs: 88 to 90, respectively, (2i) an antigen-binding domain containing a VH containing CDRs 1 to 3 containing the amino acid sequences represented by SEQ ID NOs: 113 to 115, respectively, and a VL containing CDRs 1 to 3 containing the amino acid sequences represented by SEQ ID NOs: 88 to 90, respectively, (2j) an antigen-binding domain containing a VH containing CDRs 1 to 3 containing the amino acid sequences represented by SEQ ID NOs: 116 to 118, respectively, and a VL containing CDRs 1 to 3 containing the amino acid sequences represented by SEQ ID NOs: 88 to 90, respectively, (2k) an antigen-binding domain containing a VH containing CDRs 1 to 3 containing the amino acid sequences represented by SEQ ID NOs: 119 to 121, respectively, and a VL containing CDRs 1 to 3 containing the amino acid sequences represented by SEQ ID NOs: 88 to 90, respectively, (2l) an antigen-binding domain containing a VH containing CDRs 1 to 3 containing the amino acid sequences represented by SEQ ID NOs: 122 to 124, respectively, and a VL containing CDRs 1 to 3 containing the amino acid sequences represented by SEQ ID NOs: 88 to 90, respectively, (2m) an antigen-binding domain containing a VH containing CDRs 1 to 3 containing the amino acid sequences represented by SEQ ID NOs: 125 to 127, respectively, and a VL containing CDRs 1 to 3 containing the amino acid sequences represented by SEQ ID NOs: 88 to 90, respectively, (2n) an antigen-binding domain containing a VH containing CDRs 1 to 3 containing the amino acid sequences represented by SEQ ID NOs: 128 to 130, respectively, and a VL containing CDRs 1 to 3 containing the amino acid sequences represented by SEQ ID NOs: 88 to 90, respectively, (2o) an antigen-binding domain containing a VH containing CDRs 1 to 3 containing the amino acid sequences represented by SEQ ID NOs: 131 to 133, respectively, and a VL containing CDRs 1 to 3 containing the amino acid sequences represented by SEQ ID NOs: 88 to 90, respectively, (2p) an antigen-binding domain containing a VH containing CDRs 1 to 3 containing the amino acid sequences represented by SEQ ID NOs: 134 to 136, respectively, and a VL containing CDRs 1 to 3 containing the amino acid sequences represented by SEQ ID NOs: 88 to 90, respectively, (2q) an antigen-binding domain containing a VH containing CDRs 1 to 3 containing the amino acid sequences represented by SEQ ID NOs: 137 to 139, respectively, and a VL containing CDRs 1 to 3 containing the amino acid sequences represented by SEQ ID NOs: 88 to 90, respectively, (2r-1) an antigen-binding domain containing a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with lysine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-2) an antigen-binding domain containing a VH containing CDR1 containing the amino acid sequence represented by SEQ ID NO: 137, CDR2 containing an amino acid sequence in which a modification to substitute glycine at position 17 in the amino acid sequence represented by SEQ ID NO: 138 with aspartic acid is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-3) an antigen-binding domain containing a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-4) an antigen-binding domain containing a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with leucine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-5) an antigen-binding domain containing a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with serine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-6) an antigen-binding domain containing a VH containing CDR1 containing an amino acid sequence in which a modification to substitute leucine at position 2 in the amino acid sequence represented by SEQ ID NO: 137 with valine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-7) an antigen-binding domain containing a VH containing CDR1 containing an amino acid sequence in which a modification to substitute leucine at position 2 in the amino acid sequence represented by SEQ ID NO: 137 with phenylalanine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-8) an antigen-binding domain containing a VH containing CDR1 containing an amino acid sequence in which a modification to substitute serine at position 3 in the amino acid sequence represented by SEQ ID NO: 137 with alanine and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-9) an antigen-binding domain containing a VH containing CDR1 containing an amino acid sequence in which a modification to substitute leucine at position 2 in the amino acid sequence represented by SEQ ID NO: 137 with tyrosine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-10) an antigen-binding domain containing a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid is introduced, and a VL containing CDRs 1 to 3 containing the amino acid sequences represented by SEQ ID NOs: 88 to 90, respectively, (2r-11) an antigen-binding domain containing a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid, tyrosine at position 5 with tryptophan, and tyrosine at position 6 with methionine is introduced, and a VL containing CDRs 1 to 3 containing the amino acid sequences represented by SEQ ID NOs: 88 to 90, respectively, and (2r-12) an antigen-binding domain containing a VH containing CDR1 containing an amino acid sequence in which a modification to substitute leucine at position 2 in the amino acid sequence represented by SEQ ID NO: 137 with phenylalanine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively.

Specific examples of the antigen-binding domain binding to CD116 in the present invention include any one selected from the following (2A) to (2Y) and (2Z-1) to (2Z-20):

(2A) an antigen-binding domain containing a VH containing the amino acid sequence represented by SEQ ID NO: 11 and a VL containing the amino acid sequence represented by SEQ ID NO: 12, (2B) an antigen-binding domain containing a VH containing the amino acid sequence represented by SEQ ID NO: 13 and a VL containing the amino acid sequence represented by SEQ ID NO: 14, (2C) an antigen-binding domain containing a VH containing the amino acid sequence represented by SEQ ID NO: 15 and a VL containing the amino acid sequence represented by SEQ ID NO: 16, (2D) an antigen-binding domain containing a VH containing the amino acid sequence represented by SEQ ID NO: 17 and a VL containing the amino acid sequence represented by SEQ ID NO: 18, (2E) an antigen-binding domain containing a VH containing the amino acid sequence represented by SEQ ID NO: 19 and a VL containing the amino acid sequence represented by SEQ ID NO: 20, (2F) an antigen-binding domain containing a VH containing the amino acid sequence represented by SEQ ID NO: 92 and a VL containing the amino acid sequence represented by SEQ ID NO: 30, (2G) an antigen-binding domain containing a VH containing the amino acid sequence represented by SEQ ID NO: 93 and a VL containing the amino acid sequence represented by SEQ ID NO: 30, (2H) an antigen-binding domain containing a VH containing the amino acid sequence represented by SEQ ID NO: 94 and a VL containing the amino acid sequence represented by SEQ ID NO: 30, (2I) an antigen-binding domain containing a VH containing the amino acid sequence represented by SEQ ID NO: 95 and a VL containing the amino acid sequence represented by SEQ ID NO: 30, (2J) an antigen-binding domain containing a VH containing the amino acid sequence represented by SEQ ID NO: 96 and a VL containing the amino acid sequence represented by SEQ ID NO: 30, (2K) an antigen-binding domain containing a VH containing the amino acid sequence represented by SEQ ID NO: 97 and a VL containing the amino acid sequence represented by SEQ ID NO: 30, (2L) an antigen-binding domain containing a VH containing the amino acid sequence represented by SEQ ID NO: 98 and a VL containing the amino acid sequence represented by SEQ ID NO: 30, (2M) an antigen-binding domain containing a VH containing the amino acid sequence represented by SEQ ID NO: 99 and a VL containing the amino acid sequence represented by SEQ ID NO: 30, (2N) an antigen-binding domain containing a VH containing the amino acid sequence represented by SEQ ID NO: 100 and a VL containing the amino acid sequence represented by SEQ ID NO: 30, (2O) an antigen-binding domain containing a VH containing the amino acid sequence represented by SEQ ID NO: 101 and a VL containing the amino acid sequence represented by SEQ ID NO: 30, (2P) an antigen-binding domain containing a VH containing the amino acid sequence represented by SEQ ID NO: 102 and a VL containing the amino acid sequence represented by SEQ ID NO: 30, (2Q) an antigen-binding domain containing a VH containing the amino acid sequence represented by SEQ ID NO: 103 and a VL containing the amino acid sequence represented by SEQ ID NO: 30, (2R) an antigen-binding domain containing a VH containing the amino acid sequence represented by SEQ ID NO: 176 and a VL containing the amino acid sequence represented by SEQ ID NO: 30, (2S) an antigen-binding domain containing a VH containing the amino acid sequence represented by SEQ ID NO: 177 and a VL containing the amino acid sequence represented by SEQ ID NO: 30, (2T) an antigen-binding domain containing a VH containing the amino acid sequence represented by SEQ ID NO: 178 and a VL containing the amino acid sequence represented by SEQ ID NO: 30, (2U) an antigen-binding domain containing a VH containing the amino acid sequence represented by SEQ ID NO: 179 and a VL containing the amino acid sequence represented by SEQ ID NO: 30, (2V) an antigen-binding domain containing a VH containing the amino acid sequence represented by SEQ ID NO: 182 and a VL containing the amino acid sequence represented by SEQ ID NO: 30, (2W) an antigen-binding domain containing a VH containing the amino acid sequence represented by SEQ ID NO: 183 and a VL containing the amino acid sequence represented by SEQ ID NO: 30, (2X) an antigen-binding domain containing a VH containing the amino acid sequence represented by SEQ ID NO: 184 and a VL containing the amino acid sequence represented by SEQ ID NO: 30, (2Y) an antigen-binding domain containing a VH containing the amino acid sequence represented by SEQ ID NO: 185 and a VL containing the amino acid sequence represented by SEQ ID NO: 30, (2Z-1) an antigen-binding domain containing a VH containing the amino acid sequence represented by SEQ ID NO: 190 and a VL containing the amino acid sequence represented by SEQ ID NO: 30, (2Z-2) an antigen-binding domain containing a VH containing the amino acid sequence represented by SEQ ID NO: 191 and a VL containing the amino acid sequence represented by SEQ ID NO: 30, (2Z-3) an antigen-binding domain containing a VH containing the amino acid sequence represented by SEQ ID NO: 192 and a VL containing the amino acid sequence represented by SEQ ID NO: 30, (2Z-4) an antigen-binding domain containing a VH containing the amino acid sequence represented by SEQ ID NO: 193 and a VL containing the amino acid sequence represented by SEQ ID NO: 30, (2Z-5) an antigen-binding domain containing a VH containing the amino acid sequence represented by SEQ ID NO: 194 and a VL containing the amino acid sequence represented by SEQ ID NO: 30,
(2Z-6) an antigen-binding domain containing a VH containing the amino acid sequence represented by SEQ ID NO: 195 and a VL containing the amino acid sequence represented by SEQ ID NO: 30,
(2Z-7) an antigen-binding domain containing a VH containing the amino acid sequence represented by SEQ ID NO: 196 and a VL containing the amino acid sequence represented by SEQ ID NO: 30,
(2Z-8) an antigen-binding domain containing a VH containing the amino acid sequence represented by SEQ ID NO: 197 and a VL containing the amino acid sequence represented by SEQ ID NO: 30,
(2Z-9) an antigen-binding domain containing a VH containing the amino acid sequence represented by SEQ ID NO: 198 and a VL containing the amino acid sequence represented by SEQ ID NO: 30,
(2Z-10) an antigen-binding domain containing a VH containing the amino acid sequence represented by SEQ ID NO: 199 and a VL containing the amino acid sequence represented by SEQ ID NO: 30,
(2Z-11) an antigen-binding domain containing a VH containing the amino acid sequence represented by SEQ ID NO: 200 and a VL containing the amino acid sequence represented by SEQ ID NO: 30,
(2Z-12) an antigen-binding domain containing a VH containing the amino acid sequence represented by SEQ ID NO: 201 and a VL containing the amino acid sequence represented by SEQ ID NO: 30,
(2Z-13) an antigen-binding domain containing a VH containing the amino acid sequence represented by SEQ ID NO: 202 and a VL containing the amino acid sequence represented by SEQ ID NO: 30,
(2Z-14) an antigen-binding domain containing a VH containing the amino acid sequence represented by SEQ ID NO: 203 and a VL containing the amino acid sequence represented by SEQ ID NO: 30,
(2Z-15) an antigen-binding domain containing a VH containing the amino acid sequence represented by SEQ ID NO: 204 and a VL containing the amino acid sequence represented by SEQ ID NO: 30,
(2Z-16) an antigen-binding domain containing a VH containing the amino acid sequence represented by SEQ ID NO: 205 and a VL containing the amino acid sequence represented by SEQ ID NO: 30,
(2Z-17) an antigen-binding domain containing a VH containing the amino acid sequence represented by SEQ ID NO: 206 and a VL containing the amino acid sequence represented by SEQ ID NO: 30,
(2Z-18) an antigen-binding domain containing a VH containing the amino acid sequence represented by SEQ ID NO: 207 and a VL containing the amino acid sequence represented by SEQ ID NO: 30,
(2Z-19) an antigen-binding domain containing a VH containing the amino acid sequence represented by SEQ ID NO: 208 and a VL containing the amino acid sequence represented by SEQ ID NO: 30, and
(2Z-20) an antigen-binding domain containing a VH containing the amino acid sequence represented by SEQ ID NO: 209 and a VL containing the amino acid sequence represented by SEQ ID NO: 30.

A structure of the bispecific antibody of the present invention is not particularly limited as long as the bispecific antibody contains the first antigen-binding domain and the second antigen-binding domain. From the viewpoint of improving an agonist activity to a GM-CSF receptor, the first antigen-binding domain and the second antigen-binding domain are preferably a Fab.

In the description, a case where the first antigen-binding domain is a Fab is referred to as a first Fab, and a case where the second antigen-binding domain is a Fab is referred to as a second Fab. The first Fab preferably contains a heavy chain of the first antigen-binding domain (hereinafter abbreviated as a heavy chain of the first Fab) containing a VH and CH1 domain and a light chain containing a VL and a CL, and the second Fab preferably contains a heavy chain of the second binding domain (hereinafter abbreviated as a heavy chain of the second Fab) containing a VH and CH1 domain and a light chain containing a VL and a CL.

Examples of the structure of the bispecific antibody of the present invention include structures shown in (1) to (3) below.

(1) A structure in which one first Fab ($VH_1$-CH1, VL-CL), one second Fab ($VH_2$-CH1', VL-CL), and hinge regions are contained, and a C-terminus of a heavy chain in the first Fab and a C-terminus of a heavy chain in the second Fab bind to N-termini of the hinge regions, respectively (hereinafter also abbreviated as IgG type).

From the viewpoint of stability and ease of preparation, the IgG-type bispecific antibody preferably has a structure in which Fc regions are further contained, and N-termini of the Fc regions bind to C-termini of the hinge regions. FIG. 2 shows a schematic diagram of such an IgG-type bispecific antibody.

(2) A structure in which the following first polypeptide, the following second polypeptide, and hinge regions are contained, and a C-terminus of the first polypeptide and a C-terminus of the second polypeptide bind to N-termini of the hinge regions, respectively.

The first polypeptide: a polypeptide containing at least the first Fab ($VH_1$-CH1, VL-CL) at an N-terminus thereof.

The second polypeptide: a polypeptide containing at least the second Fab ($VH_2$-CH1', VL-CL) at a C-terminus thereof.

In such an aspect, at least an antigen binding property of the first Fab in the first polypeptide and an antigen binding property of the second Fab in the second polypeptide are preferably maintained.

In such an aspect, it is preferable to has a structure in which Fc regions are further contained and N-termini of the Fc regions bind to C-termini of the hinge regions. By providing such a structure, it becomes easier to adopt a higher-order structure in which the first polypeptide binds to CD131 and the second polypeptide binds to CD116. As a result, it is considered to exhibit excellent binding properties to CD116 and CD131 and high agonist activity to a GM-CSF receptor.

Examples of such a structure include the following (2-1) to (2-4).

(2-1) A structure in which a first polypeptide containing the first Fab and the second Fab in order from an N-terminus thereof, a second polypeptide containing the first Fab and the second Fab in order from an N-terminus thereof, and hinge regions are contained. In such a structure, the first polypeptide and the second polypeptide each contain a polypeptide chain ($VH_1$-CH1-$VH_2$-CH1') in which a C-terminus of a heavy chain ($VH_1$-CH1) in the first Fab and an N-terminus of a heavy chain ($VH_2$-CH1') in the second Fab bind to each other directly or via a linker, and C-termini of the polypeptide chains bind to N-termini of the hinge regions, respectively (hereinafter, such an structure is also abbreviated as N-terminus type).

Figure 4A:
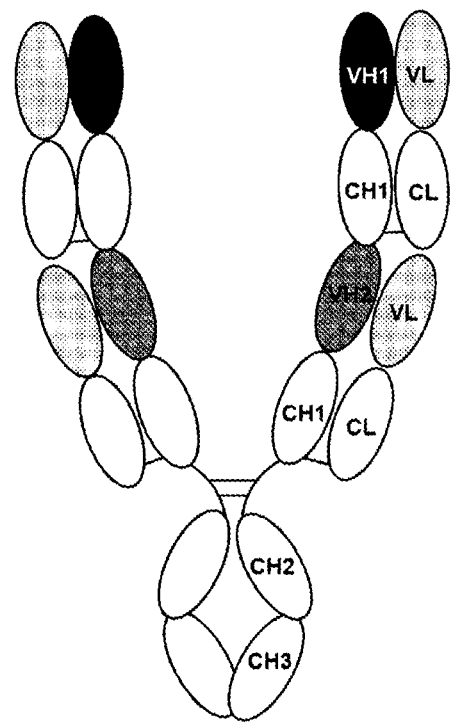
FIGS. 4A and 4B show structures of the bispecific antibody of the present invention.
Figure 16:
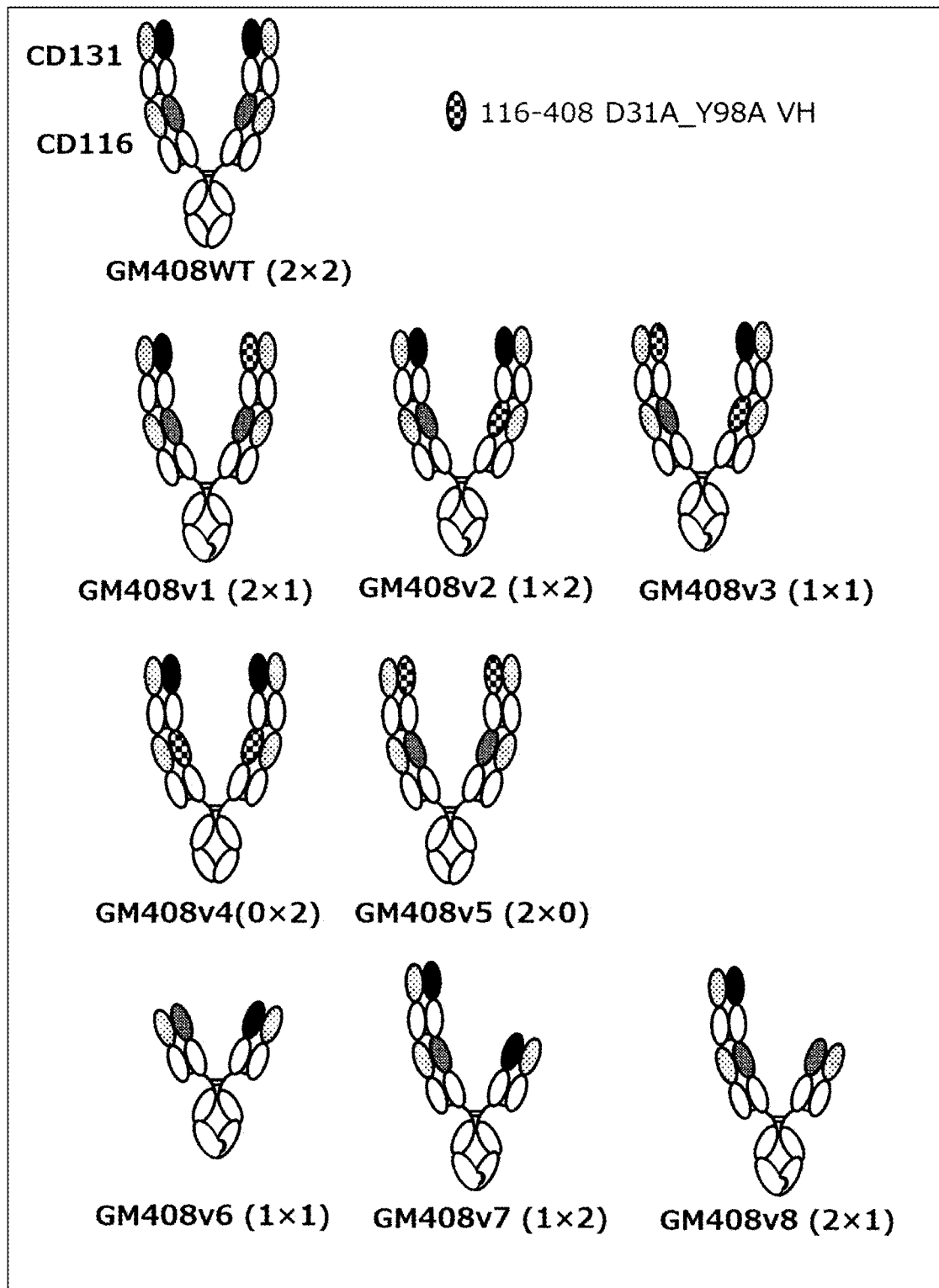
FIG. 16 is a diagram showing structures of a CD131-CD116 bispecific antibody with controlled valence, in which a 116-408 D31A_Y98 VH is a 116-408 VH with binding activity lost due to an amino acid mutation, and (valence of anti-CD116 antibody×valence of anti-CD131 antibody) is shown in parentheses.

From the viewpoint of stability, the N-terminus type bispecific antibody preferably has a structure in which Fc regions are further contained, and N-termini of the Fc regions bind to C-termini of the hinge regions. A schematic diagram of such an N-terminus type bispecific antibody is shown in FIG. 4A. As a specific embodiment, for example, GM408WT (2× 2) shown in FIG. 16 is exemplified.

(2-2) A structure in which the first polypeptide containing the first Fab and the second Fab in order from an N-terminus thereof, the second polypeptide containing the second Fab, and hinge regions are contained. In such a structure, the first polypeptide contains a polypeptide chain ($VH_1$-CH1-$VH_2$-CH1') in which a C-terminus of a heavy chain ($VH_1$-CH1) in the first Fab and an N-terminus of a heavy chain ($VH_2$-CH1') in the second Fab bind to each other directly or via a linker.

In such an aspect, it is preferable to has a structure in which Fc regions are further contained and N-termini of the Fc regions bind to C-termini of the hinge regions. As a specific embodiment, for example, GM408v8 (2× 1) shown in FIG. 16 is exemplified.

(2-3) A structure in which the first polypeptide containing the first Fab and the second Fab in order from an N-terminus thereof, the second polypeptide containing the second Fab and the second Fab in order from an N-terminus thereof, and hinge regions are contained, and a mutation is introduced into the $VH_2$ to inactivate a binding activity of the second Fab on a N-terminus side of the second polypeptide to the second antigen.

In such a structure, the first polypeptide contains a polypeptide chain ($VH_1$-CH1-$VH_2$-CH1') in which a C-terminus of a heavy chain ($VH_1$-CH1) in the first Fab and an N-terminus of a heavy chain ($VH_2$-CH1') in the second Fab bind to each other directly or via a linker. The second polypeptide contains a polypeptide chain ($VH_2$-CH1-$VH_2$-CH1') in which a C-terminus of a heavy chain ($VH_2$-CH1) in the second Fab and an N-terminus of a heavy chain ($VH_2$-CH1') in the second Fab bind to each other directly or via a linker.

In such an aspect, it is preferable to has a structure in which Fc regions are further contained and N-termini of the Fc regions bind to C-termini of the hinge regions.

(2-4) A structure in which, in the above structure (2-1), a mutation is introduced into the $VH_1$ to inactivate a binding activity of the second Fab in the second polypeptide to the second antigen. As a specific embodiment, for example, GM408v2 (1×2) shown in FIG. 16 is exemplified.

(2-5) A structure in which, in the above structure (2-3), a mutation is further introduced into the $VH_2$ of the heavy chain to inactivate a binding activity of the second Fab in the first polypeptide to the second antigen. As a specific embodiment, for example, GM408v3 (1×1) shown in FIG. 16 is exemplified.

Examples of the mutation to be introduced into the $VH_2$ of the heavy chain for inactivating the binding activity of the second Fab to the second antigen in the above (2-3) to (2-5) include D31A and Y98A.

Figure 4B:
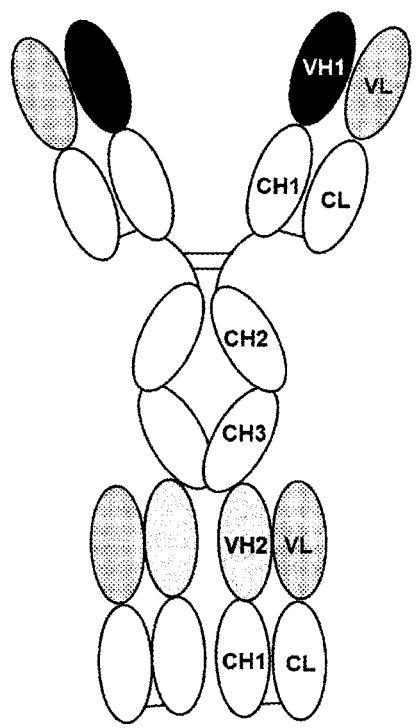

(3) A structure in which two first Fab ($VH_1$-CH1, VL-CL), two second Fab ($VH_2$-CH1', VL-CL), hinge regions, and Fc regions are contained, C-termini of heavy chains in the two first Fab bind to N-termini of the hinge regions, a C-terminus of the hinge region binds to an N-terminus of the Fc region, and N-termini of heavy chains in the two second Fab bind to C-termini of the Fc region (hereinafter also abbreviated as C-terminus type). A schematic diagram of the C-terminus type bispecific antibody is shown in FIG. 4B.

From the viewpoint of improving the agonist activity to the GM-CSF receptor, among the above structures (1) to (3), the N-terminus type bispecific antibody in (2) is preferred.

The linker used for chemically linking the antigen-binding domains is not particularly limited as long as it has a functional group necessary for chemically linking the antigen-binding domains. A linker having a polyoxyethylene group-$(CH_2CH_2O)_n$- (n is an integer of 1 to 2000) in a molecule thereof is preferred. The number n of repetitions is preferably an integer of 1 to 100, and more preferably an integer of 1 to 25.

When the non-natural amino acid contained in the antigen-binding domain of the present invention has an azide group, the linker to be used preferably contains an alkynyl group. In that case, a Huisgen [3+2] cycloaddition reaction (Kolb et al., Angew Chem Int Ed Engl. 40. 2004-21, 2001) can be used as a reaction for chemically linking the antigen-binding domain and the linker.

The peptide linker of the bispecific antibody, which is expressed as a recombinant protein by linking antigen-binding domains with an amino acid sequence of an appropriate peptide linker, is not particularly limited. Examples thereof include a so-called GS linker which is a repeating sequence of Gly-Gly-Gly-Gly-Ser, and a linker containing an immunoglobulin domain or a fragment thereof. A linker consisting of any amino acid sequence can be used as long as it can be expressed as a recombinant protein.

In the bispecific antibody and the bispecific antibody fragment thereof of the present invention, it is preferably that the first antigen-binding domain is an antigen-binding domain binding to CD131, and the second antigen-binding domain is an antigen-binding domain binding to CD116. When the first antigen-binding domain and the second antigen-binding domain each are a Fab, it is preferable that the first Fab is an antigen-binding domain binding to CD131 and the second Fab is an antigen-binding domain binding to CD116.

Examples of the bispecific antibody and the bispecific antibody fragment thereof of the present invention include a bispecific antibody in which the first Fab is one selected from the group consisting of the following (1a) to (1e), and the second Fab is one selected from the group consisting of the following (2a) to (2q) and (2r-1) to (2r-12):

(1a) an antigen-binding domain containing a VH containing CDRs 1 to 3 containing the amino acid sequences represented by SEQ ID NOs: 61 to 63, respectively, and a VL containing CDRs 1 to 3 containing the amino acid sequences represented by SEQ ID NOs: 64 to 66, respectively, (1b) an antigen-binding domain containing a VH containing CDRs 1 to 3 containing the amino acid sequences represented by SEQ ID NOs: 67 to 69, respectively, and a VL containing CDRs 1 to 3 containing the amino acid sequences represented by SEQ ID NOs: 70 to 72, respectively, (1c) an antigen-binding domain containing a VH containing CDRs 1 to 3 containing the amino acid sequences represented by SEQ ID NOs: 73 to 75, respectively, and a VL containing CDRs 1 to 3 containing the amino acid sequences represented by SEQ ID NOs: 76 to 78, respectively, (1d) an antigen-binding domain containing a VH containing CDRs 1 to 3 containing the amino acid sequences represented by SEQ ID NOs: 79 to 81, respectively, and a VL containing CDRs 1 to 3 containing the amino acid sequences represented by SEQ ID NOs: 82 to 84, respectively, and (1e) an antigen-binding domain containing a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively.

(2a) an antigen-binding domain containing a VH containing CDRs 1 to 3 containing the amino acid sequences represented by SEQ ID NOs: 31 to 33, respectively, and a VL containing CDRs 1 to 3 containing the amino acid sequences represented by SEQ ID NOs: 34 to 36, respectively, (2b) an antigen-binding domain containing a VH containing CDRs 1 to 3 containing the amino acid sequences represented by SEQ ID NOs: 37 to 39, respectively, and a VL containing CDRs 1 to 3 containing the amino acid sequences represented by SEQ ID NOs: 40 to 42, respectively, (2c) an antigen-binding domain containing a VH containing CDRs 1 to 3 containing the amino acid sequences represented by SEQ ID NO: 43 to 45, respectively, and a VL containing CDRs 1 to 3 containing the amino acid sequences represented by SEQ ID NO: 46 to 48, respectively, (2d) an antigen-binding domain containing a VH containing CDRs 1 to 3 containing the amino acid sequences represented by SEQ ID NOs: 49 to 51, respectively, and a VL containing CDRs 1 to 3 containing the amino acid sequences represented by SEQ ID NOs: 52 to 54, respectively, (2e) an antigen-binding domain containing a VH containing CDRs 1 to 3 containing the amino acid sequences represented by SEQ ID NOs: 55 to 57, respectively, and a VL containing CDRs 1 to 3 containing the amino acid sequences represented by SEQ ID NOs: 58 to 60, respectively, (2f) an antigen-binding domain containing a VH containing CDRs 1 to 3 containing the amino acid sequences represented by SEQ ID NOs: 104 to 106, respectively, and a VL containing CDRs 1 to 3 containing the amino acid sequences represented by SEQ ID NOs: 88 to 90, respectively, (2g) an antigen-binding domain containing a VH containing CDRs 1 to 3 containing the amino acid sequences represented by SEQ ID NOs: 107 to 109, respectively, and a VL containing CDRs 1 to 3 containing the amino acid sequences represented by SEQ ID NOs: 88 to 90, respectively, (2h) an antigen-binding domain containing a VH containing CDRs 1 to 3 containing the amino acid sequences represented by SEQ ID NOs: 110 to 112, respectively, and a VL containing CDRs 1 to 3 containing the amino acid sequences represented by SEQ ID NOs: 88 to 90, respectively, (2i) an antigen-binding domain containing a VH containing CDRs 1 to 3 containing the amino acid sequences represented by SEQ ID NOs: 113 to 115, respectively, and a VL containing CDRs 1 to 3 containing the amino acid sequences represented by SEQ ID NOs: 88 to 90, respectively, (2j) an antigen-binding domain containing a VH containing CDRs 1 to 3 containing the amino acid sequences represented by SEQ ID NOs: 116 to 118, respectively, and a VL containing CDRs 1 to 3 containing the amino acid sequences represented by SEQ ID NOs: 88 to 90, respectively, (2k) an antigen-binding domain containing a VH containing CDRs 1 to 3 containing the amino acid sequences represented by SEQ ID NOs: 119 to 121, respectively, and a VL containing CDRs 1 to 3 containing the amino acid sequences represented by SEQ ID NOs: 88 to 90, respectively, (2l) an antigen-binding domain containing a VH containing CDRs 1 to 3 containing the amino acid sequences represented by SEQ ID NOs: 122 to 124, respectively, and a VL containing CDRs 1 to 3 containing the amino acid sequences represented by SEQ ID NOs: 88 to 90, respectively, (2m) an antigen-binding domain containing a VH containing CDRs 1 to 3 containing the amino acid sequences represented by SEQ ID NOs: 125 to 127, respectively, and a VL containing CDRs 1 to 3 containing the amino acid sequences represented by SEQ ID NOs: 88 to 90, respectively, (2n) an antigen-binding domain containing a VH containing CDRs 1 to 3 containing the amino acid sequences represented by SEQ ID NOs: 128 to 130, respectively, and a VL containing CDRs 1 to 3 containing the amino acid sequences represented by SEQ ID NOs: 88 to 90, respectively, (2o) an antigen-binding domain containing a VH containing CDRs 1 to 3 containing the amino acid sequences represented by SEQ ID NOs: 131 to 133, respectively, and a VL containing CDRs 1 to 3 containing the amino acid sequences represented by SEQ ID NOs: 88 to 90, respectively, (2p) an antigen-binding domain containing a VH containing CDRs 1 to 3 containing the amino acid sequences represented by SEQ ID NOs: 134 to 136, respectively, and a VL containing CDRs 1 to 3 containing the amino acid sequences represented by SEQ ID NOs: 88 to 90, respectively, (2q) an antigen-binding domain containing a VH containing CDRs 1 to 3 containing the amino acid sequences represented by SEQ ID NOs: 137 to 139, respectively, and a VL containing CDRs 1 to 3 containing the amino acid sequences represented by SEQ ID NOs: 88 to 90, respectively, (2r-1) an antigen-binding domain containing a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with lysine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-2) an antigen-binding domain containing a VH containing CDR1 containing the amino acid sequence represented by SEQ ID NO: 137, CDR2 containing an amino acid sequence in which a modification to substitute glycine at position 17 in the amino acid sequence represented by SEQ ID NO: 138 with aspartic acid is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-3) an antigen-binding domain containing a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-4) an antigen-binding domain containing a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with leucine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-5) an antigen-binding domain containing a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with serine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (2r-6) an antigen-binding domain containing a VH containing CDR1 containing an amino acid sequence in which a modification to substitute leucine at position 2 in the amino acid sequence represented by SEQ ID NO: 137 with valine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-7) an antigen-binding domain containing a VH containing CDR1 containing an amino acid sequence in which a modification to substitute leucine at position 2 in the amino acid sequence represented by SEQ ID NO: 137 with phenylalanine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-8) an antigen-binding domain containing a VH containing CDR1 containing an amino acid sequence in which a modification to substitute serine at position 3 in the amino acid sequence represented by SEQ ID NO: 137 with alanine and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-9) an antigen-binding domain containing a VH containing CDR1 containing an amino acid sequence in which a modification to substitute leucine at position 2 in the amino acid sequence represented by SEQ ID NO: 137 with tyrosine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (2r-10) an antigen-binding domain containing a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid is introduced, and a VL containing CDRs 1 to 3 containing the amino acid sequences represented by SEQ ID NOs: 88 to 90, respectively, (2r-11) an antigen-binding domain containing a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid, tyrosine at position 5 with tryptophan, and tyrosine at position 6 with methionine is introduced, and a VL containing CDRs 1 to 3 containing the amino acid sequences represented by SEQ ID NOs: 88 to 90, respectively, and (2r-12) an antigen-binding domain containing a VH containing CDR1 containing an amino acid sequence in which a modification to substitute leucine at position 2 in the amino acid sequence represented by SEQ ID NO: 137 with phenylalanine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively.

Specific examples of the bispecific antibody and the bispecific antibody fragment thereof of the present invention include a bispecific antibody in which the first Fab is one selected from the group consisting of the following (1A) to (1E), and the second Fab is one selected from the group consisting of the following (2A) to (2Y) and (2Z-1) to (2Z-20):

(1A) an antigen-binding domain containing a VH containing the amino acid sequence represented by SEQ ID NO: 21 and a VL containing the amino acid sequence represented by SEQ ID NO: 22, (1B) an antigen-binding domain containing a VH containing the amino acid sequence represented by SEQ ID NO: 23 and a VL containing the amino acid sequence represented by SEQ ID NO: 24, (1C) an antigen-binding domain containing a VH containing the amino acid sequence represented by SEQ ID NO: 25 and a VL containing the amino acid sequence represented by SEQ ID NO: 26, (1D) an antigen-binding domain containing a VH containing the amino acid sequence represented by SEQ ID NO: 27 and a VL containing the amino acid sequence represented by SEQ ID NO: 28, and (1E) an antigen-binding domain containing a VH containing the amino acid sequence represented by SEQ ID NO: 29 and a VL containing the amino acid sequence represented by SEQ ID NO: 30.

(2A) an antigen-binding domain containing a VH containing the amino acid sequence represented by SEQ ID NO: 11 and a VL containing the amino acid sequence represented by SEQ ID NO: 12, (2B) an antigen-binding domain containing a VH containing the amino acid sequence represented by SEQ ID NO: 13 and a VL containing the amino acid sequence represented by SEQ ID NO: 14, (2C) an antigen-binding domain containing a VH containing the amino acid sequence represented by SEQ ID NO: 15 and a VL containing the amino acid sequence represented by SEQ ID NO: 16, (2D) an antigen-binding domain containing a VH containing the amino acid sequence represented by SEQ ID NO: 17 and a VL containing the amino acid sequence represented by SEQ ID NO: 18, (2E) an antigen-binding domain containing a VH containing the amino acid sequence represented by SEQ ID NO: 19 and a VL containing the amino acid sequence represented by SEQ ID NO: 20, (2F) an antigen-binding domain containing a VH containing the amino acid sequence represented by SEQ ID NO: 92 and a VL containing the amino acid sequence represented by SEQ ID NO: 30, (2G) an antigen-binding domain containing a VH containing the amino acid sequence represented by SEQ ID NO: 93 and a VL containing the amino acid sequence represented by SEQ ID NO: 30, (2H) an antigen-binding domain containing a VH containing the amino acid sequence represented by SEQ ID NO: 94 and a VL containing the amino acid sequence represented by SEQ ID NO: 30, (2I) an antigen-binding domain containing a VH containing the amino acid sequence represented by SEQ ID NO: 95 and a VL containing the amino acid sequence represented by SEQ ID NO: 30, (2J) an antigen-binding domain containing a VH containing the amino acid sequence represented by SEQ ID NO: 96 and a VL containing the amino acid sequence represented by SEQ ID NO: 30, (2K) an antigen-binding domain containing a VH containing the amino acid sequence represented by SEQ ID NO: 97 and a VL containing the amino acid sequence represented by SEQ ID NO: 30, (2L) an antigen-binding domain containing a VH containing the amino acid sequence represented by SEQ ID NO: 98 and a VL containing the amino acid sequence represented by SEQ ID NO: 30, (2M) an antigen-binding domain containing a VH containing the amino acid sequence represented by SEQ ID NO: 99 and a VL containing the amino acid sequence represented by SEQ ID NO: 30, (2N) an antigen-binding domain containing a VH containing the amino acid sequence represented by SEQ ID NO: 100 and a VL containing the amino acid sequence represented by SEQ ID NO: 30, (2O) an antigen-binding domain containing a VH containing the amino acid sequence represented by SEQ ID NO: 101 and a VL containing the amino acid sequence represented by SEQ ID NO: 30, (2P) an antigen-binding domain containing a VH containing the amino acid sequence represented by SEQ ID NO: 102 and a VL containing the amino acid sequence represented by SEQ ID NO: 30, (2Q) an antigen-binding domain containing a VH containing the amino acid sequence represented by SEQ ID NO: 103 and a VL containing the amino acid sequence represented by SEQ ID NO: 30, (2R) an antigen-binding domain containing a VH containing the amino acid sequence represented by SEQ ID NO: 176 and a VL containing the amino acid sequence represented by SEQ ID NO: 30, (2S) an antigen-binding domain containing a VH containing the amino acid sequence represented by SEQ ID NO: 177 and a VL containing the amino acid sequence represented by SEQ ID NO: 30, (2T) an antigen-binding domain containing a VH containing the amino acid sequence represented by SEQ ID NO: 178 and a VL containing the amino acid sequence represented by SEQ ID NO: 30, (2U) an antigen-binding domain containing a VH containing the amino acid sequence represented by SEQ ID NO: 179 and a VL containing the amino acid sequence represented by SEQ ID NO: 30, (2V) an antigen-binding domain containing a VH containing the amino acid sequence represented by SEQ ID NO: 182 and a VL containing the amino acid sequence represented by SEQ ID NO: 30, (2W) an antigen-binding domain containing a VH containing the amino acid sequence represented by SEQ ID NO: 183 and a VL containing the amino acid sequence represented by SEQ ID NO: 30, (2X) an antigen-binding domain containing a VH containing the amino acid sequence represented by SEQ ID NO: 184 and a VL containing the amino acid sequence represented by SEQ ID NO: 30, (2Y) an antigen-binding domain containing a VH containing the amino acid sequence represented by SEQ ID NO: 185 and a VL containing the amino acid sequence represented by SEQ ID NO: 30, (2Z-1) an antigen-binding domain containing a VH containing the amino acid sequence represented by SEQ ID NO: 190 and a VL containing the amino acid sequence represented by SEQ ID NO: 30, (2Z-2) an antigen-binding domain containing a VH containing the amino acid sequence represented by SEQ ID NO: 191 and a VL containing the amino acid sequence represented by SEQ ID NO: 30, (2Z-3) an antigen-binding domain containing a VH containing the amino acid sequence represented by SEQ ID NO: 192 and a VL containing the amino acid sequence represented by SEQ ID NO: 30, (2Z-4) an antigen-binding domain containing a VH containing the amino acid sequence represented by SEQ ID NO: 193 and a VL containing the amino acid sequence represented by SEQ ID NO: 30, (2Z-5) an antigen-binding domain containing a VH containing the amino acid sequence represented by SEQ ID NO: 194 and a VL containing the amino acid sequence represented by SEQ ID NO: 30, (2Z-6) an antigen-binding domain containing a VH containing the amino acid sequence represented by SEQ ID NO: 195 and a VL containing the amino acid sequence represented by SEQ ID NO: 30, (2Z-7) an antigen-binding domain containing a VH containing the amino acid sequence represented by SEQ ID NO: 196 and a VL containing the amino acid sequence represented by SEQ ID NO: 30, (2Z-8) an antigen-binding domain containing a VH containing the amino acid sequence represented by SEQ ID NO: 197 and a VL containing the amino acid sequence represented by SEQ ID NO: 30, (2Z-9) an antigen-binding domain containing a VH containing the amino acid sequence represented by SEQ ID NO: 198 and a VL containing the amino acid sequence represented by SEQ ID NO: 30, (2Z-10) an antigen-binding domain containing a VH containing the amino acid sequence represented by SEQ ID NO: 199 and a VL containing the amino acid sequence represented by SEQ ID NO: 30, (2Z-11) an antigen-binding domain containing a VH containing the amino acid sequence represented by SEQ ID NO: 200 and a VL containing the amino acid sequence represented by SEQ ID NO: 30, (2Z-12) an antigen-binding domain containing a VH containing the amino acid sequence represented by SEQ ID NO: 201 and a VL containing the amino acid sequence represented by SEQ ID NO: 30, (2Z-13) an antigen-binding domain containing a VH containing the amino acid sequence represented by SEQ ID NO: 202 and a VL containing the amino acid sequence represented by SEQ ID NO: 30, (2Z-14) an antigen-binding domain containing a VH containing the amino acid sequence represented by SEQ ID NO: 203 and a VL containing the amino acid sequence represented by SEQ ID NO: 30, (2Z-15) an antigen-binding domain containing a VH containing the amino acid sequence represented by SEQ ID NO: 204 and a VL containing the amino acid sequence represented by SEQ ID NO: 30, (2Z-16) an antigen-binding domain containing a VH containing the amino acid sequence represented by SEQ ID NO: 205 and a VL containing the amino acid sequence represented by SEQ ID NO: 30, (2Z-17) an antigen-binding domain containing a VH containing the amino acid sequence represented by SEQ ID NO: 206 and a VL containing the amino acid sequence represented by SEQ ID NO: 30, (2Z-18) an antigen-binding domain containing a VH containing the amino acid sequence represented by SEQ ID NO: 207 and a VL containing the amino acid sequence represented by SEQ ID NO: 30, (2Z-19) an antigen-binding domain containing a VH containing the amino acid sequence represented by SEQ ID NO: 208 and a VL containing the amino acid sequence represented by SEQ ID NO: 30, and (2Z-20) an antigen-binding domain containing a VH containing the amino acid sequence represented by SEQ ID NO: 209 and a VL containing the amino acid sequence represented by SEQ ID NO: 30.

Tables 1 to 3 to be described later show names of each Fab clone that binds to CD131 or CD116 and sequence numbers of the amino acid sequences of a VH, a VL, and CDRs contained therein. Hereinafter, when clone names are used, they refer to Fabs or antibodies containing the amino acid sequences of the VH and the VL.

Examples of the bispecific antibody of the bispecific antibody fragment thereof of the present invention include a bispecific antibody of a bispecific antibody fragment thereof containing the first Fab containing a VH and a VL of 131-03, 131-16, 131-18, 131-B1, or 131-B2, and a second Fab containing a VH and a VL of 116-08, 116-09, 116-18, 116-21, 116-22, 116-398, 116-412, 116-412a, 116-413, 116-413a, 116-421, 116-421a, 116-433, 116-433a, 116-435, 116-439, 116-463, 116-463a, 116-464, 116-464a, 116-465, 116-465a, 116-466, 116-466a, or 116-408, which will be described later in Examples. The bispecific antibody or the bispecific antibody fragment thereof is preferably of the N-terminus type.

Examples of the bispecific antibody of the present invention include, but are not limited to, any one selected from the group consisting of the following (x1) to (x12) and (x13-1) to (x13-12): in the following (x1) to (x12) and (x13-1) to (x13-12), the first antigen-binding domain and the second antigen-binding domain are preferably the first Fab and the second Fab, respectively, (x1) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 104 to 106, respectively, and a VL containing CDRs 1 to 3 containing the amino acid sequences represented by SEQ ID NOs: 88 to 90, respectively, (x2) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 107 to 109, respectively, and a VL containing CDRs 1 to 3 containing the amino acid sequences represented by SEQ ID NOs: 88 to 90, respectively, (x3) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 110 to 112, respectively, and a VL containing CDRs 1 to 3 containing the amino acid sequences represented by SEQ ID NOs: 88 to 90, respectively, (x4) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 113 to 115, respectively, and a VL containing CDRs 1 to 3 containing the amino acid sequences represented by SEQ ID NOs: 88 to 90, respectively, (x5) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 116 to 118, respectively, and a VL containing CDRs 1 to 3 containing the amino acid sequences represented by SEQ ID NOs: 88 to 90, respectively, (x6) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 119 to 121, respectively, and a VL containing CDRs 1 to 3 containing the amino acid sequences represented by SEQ ID NOs: 88 to 90, respectively, (x7) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 122 to 124, respectively, and a VL containing CDRs 1 to 3 containing the amino acid sequences represented by SEQ ID NOs: 88 to 90, respectively, (x8) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 125 to 127, respectively, and a VL containing CDRs 1 to 3 containing the amino acid sequences represented by SEQ ID NOs: 88 to 90, respectively, (x9) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 128 to 130, respectively, and a VL containing CDRs 1 to 3 containing the amino acid sequences represented by SEQ ID NOs: 88 to 90, respectively, (x10) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 131 to 133, respectively, and a VL containing CDRs 1 to 3 containing the amino acid sequences represented by SEQ ID NOs: 88 to 90, respectively, (x11) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 134 to 136, respectively, and a VL containing CDRs 1 to 3 containing the amino acid sequences represented by SEQ ID NOs: 88 to 90, respectively, (x12) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDRs 1 to 3 containing the amino acid sequences represented by SEQ ID NOs: 137 to 139, respectively, and a VL containing CDRs 1 to 3 containing the amino acid sequences represented by SEQ ID NOs: 88 to 90, respectively, (x13-1) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with lysine is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-2) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute glycine at position 17 in the amino acid sequence represented by SEQ ID NO: 138 with aspartic acid is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-3) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute arginine at position 9 in the amino acid sequence represented by SEQ ID NO: 138 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-4) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with leucine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-5) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing an amino acid sequence in which a modification to substitute phenylalanine at position 2 in the amino acid sequence represented by SEQ ID NO: 138 with serine and arginine at position 9 with threonine is introduced, and CDR3 containing the amino acid sequence represented by SEQ ID NO: 139, and a VL containing CDRs 1 to 3 containing the amino acid sequences represented by SEQ ID NOs: 88 to 90, respectively, (x13-6) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute leucine at position 2 in the amino acid sequence represented by SEQ ID NO: 137 with valine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (x13-7) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute leucine at position 2 in the amino acid sequence represented by SEQ ID NO: 137 with phenylalanine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (x13-8) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute serine at position 3 in the amino acid sequence represented by SEQ ID NO: 137 with alanine and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (x13-9) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute leucine at position 2 in the amino acid sequence represented by SEQ ID NO: 137 with tyrosine and serine at position 3 with alanine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively, (x13-10) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid is introduced, and a VL containing CDRs 1 to 3 containing the amino acid sequences represented by SEQ ID NOs: 88 to 90, respectively, (x13-11) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing the amino acid sequence represented by SEQ ID NO: 137, CDR2 containing the amino acid sequence represented by SEQ ID NO: 138, and CDR3 containing an amino acid sequence in which a modification to substitute leucine at position 2 in the amino acid sequence represented by SEQ ID NO: 139 with glutamic acid, tyrosine at position 5 with tryptophan, and tyrosine at position 6 with methionine is introduced, and a VL containing CDRs 1 to 3 containing the amino acid sequences represented by SEQ ID NOs: 88 to 90, respectively, and (x13-12) a bispecific antibody in which the first antigen-binding domain contains a VH containing CDRs 1 to 3 containing the amino acid sequences represented by SEQ ID NOs: 85 to 87, respectively, and a VL containing CDRs 1 to 3 containing the amino acid sequences represented by SEQ ID NOs: 88 to 90, respectively, and the second antigen-binding domain contains a VH containing CDR1 containing an amino acid sequence in which a modification to substitute leucine at position 2 in the amino acid sequence represented by SEQ ID NO: 137 with phenylalanine, serine at position 3 with alanine, and methionine at position 4 with leucine is introduced, CDR2 containing the amino acid sequence represented by SEQ ID NO: 138, and CDR3 containing the amino acid sequence represented by SEQ ID NO: 139, and a VL containing CDRs 1 to 3 containing the amino acid sequences represented by SEQ ID NOs: 88 to 90, respectively.

Specific examples of the bispecific antibody of the present invention include any one selected from the following (y1) to (y12) and (y13-1) to (y13-20): in the following (y1) to (y12) and (y13-1) to (y13-20), the first antigen-binding domain and the second antigen-binding domain are preferably the first Fab and the second Fab, respectively, (y1) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 175, and a VL containing the amino acid sequence represented by SEQ ID NO: 30, (y2) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 176, and a VL containing the amino acid sequence represented by SEQ ID NO: 30, (y3) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 177, and a VL containing the amino acid sequence represented by SEQ ID NO: 30, (y4) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 178, and a VL containing the amino acid sequence represented by SEQ ID NO: 30, (y5) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 179, and a VL containing the amino acid sequence represented by SEQ ID NO: 30, (y6) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 180, and a VL containing the amino acid sequence represented by SEQ ID NO: 30, (y7) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 181, and a VL containing the amino acid sequence represented by SEQ ID NO: 30, (y8) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 182, and a VL containing the amino acid sequence represented by SEQ ID NO: 30, (y9) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 183, and a VL containing the amino acid sequence represented by SEQ ID NO: 30, (y10) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 184, and a VL containing the amino acid sequence represented by SEQ ID NO: 30, (y11) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 185, and a VL containing the amino acid sequence represented by SEQ ID NO: 30, (y12) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 186, and a VL containing the amino acid sequence represented by SEQ ID NO: 30, (y13-1) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 190, and a VL containing the amino acid sequence represented by SEQ ID NO: 30, (y13-2) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 191, and a VL containing the amino acid sequence represented by SEQ ID NO: 30, (y13-3) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 192, and a VL containing the amino acid sequence represented by SEQ ID NO: 30, (y13-4) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 193, and a VL containing the amino acid sequence represented by SEQ ID NO: 30, (y13-5) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 194, and a VL containing the amino acid sequence represented by SEQ ID NO: 30, (y13-6) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 195, and a VL containing the amino acid sequence represented by SEQ ID NO: 30, (y13-7) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 196, and a VL containing the amino acid sequence represented by SEQ ID NO: 30, (y13-8) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 197, and a VL containing the amino acid sequence represented by SEQ ID NO: 30, (y13-9) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 198, and a VL containing the amino acid sequence represented by SEQ ID NO: 30, (y13-10) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 199, and a VL containing the amino acid sequence represented by SEQ ID NO: 30, (y13-11) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 200, and a VL containing the amino acid sequence represented by SEQ ID NO: 30, (y13-12) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 201, and a VL containing the amino acid sequence represented by SEQ ID NO: 30, (y13-13) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 202, and a VL containing the amino acid sequence represented by SEQ ID NO: 30, (y13-14) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 203, and a VL containing the amino acid sequence represented by SEQ ID NO: 30, (y13-15) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 204, and a VL containing the amino acid sequence represented by SEQ ID NO: 30, (y13-16) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 205, and a VL containing the amino acid sequence represented by SEQ ID NO: 30, (y13-17) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 206, and a VL containing the amino acid sequence represented by SEQ ID NO: 30, (y13-18) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 207, and a VL containing the amino acid sequence represented by SEQ ID NO: 30, and (y13-19) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 208, and a VL containing the amino acid sequence represented by SEQ ID NO: 30, (y13-20) a bispecific antibody in which the first antigen-binding domain contains a VH containing the amino acid sequence represented by SEQ ID NO: 29, and a VL containing the amino acid sequence represented by SEQ ID NO: 30, and the second antigen-binding domain contains a VH containing the amino acid sequence represented by SEQ ID NO: 209, and a VL containing the amino acid sequence represented by SEQ ID NO: 30.

The bispecific antibody and the bispecific antibody fragment thereof of the present invention is preferably a bispecific antibody or a bispecific antibody fragment thereof containing the first Fab containing 131-B2 and the second Fab containing 116-398, 116-412a, 116-413a, 116-421a, 116-433a, 116-435, 116-439, 116-463a, 116-464a, 116-465a, 116-466a, or 116-408.

The bispecific antibody or the bispecific antibody fragment thereof of the present invention is more preferably a bispecific antibody or a bispecific antibody fragment thereof containing two polypeptide chains in which a C-terminus of a heavy chain in the first Fab and an N-terminus of a heavy chain in the second Fab binds to each other directly or via a linker, and hinge regions, in which C-termini of the two polypeptide chains bind to N-termini of the hinge regions, respectively. Examples thereof include a bispecific antibody or a bispecific antibody fragment thereof in which the first Fab and the second Fab are any one of the following (z1) to (z12):

(z1) the first Fab contains 131-B2 and the second Fab contains 116-398, (z2) the first Fab contains 131-B2 and the second Fab contains 116-412a, (z3) the first Fab contains 131-B2 and the second Fab contains 116-413a, (z4) the first Fab contains 131-B2 and the second Fab contains 116-421a, (z5) the first Fab contains 131-B2 and the second Fab contains 116-433a, (z6) the first Fab contains 131-B2 and the second Fab contains 116-435, (z7) the first Fab contains 131-B2 and the second Fab contains 116-439, (z8) the first Fab contains 131-B2 and the second Fab contains 116-463a, (z9) the first Fab contains 131-B2 and the second Fab contains 116-464a, (z10) the first Fab contains 131-B2 and the second Fab contains 116-465a, (z11) the first Fab contains 131-B2 and the second Fab contains 116-466a, and (z12) the first Fab contains 131-B2 and the second Fab contains 116-408.

As one aspect of the bispecific antibody or the bispecific antibody thereof of the present invention, specifically, for example, the bispecific antibody or the bispecific antibody fragment thereof is of an N-terminus type as shown in FIG. 4A, and has a structure in which two heavy chains ($VH_1$-CH1-$VH_2$-CH1'-CH2-CH3) each containing a polypeptide chain ($VH_1$-CH1-$VH_2$-CH1') in which a C-terminus of a heavy chain ($VH_1$-CH1) in the first Fab and an N-terminus of a heavy chain ($VH_2$-CH1') in the second Fab bind to each other directly or via a linker, in which a C-terminus of the polypeptide chain binds to an N-terminus of the hinge region, and an N-terminus of the Fc region (CH2-CH3) binds to a C-terminus of the hinge region, and four light chains (VL-CL) are contained. In the heavy chain, the $VH_1$ preferably contains the amino acid sequence represented by any one of SEQ ID NOs: 21, 23, 25, 27, and 29, and more preferably contains the amino acid sequence represented by SEQ ID NO: 29, and the $VH_2$ preferably contains the amino acid sequence represented by any one of SEQ ID NOs: 175 to 186.

In the above aspect, ($VH_1$-CH1-$VH_2$) in the heavy chain ($VH_1$-CH1-$VH_2$-CH1'-CH2-CH3) is preferably any one selected from the following (v1) to (v12) and (v13-1) to (v13-20):

(v1) ($VH_1$-CH1-$VH_2$) containing a $VH_1$ containing the amino acid sequence represented by SEQ ID NO: 29, a CH1 containing the amino acid sequence represented by SEQ ID NO: 144, and a $VH_2$ containing the amino acid sequence represented by SEQ ID NO: 175 in order from an N-terminus, (v2) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 176 in order from an N-terminus, (v3) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 177 in order from an N-terminus, (v4) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 178 in order from an N-terminus, (v5) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 179 in order from an N-terminus, (v6) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 180 in order from an N-terminus, (v7) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 181 in order from an N-terminus, (v8) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 182 in order from an N-terminus, (v9) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 183 in order from an N-terminus, (v10) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 184 in order from an N-terminus, (v11) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 185 in order from an N-terminus, (v12) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 186 in order from an N-terminus, (v13-1) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 190 in order from an N-terminus, (v13-2) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 191 in order from an N-terminus, (v13-3) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 192 in order from an N-terminus, (v13-4) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 193 in order from an N-terminus, (v13-5) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 194 in order from an N-terminus, (v13-6) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 195 in order from an N-terminus, (v13-7) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 196 in order from an N-terminus, (v13-8) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 197 in order from an N-terminus, (v13-9) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 198 in order from an N-terminus, (v13-10) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 199 in order from an N-terminus, (v13-11) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 200 in order from an N-terminus, (v13-12) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 201 in order from an N-terminus, (v13-13) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 202 in order from an N-terminus, (v13-14) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 203 in order from an N-terminus, (v13-15) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 204 in order from an N-terminus, (v13-16) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 205 in order from an N-terminus, (v13-17) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 206 in order from an N-terminus, (v13-18) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 207 in order from an N-terminus, (v13-19) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 208 in order from an N-terminus, and (v13-20) (VH$_1$-CH1-VH$_2$) containing a VH$_1$ containing the amino acid sequence represented by SEQ ID NO: 29, a CH1 containing the amino acid sequence represented by SEQ ID NO: 144, and a VH$_2$ containing the amino acid sequence represented by SEQ ID NO: 209 in order from an N-terminus.

In the above aspect, the (CH1'-CH2-CH3) in the heavy chain preferably contains the amino acid sequence represented by any one of SEQ ID NO: 145 to 172. In the above aspect, the VL in the light chain (VL-CL) more preferably contains the amino acid sequence represented by SEQ ID NO: 30.

The bispecific antibody of the present invention also includes a bispecific antibody that competes with any one of the above-described bispecific antibodies in binding to CD116 and/or CD131.

Further, the bispecific antibody of the present invention also includes a bispecific antibody that recognizes an epitope same as an epitope of CD116 and/or CD131 recognized by any of the above bispecific antibodies, a bispecific antibody that recognizes a part of an epitope of CD116 and/or CD131 recognized by any of the above bispecific antibodies, and a bispecific antibody that recognizes an epitope containing an epitope of CD116 and/or CD131 recognized by any of the above bispecific antibodies.

The bispecific antibody of the present invention may or may not have an effector activity due to the constant region of the antibody, and one not having an effector activity is preferred.

The effector activity refers to an antibody-dependent cellular cytotoxicity activity caused through the Fc region of the antibody, and examples thereof include an antibody-dependent cellular cytotoxicity activity (ADCC activity), a complement-dependent cytotoxicity activity (CDC activity), and an antibody-dependent cellular phagocytosis activity (ADCP activity) and an opsonin effect due to phagocytes such as macrophages and dendritic cells.

In the present invention, the ADCC activity and the CDC activity can be measured using a known measurement method [Cancer Immunol. Immunother., 36, 373 (1993)].

The ADCC activity refers to an activity in which an antibody that binds to an antigen on a target cell binds to an Fc receptor of an immune cell through the Fc region of the antibody to activate the immune cell (natural killer cell or the like), thereby injuring the target cell.

The Fc receptor (FcR) is a receptor that binds to the Fc region of the antibody, and induces various effector activities for binding the antibody. Each FcR corresponds to an antibody subclass, and IgG, IgE, IgA, and IgM specifically bind to FcγR, FcεR, FcαR, and FcμR, respectively. Further, FcγR includes subtypes of FcγRI (CD64), FcγRII (CD32), and FcγRIII (CD16), and each subtype includes isoforms FcγRIA, FcγRIB, FcγRIC, FcγRIIA, FcγRIIB, FcγRIIC, FcγRIIIA, and FcγRIIIB. These different FcγRs are present on different cells [Annu. Rev. Immunol. 9:457-492 (1991)]. In humans, FcγRIIIB is specifically expressed in neutrophils, and FcγRIIIA is expressed in monocytes, natural killer cells (NK cells), macrophages, and some T cells. An NK cell-dependent ADCC activity is induced through antibody binding to FcγRIIIA.

The term "CDC activity" refers to an activity in which an antibody that binds to an antigen on a target cell activates a series of cascades (complement activation pathway) consisting of a group of complement-related proteins in the blood, thereby injuring the target cell. Protein fragments generated by complement activation induce migration and activation of immune cells. The cascade of CDC activity is initiated by first binding of C1q to the Fc region and then to two serine proteases, C1r and C1s, to form a C1 complex.

The CDC activity or ADCC activity of the bispecific antibody or the antibody fragment thereof of the present invention to antigen-expressing cells can be evaluated by a known measurement method [Cancer Immunol. Immunother., 36, 373 (1993)].

As a method for controlling the effector activity of the bispecific antibody of the present invention, there has been known a method for controlling an amount of fucose (also called core fucose) that alpha-1,6-binds to N-acetylglucosamine (GlcNAc) present at a reducing end of an N-linked complex-type sugar chain that binds to asparagine (Asn) at position 297 in an Fc region (constant region consisting of CH2 and CH3 domains) of an antibody (WO2005/035586, WO2002/31140, and WO00/61739), and a method for controlling by modifying amino acid residues in an Fc region of an antibody (WO00/42072).

By controlling an amount of fucose added to the bispecific antibody, the ADCC activity of the antibody can be increased or reduced. For example, as a method for reducing an amount of fucose that binds to an N-linked complex sugar chain that binds to an Fc of an antibody, a bispecific antibody having high ADCC can be obtained by expressing the bispecific antibody using host cells from which an α1,6-fucosyltransferase gene is deleted. On the other hand, as a method for increasing an amount of fucose that binds to an N-linked complex sugar chain that binds to an Fc of a bispecific antibody, a bispecific antibody having low ADCC activity can be obtained by expressing the antibody using host cells with an α1,6-fucosyltransferase gene introduced.

The ADCC activity and the CDC activity can be increased or reduced by modifying amino acid residues in the Fc region of the bispecific antibody. For example, the CDC activity of the bispecific antibody can be increased by using the amino acid sequence of the Fc region described in US Patent Application Publication No. 2007/0148165. The ADCC activity or the CDC activity can be increased or reduced by performing an amino acid modification described in U.S. Pat. Nos. 6,737,056, 7,297,775, or U.S. Pat. No. 7,317,091.

Further, by combining the above-described methods, a bispecific antibody whose effector activity is controlled may be acquired.

The stability of the bispecific antibody of the present invention can be evaluated by measuring an amount of aggregates (oligomers) formed during a purification process or in a sample stored under certain conditions. That is, when the amount of aggregates decreases under the same conditions, it is evaluated that the stability of the antibody is improved. The amount of aggregates can be measured by separating aggregated antibodies and non-aggregated antibodies using appropriate chromatography including gel filtration chromatography.

The productivity of the bispecific antibody of the present invention can be evaluated by measuring an amount of antibodies produced from antibody-producing cells in a culture medium. More specifically, the productivity can be evaluated by measuring an amount of antibodies contained in a culture supernatant after removing the producing cells from the culture medium using an appropriate method such as HPLC or ELISA.

In the present invention, the antibody fragment is a protein containing an antigen-binding site and having an antigen-binding activity to an antigen. Examples thereof include Fab, Fab', F(ab')$_2$, scFv, Diabody, dsFv, or a VHH or CDR-containing peptide.

The Fab is an antibody fragment obtained by treating an IgG antibody with a proteolytic enzyme papain (obtained by cleaving at an amino acid residue at position 224 in an H chain) and having a molecular weight of about 50000 and an antigen-binding activity, in which about half of the H chain on an N-terminus side and an entire L chain bind to each other by a disulfide bond (S—S bond).

The F(ab')$_2$ is an antibody fragment obtained by treating an IgG antibody with a proteolytic enzyme pepsin (obtained by cleaving at an amino acid residue at position 234 in an H chain) and having a molecular weight of about 100000 and an antigen-binding activity, which is slightly larger than that of Fab bound through an S—S bond in a hinge region.

The Fab' is an antibody fragment obtained by cleaving the S—S bond in the hinge region of the F(ab')$_2$ and having a molecular weight of about 50000 and an antigen-binding activity.

The scFv is a VH-P-VL or VL-P-VH polypeptide obtained by linking one VH and one VL by a suitable peptide linker (P) of 12 or more residues, and is an antibody fragment having an antigen-binding activity.

The Diabody is an antibody fragment obtained by forming a dimer with scFvs having the same or different antigen binding specificity, and is an antibody fragment having an divalent antigen-binding activity to the same antigen or a specific antigen-binding activity to different antigens.

The dsFv refers to a polypeptide in which one amino acid residue each in a VH and a VL is substituted with a cysteine residue, which are linked via an S—S bond between the cysteine residues.

The VHH, also referred to as a nanobody, refers to a heavy chain variable region in a VHH antibody and is capable of binding an antigen without the presence of other polypeptides.

The VHH antibody is an antibody present in camelid animals such as alpacas and cartilaginous fish such as sharks, and consists only of heavy chains without light chains and CH1.

A CDR-containing peptide includes at least one region of a CDR of a VH or a VL. A peptide containing a plurality of CDRs can be prepared by binding CDRs directly or via a suitable peptide linker. The CDR-containing peptide can be produced by constructing a DNA encoding CDRs of a VH and a VL of the bispecific antibody of the present invention, inserting the DNA into a prokaryotic expression vector or an eukaryotic expression vector, and expressing the CDR-containing peptide by introducing the expression vector into prokaryotes or eukaryotes. The CDR-containing peptide can also be produced by a chemical synthesis method such as an Fmoc method or a tBoc method.

In the present invention, the bispecific antibody fragment essentially consists of a partial structure of the bispecific antibody, and may be a fragment of any bispecific antibody as long as it has an antigen-binding activity for two types of antigens.

The bispecific antibody of the present invention also includes a protein obtained by fusing an Fc to the bispecific antibody or the bispecific antibody fragment thereof of the invention, a fusion protein obtained by further binding an antibody fragment to the protein, an Fc fusion protein (also referred to as an immunoadhesin) obtained by binding the Fc to a naturally occurring ligand or receptor, and an Fc fusion protein obtained by fusing a plurality of Fc regions. An Fc region to which a technique aiming at enhancing or reducing the effector activity of the antibody, stabilizing the antibody, and controlling blood half-life is applied can also be used for the bispecific antibody of the present invention.

Examples of the technique aiming at controlling blood half-life include a method of inhibiting antibody recycling by cleaving binding to FcRn at pH 6.0.

As the method of inhibiting antibody recycling by cleaving binding to an FcRn at pH 6.0, for example, it is preferred to introduce an amino acid residue modification into at least one selected from Ile at position 253, His at position 310, His at position 435, and Tyr at position 436 as represented by the EU index. Specific examples of such modification include H435F.

It is considered that FcRn does not bind to an Fc region outside cells (pH 7.0 to 7.5), but binds to IgG taken into the cell within early endosomes (pH 6.0), and maintains a concentration in blood by recycling IgG to the outside of the cell (Biochemistry, 34, 14649 (1995) DOI: 10.1021/bi00045a005; Nat. Rev. Immunol., 7, 715 (2007) DOI: 10.1038/nri2155). A residue important for binding between the Fc region and FcRn at pH 6.0 is identified as Ile at position 253, His at position 310, His at position 435, and Tyr at position 436 as represented by the above EU index (J. Immunol., 176, 346 (2006); Int. Immunol., 13, 993 (2001); J. Biol. Chem., 276, 6591 (2001); J. Immunol., 169, 5171 (2002)), as a result of a search for a site where the binding activity is significantly reduced by introducing an amino acid mutation (substitution to Ala).

The bispecific antibody and the bispecific antibody fragment thereof of the present invention includes an antibody derivative obtained by chemically or genetically binding a radioactive isotope, a low-molecular drug, a high-molecular drug, a protein, or an antibody drug to the bispecific antibody or the bispecific antibody fragment thereof of the present invention.

The derivative of the bispecific antibody in the present invention can be produced by binding, by a chemical method [Introduction to Antibody Engineering, Chijin Shokan (1994)], a radioactive isotope, a low-molecular drug, a high-molecular drug, an immunostimulant, a protein, or an antibody drug to an N-terminus side or a C-terminus side of the bispecific antibody or the bispecific antibody fragment thereof of the present invention, an appropriate substituent or a side chain in the bispecific antibody or the bispecific antibody fragment thereof, and further a sugar chain in the bispecific antibody or the bispecific antibody fragment thereof.

The derivative of the bispecific antibody in the present invention can be produced by a genetic engineering technique in which a DNA encoding the bispecific antibody or the bispecific antibody fragment thereof of the present invention and a DNA encoding a desired protein or an antibody drug are linked and inserted into an expression vector, and the expression vector is introduced into an appropriate host cell to express the derivative.

Examples of the radioactive isotope include $^{111}$In, $^{131}$I, $^{125}$I, $^{90}$Y, $^{64}$Cu, $^{99}$Tc, $^{77}$Lu, and $^{211}$At. The radioactive isotope can directly bind to the antibody by a chloramine T method or the like. A substance for chelating the radioactive isotope may bind to the antibody. Examples of the chelating reagent include 1-isothiocyanatebenzyl-3-methyldiethylenetriaminepentaacetic acid (MX-DTPA).

Examples of the low-molecular drug include an alkylating agent, nitrosourea, an antimetabolite, an antibiotic, a plant alkaloid, a topoisomerase inhibitor, a hormone therapy agent, a hormone antagonist, an aromatase inhibitor, a P-glycoprotein inhibitor, a platinum complex derivative, an anticancer agent such as an M-phase inhibitor or a kinase inhibitor [Clinical Oncology, Cancer and Chemotherapy (1996)], a steroidal drug such as hydrocortisone or prednisone, a non-steroidal drug such as aspirin or indomethacin, an immunomodulator such as gold thiomalate or penicillamine, an immunosuppressant such as cyclophosphamide or azathioprine, and an anti-inflammatory agent such as an antihistamine such as chlorpheniramine maleate or clemacitin [Inflammation and anti-inflammatory therapy, Ishiyaku Pub, Inc. (1982)].

Examples of the anticancer agent include amifostine (ethiol), cisplatin, dacarbazine (DTIC), dactinomycin, mechlorethamine (nitrogen mustard), streptozocin, cyclophosphamide, ifosfamide, carmustine (BCNU), iomustine (CCNU), doxorubicin (Adriamycin), epirubicin, gemcitabine (Gemzar), daunorubicin, procarbazine, mitomycin, cytarabine, etoposide, 5-fluorouracil, fluorouracil, vinblastine, vincristine, bleomycin, daunomycin, pepromycin, estramustine, paclitaxel (Taxol), docetaxel (Taxotea), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegasparagase, pentostatin, pipobroman, streptozocin, tamoxifen, goserelin, leuprorenin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, tomdex, azacitidine, UFT, oxaloplatin, gefitinib (Iressa), imatinib (STI571), erlotinib, an FMS-like tyrosine kinase 3 (Flt3) inhibitor, a vascular endothelial growth facotr receptor (VEGFR) inhibitor, a fibroblast growth factor receptor (FGFR) inhibitor, an epidermal growth factor receptor (EGFR) inhibitor such as Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestins, estrogens, anastrozole (Arimidex), leuprolide, aspirin, indomethacin, celecoxib, azathioprine, penicillamine, gold thiomalate, chlorpheniramine maleate, chlorpheniramine, clemacitin, tretinoin, bexarotene, arsenic, bortezomib, allopurinol, calicheamicin, ibritumomab tiuxetan, targretin, ozogamine, clarithromacin, leucovorin, ketoconazole, aminoglutethimide, suramin, methotrexate, and maytansinoid or a derivative thereof.

Examples of the method of binding the low-molecular drug with the bispecific antibody or the bispecific antibody fragment thereof of the present invention include a method of binding a drug with an amino group of the antibody via glutaraldehyde, and a method of bonding an amino group of a drug and a carboxy group of the antibody via water-soluble carbodiimide.

Examples of the high-molecular drug include polyethylene glycol (PEG), albumin, dextran, polyoxyethylene, a styrene maleic acid copolymer, polyvinylpyrrolidone, a pyran copolymer, or hydroxypropyl methacrylamide. By binding the high molecular weight compound to the bispecific antibody or the antibody fragment thereof of the present invention, effects such as (1) improvement of stability with respect to various chemical, physical, or biological factors, (2) significant extension of blood half-life, and (3) loss of immunogenicity or prevention of antibody production are expected [Bioconjugate pharmaceuticals, Hirokawa Shoten (1993)].

Examples of the method of binding a PEG with the bispecific antibody of the present invention include a method for reacting with a PEGylation modification reagent [Bioconjugate pharmaceuticals, Hirokawa Shoten (1993)]. Examples of the PEGylation modification reagent include a modifier for a ε-amino group of lysine (JPS61-178926A), a modifier for a carboxy group of aspartic acid and glutamic acid (JPS56-23587A), or a modifier for a guanidino group of arginine (JPH2-117920A).

The immunostimulant may be a natural product known as an immunoadjuvant, and specific examples thereof include drugs that enhance immunity, such as β (1->3) glucan (for example, lentinan or schizophyllan), or a-galactosylceramide (KRN7000).

Examples of the protein include a cytokine or a growth factor that activates immunocompetent cells such as NK cells, macrophages, or neutrophils, or a toxin protein.

Examples of the cytokine or growth factor include interferon (hereinafter referred to as IFN)-α, IFN-β, IFN-γ, interleukin (hereinafter referred to as IL)-2, IL-12, IL-15, IL-18, IL-21, and IL-23, a granulocyte-colony stimulating factor (G-CSF), a granulocyte/macrophage-colony stimulating factor (GM-CSF), or a macrophage-colony stimulating factor (M-CSF).

Examples of the toxin protein include ricin, diphtheria toxin, or ONTAK, and the toxin protein also includes a protein toxin obtained by introducing a mutation into a protein to adjust toxicity.

A fusion antibody with a protein or antibody drug can be produced by linking a cDNA encoding a protein to a cDNA encoding the bispecific antibody or the antibody fragment of the present invention, constructing a DNA encoding the fusion antibody, inserting the DNA into a prokaryotic or eukaryotic expression vector, and introducing the expression vector into prokaryotes or eukaryotes to express the fusion antibody.

When using the above antibody derivatives as a detection method, a quantitative method, a detection reagent, a quantitative reagent, or a diagnostic agent, examples of a drug binding to the bispecific antibody or the antibody fragment thereof of the present invention include labels used in a general immunological detection method or measurement method. Examples of the label include an enzyme such as alkaline phosphatase, peroxidase, or luciferase, a luminescent substance such as an acridinium ester or a lophine, or a fluorescent substance such as fluorescein isothiocyanate (FITC) or tetramethylrhodamine isothiocyanate (RITC), Alexa (registered trademark) Fluor 488, or R-phycoerythrin (R-PE).

The present invention includes a bispecific antibody having a cellular cytotoxicity activity, such as a CDC activity or an ADCC activity, and a bispecific antibody fragment thereof. The CDC activity or ADCC activity of the bispecific antibody or the bispecific antibody fragment thereof of the present invention to antigen-expressing cells can be evaluated by a known measurement method [Cancer Immunol. Immunother., 36, 373 (1993)].

The present invention relates to a composition containing a bispecific antibody that specifically recognizes and binds to CD116 and CD131 or a bispecific antibody fragment thereof, or a therapeutic agent for a disease associated with at least one of CD116 and CD131, preferably a disease associated with cells expressing CD116 and CD131, which contains the bispecific antibody or the bispecific antibody fragment thereof as an active ingredient.

The disease associated with at least one of CD116 and CD131 may be any disease associated with at least one of CD116 and CD131, and examples thereof include a disease associated with a GM-CSF, cancer, leukopenia, various infectious diseases, an Alzheimer's disease, and a disease associated with a GM-CSF neutralizing antibody.

In the present invention, examples of the disease associated with a GM-CSF or a disease associated with a GM-CSF neutralizing antibody include melanoma, head and neck cancer, breast cancer, gastrointestinal cancer, pancreatic cancer, hepatocellular carcinoma, prostate cancer, colorectal cancer, lung cancer, renal cell cancer, ovarian cancer, leukopenia due to chemotherapy, leukopenia due to bone marrow transplantation, leukopenia due to aplastic anemia, leukopenia due to myelodysplastic syndrome, recovery of bone marrow function in bone marrow transplantation, acute myeloid leukemia, chronic myelomonocytic leukemia, sepsis, mycosis, HIV infection, influenza virus infection, a non-tuberculous mycobacterial infection, acute respiratory distress syndrome, pulmonary alveolar proteinosis, and a Crohn's disease.

The therapeutic agent containing the bispecific antibody or the bispecific antibody fragment thereof of the present invention, or a derivative thereof may contain only the bispecific antibody or the bispecific antibody fragment thereof, or a derivative thereof as an active ingredient, and the therapeutic agent is generally preferred to be provided as a pharmaceutical preparation mixed with one or more pharmacologically acceptable carriers and produced by any method known in the art of preparation.

It is preferred to use a most effective route of administration for treatment. Examples thereof include oral administration and parenteral administration such as intrapulmonary administration, buccal, tracheobronchial, intrarectal, subcutaneous, intramuscular, or intravenous administration. Among them, intravenous or intrapulmonary administration is preferred.

Examples of a dosage form include inhalants, sprays, capsules, tablets, powders, granules, syrups, emulsions, suppositories, injections, ointments, and tapes.

A dosage or the number of doses varies depending on a desired therapeutic effect, an administration method, a treatment period, an age, a body weight, or the like, and is generally 10 µg/kg to 10 mg/kg per day for adults.

Further, the present invention also relates to an immunological detection or measurement reagent for at least one of CD116 and CD131, which contains the bispecific antibody or the bispecific antibody fragment thereof of the present invention, or a diagnostic agent for a disease associated with at least one of CD116 and CD131, and preferably a disease associated with cells expressing CD116 and CD131. The present invention relates to an immunological detection or measurement method for at least one of CD116 and CD131 using the bispecific antibody or the bispecific antibody fragment thereof of the present invention, a therapeutic method for a disease associated with at least one of CD116 and CD131, and preferably a disease associated with cells expressing CD116 and CD131, and a diagnostic method for a disease associated with at least one of CD116 and CD131, and preferably a disease associated with cells expressing CD116 and CD131.

In the present invention, any known method may be used as a method for detecting or measuring an amount of at least one of CD116 and CD131. Examples thereof include an immunological detection or measurement method.

An immunological detection or measurement method is a method for detecting or measuring an antibody amount or antigen amount using a labeled antigen or antibody. Examples of the immunological detection or measurement method include radioimmunoassay (RIA), enzyme immunoassay (EIA or ELISA), fluorescence immunoassay (FIA), luminescent immunoassay, Western blotting, or a physicochemical method.

By detecting or measuring cells expressing at least one of CD116 and CD131 using the bispecific antibody or the bispecific antibody fragment thereof of the present invention, a disease associated with at least one of CD116 and CD131, and preferably a disease associated with cells expressing CD116 and CD131 can be diagnosed.

Known immunological detection methods can be used to detect cells expressing at least one of CD116 and CD131, and examples thereof include an immunoprecipitation method, an immunocytostaining method, an immunohistological staining method, and a fluorescent antibody staining method. Examples thereof include a fluorescent antibody staining method such as an FMAT 8100 HTS system (manufactured by Applied Biosystems).

In the present invention, a biological sample to be detected or measured for at least one of CD116 and CD131 is not particularly limited as long as it may contain cells expressing at least one of CD116 and CD131, such as tissue cells, blood, plasma, serum, a pancreatic fluid, urine, feces, a tissue fluid, or a culture medium.

The diagnostic agent containing the bispecific antibody or the bispecific antibody fragment thereof of the present invention, or the derivative thereof may contain a reagent for performing an antigen-antibody reaction and a detection reagent for the reaction, depending on an intended diagnostic method. Examples of the reagent for performing an antigen-antibody reaction include a buffer and a salt.

Examples of the detection reagent include a labeled secondary antibody that binds to the bispecific antibody or the bispecific antibody fragment thereof, or the derivative thereof, and a reagent used in a general immunological detection or measurement method, such as substrates compatible with labels.

Hereinafter, a method for preparing the bispecific antibody of the present invention, a method for evaluating an activity of the bispecific antibody or the bispecific antibody fragment thereof, and a therapeutic method and a diagnostic method for a disease using the bispecific antibody or the bispecific antibody fragment thereof will be specifically described.

1. Method for Preparing Monoclonal Antibody

A method for producing a monoclonal antibody in the present invention includes the following working steps. That is, the working steps include (1) at least one of purifying antigens used as an immunogen and preparing cells overexpressing the antigens on a cell surface, (2) a step of extracting blood after immunizing an animal with the antigens and testing an antibody titer thereof to determine a time to extract spleen or the like, thereby preparing antibody-producing cells, (3) preparing myeloma cells (myelomas), (4) performing cell fusion between the antibody-producing cells and the myelomas, (5) selecting a target antibody-producing hybridoma group, (6) separating (cloning) monoclonal cells from the hybridoma group, (7) culturing the hybridomas for mass production of the monoclonal antibody or breeding animals grafted with the hybridomas according to the case, and (8) examining a physiological activity and an antigen-binding specificity of the monoclonal antibody thus produced, or testing properties thereof as a labeling reagent.

Hereinafter, a method for preparing a monoclonal antibody binding to CD116 and a monoclonal antibody binding to CD131, which are used for preparing the bispecific antibody binding to CD116 and CD131 in the present invention, will be described in detail along the above steps. The method for preparing the antibody is not limited thereto, and, for example, antibody-producing cells other than spleen cells and myelomas can also be used.

(1) Purification of Antigens

Cells expressing CD116 or CD131 can be obtained by introducing an expression vector containing a cDNA encoding a full length of CD116 or CD131 or a partial length thereof into *Escherichia coli*, yeast, insect cells, or animal cells. At least one of CD116 and CD131 can be purified from various cultured human tumor cells or human tissues that express at least one of CD116 or CD131 in large amounts and used as antigens. The cultured tumor cells or tissues can also be used as they are as antigens. Further, a synthetic peptide having a partial sequence of CD116 or CD131 can be prepared by a chemical synthesis method such as an Fmoc method or a tBoc method and used as antigens.

CD116 or CD131 used in the present invention can be produced by expressing a DNA encoding the CD116 or CD131 in a host cell using a method described in Molecular Cloning, A Laboratory Manual, Second Edition, Cold Spring Harbor Laboratory Press (1989) and Current Protocols In Molecular Biology, John Wiley & Sons (1987-1997), and the like, for example, by the following method.

A recombinant vector is prepared by inserting a full-length cDNA containing a portion encoding CD116 or CD131 downstream of a promoter of an appropriate expression vector. Instead of the full-length cDNA described above, a DNA fragment of an appropriate length containing a polypeptide-encoding portion prepared based on the full-length cDNA may be used. Next, by introducing the obtained recombinant vector into a host cell compatible with the expression vector, a transformant producing CD116 or CD131 can be obtained.

Any expression vectors can be used as long as it is capable of autonomous replication in a host cell to be used or integration into a chromosome, and contains an appropriate promoter at a position where a DNA encoding CD116 or CD131 can be transcribed.

As the host cell, any cells that can express a target gene can be used, such as microorganisms belonging to the genus *Escherichia* such as *Escherichia coli*, yeast, insect cells, or animal cells.

When using prokaryotes such as *Escherichia coli* as the host cell, the recombinant vector is preferably a vector that is capable of autonomous replication in prokaryotes and contains a promoter, a ribosome binding sequence, a DNA containing a portion encoding CD116 or CD131, and a transcription termination sequence. Although the recombinant vector does not necessarily have a transcription termination sequence, it is preferred to place the transcription termination sequence immediately below a structural gene. Further, the recombinant vector may contain a gene that controls a promoter.

As the recombinant vector, it is preferred to use a plasmid in which a distance between the Shine-Dalgarno sequence, which is a ribosome binding sequence, and an initiation codon is adjusted to an appropriate distance (for example, 6 bases to 18 bases).

In a nucleotide sequence of the DNA encoding CD116 or CD131, bases can be substituted such that the codon is optimal for expression in the host, thereby improving a production rate of the target CD116 or CD131.

Any expression vector can be used as long as it can function in a host cell to be used. Examples thereof include pBTrp2, pBTac1, and pBTac2 (manufactured by Roche Diagnostics), pKK233-2 (manufactured by Pharmacia), pSE280 (manufactured by Invitrogen), pGEMEX-1 (manufactured by Promega), pQE-8 (manufactured by Qiagen), pKYP10 (JPS58-110600A), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK (−) (manufactured by Stratagene Corporation), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), JPS60-221091A], pGKA2 [prepared from *Escherichia coli* IGKA2 (FERM BP-6798), JPS60-221091A], pTerm2 (U.S. Pat. Nos. 4,686,191, 4,939,094, U.S. Pat. No. 5,160,735), pSupex, pUB110, pTP5, pC194, and pEG400 [J. Bacteriol., 172, 2392 (1990)], pGEX (manufactured by Pharmacia), a pET system (manufactured by Novagen), or pME18SFL3 (manufactured by Toyobo Co., Ltd.).

Any promoter may be used as long as it functions in a host cell to be used. Examples thereof include a promoter derived from *Escherichia coli* or a phage, such as a trp promoter (Ptrp), a lac promoter, a PL promoter, a PR promoter, or a T7 promoter. Examples thereof include a tandem promoter with two Ptrps arranged in series, a tac promoter, a lacT7 promoter, and an artificially designed promoter such as a let I promoter.

Examples of the host cell include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, or *Escherichia coli* DH5a.

As a method for introducing a recombinant vector into a host cell, any method can be used as long as it introduces a DNA into a host cell to be used, such as a method using calcium ions [Proc. Natl. Acad. Sci. USA, 69, 2110 (1972), Gene, 17, 107 (1982), Molecular & General Genetics, 168, 111 (1979)].

When using an animal cell as a host, any expression vector that functions in an animal cell can be used. Examples thereof include pcDNAI (manufactured by Invitrogen), pcDM8 (manufactured by Funakoshi), PAGE107 [JPH3-22979A; Cytotechnology, 3, 133 (1990)], pAS3-3 (JPH2-227075A), pCDM8 [Nature, 329, 840 (1987)], pcDNAI/Amp (manufactured by Invitrogen), pcDNA3.1 (manufactured by Invitrogen), pREP4 (manufactured by Invitrogen), pAGE103 [J. Biochemistry, 101, 1307 (1987)], and pAGE210, pME18SFL3, or pKANTEX93 (WO97/10354).

Any promoter can be used as long as it can function in an animal cell, and examples thereof include a cytomegalovirus (CMV) immediate early (IE) gene promoter, a SV40 early promoter, a retrovirus promoter, a metallothionein promoter, a heat shock promoter, an SRα promoter, or a Moloney murine leukemia virus promoter or enhancer. A human CMV IE gene enhancer may be used together with the promoter.

Examples of the host cell include human Burkitt's lymphoma cells Namalwa, African green monkey kidney-derived cells COS, Chinese hamster ovary-derived cells CHO, and human leukemia cells HBT5637 (JPS63-000299A).

Any method for introducing a DNA into an animal cell can be used as the method for introducing a recombinant vector into a host cell, and examples thereof include an electroporation method [Cytotechnology, 3, 133 (1990)], a calcium phosphate method (JP2-227075A), or a lipofection method [Proc. Natl. Acad. Sci. USA, 84, 7413 (1987)].

CD116 or CD131 can be produced by culturing, in a medium, a transformant derived from a microorganism, an animal cell, or the like having a recombinant vector with the DNA encoding CD116 or CD131 obtained as described above incorporated, producing and accumulating the CD116 and/or CD131 in a culture, and collecting the CD116 and/or CD131 from the culture. The transformant can be cultured in a medium according to a general method used for culturing hosts.

When expressed in cells derived from eukaryotes, CD116 or CD131 with an added sugar or sugar chain can be obtained.

When culturing a microorganism transformed with a recombinant vector using an inducible promoter, an inducer may be added to the medium as necessary. For example, when culturing a microorganism transformed with a recombinant vector using a lac promoter, isopropyl-B-D-thiogalactopyranoside or the like may be added to each medium, and when culturing a microorganism transformed with a recombinant vector using a trp promoter, indole acrylic acid or the like may be added to each medium.

Examples of the medium for culturing the obtained transformant using an animal cell as a host include a generally used RPMI1640 medium [The Journal of the American Medical Association, 199, 519 (1967)], an Eagle's MEM medium [Science, 122, 501 (1952)], a Dulbecco's modified MEM medium [Virology, 8, 396 (1959)], a 199 medium [Proc. Soc. Exp. Biol. Med., 73, 1 (1950)], an Iscove's Modified Dulbecco's Medium (IMDM) medium, and a medium containing fetal bovine serum (FBS). The culture is generally performed for 1 day to 7 days under conditions of pH 6 to 8, 30° C. to 40° C., and the presence of 5% $CO_2$. If necessary during culture, an antibiotic such as kanamycin and penicillin may be added to the medium.

As a method for expressing the gene encoding CD116 or CD131, in addition to direct expression, a method such as secretory production or fusion protein expression [Molecular Cloning, A Laboratory Manual, Second Edition, Cold Spring Harbor Laboratory Press (1989)] can be used. Examples of the method for producing CD116 or CD131 include a method for producing CD116 or CD131 within a host cell, a method for secreting CD116 or CD131 outside a host cell, and a method for producing CD116 or CD131 on an outer membrane of a host cell. An appropriate method can be selected by changing a host cell to be used and a structure of CD116 or CD131 to be produced.

For example, an antigen fusion protein can be prepared by preparing a DNA obtained by linking a DNA encoding an Fc region of an antibody, a DNA encoding glutathione S-transferase (GST), or a DNA encoding a FLAG tag, or a DNA encoding a Histidine tag to a DNA encoding an amino acid sequence of an extracellular region, and expressing and purifying the antigen fusion protein. Specific examples thereof include an Fc fusion protein obtained by binding an extracellular region of CD116 or CD131 to an Fc region of human IgG, and a fusion protein of an extracellular region of CD116 or CD131 with glutathione S-transferase (GST).

When CD116 or CD131 is produced within a host cell or on an outer membrane of a host cell, CD116 or CD131 can be actively secreted outside the host cell by using a method of Paulson et al. [J. Biol. Chem., 264, 17619 (1989)], a method of Rowe et al. [Proc. Natl. Acad. Sci., USA, 86, 8227 (1989), Genes Develop., 4, 1288 (1990)], and a method described in JPH05-336963A or WO1994/23021. A production amount of CD116 or CD131 can also be increased using a gene amplification system (JPH2-227075A) using a dihydrofolate reductase gene, or the like.

The produced CD116 or CD131 can be isolated and purified, for example, as follows.

When CD116 or CD131 is expressed in a dissolved state in cells, the cells are collected by centrifugation after the end of the culture, suspended in an aqueous buffer solution, and then disrupted with an ultrasonic disintegrator, a French press, a Manton-Gaurin homogenizer, a Dyno mill, or the like to obtain a cell-free extract. From a supernatant obtained by centrifuging the cell-free extract, a purified protein can be obtained by using a general protein isolation and purification method, that is, a method such as a solvent extraction method, a salting-out method with ammonium sulfate or the like, a desalting method, a precipitation method with an organic solvent, diethylaminoethyl (DEAE)-Sepharose, an anion exchange chromatography method using a resin such as DIAION HPA-75 (manufactured by Mitsubishi Chemical Corporation), a cation exchange chromatography method using a resin such as S-Sepharose FF (manufactured by Pharmacia), a hydrophobic chromatography method using a resin such as butyl sepharose and phenyl sepharose, a gel filtration method using molecular sieves, an affinity chromatography method, a chromatofocusing method, and an electrophoresis method such as isoelectric focusing, alone or in combination.

When CD116 or CD131 is expressed in an insoluble form in cells, the cells are collected and disrupted in the same manner as above, and centrifuged to collect an insoluble form of CD116 or CD131 as a precipitate fraction. The collected insoluble form of CD116 or CD131 is solubilized with a protein denaturant. After recovering CD116 or CD131 to a normal three-dimensional structure by diluting or dialyzing the solubilized solution, a purified protein of a polypeptide can be obtained by an isolation and purification method same as that described above.

When CD116 or CD131 or a derivative such as a glycosylated derivative thereof is secreted extracellularly, the CD116 or CD131 or the derivative such as a glycosylated derivative thereof can be collected in a culture supernatant. A soluble fraction can be obtained by processing the culture supernatant using a method such as centrifugation same as that described above, and a purified protein can be obtained from the soluble fraction by using an isolation and purification method same as that described above.

CD116 or CD131 used in the present invention can also be produced by a chemical synthesis method such as an Fmoc method or a tBoc method. Specifically, for example, CD116 or CD131 can be produced by chemical synthesis using a peptide synthesizer manufactured by Advanced Chem Tech Inc., PerkinElmer, Pharmacia, Protein Technology Instruments, Synthecell-Vega, Perceptiv, or Shimadzu.

(2) Step of Preparing Antibody-Producing Cells

An animal such as mice, rats, hamsters, rabbits, cows, or alpacas is immunized with the antigens obtained in (1), and antibody-producing cells from a spleen, a lymph node, or a peripheral blood of the animal are collected. Examples of the immune animal include human-derived antibody producing-transgenic mice described in the literature of Tomitsuka et al. [Tomizuka. et al., Proc Natl Acad Sci USA., 97, 722 (2000)], and CD116 or CD131 conditional knockout mice for increasing immunogenicity.

The immunization is performed by administering the antigens with a suitable adjuvant such as complete Freund's adjuvant or aluminum hydroxide gel and *Bordetella pertussis* vaccine. An immunogen administration method for mouse immunization may be subcutaneous injection, intraperitoneal injection, intravenous injection, intradermal injection, intramuscular injection, or footpad injection, and intraperitoneal injection, footpad injection, or intravenous injection is preferred. When the antigen is a partial peptide, a conjugate with a carrier protein such as a bovine serum albumin (BSA) or a keyhole limpet hemocyanin (KLH) is prepared and used as an immunogen.

After the first administration, the antigen is administered 5 times to 10 times every 1 week to 2 weeks. Blood is collected from a fundus venous plexus 3 days to 7 days after each administration, and an antibody titer of the serum thereof is measured using enzyme immunoassay [Antibodies-A Laboratory Manual, Cold Spring Harbor Laboratory (1988)] or the like. When an animal whose serum exhibits a sufficient antibody titer to the antigen used for immunization is used as a source of fusion antibody-producing cells, an effect of subsequent operations can be enhanced.

Tissues containing antibody-producing cells, such as a spleen, are excised from the immunized animal 3 days to 7 days after the final administration of the antigen, and the antibody-producing cells are collected. The antibody-producing cells are plasma cells and progenitor cells thereof, i.e., lymphocytes, and can be obtained from any part of an individual, and generally from a spleen, a lymph node, bone marrow, a tonsil, peripheral blood, or an appropriate combination of these, and spleen cells are the most generally used. When using spleen cells, the spleen is shredded and loosened, followed by centrifuging, and then erythrocytes are further removed to obtain fusion antibody-producing cells.

(3) Step of Preparing Myelomas

As myelomas, cells without an autoantibody-producing ability that are derived from a mammal such as mice, rats, guinea pigs, hamsters, rabbits, or humans can be used. Generally, an established cell line obtained from a mouse, such as an 8-azaguanine-resistant mouse (BALB/c-derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], and P3-X63-Ag8 (X63) [Nature, 256, 495 (1975)] can be used. The cell line is subcultured in an appropriate culture medium, for example, an 8-azaguanine medium [RPMI-1640 medium supplemented with glutamine, 2-mercaptoethanol, gentamicin, FCS and 8-azaguanine], an Iscove's Modified Dulbecco's Medium (hereinafter referred to as "IMDM"), or a Dulbecco's Modified Eagle Medium (hereinafter referred to as "DMEM"). The above cell line is subcultured in a normal medium (for example, a DMEM medium supplemented with 10% FCS) 3 days to 4 days before cell fusion to ensure a cell number of $2 \times 10^7$ or more on the day of fusion.

(4) Cell Fusion

The fusion antibody-producing cells obtained in (2) and the myeloma cells obtained in (3) are thoroughly washed with a Minimum Essential Medium (MEM) or PBS (1.83 g of disodium phosphate, 0.21 g of monopotassium phosphate, 7.65 g of sodium chloride, 1 liter of distilled water, pH 7.2), and mixed such that fusion antibody-producing cells: myeloma cells=5:1 to 10:1, followed by performing centrifugation and then removing a supernatant. After thoroughly loosening precipitated cell aggregates, a mixed solution of polyethylene glycol-1000 (PEG-1000), a MEM medium and dimethyl sulfoxide is added thereto at 37° C. while stirring. Further, 1 mL to 2 mL of the MEM medium is added several times every 1 minute to 2 minutes, and then the MEM medium is added to make a total amount to 50 mL. After centrifugation, a supernatant is removed, precipitated cell aggregates are gently loosened, and cells are then gently suspended in an HAT medium [a normal medium supplemented with hypoxanthine, thymidine, and aminopterin]. The suspension is cultured at 37° C. for 7 days to 14 days in a 5% $CO_2$ incubator.

The cell fusion can also be performed by the following method. The spleen cells and the myeloma cells are thoroughly washed with a serum-free medium (for example, DMEM) and phosphate buffered saline (hereinafter referred to as a "phosphate buffer solution"), and mixed such that a ratio of the number of spleen cells to the number of myeloma cells is about 5:1 to 10:1, followed by performing centrifugation. After removing a supernatant and thoroughly loosening precipitated cell aggregates, a serum-free medium supplemented with 1 mL of 50% (w/v) polyethylene glycol (molecular weight 1000 to 4000) is added dropwise while stirring. Thereafter, 10 mL of serum-free medium is slowly added thereto, followed by performing centrifugation. A supernatant is discarded again, and precipitated cells are suspended in a normal medium (hereinafter referred to as HAT medium) supplemented with an appropriate amount of hypoxanthine-aminopterin-thymidine (HAT) solution and human interleukin-2 (IL-2), and the resultant is dispensed into each well of a culture plate (hereinafter referred to as plate) and cultured at 37° C. for about 2 weeks in the presence of 5% carbon dioxide gas. The HAT medium is supplemented as appropriate during the processing.

(5) Selection of Hybridoma Group

When the myeloma cells used for fusion are an 8-azaguanine resistant strain, that is, a hypoxanthine guanine phosphoribosyltransferase (HGPRT)-deficient strain, unfused myeloma cells and fused cells between myeloma cells cannot survive in the HAT medium. On the other hand, fused cells between antibody-producing cells and hybridomas between antibody-producing cells and myeloma cells can survive in the HAT medium, and the fused cells between antibody-producing cells eventually reach an end of a lifespan thereof. Therefore, by continuing culturing in the HAT medium, only hybridomas of antibody-producing cells and myeloma cells can survive, and as a result, hybridomas can be obtained.

For hybridomas grown into a colony, the medium is replaced with a medium obtained by removing aminopterin from the HAT medium (hereinafter referred to as HT medium). Thereafter, a portion of a culture supernatant can be collected, and antibody-producing hybridomas can be selected using an antibody titer measurement method to be described later. Examples of a method for measuring an antibody titer include various known techniques, such as radioisotope immunoassay (RIA), enzyme-linked immunosorbent assay (ELISA), a fluorescent antibody method, and passive hemagglutination assay. RIA or ELISA is preferred from the viewpoint of detection sensitivity, rapidity, accuracy, possibility of operation automation, or the like.

Hybridomas that are found to produce a desired antibody by measuring an antibody titer are transferred to another plate for cloning. Examples of the cloning method include a limiting dilution method in which cells are diluted and cultured such that one well of a plate contains one cell, a soft agar method in which a colony is collected by culturing in a soft agar medium, a method in which one cell is isolated using a micromanipulator, and a method in which one cell is isolated using a cell sorter.

Cloning, for example, by limiting dilution method, is repeated 2 times to 4 times for wells with antibody titers observed, and those with stable antibody titers observed are selected as hybridoma strains that produce monoclonal antibodies to CD116 or CD131.

(6) Preparation of Monoclonal Antibody

The monoclonal antibody-producing hybridomas obtained in (5) are intraperitoneally injected into 8- to 10-week-old mice or nude mice treated with pristane [intraperitoneally administered with 0.5 mL of 2,6,10,14-tetramethylpentadecane (pristane) and kept for 2 weeks]. The hybridomas turn into ascites cancer in 10 days to 21 days. An ascites fluid is collected from the mice, centrifuged to remove solids, followed by salting out with 40% to 50% ammonium sulfate and purifying using a caprylic acid precipitation method, a DEAE-Sepharose column, a Protein A column, or a gel filtration column, and IgG or IgM fractions are collected and used as purified monoclonal antibodies. By propagating the hybridomas intraperitoneally in mice of the same strain (e.g., BALB/c) or Nu/Nu mice, rats, guinea pigs, hamsters, or rabbits, an ascites fluid containing large amounts of monoclonal antibodies binding to CD116 or CD131 can be obtained.

After culturing the monoclonal antibody-producing hybridomas obtained in (5) in an RPMI1640 medium supplemented with 10% FBS, a supernatant is removed by centrifugation, and the resultant is suspended in a GIT medium or a Hybridoma-SFM medium supplemented with 5% Daigo GF21, and cultured for 3 days to 7 days by flask culture, spinner culture, bag culture, or the like. The obtained cell suspension can be centrifuged, the supernatant can be purified by a Protein A column or a protein G column, an IgG fraction can be collected to obtain purified monoclonal antibodies. As a simple purification method, a commercially available monoclonal antibody purification kit (for example, an MAbTrap GII kit; manufactured by Amersham Pharmacia Biotech Inc.) can also be used.

Determination of the antibody subclass is performed by enzyme immunoassay using a subclass typing kit. A protein amount can be quantified by a Lowry method or a method of calculating from absorbance at 280 nm [1.4 (OD280)= Immunoglobulin 1 mg/mL].

(7) Binding Assay of Monoclonal Antibody to CD116 or CD131

A binding activity of a monoclonal antibody to CD116 or CD131 can be measured by a binding assay system such as an Ouchterlony method, ELISA, RIA, a flow cytometry method (FCM), or surface plasmon resonance (SPR).

Although the Ochterrony method is simple, it requires a concentration operation when the antibody concentration is low. On the other hand, when using ELISA or RIA, the culture supernatant is directly reacted with an antigen-adsorbed solid phase, and antibodies corresponding to various immunoglobulin isotypes and subclasses are used as secondary antibodies. Therefore, the isotype and subclass of an antibody can be identified and the binding activity of the antibody can be measured.

As a specific example of the procedure, purified or partially purified recombinant CD116 or CD131 is adsorbed onto a solid phase surface such as a 96-well plate for ELISA, and further, a solid phase surface to which no antigen is adsorbed is blocked with a protein unrelated to the antigen, such as bovine serum albumin (BSA). After washing the ELISA plate with phosphate buffer saline (PBS) and PBS containing 0.05% Tween 20 (Tween-PBS), a serially diluted first antibody (for example, mouse serum or culture supernatant) is allowed to react to bind the antibody to the antigen immobilized on the plate. Next, an anti-immunoglobulin antibody labeled with biotin, an enzyme (a horse radish peroxidase; an HRP, an alkaline phosphatase; an ALP; or the like), a chemiluminescent substance, a radioactive compound, or the like is dispensed as a second antibody, and the second antibody is allowed to react with the first antibody binding to the plate. After thorough washing with Tween-PBS, a reaction is performed depending on the labeling substance of the second antibody, and a monoclonal antibody that specifically reacts with the target antigen is selected.

In the FCM method, a binding activity of an antibody to an antigen-expressing cell can be measured [Cancer Immunol. Immunother., 36, 373 (1993)]. When an antibody binds to a membrane protein antigen expressed on a cell membrane, it means that the antibody recognizes and binds to a three-dimensional structure of a naturally occurring antigen.

Examples of the SPR method include kinetics analysis using Biacore. For example, Biacore T100 is used to measure the kinetics of binding between an antigen and a test substance, and the results are analyzed using analysis software attached to the device. As a specific example of the procedure, anti-mouse IgG antibodies are immobilized on a sensor chip CM5 by an amine coupling method, then appropriate amount of test substance such as a hybridoma culture supernatant or purified monoclonal antibodies flows and binds thereto, and further, antigens of a plurality of known concentrations flow thereto to measure binding and dissociation.

Next, the obtained data is subjected to kinetics analysis using a 1:1 binding model using software attached to the device, and various parameters are obtained. After CD116 or CD131 is immobilized on the sensor chip by, for example, an amine coupling method, purified monoclonal antibodies of a plurality of known concentrations flow thereto to measure binding and dissociation. The obtained data is subjected to kinetics analysis using a bivalent binding model using software attached to the device, and various parameters are obtained.

In the present invention, an antibody binding to CD116 or CD131 in competition with an antibody to CD116 or CD131 can be selected by allowing a test antibody to coexist and react in the above-described binding assay system. That is, by screening for antibodies that are inhibited from binding to the antigen when the test antibody is added, antibodies in competition with the antibodies obtained above for binding to CD116 or CD131 can be obtained.

(8) Identification of Epitope of Monoclonal Antibody to CD116 or CD131

In the present invention, identification of an epitope recognized and bound by the antibody can be performed as follows.

For example, when a partial deletion variant of an antigen, a mutant obtained by modifying amino acid residues that differ between species, or a mutant obtained by modifying a specific domain is prepared, and reactivity of the antibody to the deletion variant or the mutant is lowered, it is revealed that a deletion site and an amino acid modified site are epitopes of the antibody. Such a partial deletion variant and mutant of the antigen may be obtained as a secretion protein by using an appropriate host cell, for example, *Escherichia coli*, yeast, plant cells, or mammalian cells, or may be prepared as an antigen-expressing cell by being expressed on a cell membrane of a host cell. In the case of a membrane-type antigen, it is preferred to express the membrane-type antigen on a membrane of a host cell in order to express the membrane-type antigen while maintaining a three-dimensional structure thereof. A synthetic peptide that mimics a primary structure or three-dimensional structure of the antigen can be prepared, and the reactivity of the antibody can be confirmed. The synthetic peptide can be prepared using a known peptide synthesis technique, for example, a method of preparing various partial peptides of a molecule thereof.

For example, for an extracellular region of human and mouse CD116 or CD131, an antibody epitope is identified by preparing a chimeric protein by appropriately combining domains that constitute each region, and confirming a reactivity of the antibody to the protein. Thereafter, the epitope can be specified in more detail by synthesizing various oligopeptides of the corresponding portion thereof or mutants of the peptide using an oligopeptide synthesis technique well known to those skilled in the art, and confirming the reactivity of the antibody to the peptide. As a simple method for obtaining many types of oligopeptides, commercially available kits [for example, a SPOTs kit (manufactured by Genosys Biotechnologies), or a series of multipin peptide synthesis kits using a multipin synthesis method (manufactured by Chiron Corporation)] can also be used.

An antibody fragment binding to CD116 or CD131, such as Fab, can be isolated and obtained by a technique such as a phage display method and a yeast display method, in addition to the above-described method using hybridomas [Emmanuelle Laffy et. al., Human Antibodies 14, 33-55, (2005)].

An antibody binding to an epitope which is the same as an epitope bound by the antibody binding to CD116 or CD131 can be obtained by identifying an epitope of the antibody obtained in the above-described binding assay system, preparing a partial synthetic peptide of the epitope, a synthetic peptide that mimics the three-dimensional structure of the epitope, or a recombinant of the epitope, and performing immunization.

For example, when the epitope is a membrane protein, an antibody specific to the epitope can be prepared more efficiently by preparing a recombinant fusion protein by linking an entire extracellular region or a partial extracellular domain to an appropriate tag, for example, an FLAG tag, a Histidine tag, a GST protein, or an antibody Fc region, and immunizing with the recombinant protein.

2. Preparation of Recombinant Antibody

Examples of producing a recombinant antibody are outlined in P. J. Delves., ANTIBODY PRODUCTION ESSENTIAL TECHNIQUES., 1997 WILEY, P. Shepherd and C. Dean. Monoclonal Antibodies., 2000 OXFORD UNIVERSITY PRESS and J. W. Goding., Monoclonal Antibodies: principles and practice., 1993 ACADEMIC PRESS, and methods for producing a chimeric antibody, a humanized antibody, and a human antibody are shown below. Recombinant mouse, rat, hamster, and rabbit antibodies can also be prepared in a similar manner.

(1) Acquisition of cDNA Encoding V Region of Monoclonal Antibody from Hybridoma

Acquisition of a cDNA encoding a VH and a VL of a monoclonal antibody can be performed, for example, as follows.

First, an mRNA is extracted from a hybridoma producing a monoclonal antibody, and a cDNA is synthesized. Next, the synthesized cDNA is cloned into a vector such as a phage or a plasmid to prepare a cDNA library. From the library, a recombinant phage or a recombinant plasmid having the cDNA encoding the VH or the VL is isolated using, as a probe, a DNA encoding a C region portion or a V region portion of the antibody. A complete nucleotide sequence of the VH or the VL in the isolated recombinant phage or recombinant plasmid is determined, and a complete amino acid sequence of the VH or the VL is estimated from the nucleotide sequence.

As a non-human animal used for preparing hybridomas, mice, rats, hamsters, rabbits, and the like can be used, and any animals can be used as long as hybridomas can be prepared.

For preparation of a total RNA from the hybridomas, a guanidine thiocyanate method [Methods in Enzymol, 154, 3 (1987)] or a kit such as an RNA easy kit (manufactured by Qiagen) is used.

For preparation of an mRNA from the total RNA, an oligo (dT) immobilized cellulose column method [Molecular Cloning, A Laboratory Manual, Second Edition, Cold Spring Harbor Laboratory Press (1989)] or a kit such as an Oligo-dT30<Super>mRNA Purification Kit (manufactured by Takara Bio Inc.) is used. The mRNA can also be prepared using a kit such as a Fast Track mRNA Isolation Kit (manufactured by Invitrogen) or a QuickPrep mRNA Purification Kit (manufactured by Pharmacia).

For synthesis of the cDNA and preparation of the cDNA library, a known method [Molecular Cloning, A Laboratory Manual, Second Edition, Cold Spring Harbor Laboratory Press (1989), Current Protocols in Molecular Biology. Supplement 1, John Wiley & Sons (1987-1997)], SuperScript Plasmid System for cDNA Synthesis and Plasmid Cloning (manufactured by Invitrogen), or a ZAP-cDNA Synthesis Kit (manufactured by Stratagene) is used.

When preparing the cDNA library, any vector can be used as long as it can incorporate a cDNA synthesized using an mRNA extracted from a hybridoma as a template.

For example, ZAP Express [Strategies, 5, 58 (1992)], pBluescript II SK (+) [Nucleic Acids Research, 17, 9494 (1989)], AZAPII (manufactured by Stratagene), λgt10, λgt11 [DNA Cloning: A Practical Approach, I, 49 (1985)], Lambda BlueMid (manufactured by Clontech), λExCell, pT7T3-18U (manufactured by Pharmacia), pcD2 [Mol. Cell. Biol., 3, 280 (1983)], or pUC18 [Gene, 33, 103 (1985)] is used.

Any *Escherichia coli* that can be used to introduce, express, and maintain the cDNA library constructed using a phage or plasmid vector can be used. For example, XL1-Blue MRF' [Strategies, 5,81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], or JM105 [Gene, 38, 275 (1985)] is used.

For selection of a clone of the cDNA encoding the VH or the VL of a non-human antibody from the cDNA library, a colony hybridization method using an isotope- or fluorescently labeled probe, a plaque hybridization method [Molecular Cloning, A Laboratory Manual, Second Edition, Cold Spring Harbor Laboratory Press (1989)], or the like is used.

The cDNA encoding the VH or the VL can also be prepared by preparing primers and performing a Polymerase Chain Reaction method [Molecular Cloning, A Laboratory Manual, Second Edition, Cold Spring Harbor Laboratory Press (1989), Current Protocols in Molecular Biology. Supplement 1, John Wiley & Sons (1987-1997)] using a cDNA synthesized from the mRNA or the cDNA library as a template.

After cleaving the selected cDNA with an appropriate restriction enzyme, or the like, cloning into a plasmid such as pBluescript SK (−) (manufactured by Stratagene) is performed, and a nucleotide sequence of the cDNA is determined by a commonly used nucleotide sequence analysis method. For example, after performing a reaction such as a dideoxy method [Proc. Natl. Acad. Sci. USA, 74, 5463 (1977)], analysis is performed using an automatic nucleotide sequence analyzer such as an A. L. F. DNA sequencer (manufactured by Pharmacia).

By estimating complete amino acid sequences of the VH and the VL from the determined complete nucleotide sequences, and comparing with complete amino acid sequences of a VH and a VL of a known antibody [Sequences of Proteins of Immunological Interest, US Dept. Health and Human Services (1991)], it is confirmed whether the obtained cDNA encodes the complete amino acid sequence of each VH and VL of the antibody, which includes a secretion signal sequence.

Regarding the complete amino acid sequence of each VH and VL of the antibody, which includes a secretion signal sequence, by comparing with complete amino acid sequences of a VH and a VL of a known antibody [Sequences of Proteins of Immunological Interest, US Dept. Health and Human Services (1991)], a length and an N-terminus amino acid sequence of the secretion signal sequence can be estimated, and further, the subgroup to which they belong can be identified.

Amino acid sequences of CDRs of the VH and the VL can be estimated by comparing with amino acid sequences of a VH and a VL of a known antibody [Sequences of Proteins of Immunological Interest, US Dept. Health and Human Services (1991)].

For the obtained complete amino acid sequences of the VH and the VL, for example, by performing a homology search by BLAST [J. Mol. Biol., 215, 403 (1990)] using any database such as SWISS-PROT or PIR-Protein, it is confirmed whether the complete amino acid sequences of the VH and the VL are novel.

(2) Construction of Recombinant Antibody Expression Vector

A recombinant antibody expression vector can be constructed by cloning a DNA encoding at least one of a CH and a CL of a human antibody into an animal cell expression vector.

As a C region of a human antibody, a CH and a CL of any human antibody can be used, and for example, a CH of the γ1 subclass and a CL of the κ class of a human antibody can be used. Although a cDNA is used as the DNA encoding a CH and a CL of a human antibody, a chromosomal DNA consisting of exon and intron can also be used.

As an animal cell expression vector, any vector can be used as long as it can incorporate a gene encoding a C region of a human antibody to express. For example, PAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], or pSEIUK1Sed1-3 [Cytotechnol., 13, 79 (1993)], INPEP4 (manufactured by Biogen-IDEC), N5KG1val (U.S. Pat. No. 6,001,358), N5KG4PE R409K (described in WO2006/033386), an N5KG2 vector (described in WO2003/033538), or a transposon vector (WO2010/143698) can be used.

As a promoter and an enhancer for the animal cell expression vector, an SV40 early promoter [J. Biochem., 101, 1307 (1987)], a moloney murine leukemia virus LTR [Biochem. Biophys. Res. Commun., 149, 960 (1987)], a CMV promoter (U.S. Pat. No. 5,168,062), or an immunoglobulin H chain promoter [Cell, 41, 479 (1985)], an enhancer [Cell, 33, 717 (1983)], and the like can be used.

For expression of the recombinant antibody, from the viewpoints of ease of vector construction, ease of introduction into animal cells, and balance in expression levels of an H chain and an L chain of the antibody within cells, and the like, a vector carrying both genes of the H chain and the L chain of the antibody (tandem vector) [J. Immunol. Methods, 167, 271 (1994)] is used, and a combination of a plurality of vectors (separate vectors) each carrying the genes of the H chain and the L chain of the antibody can also be used.

As a tandem-type recombinant antibody expression vector, pKANTEX93 (WO97/10354), pEE18 [Hybridoma, 17, 559 (1998)], N5KG1val (U.S. Pat. No. 6,001,358), N5KG4PE R409K (described in WO2006/033386), an N5KG2 vector (described in WO2003/033538), a Tol2 transposon vector (WO2010/143698), or the like is used.

(3) Construction of Chimeric Antibody Expression Vector

By cloning the cDNA encoding a VH or a VL of a non-human antibody obtained in (1), upstream of each gene encoding a CH or a CL of a human antibody in the recombinant antibody expression vector obtained in (2), a chimeric antibody expression vector can be constructed.

First, in order to link a 3' end side of the cDNA encoding a VH or a VL of a non-human antibody and a 5' end side of a CH or a CL of a human antibody, cDNAs of a VH and a VL are prepared in such a way that a nucleotide sequence of a linking portion encodes an appropriate amino acid and is an appropriate restriction enzyme recognition sequence. Next, the prepared cDNAs of the VH and the VL are cloned, respectively, upstream of each gene encoding a CH or a CL of a human antibody in the recombinant antibody expression vector obtained in (2) such that they are expressed in an appropriate form, and a chimeric antibody expression vector is constructed.

By amplifying the cDNA encoding a VH or a VL of a non-human antibody by PCR using a synthetic DNA having recognition sequences for appropriate restriction enzymes at both ends, and cloning the cDNA into the recombinant antibody expression vector obtained in (2), the chimeric antibody expression vector can also be constructed.

(4) Preparation of cDNA Encoding V Region of Humanized Antibody

A cDNA encoding a VH or a VL of a humanized antibody can be prepared as follows. First, an amino acid sequence of a framework region (hereinafter referred to as FR) of a VH or a VL of a human antibody to which amino acid sequences of CDRs of a VH or a VL of the non-human antibody obtained in (1) are to be grafted is selected.

The selected amino acid sequence of the FR may be any amino acid sequence derived from a human antibody. For example, an amino acid sequence of an FR of a human antibody registered in a database such as a Protein Data Bank, or a common amino acid sequence of each subgroup of an FR of a human antibody [Sequences of Proteins of Immunological Interest, US Dept. Health and Human Services (1991)] is used. In order to prevent a decrease in binding activity of the antibody, an amino acid sequence of a human FR that has as high a homology as possible (60% or more) with an amino acid sequence of an FR of a VH or a VL of an original non-human antibody can be selected.

Next, amino acid sequences of CDRs of the original non-human antibody are grafted to the amino acid sequence of the FR of the VH or the VL of the selected human antibody to design an amino acid sequence of a VH or a VL of a humanized antibody. By converting the designed amino acid sequence into a DNA sequence in consideration of the usage frequency of codons found in the nucleotide sequence of an antibody gene [Sequences of Proteins of Immunological Interest, US Dept. Health and Human Services (1991)], a cDNA sequence of the VH or the VL of the humanized antibody is designed.

Based on the designed cDNA sequence, several synthetic DNAs having a length of about 100 to 150 bases are synthesized, and a PCR reaction is performed using the synthesized DNA. In this case, from the viewpoint of the reaction efficiency in the PCR reaction and the length of the DNA that can be synthesized, preferably 4 to 6 synthetic DNAs are designed for each of the H chain and the L chain. A synthetic DNA of the full-length variable region can also be synthesized and used.

Further, by introducing recognition sequences for appropriate restriction enzymes into 5' ends of the synthetic DNA located at both ends, the cDNA encoding the VH or the VL of the humanized antibody can be easily cloned into the recombinant antibody expression vector obtained in (2). After the PCR reaction, each amplified product was cloned into a plasmid such as pBluescript SK (−) (manufactured by Stratagene), and a nucleotide sequence is determined by a method same as that described in (1) to obtain a plasmid having a DNA sequence encoding an amino acid sequence of a VH or a VL of a desired humanized antibody.

(5) Modification of Amino Acid Sequence of V Region of Humanized Antibody

When only CDRs of a VH and a VL of a non-human antibody are grafted onto the FRs of the VH and the VL of the human antibody, the antigen-binding activity of the humanized antibody is lower than that of the original non-human antibody [BIO/TECHNOLOGY, 9, 266 (1991)]. Therefore, by identifying, among the amino acid sequences of the FRs of the VH and the VL of the human antibody, an amino acid residue directly associated with binding to an antigen, an amino acid residue interacting with an amino acid residue of a CDR, and an amino acid residue maintaining a three-dimensional structure of an antibody and indirectly associated with binding to an antigen, and substituting those amino acid residues with amino acid residues of the original non-human antibody, the reduced antigen-binding activity of the humanized antibody can be increased.

In order to identify the FR amino acid residues associated with the antigen-binding activity, the three-dimensional structure of the antibody can be constructed and analyzed by using X-ray crystal analysis [J. Mol. Biol., 112, 535 (1977)], computer modeling [Protein Engineering, 7, 1501 (1994)], or the like. A modified humanized antibody having a necessary antigen-binding activity can be obtained by preparing several types of variants of each antibody, repeatedly examining each correlation with the antigen-binding activity, and performing trial and error.

The amino acid residues of the FRs of the VH and the VL of the human antibody can be modified by performing the PCR reaction described in (4) using a synthetic DNA for modification. The nucleotide sequence of the amplified product after the PCR reaction is determined by the method described in (1) to confirm that the desired modification is made.

(6) Construction of Humanized Antibody Expression Vector

By cloning the cDNA encoding the VH or the VL of the constructed humanized antibody upstream of a gene encoding the CH or the CL of the human antibody in the recombinant antibody expression vector obtained in (2), a humanized antibody expression vector can be constructed.

For example, by introducing recognition sequences for appropriate restriction enzymes to 5' ends of the synthetic DNA used in constructing the VH and the VL of the humanized antibody obtained in (4) and (5) at both ends, the synthetic DNA is cloned upstream of a gene encoding the CH or the CL of the human antibody in the recombinant antibody expression vector obtained in (2) such that the synthetic DNA is expressed in an appropriate form.

(7) Construction of Human Antibody Expression Vector

When monoclonal antibody-producing hybridomas are established using a human antibody-producing animal as an immune animal, amino acid sequences and cDNA sequences of a VH and a VL of a human antibody can be obtained in (1). Therefore, by cloning the gene encoding the VH or the VL of the human antibody obtained in (1) upstream of the gene encoding the CH or the CL of the human antibody in the recombinant antibody expression vector obtained in (2), a human antibody expression vector can be constructed.

(8) Transient Expression of Recombinant Antibody

The recombinant antibody expression vectors obtained in (3), (6), and (7) and expression vectors obtained by modifying the recombinant antibody expression vectors can be used to cause the recombinant antibody to be expressed in a transient manner, and the antigen-binding activity of the obtained various types of recombinant antibody can be efficiently evaluated.

Any host cell that can express a recombinant antibody can be used as the host cell into which the expression vector is to be introduced, and for example, COS-7 cells [American Type Culture Collection (ATCC) number: CRL1651] is used. For introduction of the expression vector into COS-7 cells, a DEAE-dextran method [Methods in Nucleic Acids Res., CRC press (1991)], or a lipofection method [Proc. Natl. Acad. Sci. USA, 84, 7413 (1987)] is used.

After introduction of the expression vector, an expression level and an antigen-binding activity of the recombinant antibody in a culture supernatant are measured using enzyme immunoassay [Monoclonal Antibodies-Principles and practice, Third Edition, Academic Press (1996), Antibodies-A Laboratory Manual, Cold Spring Harbor Laboratory (1988), Monoclonal Antibody Laboratory Manual, Kodansha Scientific (1987)], and the like.

(9) Acquisition of Stable Expression Strain of Recombinant Antibody and Preparation of Recombinant Antibody By introducing the recombinant antibody expression vectors obtained in (3), (6), and (7) into appropriate host cells, transformants that stably express the recombinant antibody can be obtained.

Examples of the method for introducing an expression vector into a host cell include an electroporation method [JPH2-257891A, Cytotechnology, 3, 133 (1990)], a calcium ion method, an electroporation method, a spheroplast method, a lithium acetate method, a calcium phosphate method, and a lipofection method. Examples of a method for introducing a gene into an animal to be described later include a microinjection method, a method of introducing genes into ES cells using an electroporation method or a lipofection method, and a nuclear transplantation method.

Any host cell that can express the recombinant antibody can be used as the host cell into which the recombinant antibody expression vector is to be introduced. For example, mouse SP2/0-Ag14 cells (ATCC CRL1581), mouse P3X63-Ag8.653 cells (ATCC CRL1580), Chinese hamster CHO-K1 cells (ATCC CCL-61), DUKXB11 (ATCC CCL-9096), Pro-5 cells (ATCC CCL-1781), CHO-S cells (Life Technologies, Cat No. 11619), CHO cells deficient in dihydrofolate reductase gene (dhfr) (CHO/DG44 cells) [Proc. Natl. Acad. Sci. USA, 77, 4216 (1980)], Lec13 cells with acquired lectin resistance [Somatic Cell and Molecular genetics, 12, 55 (1986)], CHO cells from which an $\alpha$1,6-fucosyltransferase gene is deleted (WO2005/035586, WO02/31140), and rat YB2/3HL.P2.G11.16Ag.20 cells (ATCC No.: CRL1662) are used.

A host cell in which an activity of a protein such as an enzyme associated with synthesis of intracellular sugar nucleotide GDP-fucose, a protein such as an enzyme associated with sugar chain modification in which 1-position of fucose $\alpha$-binds to 6-position of N-acetylglucosamine at a reducing end of an N-glycoside-linked complex sugar chain, or a protein associated with transport of intracellular sugar nucleotide GDP-fucose to a Golgi body is reduced or deleted, for example, CHO cells from which an $\alpha$1,6-fucosyltransferase gene is deleted (WO2005/035586, WO02/31140) can also be used.

After introduction of the expression vector, a transformant that stably expresses the recombinant antibody is selected by culturing in an animal cell culture medium containing a drug such as G418 sulfate (hereinafter referred to as G418) (JPH2-257891A).

Examples of the animal cell culture medium include a RPMI 1640 medium (manufactured by Invitrogen), a GIT medium (manufactured by Japan Pharmaceutical Co., Ltd.), an EX-CELL 301 medium (manufactured by JRH Co., Ltd.), an EX-CELL 302 medium (manufactured by JRH Co., Ltd.), an EX-CELL 325 medium (manufactured by JRH Co., Ltd.), an IMDM medium (manufactured by Invitrogen), a Hybridoma-SFM medium (manufactured by Invitrogen), and a medium supplemented with various additives such as FBS. The obtained transformant is cultured in a medium to express and accumulate the recombinant antibody in the culture supernatant. An expression level and an antigen-binding activity of the recombinant antibody in the culture supernatant can be measured by ELISA or the like. The expression level of the recombinant antibody produced by the transformant can be increased by using a DHFR amplification system (JPH2-257891A), or the like.

The recombinant antibody can be purified from the culture supernatant of the transformant using a Protein A column [Monoclonal Antibodies-Principles and practice, Third edition, Academic Press (1996), Antibodies-A Laboratory Manual, Cold Spring Harbor Laboratory (1988)]. Alternatively, purification can be performed by combining methods used for protein purification, such as gel filtration, ion exchange chromatography, and ultrafiltration.

Examples of one embodiment of the present invention include a method for purifying a composition containing an antibody, the method including purifying an antibody containing an Fc region by Protein A column chromatography, in which the antibody is an antibody with an H435F mutation introduced in an Fc region. The antibody with an H435F mutation introduced in an Fc region has excellent binding properties to a Protein A column, and high purification efficiency can be achieved by purifying the antibody by the Protein A column chromatography.

A molecular weight of the H chain, the L chain, or the entire antibody molecule of the purified recombinant antibody can be measured using polyacrylamide gel electrophoresis [Nature, 227, 680 (1970)], Western blotting [Monoclonal Antibodies-Principles and practice, Third edition, Academic Press (1996), Antibodies-A Laboratory Manual, Cold Spring Harbor Laboratory (1988)], or the like.

(10) Acquisition of Antibody with Non-Natural Amino Acid Residue Introduced or Antibody Fragment An antibody with a non-natural amino acid residue introduced or an antibody fragment can be obtained according to a method described in WO2017/030156.

3. Preparation of Bispecific Antibody

The bispecific antibody of the present invention can be prepared by, for example, preparing the first antigen-binding domain binding to CD131 and the second antigen-binding domain binding to CD116, respectively, and linking the domains.

3-1. Preparation of First Antigen-Binding Domain Binding to CD116

When the first antigen-binding domain is an antibody or an antibody fragment, DNA sequences encoding amino acid sequences of CDRs and variable regions of the antibody are determined by the methods described in 1. and 2. described above. Further, an antigen-binding domain containing the CDRs or the variable regions is designed, and a DNA sequence encoding the amino acid sequence of the antigen-binding domain is designed. The antigen-binding domain can be prepared, for example, by incorporating the DNA sequence into the recombinant antibody expression vector described in 2. (2) and expressing the antigen-binding domain.

Specifically, for example, when the first antigen-binding domain is Fab, the DNA sequences of the CDRs of the antibody are determined by the methods described in 1. and 2. described above. Further, a DNA sequence encoding a polypeptide chain obtained by linking a VH sequence containing the determined CDRs of the heavy chain and a CH1 sequence, and a DNA sequence encoding a polypeptide chain obtained by linking a VL sequence containing the determined CDRs of the light chain and a CL sequence are designed. The antigen-binding domain can be prepared, for example, by incorporating the DNA sequence into the recombinant antibody expression vector described in 2. (2) and expressing the antigen-binding domain.

When the first antigen-binding domain is a polypeptide containing a CD116-binding portion of a protein capable of binding to GM-CSF or CD116, the first antigen-binding domain can be prepared by designing a DNA sequence encoding the polypeptide, incorporating the DNA sequence into the recombinant antibody expression vector described in 2.(2), for example, and expressing the antigen-binding domain.

The antigen-binding activity of the prepared antigen-binding domain can be evaluated by the method described above, and those that retain the antigen-binding activity can be selected.

3-2. Preparation of Second Antigen-Binding Domain Binding to CD131

The antigen-binding domain binding to CD131 can be prepared by a method same as that in the 3-1. described above. The bispecific antibody of the present invention can also be prepared by the method described above when a recombinant protein is expressed by linking the first and second antigen-binding domains with an appropriate amino acid sequence.

3-3. Linking of Two Antigen-Binding Domains

The antigen-binding domains binding to CD116 and CD131 prepared in the 3-1. and 3-2. described above are linked by the following method to prepare a bispecific antibody.

Amino acid residues contained in the antigen-binding domains can be chemically linked via any linker. An amino acid residue used for linking may be a natural amino acid residue or a non-natural amino acid residue. Examples of the natural amino acid residue include cysteine, tyrosine, serine, threonine, lysine, glutamic acid, and aspartic acid. Examples of the non-natural amino acid residue include a Z lysine derivative (N6-((benzyloxy)carbonyl)-L-lysine derivative) disclosed in WO2017/030156, TCO*-Lys (N6-(((trans-cyclooct-2-en-1-yl)oxy)carbonyl)-L-lysine), and BCN-Lys (N6-((bicyclo[6.1.0]non-4-yn-9-ylmethoxy) carbonyl)-L-lysine).

As the method for linking the antigen-binding domains, it is preferred to use chemical linking via a non-natural amino acid residue because it allows selective reaction with a linker without affecting other amino acids contained in the antigen-binding domains.

The method used for linking the antigen-binding domains is not particularly limited, and any method for chemically linking a desired amino acid residue and a linker can be used. Examples thereof include chemical linkage using a chemical reaction [Introduction to Antibody Engineering, Chijin Shokan (1994), Kolb et al., Angew Chem Int Ed Engl. 40. 2004-21, 2001].

The linker used for chemically linking the antigen-binding domains is not particularly limited as long as it has a functional group necessary for reacting with the amino acid residues contained in the antigen-binding domains. For example, when linking two antigen-binding domains each containing an Ad-Z lysine derivative, the antigen-binding domains can be linked by using a linker having two alkynyl group in one molecule.

When the antigen-binding domains prepared in 3-1. and 3-2. are Fab, a part or all of hinge regions of the antibody may be added to a C-terminus side of each of the antigen-binding domains, and a bispecific antibody having a structure of (Fab') 2 may be prepared by an S—S bond. An Fc can also be added thereto to prepare an IgG antibody type bispecific antibody.

4. Activity Evaluation of Bispecific Antibody or Bispecific Antibody Fragment Thereof of Present Invention The activity evaluation of the purified bispecific antibody or bispecific antibody fragment thereof can be performed as follows.

The binding activity of the bispecific antibody of the present invention to a cell line expressing at least one of CD116 and CD131 can be measured using the binding assay system described in 1.(7) described above.

The CDC activity or ADCC activity to cells expressing at least one of CD116 and CD131 can be measured by known measurement methods [Cancer Immunol. Immunother., 36, 373 (1993)].

The agonist activity of the bispecific antibody of the present invention to a GM-CSF receptor can be measured by the following method. For example, TF-1 cells that proliferate in a GM-CSF-dependent manner are seeded in a 96-well plate and cultured for a certain period of time after a GM-CSF or the bispecific antibody of the invention are added thereto, and then a proliferation ratio of the cells is measured by measuring a luminescence intensity due to an ATP luciferase reaction.

In the above method, when the TF-1 cell proliferation ratio in a GM-CSF non-addition group is taken as 0% and the cell proliferation ratio in a GM-CSF addition group is taken as 100%, the agonist activity is considered to be present when the cell proliferation ratio is 30% or more in a group to which the bispecific antibody or the bispecific antibody fragment thereof is added. The agonist activity of the bispecific antibody or the bispecific antibody fragment thereof is preferably 40% or more, more preferably 50% or more, still more preferably 60% or more, and even more preferably 70% or more when the agonist activity of the GM-CSF is taken as 100%.

The agonist activity of the bispecific antibody of the present invention to the GM-CSF receptor can be evaluated by an activity of inducing differentiation from monocytes to macrophages. The activity of inducing differentiation can be measured by the following method. For example, after seeding monocytes in a 96-well plate, adding a bispecific antibody and culturing for a certain period of time, changes in expression levels of CD14 and CD206 are analyzed by a flow cytometry method.

Signal transduction from CD116 and CD131 into cells can be evaluated by detecting phosphorylation of intracellular proteins by Western blotting or the like.

5. Therapeutic Method for Disease Using Bispecific Antibody and Antibody Fragment Thereof of Present Invention The bispecific antibody or the antibody fragment thereof of the present invention can be used for treating a disease associated with a GM-CSF and a disease associated with a GM-CSF neutralizing antibody. Examples thereof include melanoma, head and neck cancer, breast cancer, gastrointestinal cancer, pancreatic cancer, hepatocellular carcinoma, prostate cancer, colorectal cancer, lung cancer, renal cell cancer, ovarian cancer, leukopenia due to chemotherapy, leukopenia due to bone marrow transplantation, leukopenia due to aplastic anemia, leukopenia due to myelodysplastic syndrome, recovery of bone marrow function in bone marrow transplantation, acute myeloid leukemia, chronic myelomonocytic leukemia, sepsis, mycosis, HIV infection, influenza virus infection, a non-tuberculous mycobacterial infection, acute respiratory distress syndrome, pulmonary alveolar proteinosis, a Crohn's disease, an Alzheimer's disease, and various infectious diseases.

The therapeutic agent containing the bispecific antibody or the bispecific antibody fragment thereof of the present invention, or a derivative thereof may contain only the antibody or the antibody fragment thereof, or the derivative thereof as an active ingredient, and the therapeutic agent is generally to be provided as a pharmaceutical preparation mixed with one or more pharmacologically acceptable carriers and produced by any method known in the art of preparation.

Examples of the administration route include oral administration, and parenteral administration such as buccal, tracheobronchial, intrarectal, subcutaneous, intramuscular, or intravenous administration. Examples of a dosage form include sprays, capsules, tablets, powders, granules, syrups, emulsions, suppositories, injections, ointments, and tapes. Various preparations can be produced by an ordinary method using a commonly used excipient, extender, binder, wetting agent, disintegrator, surfactant, lubricant, dispersant, buffer, preservative, solubilizing agent, antiseptic, colorant, flavor, or stabilizer.

Examples of the excipient include lactose, fructose, glucose, corn starch, sorbitol, crystalline cellulose, sterile water, ethanol, glycerol, saline, and a buffer solution. Examples of the disintegrator include starch, sodium alginate, gelatin, calcium carbonate, calcium citrate, dextrin, magnesium carbonate, and synthetic magnesium silicate.

Examples of the binder include methylcellulose or a salt thereof, ethylcellulose, gum arabic, gelatin, hydroxypropylcellulose, and polyvinylpyrrolidone. Examples of the lubricant include talc, magnesium stearate, polyethylene glycol, and hydrogenated vegetable oil.

Examples of the stabilizer include an amino acid such as arginine, histidine, lysine, and methionine, human serum albumin, gelatin, dextran 40, methylcellulose, sodium sulfite, and sodium metasulfite.

Examples of the other additives include syrup, vaseline, glycerin, ethanol, propylene glycol, citric acid, sodium chloride, sodium nitrite, and sodium phosphate.

Examples of the preparation suitable for oral administration include an emulsion, a syrup, a capsule, a tablet, a powder, and a granule.

A liquid preparation such as an emulsion or a syrup can be produced using, as an additive, water, sugars such as sucrose, sorbitol or fructose, glycols such as polyethylene glycol or propylene glycol, oils such as sesame oil, olive oil, or soybean oil, antiseptics such as a p-hydroxybenzoic acid ester, or flavors such as strawberry flavor or peppermint.

The capsule, the tablet, the powder, the granule, and the like can be produced using, as an additive, an excipient such as lactose, glucose, sucrose, or mannitol, a disintegrator such as starch or sodium alginate, a lubricant such as magnesium stearate or talc, a binder such as polyvinyl alcohol, hydroxypropyl cellulose, or gelatin, a surfactant such as a fatty acid ester, or a plasticizer such as glycerin.

Examples of the preparation suitable for parenteral administration include an injection, suppository, and a spray. The injection can be produced using a salt solution, a glucose solution, or a carrier formed of a mixture of both.

The suppository can be produced using a carrier such as cacao butter, hydrogenated aliphatic, or carboxylic acid. The spray can be produced using a carrier that does not stimulate the oral cavity and the respiratory tract mucosa of a recipient and that allows the monoclonal antibody and the antibody fragment thereof of the present invention to be dispersed as fine particles and facilitate absorption. Examples of the carrier include lactose and glycerin. The preparation can also be produced as an aerosol or a dry powder. Further, a component shown as an additive in an appropriate preparation for oral administration can also be added to the above parental agent.

An effective amount of the bispecific antibody of the invention administered in combination with a suitable diluent and a pharmacologically acceptable carrier is 0.0001 mg to 100 mg per kg body weight at a time, and the bispecific antibody is administered at intervals of 2 days to 8 weeks.

6. Diagnostic Method for Disease Using Bispecific Antibody or Bispecific Antibody Fragment Thereof of Present Invention By detecting or measuring cells expressing at least one of CD116 and CD131 using the bispecific antibody or the bispecific antibody fragment thereof of the invention, a disease associated with a GM-CSF or a disease associated with a GM-CSF neutralizing antibody can be diagnosed.

The diagnosis of the disease associated with a GM-CSF can be performed by, for example, detecting and measuring at least one of CD116 and CD131 as follows.

First, biological samples collected from living bodies of a plurality of healthy persons are subjected to one of detection and measurement of at least of CD116 and CD131 by using the following immunological technique using the bispecific antibody or the bispecific antibody fragment thereof of the present invention and a derivative thereof, and an abundance of at least one of CD116 and CD131 in the biological samples of the healthy person is examined.

Next, an abundance of at least one of CD116 and CD131 is similarly examined for a biological sample of a subject, and the abundance thereof is compared with the abundance of healthy people. When the abundance of at least one of CD116 and CD131 of the subject is increased or reduced as compared with the healthy person, it can be diagnosed that the disease is associated with a GM-CSF.

The immunological technique is a method of detecting and measuring an antibody amount or an antigen amount by using an antigen or an antibody subjected to labeling.

Examples thereof include a radiolabeled immunoantibody method, enzyme immunoassay, fluorescence immunoassay, luminescent immunoassay, Western blotting, or a physicochemical method.

Examples of the radiolabeled immunoantibody method include a method in which an antigen, a cell expressing an antigen, or the like is allowed to react with the bispecific antibody or the antibody fragment thereof of the present invention, followed by further allowing to react with a radiolabeled anti-immunoglobulin antibody or binding fragment, and then measurement is performed using a scintillation counter or the like.

Examples of the enzyme immunoassay include a method in which, for example, an antigen, a cell expressing an antigen, or the like is allowed to react with the bispecific antibody or the bispecific antibody fragment thereof of the present invention, followed by further allowing to react with a labeled anti-immunoglobulin antibody and binding fragment, and then a color developing dye is measured with an absorptiometer. Examples thereof include sandwich ELISA.

As a label used in the enzyme immunoassay, a known enzyme label [Enzyme Immunoassay, Igaku Shoin (1987)] can be used. For example, an alkaline phosphatase label, a peroxidase label, a luciferase label, or a biotin label is used.

The sandwich ELISA is a method in which an antibody is conjugated to a solid phase, then an antigen to be detected or measured is trapped, and a second antibody is allowed to react with the trapped antigen. In the ELISA, two types of antibodies or antibody fragments that bind to the antigen to be detected or measured and have different antigen-binding sites are prepared, and among them, a first antibody or an antibody fragment thereof is adsorbed onto a plate (for example, a 96-well plate) in advance, and then a second antibody or an antibody fragment thereof is labeled with a fluorescent substance such as FITC, an enzyme such as peroxidase, or biotin. Cells isolated from a living body or a lysate thereof, tissues or a lysate thereof, cell culture supernatant, serum, a pleural fluid, an ascites fluid, or an eye fluid is allowed to react with the plate to which the above antibody is adsorbed, followed by allowing to react with a labeled antibody or an antibody fragment to perform a detection reaction depending on the labeling substance. An antigen concentration in a test sample is calculated from a calibration curve prepared by stepwise diluting a known antigen.

As the antibody used in the sandwich ELISA, either a polyclonal antibody or a monoclonal antibody may be used, and Fab, Fab', or an antibody fragment such as $F(ab')_2$ may be used. The combination of two types of antibodies used in the sandwich ELISA may be a combination of monoclonal antibodies binding to different epitopes and antibody fragments thereof, or a combination of a polyclonal antibody and a monoclonal antibody or an antibody fragment thereof.

As the fluorescence immunoassay, for example, a method described in the literature [Monoclonal Antibodies-Principles and practice, Third edition, Academic Press (1996), Monoclonal Antibody Experiment Manual, Kodansha Scientific (1987)] is used. As the label used in the fluorescence immunoassay, a known fluorescent label [Fluorescent Antibody Method, Soft Science Co., Ltd. (1983)] can be used. For example, FITC or RITC is used.

As the luminescent immunoassay, for example, the measurement is performed by a method described in, for example, the literature [Bioluminescence, Chemiluminescence Clinical Examination 42, Hirokawa Shoten (1998)]. Examples of the label used in the luminescent immunoassay include a known luminescent label. For example, acridinium ester or lophine is used.

As the Western blotting, after fractionating antigens or cells expressing the antigens using SDS (sodium dodecyl sulfate)-PAGE [Antibodies-A Laboratory Manual Cold Spring Harbor Laboratory (1988)], the gel is blotted onto a polyvinylidene difluoride (PVDF) membrane or a nitrocellulose membrane, the membrane is allowed to react with an antibody binding to the antigen or an antibody fragment thereof, followed by further allowing to react with an anti-IgG antibody or an antibody fragment thereof labeled with a fluorescent substance such as FITC, an enzyme label such as peroxidase, or a biotin label, and then measurement is performed by visualizing the label. An example is shown below.

First, cells or tissues expressing a polypeptide having a desired amino acid sequence are lysed, and 0.1 μg to 30 μg of protein per lane is migrated by SDS-PAGE under reducing conditions. Next, the migrated proteins are transferred to a PVDF membrane and allowed to react with PBS containing 1% to 10% BSA (hereinafter referred to as BSA-PBS) at room temperature for 30 minutes to perform a blocking operation. Here, the resultant is allowed to react with the bispecific antibody of the present invention, followed by washing with PBS containing 0.05% to 0.1% Tween-20 (Tween-PBS) and allowing to react with peroxidase-labeled goat anti-mouse IgG at room temperature for 2 hours. The antigen is detected by washing with Tween-PBS and detecting a band binding to the antibody using ECL Western Blotting Detection Reagents (manufactured by Amersham plc) or the like. As the antibody used for detection in the Western blotting, an antibody capable of binding to a polypeptide not retaining a natural three-dimensional structure is used.

As the physicochemical method, for example, aggregates are formed by binding at least one of CD116 and CD131, which are antigens, and the bispecific antibody or the bispecific antibody fragment thereof of the present invention, thereby detecting the aggregates. As the physicochemical method, a capillary method, a single radial immunodiffusion method, turbidimetric inhibition immunoassay, or latex turbidimetric inhibition immunoassay [Clinical Testing Projection, Kanehara (1998)] can also be used.

In the latex turbidimetric inhibition immunoassay, when a carrier such as polystyrene latex with a particle size of about 0.1 μm to 1 μm that is sensitized with an antibody or antigen is used and an antigen-antibody reaction is caused by the corresponding antigen or antibody, scattered light in the reaction solution increases and transmitted light decreases. By detecting this change as absorbance or integrating sphere turbidity, the antigen concentration in the test sample is measured.

On the other hand, known immunological detection methods can be used to detect or measure cells expressing at least one of CD116 and CD131, and an immunoprecipitation method, an immunocytostaining method, an immunohistological staining method, a fluorescent antibody staining method, or the like is preferably used.

In the immunoprecipitation method, cells expressing at least one of CD116 and CD131, or the like are allowed to react with the bispecific antibody or the antibody fragments thereof of the present invention, and then a carrier having a binding ability specific to immunoglobulin, such as Protein G Sepharose, is added to precipitate an antigen-antibody complex.

The immunoprecipitation method can also be performed by the following method. First, the bispecific antibody or the bispecific antibody fragment thereof of the present invention is immobilized on a 96-well plate for ELISA, and then blocked with BSA-PBS. Next, after discarding the BSA-PBS and thoroughly washing with PBS, a lysate of cells or tissues expressing at least one of CD116 and CD131 is allowed to react. After thoroughly washing the plate, the immunoprecipitate is extracted with a SDS-PAGE sample buffer and detected by Western blotting as described above.

The immunocytostaining method or immunohistological staining method is a method in which cells or tissues expressing antigens are treated with a surfactant, methanol, or the like to improve antibody permeability according to the case, allowed to react with the bispecific antibody of the present invention, and further allowed to react with an anti-immunoglobulin antibody or binding fragment thereof labeled with a fluorescent label such as FITC, an enzyme label such as peroxidase, or a biotin label, and then the label is visualized and viewed under a microscope. Detection can be performed using a fluorescent antibody staining method in which cells are allowed to react with a fluorescently labeled antibody and analyzed using a flow cytometer

[Monoclonal Antibodies-Principles and practice, Third edition, Academic Press (1996), Monoclonal Antibody Experiment Manual, Kodansha Scientific (1987)]. Particularly, the bispecific antibody or the bispecific antibody fragment thereof of the present invention can detect, by the fluorescent antibody staining method, at least one of CD116 and CD131 expressed on cell membranes.

In the fluorescent antibody staining method, when using an FMAT 8100 HTS system (manufactured by Applied Biosystems) or the like, an antigen amount and an antibody amount can be measured without separating the formed antibody-antigen complex and a free antibody or antigen not involved in the formation of the antibody-antigen complex.

EXAMPLE

[Example 1] Preparation of CD131 and CD116 Expression Vectors and Soluble Antigens (1) Preparation of Human, Monkey, and Mouse CD131 Expression Vectors From the nucleotide sequence of a human CD131 gene (Genbank Accession Number: M59941), the nucleotide sequence of a monkey CD131 gene (Genbank Accession Number: XP_015312724_1), and the nucleotide sequence of a mouse CD131 gene (Genbank Accession Number: M34397), full-length amino acid sequences of human, monkey, and mouse CD131 were obtained and converted to codons optimal for expression in mammalian cells to obtain nucleotide sequences encoding full-length human, monkey, and mouse CD131.

DNAs each having the full-length nucleotide sequences (SEQ ID NO: 1, SEQ ID NO: 2) of human and monkey CD131 were totally synthesized, and inserted into pEF6-myc-His vectors (manufactured by Thermo Fisher Scientific) using an Infusion-HD Cloning Kit (manufactured by Clontech) to obtain human and monkey CD131 full-length expression vectors.

DNAs each having the nucleotide sequences (SEQ ID NO: 3, SEQ ID NO: 4, SEQ ID NO: 5) of extracellular regions of human, monkey, and mouse CD131, and a DNA having a nucleotide sequence with a signal sequence, a human Fc sequence, and a His tag sequence added were fully synthesized, and inserted into pCI vectors (manufactured by Promega) using an Infusion-HD Cloning Kit (manufactured by Clontech) to obtain human, monkey, and mouse CD131 soluble antigen expression vectors.

(2) Preparation of Human, Monkey, and Mouse CD116 Expression Vectors

From the nucleotide sequence of a human CD116 gene (Genbank Accession Number: X17648) and the nucleotide sequence of a mouse CD116 gene (Genbank Accession Number: M85078), full-length amino acid sequences of human and mouse CD116 were obtained. For the monkey CD116, cloning was performed from cynomolgus monkey total RNA to obtain full-length nucleotide sequence and amino acid sequence information. The amino acid sequences were converted into codons optimal for expression in mammal cells, and nucleotide sequences encoding full-length human, monkey, and mouse CD116 were obtained.

The full-length nucleotide sequences (SEQ ID NO: 6, SEQ ID NO: 7) of human and monkey CD116 were totally synthesized, inserted into pCI vectors (manufactured by Promega) using an Infusion-HD Cloning Kit (manufactured by Clontech) to obtain human and monkey CD116 full-length expression vectors.

DNAs each having the nucleotide sequences (SEQ ID NO: 8, SEQ ID NO: 9, SEQ ID NO: 10) of extracellular regions of human, monkey, and mouse CD116, and a DNA having a nucleotide sequence with a signal sequence, a human Fc sequence, and a His tag sequence added were fully synthesized, and inserted into pCI vectors (manufactured by Promega) using an Infusion-HD Cloning Kit (manufactured by Clontech) to obtain human, monkey, and mouse CD116 soluble antigen expression vectors.

(3) Preparation of Soluble CD131 Protein and Soluble CD116 Protein

Using an Expi293 (trademark) Expression System (manufactured by Thermo Fisher Scientific), the human, monkey, mouse CD131 soluble antigen expression vectors (human Fc fusions or His-tag fusions) prepared in (1), and the human, monkey and mouse CD116 soluble antigen expression vectors (human Fc fusions or His-tag fusions) prepared in (2) were introduced into Expi293F cells, followed by culturing and expressing proteins in a transient manner. The culture supernatant was collected 4 days to 5 days after vector introduction, and filtered with a membrane filter (manufactured by MILLIPORE) having a pore diameter of 0.22 μm.

The culture supernatant was subjected to affinity purification using a Protein A resin (MabSelect, manufactured by GE Healthcare) or a complete His-Tag Purification Resin (manufactured by Roche).

Purification of the human Fc fusion using a Protein A resin was carried out by adsorbing the protein in the culture supernatant to Protein A, then washing with D-PBS(-), eluting with 20 mM sodium citrate and 50 mM NaCl buffer (pH 3.4), and collecting into a tube containing 1M sodium phosphate buffer solution (pH 7.0).

Purification of the His-tag fusion using a complete His-Tag Purification Resin was carried out by adsorbing the protein in the culture supernatant to a resin equilibrated with 20 mM phosphoric acid and 500 mM NaCl buffer, washing with 20 mM phosphoric acid, 500 mM NaCl, and 5 mM imidazole buffer, eluting with 20 mM phosphoric acid, 500 mM NaCl, and 250 mM imidazole buffer, and collecting into a tube.

Next, an eluate was replaced with D-PBS(-) using NAP-25 (manufactured by GE Healthcare), followed by filtration sterilization using a membrane filter Millex-Gv (manufactured by Millipore Inc.) having a pore diameter of 0.22 μm.

A concentration of the obtained protein was calculated by measuring an absorbance at a wavelength of 280 nm and using an absorbance coefficient estimated from the amino acid sequence of each protein.

[Example 2] Preparation of Anti-Human CD131 Monoclonal Antibody and Anti-Human CD116 Monoclonal Antibody (1) Immunization of Animal and Preparation of Antibody-Producing Cells Human CD131-Fc (manufactured by R&D Systems), or the human CD131 soluble antigen (human Fc fusion) or the human CD116 soluble antigen (human Fc fusion), which was prepared in Example 1, was administered as an immunogen to human antibody-producing mice [Ishida & Lonberg, IBC's 11th Antibody Engineering, Abstract 2000; Ishida, I. et al., Cloning & Stem Cells 4, 91-102 (2002), and Ishida Isao (2002) Experimental Medicine 20, 6, 846-851] at 20 μg/mouse or 50 μg/mouse, 4 times to 6 times in total. Only during a first immunization, an Alum gel (0.25 mg/mouse or 2 mg/mouse) and an inactive *Bordetella per-* tussis suspension (manufactured by Nacalai Tesque, Inc.) (1×10$^9$/mouse) were added as an adjuvant.

A second immunization was performed 2 weeks after the first immunization, a third immunization was performed one week later thereafter, and a final immunization was performed two weeks after the third immunization. Some individuals were subjected to an addition immunization twice at intervals of 2 weeks from the third immunization, and then subjected to final immunization after 2 weeks. The mice were dissected 4 days after the final immunization, and the lymph nodes or spleen were surgically excised. After homogenizing the excised lymph nodes or spleen, cells were transferred to a tube through a cell strainer (manufactured by Falcon Corporation) and centrifuged to precipitate the cells.

The obtained spleen cells were mixed with a red blood cell removing reagent (manufactured by Sigma-Aldrich Corporation), followed by allowing to react in a hot water bath at 37° C. for 1 minute, and then the mixture was diluted with an MEM medium (manufactured by Sigma-Aldrich Corporation), and further centrifuged. The obtained splenocytes or lymphocytes were washed twice with an MEM medium, and then used for hybridoma production or antibody library production.

(2) Preparation of Hybridomas

An 8-azaguanine-resistant mouse myeloma cell line p3-U1 [P3X63Ag8U. 1, ATCC: CRL-1597, European Journal of Immunology, 6, 511 (1976)] was cultured in an RPMI 1640 medium (manufactured by Wako Pure Chemical Corporation) supplemented with 10% FBS (manufactured by Access Biologicals) and gentamicin (20 μg/mL), and expanded and cultured until the number of cells required for cell fusion (3×10$^7$ cells or more) was reached.

The mouse splenocytes or lymphocytes obtained in (1) and myeloma cells were mixed at a ratio of 2:1 and centrifuged (1500 rpm, 5 minutes). After loosening the obtained precipitate fraction (cell group), cell fusion was performed using GenomONE-CF (manufactured by Ishihara Sangyo Kaisha, Ltd.). The cell group was allowed to react on ice for 5 minutes, and incubated at 37° C. for 15 minutes.

Thereafter, a cloning medium CM-B (manufactured by Sekisui Medical Co., Ltd.) supplemented with 10% FBS (manufactured by Access Biologicals), an HAT supplement (manufactured by Thermo Fisher Scientific), and gentamicin (20 μg/mL) was added thereto, and the cell group was suspended to 2.5×10$^6$ cells/18 mL to 5×10$^6$ cells/18 mL, seeded in a 96-well plate at 200 μL each except a row A, and incubated at conditions of 37° C. and 5% CO$_2$ for 8 days to 10 days. The medium exchange was performed using an HAT medium 1 day to 2 days before screening, and the culture supernatant 1 day to 2 days after the medium exchange was used to screen hybridomas as described below.

(3) Screening of Anti-Human CD131 Antibody-Producing Hybridomas

Anti-human CD131 antibody-producing hybridomas were screened by ELISA and FCM. For screening by ELISA, a solid phase antigen ELISA system was used in which the human CD131 soluble antigen (His-tag form), the monkey CD131 soluble antigen (His-tag form), and the mouse CD131 soluble antigen (His-tag form), which are prepared in Example 1-(3) were immobilized.

Various antigen proteins prepared at 5 μg/mL in D-PBS(−) (manufactured by Nacalai Tesque, Inc.) were dispensed into a 96-well or 384-well ELISA plate (MAXISORP NUNC-IMMNO PLATE, manufactured by Thermo Fisher Scientific) at 50 μL/well or 25 μL/well, followed by allowing to stand at 4° C. overnight for adsorption and then washing 2 times to 3 times with PBS, and 1% BSA-PBS (manufactured by Nacalai Tesque, Inc.) was dispensed thereto at 100 μL/well or 50 μL/well, followed by allowing to stand at room temperature for 1 hour for blocking.

Next, the hybridoma supernatant was dispensed thereto at 50 μL/well or 25 μL/well, followed by allowing to stand at room temperature for 1 hour. The plate was washed 3 times with PBST, and then a peroxidase labeled Goat Anti-Human IgG, Fc γ-fragment specific antibody (Cat #109-035-008, manufactured by Jackson ImmunoResearch, Inc.) diluted with 1% BSA-PBS was dispensed thereto at 50 μL/well or 25 μL/well, followed by allowing to stand at room temperature for 1 hour.

The plate was washed 3 times with PBST, an ABTS (2,2'-Azino-bis(3-ethylbenzothiazoline-6-sulfonic Acid, manufactured by Wako, Cat #016-08521) substrate solution or a TMB substrate solution (manufactured by Thermo Fisher Scientific) was added thereto at 50 μL/well or 25 μL/well to develop color, and when appropriate color development was obtained, the color development was stopped by adding an equal amount of 1% SDS solution or 0.5 mol/L sulfuric acid, and then an absorbance (415 nm to 490 nm) at a sample wavelength of 415 nm and a reference wavelength of 490 nm or an absorbance (450 nm to 570 nm) at a sample wavelength of 450 nm and a reference wavelength of 570 nm was measured using a plate reader (Spectra Max manufactured by Molecular Devices, or SPARK 10M manufactured by TECAN).

For screening by FCM, cells into which the human and monkey CD131 full-length expression vectors prepared in Example 1-(1) were transiently introduced and cells into which no human and monkey CD131 full-length expression vectors were introduced were used in an Expi293 (trademark) Expression System (manufactured by Thermo Fisher Scientific). The respective cells were suspended in 1% BSA-PBS (manufactured by Nacalai Tesque, Inc.), dispensed into a 96-well plate at 1×10$^5$ cells/well to 2×10$^5$ cells/well, incubated on ice for 30 minutes, and then centrifuged (2000 rpm, 2 minutes). After removing the supernatant, the hybridoma supernatant was dispensed at 20 μL/well to 50 μL/well and allowed to react on ice for 30 minutes. After centrifugation and washing with 1% BSA-PBS once or twice, an APC-labeled F(ab')$_2$ Fragment Goat Anti-Human IgG, Fcγ fragment specific antibody (Cat #109-136-098, manufactured by Jackson ImmunoResearch) diluted with 1% BSA-PBS was dispensed at 50 μL/well, followed by allowing to react on ice for 30 minutes in the dark. After centrifugation and washing with 1% BSA-PBS three times, the resultant was suspended in 1% BSA-PBS, and a fluorescence intensity was measured using a flow cytometer (FACS Canto II manufactured by BD Biosciences, or CyAn ADP manufactured by BECKMAN COULTER).

(4) Screening of Anti-Human CD116 Antibody-Producing Hybridomas

Anti-human CD116 antibody-producing hybridomas were screened by ELISA and FCM. For screening by ELISA, an indirect solid phase antigen ELISA system was used in which the human CD116 soluble antigen (His-tag form), monkey CD116 soluble antigen (His-tag form), and mouse CD116 soluble antigen (His-tag form), which are prepared in Example 1-(3) were captured on a plate immobilized with a Tetra His Antibody (Cat #34670, manufactured by Qiagen).

Tetra His Antibodies prepared at 5 μg/mL in D-PBS(−) (manufactured by Nacalai Tesque, Inc.) were dispensed into a 96-well or 384-well ELISA plate (MAXISORP NUNC- IMMNO PLATE, manufactured by Thermo Fisher Scientific) at 50 µL/well or 25 µL/well, followed by allowing to stand at 4° C. overnight for adsorption and then washing 2 times to 3 times with PBS, and 1% BSA-PBS (manufactured by Nacalai Tesque, Inc.) was dispensed thereto at 100 µL/well or 50 µL/well, followed by allowing to stand at room temperature for 1 hour for blocking.

Next, the human CD116 soluble antigen (His-tag form), the monkey CD116 soluble antigen (His-tag form), and the mouse CD116 soluble antigen (His-tag form) that are prepared in Example 1-(3) and diluted at 5 µg/mL with 1% BSA-PBS were dispensed at 50 µL/well or 25 µL/well, followed by allowing to stand at room temperature for 1 hour. After washing the plate 3 times with PBST, the hybridoma supernatant diluted with 1% BSA-PBS was dispensed at 50 µL/well or 25 µL/well, followed by allowing to stand at room temperature for 1 hour. The plate was washed 3 times with PBST, and then a peroxidase labeled Goat Anti-Human IgG, Fc antibody (Cat #17507, manufactured by IBL Inc.) diluted with 1% BSA-PBS was dispensed at 50 µL/well or 25 µL/well, followed by allowing to stand at room temperature for 1 hour.

The plate was washed 3 times with PBST, an ABTS (2,2'-Azino-bis(3-ethylbenzothiazoline-6-sulfonic Acid, manufactured by Wako, Cat #016-08521) substrate solution or a TMB substrate solution (manufactured by Thermo Fisher Scientific) was added thereto at 50 µL/well or 25 µL/well to develop color, and when appropriate color development was obtained, the color development was stopped by adding an equal amount of 1% SDS solution or 0.5 mol/L sulfuric acid, and then an absorbance (415 nm to 490 nm) at a sample wavelength of 415 nm and a reference wavelength of 490 nm or an absorbance (450 nm to 570 nm) at a sample wavelength of 450 nm and a reference wavelength of 570 nm was measured using a plate reader (Spectra Max manufactured by Molecular Devices, or SPARK 10M manufactured by TECAN).

For screening by FCM, cells into which the human and monkey CD131 full-length expression vectors prepared in Example 1-(2) were transiently introduced and cells into which no human and monkey CD116 full-length expression vectors were introduced were used in an Expi293 (trademark) Expression System (manufactured by Thermo Fisher Scientific). The respective cells were suspended in 1% BSA-PBS (manufactured by Nacalai Tesque, Inc.), dispensed into a 96-well plate at $1 \times 10^5$ cells/well to $2 \times 10^5$ cells/well, incubated on ice for 30 minutes, and then centrifuged (2000 rpm, 2 minutes).

After removing the supernatant, the hybridoma supernatant was dispensed at 20 µL/well to 50 µL/well and allowed to react on ice for 30 minutes. After centrifugation and washing with 1% BSA-PBS once or twice, an APC-labeled F(ab')$_2$ Fragment Goat Anti-Human IgG, Fcγ fragment specific antibody (Cat #109-136-098, manufactured by Jackson ImmunoResearch) diluted with 1% BSA-PBS was dispensed at 50 µL/well, followed by allowing to react on ice for 30 minutes in the dark.

After centrifugation and washing with 1% BSA-PBS three times, the resultant was suspended in 1% BSA-PBS, and a fluorescence intensity was measured using a flow cytometer (FACS Canto II manufactured by BD Biosciences, or CyAn ADP manufactured by BECKMAN COULTER).

(5) Isolation of Hybridomas and Analysis of Antibody Gene Sequence

Hybridomas in a positive well selected by the hybridoma screening were seeded into a 96-well plate dispensed with an HAT medium using a cell sorter (SH800, manufactured by SONY Corporation), followed by performing single cloning.

The cells in the well were cultured at conditions of 37° C. and 5% $CO_2$ until the number of cells in the well reaches an appropriate number for screening, and the obtained single clone hybridoma culture supernatant was used to perform screening according to the method described in (2) and (3) again to establish anti-CD131 monoclonal antibody-producing hybridomas and anti-CD116 monoclonal antibody-producing hybridomas.

Total RNA was prepared from the obtained hybridomas using MagNApure 96 (manufactured by Roche) and an MagNA Pure 96 Cellular RNA Large Volume Kit (manufactured by Roche). Using the prepared total RNA as a template, a cDNA was prepared using an SMARTer RACE 5'/3' Kit (manufactured by Clontech).

Using the cDNA corresponding to each obtained hybridoma as a template, a PCR reaction using a combination of a universal primer A mix (containing a forward primer) attached to the kit and a reverse primer encoding a human IgG heavy chain constant region or a light chain constant region was performed using a PrimeSTAR Max DNA Polymerase (manufactured by Takara Bio Inc.) to amplify a heavy chain antibody gene fragment and a light chain antibody gene fragment.

The amplified heavy chain antibody gene fragment and light chain antibody gene fragment were subjected to DNA sequence analysis according to a direct sequence method, or DNA sequence analysis according to a sub cloning method using a Zero Blunt TOPO PCR CloningKit for Sequencing (manufactured by Invitrogen) to perform sequence identification.

The DNA sequence analysis according to the direct sequence method was performed by adding 4 µL of ExoSAP-IT-Express (manufactured by Thermo Fisher Scientific) to 10 µL of the PCR product, performing a reaction at 37° C. for 4 minutes and 80° C. for 1 minute, and then using a sample diluted with sterilized water as a template and using a primer corresponding to a terminus sequence of a primer used for Nested-PCR.

The DNA sequence analysis according to the sub cloning method using a Zero Blunt TOPO PCR Cloning Kit for Sequencing (manufactured by Invitrogen) was performed according to the following procedure. After the PCR product was inserted into a pCR4 vector (manufactured by Invitrogen), the obtained plasmid was introduced into an *Escherichia coli* DH5α strain.

The DNA sequence analysis was performed using the plasmid extracted from the obtained transformant using an automatic plasmid extractor (manufactured by Kurabo Industries Ltd.) as a template and using an M13 primer attached to the Zero Blunt TOPO PCR CloningKit for Sequencing.

From the DNA sequence analysis results, a nucleotide sequence encoding a full-length VH or a nucleotide sequence encoding a VL was confirmed, and amino acid sequences of the antibody to CD131 and the antibody to CD116, which are expressed by each hybridoma, were determined. Tables 1 and 2 show a correspondence between clone names, VH, VL, and CDR amino acid sequences and sequence numbers.

Table 1 shows a clone name of the CD131 antibody, and sequence numbers of an amino acid sequence deduced from the complete nucleotide sequence encoding a VH, amino acid sequences of CDRs 1 to 3 of the VH (hereinafter sometimes referred to as HCDRs 1 to 3), an amino acid sequence deduced from the complete nucleotide sequence encoding a VL, and amino acid sequences of CDRs 1 to 3 of the VL (hereinafter also referred to as LCDRs 1 to 3).

Table 2 shows a clone name of the CD116 antibody, and sequence numbers of an 5 amino acid sequence deduced from the complete nucleotide sequence encoding a VH, amino acid sequences of CDRs 1 to 3 of the VH (hereinafter sometimes referred to as HCDRs 1 to 3), an amino acid sequence deduced from the complete nucleotide sequence encoding a VL, and amino acid sequences of CDRs 1 to 3 of the VL (hereinafter also referred to as LCDRs 1 to 3).

(manufactured by Agilent Technologies), a CD116 antibody phage library containing the VL nucleotide sequence represented by SEQ ID NO: 91 and a VH gene library was obtained.

(7) Screening of Anti-Human CD116 Antibody by Phage Display Method

Using the CD116 antibody phage library obtained in Example 2-(6), an anti-CD116 monoclonal antibody containing an L chain of a CD131 antibody containing the amino acid sequence represented by SEQ ID NO: 30 was obtained by the following phage display method.

TABLE 1

| Clone name | VH full-length amino acid SEQ ID NO: | HCDR1 amino acid SEQ ID NO: | HCDR2 amino acid SEQ ID NO: | HCDR3 amino acid SEQ ID NO: | VL full-length amino acid SEQ ID NO: | LCDR1 amino acid SEQ ID NO: | LCDR2 amino acid SEQ ID NO: | LCDR3 amino acid SEQ ID NO: |
|---|---|---|---|---|---|---|---|---|
| 131-03 | 21 | 61 | 62 | 63 | 22 | 64 (same as 34) | 65 (same as 35) | 66 |
| 131-16 | 23 | 67 | 68 | 69 | 24 | 70 | 71 | 72 |
| 131-18 | 25 | 73 | 74 | 75 | 26 | 76 (same as 70) | 77 (same as 71) | 78 |
| 131-B1 | 27 | 79 | 80 | 81 | 28 | 82 (same as 70) | 83 (same as 71) | 84 |
| 131-B2 | 29 | 85 | 86 | 87 (same as 81) | 30 (same as 28) | 88 (same as 70) | 89 (same as 71) | 90 (same as 84) |

TABLE 2

| Clone name | VH full-length amino acid SEQ ID NO: | HCDR1 amino acid SEQ ID NO: | HCDR2 amino acid SEQ ID NO: | HCDR3 amino acid SEQ ID NO: | VL full-length amino acid SEQ ID NO: | LCDR1 amino acid SEQ ID NO: | LCDR2 amino acid SEQ ID NO: | LCDR3 amino acid SEQ ID NO: |
|---|---|---|---|---|---|---|---|---|
| 116-08 | 11 | 31 | 32 | 33 | 12 | 34 | 35 | 36 |
| 116-09 | 13 | 37 | 38 | 39 | 14 | 40 | 41 | 42 (same as 40) |
| 116-18 | 15 | 43 (same as 37) | 44 (same as 38) | 45 | 16 | 46 | 47 (same as 41) | 48 |
| 116-21 | 17 | 49 (same as 37) | 50 (same as 38) | 51 | 18 | 52 (same as 40) | 53 (same as 41) | 54 (same as 40) |
| 116-22 | 19 | 55 | 56 | 57 | 20 | 58 | 59 | 60 |

(6) Preparation of Anti-Human CD116 Antibody Phage Library

A CD116 antibody phage library having an L chain of a CD131 antibody that has the amino acid sequence represented by SEQ ID NO: 30 and is obtained in Example 2-(5) was prepared by the following method. An RNA was extracted from the lymph node cells or spleen cells obtained in Example 2-(1) using an RNeasy Mini Plus kit (manufactured by QIAGEN), a cDNA was amplified by an SMARTer RACE cDNA amplification kit (manufactured by Clontech), and a VH gene fragment was further amplified by PCR.

The VH DNA fragment and the VL DNA fragment having the nucleotide sequence represented by SEQ ID NO: 91 were inserted into a vector in which a tag sequence of phage pCANTAB 5E (manufactured by Amersham Pharmacia) was changed to an FLAG-His tag and a trypsin recognition sequence, and *Escherichia coli* TG1 (manufactured by Lucigen Corporation) was transformed to obtain an *Escherichia coli* library.

By amplifying the obtained *Escherichia coli* library and infecting VCSM13 Interference Resistant Helper Phage The human CD116 soluble antigen (His-tag form) and the monkey CD116 soluble antigen (His-tag form), which are prepared in Example 1-(3), were biotinylated using an EZ-Link Sulfo-HNS-LC-Biotin, No-Weight Format (manufactured by Thermo Fisher Scientific), and the biotinylated human CD116 soluble antigen (His-tag form) and the biotinylated monkey CD116 soluble antigen (His-tag form) were obtained.

After the biotinylated human CD116 soluble antigen (His-tag form) and a CD116 immunohuman antibody M13 phage library were allowed to react at room temperature for 1 hour to 2 hours, the resultant was added to MAXISORP STARTUBE that is immobilized with streptavidin (manufactured by Thermo Fisher Scientific) and blocked using a SuperBlock Blocking Buffer (manufactured by Thermo Fisher Scientific).

After reacting at room temperature for 30 minutes to 1 hour, washing was performed with D-PBS(−) and PBS containing 0.1% Tween 20 (hereinafter referred to as PBS-T, manufactured by Wako Pure Chemical Industries, Ltd.), and then phages were eluted with 0.25% trypsin (manufactured by Nacalai Tesque, Inc.). TG1 competent cells were infected with the eluted phages, thereby amplifying the phages.

The obtained phages were allowed to react again with the biotinylated human CD116 soluble antigen (His-tag form) immobilized on the MAXISORP STARTUBE, then the tube was washed, and the phages were eluted. The operation was repeated to concentrate phages displaying antibody molecules that specifically bind to human CD116 and monkey CD116.

A plasmid was prepared from transformed *Escherichia coli* obtained by infecting TG1 with the concentrated phages. A Mix&Go Competent Cells-Strain TG1 (manufactured by Zymo Research) was transformed using the prepared plasmid, followed by seeding onto a SOBAG plate (2.0% tryptone, 0.5% Yeast extract, 0.05% NaCl, 2.0% glucose, 10 mM $MgCl_2$, 100 μg/mL ampicillin, and 1.5% agar) to form a colony. After the colony was inoculated and cultured for several hours, 1 mM IPTG (manufactured by Nacalai Tesque, Inc.) was added thereto, followed by culturing again to obtain a monoclonal *Escherichia coli* culture supernatant.

Using the obtained monoclonal *Escherichia coli* culture supernatant, screening for clones that bind to both human CD116 and monkey CD116 was performed by ELISA and FCM described below.

In screening by ELISA, a MAXISORP plate (manufactured by NUNC Corporation) was immobilized with streptavidin (manufactured by Thermo Fisher Scientific) and blocked using 1% BSA-PBS (manufactured by Nacalai Tesque, Inc.), and then the biotinylated human CD116 soluble antigen (His-tag form) or the biotinylated monkey CD116 soluble antigen (His-tag form) binds thereto. Each *Escherichia coli* culture supernatant was added to each well of the plate and allowed to react for 60 minutes at room temperature, and then each well was washed 3 times with PBS-T.

Next, HRP-labeled Goat poly, anti-human IgG $F(ab')_2$ (manufactured by Abcam) was diluted 1000 times with 1% BSA-PBS, and 50 μL thereof was added to each well, followed by incubating at room temperature for 30 minutes. After washing the microplate 3 times with PBS-T, 50 μL of TMB color developing substrate solution (manufactured by DAKO) was added to each well, followed by incubating at room temperature for 10 minutes. A 2N HCl solution (50 μL/well) was added to each well to stop the color developing reaction, and an absorbance at a wavelength of 450 nm (reference wavelength: 570 nm) was measured using a plate reader (EnSpire: manufactured by PerkinElmer).

For screening by FCM, cells into which the human and monkey CD131 full-length expression vectors prepared in Example 1-(2) were transiently introduced and cells into which no human and monkey CD116 full-length expression vectors were introduced were used in an Expi293 (trademark) Expression System (manufactured by Thermo Fisher Scientific). The respective cells were suspended in 1% BSA-PBS (manufactured by Nacalai Tesque, Inc.), dispensed into a 96-well plate at $1 \times 10^5$ cells/well to $2 \times 10^5$ cells/well, incubated on ice for 30 minutes, and then centrifuged (2000 rpm, 2 minutes).

After removing the supernatant, the *Escherichia coli* culture supernatant and an anti-FLAG M2 Antibody (manufactured by SIGMA) were dispensed at 20 μL/well to 50 μL/well, followed by allowing to react on ice for 30 minutes. After centrifugation and washing with 1% BSA-PBS once or twice, an APC-labeled Goat anti-Mouse IgG (H+L) antibody (manufactured by Southern Bio) diluted with 1% BSA-PBS was dispensed at 50 μL/well, followed by allowing to react on ice for 30 minutes in the dark.

After centrifugation and washing with 1% BSA-PBS three times, the resultant was suspended in 1% BSA-PBS, and a fluorescence intensity was measured using a flow cytometer (FACS Canto II manufactured by BD Biosciences, or CyAn ADP manufactured by BECKMAN COULTER).

As a result of the screening, the VH sequences of clones that bind to both human CD116 and monkey CD116 were analyzed, and the obtained results are shown in Table 3.

Table 3 shows a clone name of an anti-CD116 antibody whose VL amino acid sequence is SEQ ID NO: 30, and sequence numbers of an amino acid sequence deduced from the complete nucleotide sequence encoding a VH and amino acid sequences of CDRs 1 to 3 of the VH (hereinafter sometimes referred to as HCDRs 1 to 3).

TABLE 3

| Clone name | VH full-length amino acid SEQ ID NO: | HCDR1 amino acid SEQ ID NO: | HCDR2 amino acid SEQ ID NO: | HCDR3 amino acid SEQ ID NO: | VL full-length amino acid SEQ ID NO: | LCDR1 amino acid SEQ ID NO: | LCDR2 amino acid SEQ ID NO: | LCDR3 amino acid SEQ ID NO: |
|---|---|---|---|---|---|---|---|---|
| 116-398 | 92 | 104 | 105 | 106 | 30 (same as 28) | 88 (same as 70) | 89 (same as 71) | 90 (same as 84) |
| 116-412 | 93 | 107 | 108 | 109 (same as 106) | 30 (same as 28) | 88 (same as 70) | 89 (same as 71) | 90 (same as 84) |
| 116-413 | 94 | 110 (same as 107) | 111 | 112 (same as 106) | 30 (same as 28) | 88 (same as 70) | 89 (same as 71) | 90 (same as 84) |
| 116-421 | 95 | 113 (same as 107) | 114 (same as 105) | 115 (same as 106) | 30 (same as 28) | 88 (same as 70) | 89 (same as 71) | 90 (same as 84) |
| 116-433 | 96 | 116 (same as 125) | 117 (same as 105) | 118 (same as 106) | 30 (same as 28) | 88 (same as 70) | 89 (same as 71) | 90 (same as 84) |
| 116-435 | 97 | 119 (same as 104) | 120 (same as 105) | 121 (same as 106) | 30 (same as 28) | 88 (same as 70) | 89 (same as 71) | 90 (same as 84) |

TABLE 3-continued

| Clone name | VH full-length amino acid SEQ ID NO: | HCDR1 amino acid SEQ ID NO: | HCDR2 amino acid SEQ ID NO: | HCDR3 amino acid SEQ ID NO: | VL full-length amino acid SEQ ID NO: | LCDR1 amino acid SEQ ID NO: | LCDR2 amino acid SEQ ID NO: | LCDR3 amino acid SEQ ID NO: |
|---|---|---|---|---|---|---|---|---|
| 116-439 | 98 | 122 (same as 107) | 123 (same as 105) | 124 (same as 106) | 30 (same as 28) | 88 (same as 70) | 89 (same as 71) | 90 (same as 84) |
| 116-463 | 99 | 125 (same as 116) | 126 (same as 105) | 127 (same as 106) | 30 (same as 28) | 88 (same as 70) | 89 (same as 71) | 90 (same as 84) |
| 116-464 | 100 | 128 (same as 107) | 129 (same as 105) | 130 (same as 106) | 30 (same as 28) | 88 (same as 70) | 89 (same as 71) | 90 (same as 84) |
| 116-465 | 101 | 131 (same as 107) | 132 | 133 (same as 106) | 30 (same as 28) | 88 (same as 70) | 89 (same as 71) | 90 (same as 84) |
| 116-466 | 102 | 134 (same as 107) | 135 | 136 (same as 106) | 30 (same as 28) | 88 (same as 70) | 89 (same as 71) | 90 (same as 84) |
| 116-408 | 103 | 137 (same as 107) | 138 (same as 105) | 139 | 30 (same as 28) | 88 (same as 70) | 89 (same as 71) | 90 (same as 84) |

[Example 3] Preparation and Activity Evaluation of IgG-Type Bispecific Antibody Binding to CD131 and CD116

(1) Preparation of IgG-Type Bispecific Antibody Binding to CD131 and CD116

An IgG-type bispecific antibody expression vector containing the anti-CD131 antibody sequence and the anti-CD116 antibody sequence, which are obtained in Example 2, was prepared. A structure of the IgG-type bispecific antibody is based on the paper Mabs, 7, 377 (2015) and the paper Protein Engineering, Design & Selection, 29, 457, (2016), and the IgG-type bispecific antibody is a bispecific antibody having a heterogeneous H chain using Kobs-into-Holes as shown in FIG. 2, and is hereinafter referred to as an IgG-type CD131-CD116 bispecific antibody.

Using, as a common backbone, a pCI vector manufactured by Promega, a restriction enzyme site necessary for expressing human antibody genes was introduced downstream of a signal sequence, and vectors for H chain and L chain expression were prepared by two types of total synthesis as shown below.

As an antibody expression vector to the first antigen (CD116), a DNA fragment containing a nucleotide sequence encoding the amino acid sequence represented by any one of SEQ ID NOs: 11, 13, 15, 17, and 19 as an H chain variable region and a DNA fragment containing a nucleotide sequence encoding the amino acid sequence represented by SEQ ID NO: 140, which contains an F126C/C220A mutation that prevents mispairing of an L chain, an S354C/T366W mutation to make a hetero heavy chain, and an L234A/L235A/P329G mutation that deletes an effector activity, as an H chain constant region sequence are linked, and a DNA fragment containing a nucleotide sequence encoding the amino acid sequence represented by any of SEQ ID NOs: 12, 14, 16, 18, and 20 as an L chain variable region and a DNA fragment containing a nucleotide sequence encoding the amino acid sequence represented by SEQ ID NO: 141, which contains an S121C/C214S mutation that prevents mispairing of an L chain, as an L chain constant region are linked.

Similarly, as an antibody expression vector to the second antigen (CD131), a DNA fragment containing the amino acid sequence represented by any of SEQ ID NOs: 21, 23, 25, 27 and 29 as an H chain variable region and a DNA fragment containing a nucleotide sequence encoding the amino acid sequence represented by SEQ ID NO: 142, which contains Y349C/T366S/L368A/Y407V/H435R/Y436F mutations to make a hetero H chain, as an H chain constant region sequence are linked, and a DNA fragment containing the amino acid sequence represented by any of SEQ ID NOs: 22, 24, 26, 28 and 30 as an L chain variable region and a DNA fragment containing a nucleotide sequence encoding the amino acid sequence represented by SEQ ID NO: 143 as an L chain constant region sequence are linked.

The antibody expression vector to the first antigen (CD116) and the antibody expression vector to the second antigen (CD131) was co-transfected into Expi293 cells in any combination using an Expi293 (trademark) Expression System (manufactured by Thermo Fisher Scientific), and after 16 hours, a Transfection Enhancer was added to express a total of 25 types of IgG-type bispecific antibodies in a transient expression system.

The culture supernatant was collected 3 days to 5 days after vector introduction, and filtered with a membrane filter (manufactured by MILLIPORE) having a pore diameter of 0.22 μm, and then the antibody was affinity purified using a Protein A resin (POROS MabCapture A Affinity Chromatography Resin, manufactured by Thermo Scientific). As a washing liquid, 20 mM sodium citrate and 150 mM NaCl buffer solution (pH 6.0) were used. The antibody adsorbed to the Protein A was eluted by 40 mM sodium acetate and 500 mM calcium chloride buffer solution (pH 4.6) and collected into a tube containing a 1M sodium phosphate buffer solution (pH 7.0).

Next, an eluate was replaced with D-PBS(−) using NAP-25 (manufactured by GE Healthcare), followed by filtration sterilization using a membrane filter Millex-Gv (manufactured by Millipore Inc.) having a pore diameter of 0.22 μm.

A concentration of the obtained IgG-type CD131-CD116 bispecific antibody was calculated by measuring an absorbance at a wavelength of 280 nm and using an absorbance coefficient estimated from the amino acid sequence of each antibody.

(2) Agonist Activity Analysis of IgG-Type CD131-CD116 Bispecific Antibody

Agonist activities of the 25 types of CD131-CD116 bispecific antibodies prepared above were analyzed by the following method. In the activity analysis, a TF-1 cell line (ATCC, CRL-2003) exhibiting a proliferation activity depending on GM-CSF signals was used.

Figure 3A:
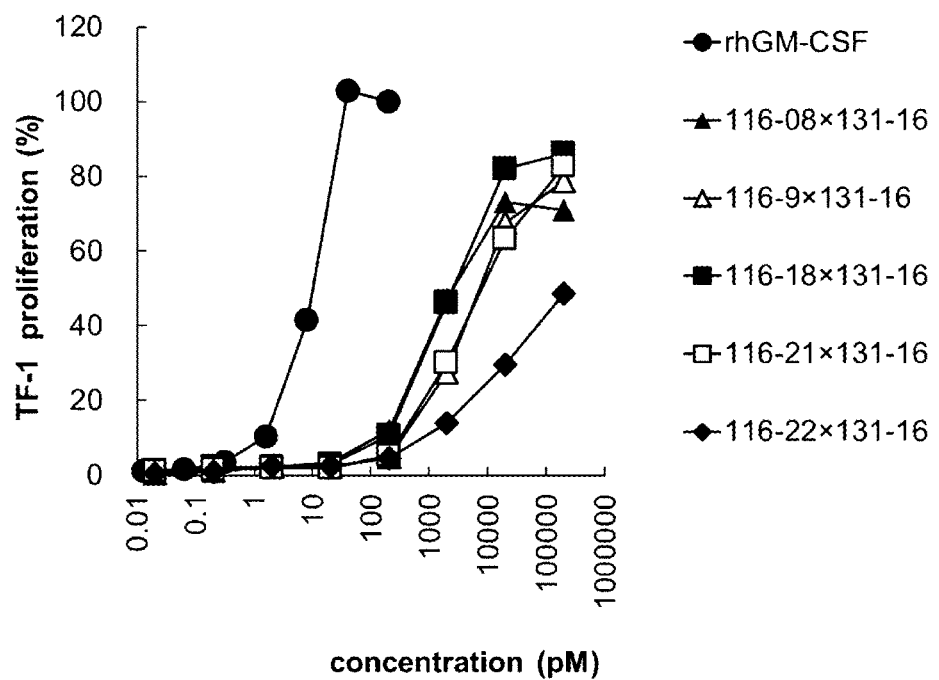
FIGS. 3A and 3B show a GM-CSF receptor agonist activity of the IgG-type CD131-CD116 bispecific antibody to TF-1 cells. The agonist activity is shown as a TF-1 cell proliferation ratio, where an activity when 200 pM of recombinant human GM-CSF (rhGM-CSF) is added is taken as 100%.
Figure 3B:
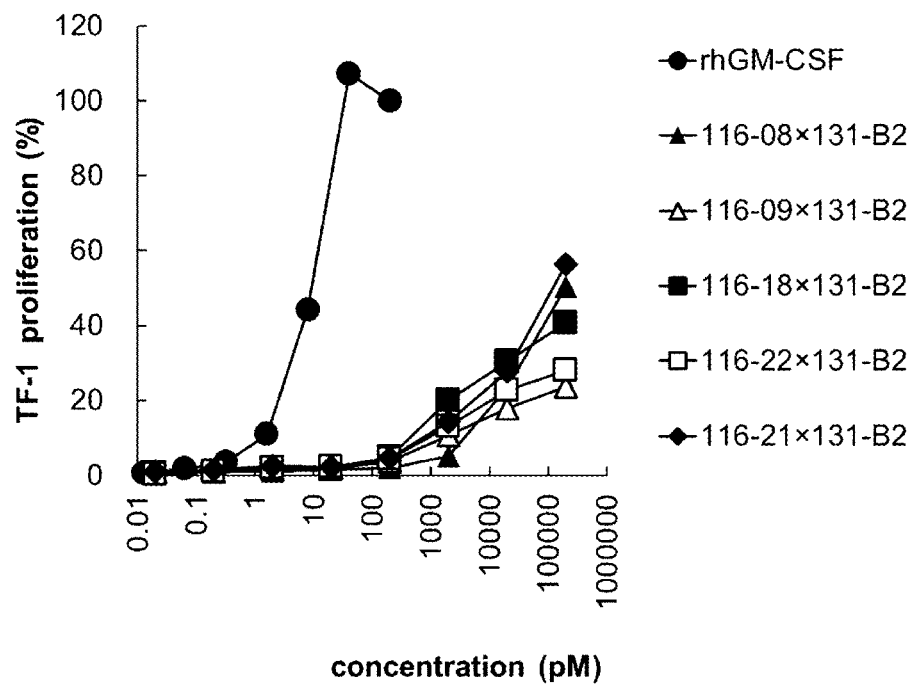

As shown in FIGS. 3A and 3B, each of the IgG-type CD131-CD116 bispecific antibody exhibited the agonist activity.

[Example 4] Preparation and Activity Evaluation of Bispecific Antibody Binding to CD131 and CD116

(1) Preparation of Bispecific Antibody Binding to CD131 and CD116

A bispecific antibody shown in Table 4 and containing the anti-CD131 antibody sequence and the anti-CD116 antibody sequence, which are obtained in Example 2, was prepared.

TABLE 4

| Bispecific antibody name | Anti-CD116 antibody | | | Anti-CD131 antibody | | |
|---|---|---|---|---|---|---|
| | Clone name | VH full-length amino acid SEQ ID NO: | VL full-length amino acid SEQ ID NO: | Clone name | VH full-length amino acid SEQ ID NO: | VL full-length amino acid SEQ ID NO: |
| GM398 | 116-398 | 175 (same as 92) | 30 (same as 28) | 131-B2 | 29 | 30 (same as 28) |
| GM412 | 116-412a | 176 | 30 (same as 28) | 131-B2 | 29 | 30 (same as 28) |
| GM413 | 116-413a | 177 | 30 (same as 28) | 131-B2 | 29 | 30 (same as 28) |
| GM421 | 116-421a | 178 | 30 (same as 28) | 131-B2 | 29 | 30 (same as 28) |
| GM433 | 116-433a | 179 | 30 (same as 28) | 131-B2 | 29 | 30 (same as 28) |
| GM435 | 116-435 | 180 (same as 97) | 30 (same as 28) | 131-B2 | 29 | 30 (same as 28) |
| GM439 | 116-439 | 181 (same as 98) | 30 (same as 28) | 131-B2 | 29 | 30 (same as 28) |
| GM463 | 116-463a | 182 | 30 (same as 28) | 131-B2 | 29 | 30 (same as 28) |
| GM464 | 116-464a | 183 | 30 (same as 28) | 131-B2 | 29 | 30 (same as 28) |
| GM465 | 116-465a | 184 | 30 (same as 28) | 131-B2 | 29 | 30 (same as 28) |
| GM466 | 116-466a | 185 | 30 (same as 28) | 131-B2 | 29 | 30 (same as 28) |
| GM408 | 116-408 | 186 (same as 103) | 30 (same as 28) | 131-B2 | 29 | 30 (same as 28) |

TF-1 cells, which were subcultured and maintained in an RPMI 1640 medium (nacalai tesque) supplemented with 2 ng/mL recombinant human GM-CSF (R&D Systems), 10% FBS, and 50 µg/mL Gentamicin Sulfate Solution, were centrifuged, washed 3 times with an Macrophage-SFM medium (GIBCO), suspended in an Macrophage-SFM medium to 2.5×10⁵ cells/mL, and dispensed into a 96-well plate (Greiner) at 80 µL per well and 2.0×10⁴ cells/well.

Thereafter, each IgG-type CD131-CD116 bispecific antibody sample was prepared using a Macrophage-SFM medium at 5 times the final concentration and added at 20 µL/well, followed by culturing under conditions of 37° C. and 5% CO₂ for 3 days. After 3 days, a luminescence reagent CellTiter-Glo2.0 (Promega) was added at 100 µL/well, and then a luminescence intensity due to an ATP luciferase reaction was measured using a microplate reader ARVO (PerkinElmer).

A proliferation ratio of the TF-1 cells due to each IgG-type CD131-CD116 bispecific antibody was calculated with an average value of luminescence of a group to which 200 pM of recombinant human GM-CSF was added as 100%. The representative results are shown in FIGS. 3A and 3B.

A structure of the bispecific antibody had an N-terminus type structure shown in FIG. 4A, and the bispecific antibody was an bispecific antibody in which the VH1 is a VH of an anti-CD131 antibody (an amino acid sequence thereof is represented by SEQ ID NO: 29), the CH1 is a CH1 of human IgG4 (an amino acid sequence thereof is represented by SEQ ID NO: 144), the VH2 is a VH of an anti-CD116 antibody, and a constant region contains a constant region sequence of a human antibody such as human IgG4PE R409K (an amino acid sequence thereof is represented by SEQ ID NO: 145) described in WO2006/033386, a wild-type IgG1, and a human IgG1 LALAGA mutant (an amino acid sequence thereof is represented by SEQ ID NO: 146) described in WO2006/031653, or modified sequences thereof (amino acid sequences are represented by SEQ ID NOs: 147 to 172). Such a bispecific antibody is hereinafter referred to as a CD131-CD116 bispecific antibody.

As the L chain expression vector, a pCI-OtCMCMV_hK vector having a signal sequence and a human L chain (κ-chain) constant region sequence was used. As the H chain expression vector, a pCI-OtCAG_hG4PE (R409K) vector having a signal sequence and a human IgG4PE R409K, or a pCI-OtCAG_hG1LAGA vector having a human IgG1LALAGA was used. The vectors were prepared by total synthesis using, as a common backbone, a pCI vector manufactured by Promega and introducing a restriction enzyme site necessary for expressing human antibody genes.

A DNA fragment having the nucleotide sequence of the totally synthesized VL represented by SEQ ID NO: 91 was inserted into an appropriate restriction enzyme site of the pCI-OtCMV_hK vector to obtain an L-chain expression vector for the CD131-CD116 bispecific antibody.

A DNA fragment having a nucleotide sequence of the anti-CD131 antibody VH represented by SEQ ID NO: 173, a DNA fragment having a nucleotide sequence encoding a CH1 of a human IgG4 represented by SEQ ID NO: 177, and a DNA fragment having a nucleotide sequence encoding an amino acid sequence of any one of anti-CD116 antibody VHs whose amino acid sequences are represented by SEQ ID NOs: 175 to 186 were prepared by total synthesis or PCR amplification, the three DNA fragments were linked by assemble PCR, and then inserted into an appropriate restriction enzyme site of a pCI-OtCAG_hG4PE (R409K) or a pCI-OtCAG_hG1LALAGA vector to obtain an H chain expression vector for CD131-CD116 bispecific antibody.

The L chain expression vector and the H chain expression vector for the prepared CD131-CD116 bispecific antibody were transfected by the following method, and a CD131-CD116 bispecific antibody were expressed and purified.

The L chain expression vector and the H chain expression vector for the CD131-CD116 bispecific antibody were co-transfected into Expi293 cells using an Expi293 (trademark) Expression System (manufactured by Thermo Fisher Scientific), and after 16 hours, a Transfection Enhancer was added to express the antibody in a transient expression system.

The culture supernatant was collected 3 days to 5 days after vector introduction, filtered with a membrane filter (manufactured by MILLIPORE) having a pore diameter of 0.22 μm, and then the antibody was affinity purified using a Protein A resin (MabSelect, manufactured by GE Healthcare). D-PBS(-) was used as a washing liquid. The antibody adsorbed to the Protein A was eluted by 20 mM sodium citrate and 50 mM NaCl buffer solution (pH 3.4) and collected into a tube containing a 1M sodium phosphate buffer solution (pH 7.0).

Next, an eluate was replaced with D-PBS(-) using NAP-25 (manufactured by GE Healthcare), followed by filtration sterilization using a membrane filter Millex-Gv (manufactured by Millipore Inc.) having a pore diameter of 0.22 μm.

A concentration of the obtained CD131-CD116 bispecific antibody was calculated by measuring an absorbance at a wavelength of 280 nm and using an absorbance coefficient estimated from the amino acid sequence of each antibody. In order to analyze an influence of the presence or absence of an Fc region of the obtained CD131-CD116 bispecific antibody on agonist activity, a bispecific antibody whose Fc region is wild-type IgG1 was treated with an enzyme IdeS (manufactured by Promega) according to the attached protocol, and a bispecific antibody with an Fc region removed was prepared by performing size exclusion chromatography using a Superdex200 increase column (manufactured by GE Healthcare).

(2) Binding Activity Analysis of CD131-CD116 Bispecific Antibody

An antigen-binding activity of the CD131-CD116 bispecific antibody prepared above was analyzed by Enzyme-Linked Immuno Sorbent Assay (ELISA).

The human CD131 or CD116 soluble antigen (His-tag form) prepared in Example 1 and prepared at 5 μg/mL in D-PBS(-) (manufactured by Nacalai Tesque, Inc.) was dispensed into a 96-well or 384-well ELISA plate (MAX-ISORP NUNC-IMMNO PLATE, manufactured by Thermo Fisher Scientific) at 50 μL/well or 25 μL/well, followed by allowing to stand at 4° C. overnight for adsorption and then washing 2 times to 3 times with PBS, and 1% BSA-PBS (manufactured by Nacalai Tesque, Inc.) was dispensed thereto at 100 μL/well or 50 μL/well, followed by allowing to stand at room temperature for 1 hour for blocking. Next, the CD131-CD116 bispecific antibody solution was dispensed thereto at 50 μL/well or 25 μL/well, followed by allowing to stand at room temperature for 1 hour. The plate was washed 3 times with PBST, and then a peroxidase labeled Goat Anti-Human IgG, Fc γ-fragment specific antibody (Cat #109-035-008, manufactured by Jackson ImmunoResearch, Inc.) diluted with 1% BSA-PBS was dispensed at 50 μL/well or 25 μL/well, followed by allowing to stand at room temperature for 1 hour. The plate was washed 3 times with PBST, an ABTS (2,2'-Azino-bis(3-ethylbenzothiazoline-6-sulfonic Acid, manufactured by Wako, Cat #016-08521) substrate solution or a TMB substrate solution (manufactured by Thermo Fisher Scientific) was added thereto at 50 μL/well or 25 μL/well to develop color, and when appropriate color development was obtained, the color development was stopped by adding an equal amount of 1% SDS solution or 0.5 mol/L sulfuric acid, and then an absorbance (415 nm to 490 nm) at a sample wavelength of 415 nm and a reference wavelength of 490 nm or an absorbance (450 nm to 570 nm) at a sample wavelength of 450 nm and a reference wavelength of 570 nm was measured using a plate reader (Spectra Max manufactured by Molecular Devices, or SPARK 10M manufactured by TECAN).

As a result, it was confirmed that the CD131-CD116 bispecific antibody binds to human CD131 and CD116.

(3) Agonist Activity Analysis of CD131-CD116 Bispecific Antibody

The 7 types of CD131-CD116 bispecific antibodies (GM398, GM408, GM413, GM435, GM463, GM464, GM466, and constant regions all using IgG4PE R409K) prepared as described above were analyzed in the same manner as in Example 3-(2). The results are shown in FIG. 5.

Figure 5:
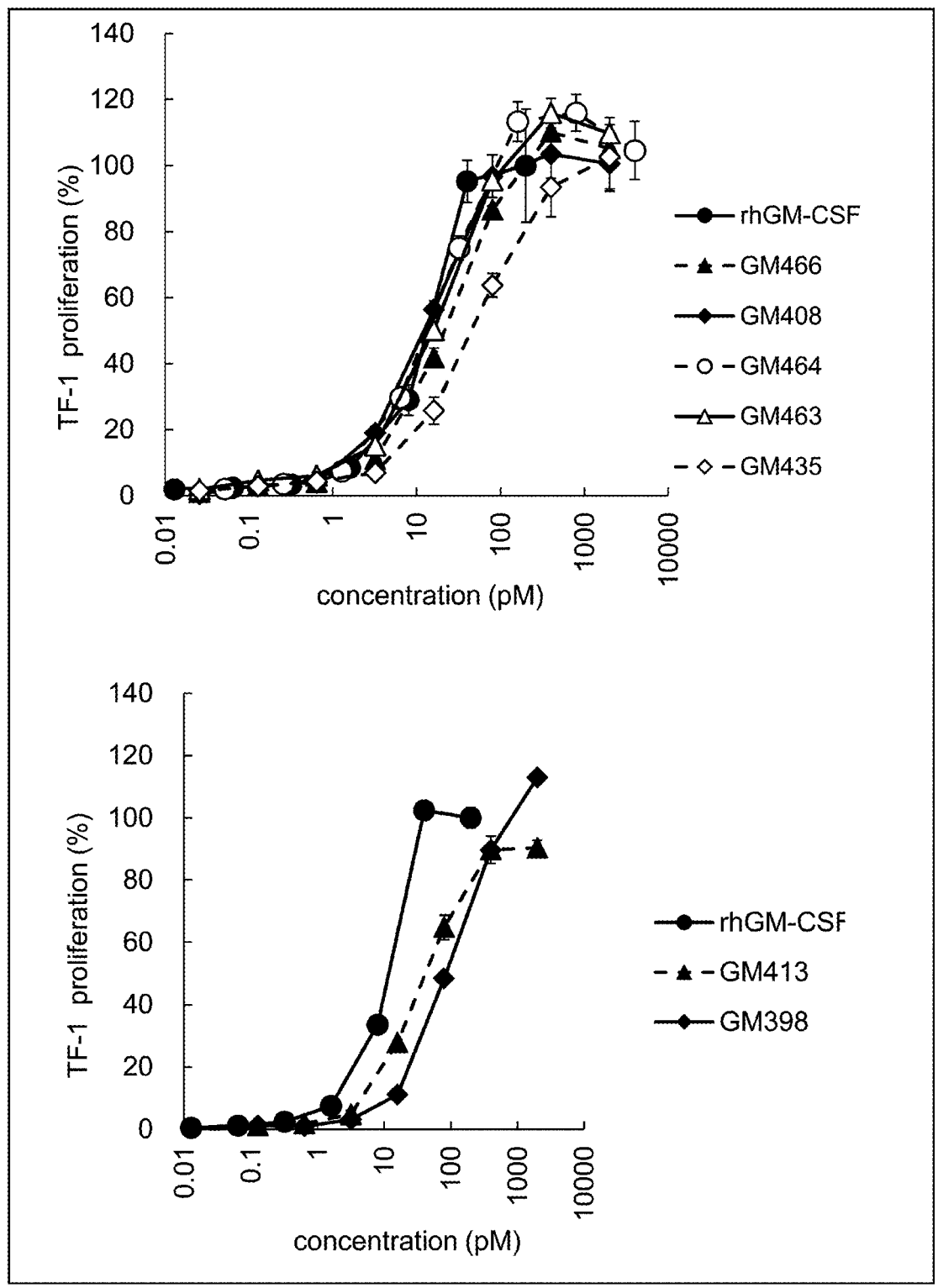
FIG. 5 shows a GM-CSF receptor agonist activity of the CD131-CD116 bispecific antibody to TF-1 cells, in which the agonist activity is shown as a TF-1 cell proliferation ratio, where an activity when 200 pM of recombinant human GM-CSF (rhGM-CSF) is added is taken as 100%, IgG4PE R409K is used for all constant regions, and a horizontal axis represents a concentration of the antibody.
Figure 6:
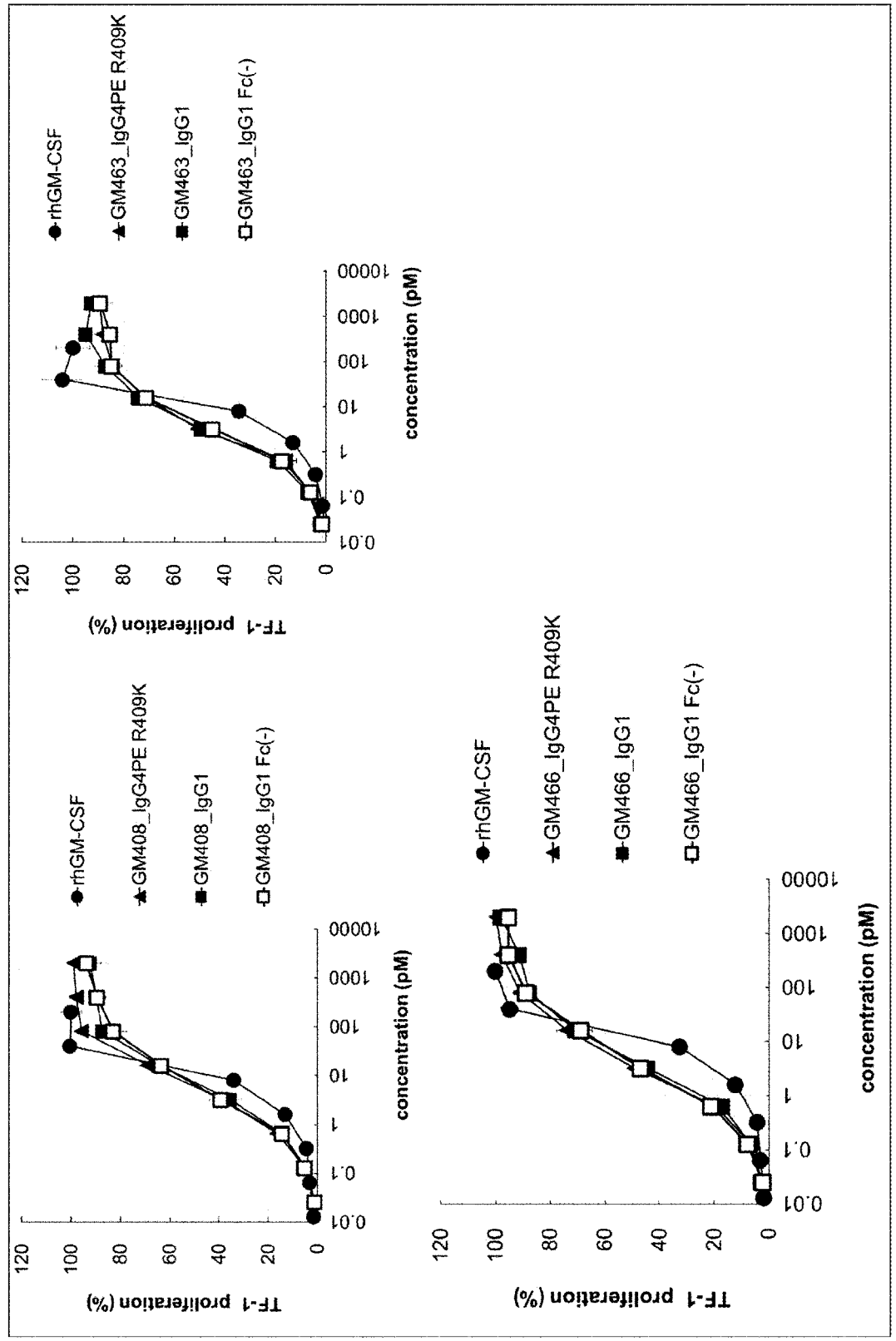
FIG. 6 shows a GM-CSF receptor agonist activity of the CD131-CD116 bispecific antibody with a mutation inserted in an Fc region to TF-1 cells, the agonist activity is shown as a TF-1 cell proliferation ratio, where an activity when 200 pM of recombinant human GM-CSF (rhGM-CSF) is added is taken as 100% (mean value±standard deviation of n=3), and a horizontal axis represents a concentration of the antibody.
Figure 7:
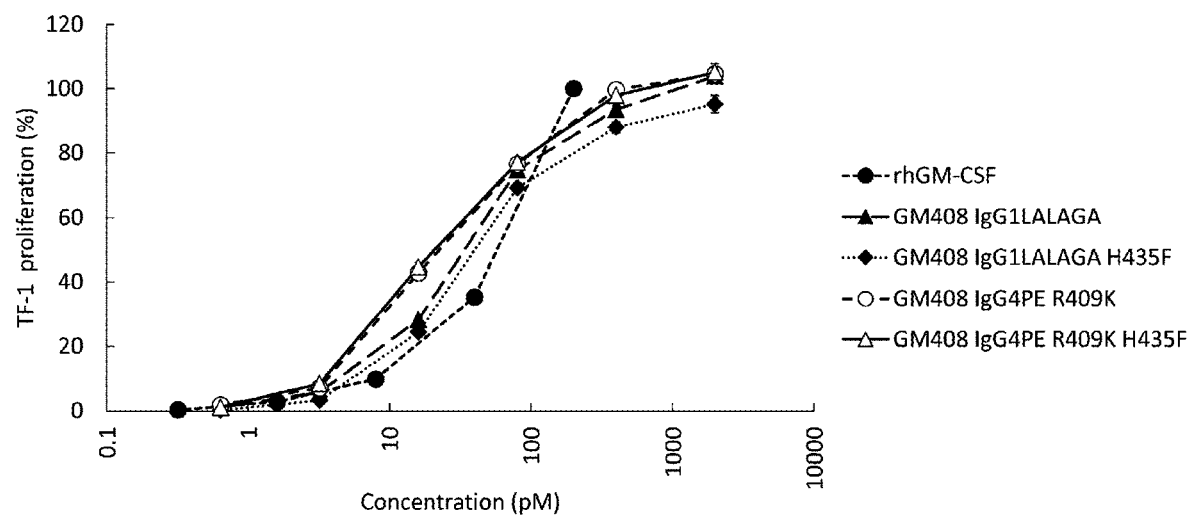
FIG. 7 shows a GM-CSF receptor agonist activity of the CD131-CD116 bispecific antibody with a mutation inserted in an Fc region to TF-1 cells, in which the agonist activity is shown as a TF-1 cell proliferation ratio, where an activity when 200 pM of recombinant human GM-CSF (rhGM-CSF) is added is taken as 100%, a horizontal axis represents a concentration of the antibody.

As shown in FIG. 5, all CD131-CD116 bispecific antibodies exhibited agonist activity comparable to that of a recombinant human GM-CSF. As shown in FIG. 6, when analyzing the influence of the presence or absence of an Fc region on agonist activity for the three types of bispecific antibodies (GM408, GM463, and GM466), it was found that the agonist activity was not affected by the presence or absence of the Fc region. Further, as shown in FIG. 7, it was confirmed that the agonist activity was not affected by introduction of mutations into the Fc region.

It was found that, in Example 4 (1), 43 types of CD131-CD116 bispecific antibodies each having a different VH sequence of the anti-CD116 antibody were prepared in combination with 131-16 (the amino acid sequence of the VH is represented by SEQ ID NO: 23, and the amino acid sequence of the VL is represented by SEQ ID NO: 24), CD131-CD116 bispecific antibodies each having a different VH sequence of the anti-CD116 antibody were prepared in combination with 131-B2 (the amino acid sequence of the VH is represented by SEQ ID NO: 29, and the amino acid sequence of the VL is represented by SEQ ID NO: 30), and the agonist activities thereof were analyzed, and as a result, the above 7 types of bispecific antibodies showed particularly high agonist activity.

(4) Agonist Activity of CD131-CD116 Bispecific Antibody to Human CD14-Positive Monocytes Human monocytes are differentiated into macrophages in vitro by being cultured with addition of a recombinant human GM-CSF, and during this process, expression of CD14, which is a marker molecule for monocytes, decreases, and expression of CD206, which is a marker molecule for macrophages, increases. Therefore, the agonist activity of the CD131-CD116 bispecific antibody to human monocytes was evaluated using changes in CD206 expression accompanying differentiation of monocytes into macrophages as an indicator. In addition, evaluation was performed by observing cell morphology.

The present evaluation was conducted on the 7 types of CD131-CD116 bispecific antibodies (GM398, GM408, GM413, GM435, GM463, GM464, GM466, constant regions all using IgG4PE R409K) whose agonist activity was evaluated in Example 4 (3).

Human CD14-positive monocytes were prepared from frozen human peripheral blood mononuclear cells (All Cells) using human CD14 microbeads (Miltenyi) and an LS Column (Miltenyi Biotec). The prepared CD14-positive monocytes were prepared to $1.6 \times 10^6$ cells/mL with a culture medium [RPMI 1640 (Nacalai tesque)+10% FBS+1% Penicillin-Streptomycin, Mixed Solution (nacalai que)], and seeded on a 96-well flat bottom plate (Nunc) under conditions of 50 µL/well.

The CD131-CD116 bispecific antibody (GM464) prepared in a medium to a final concentration of 4000 pM, 800 pM, 160 pM, 32 pM, 6.4 pM, and 1.28 pM, the CD131-CD116 bispecific antibodies (GM398, GM408, GM413, GM435, GM463, GM466, constant regions all using IgG4PE R409K) prepared in a medium to a final concentration of 2000 pM, 400 pM, 80 pM, 16 pM, 3.2 pM, and 0.64 pM, and a recombinant human GM-CSF (R&D Systems) were added thereto at 50 µL/well, followed by co-culturing with CD14-positive monocytes for 7 days under conditions of 37° C. and 5% $CO_2$.

After 7 days, the morphology of the cells cultured with the CD131-CD116 bispecific antibody or the recombinant human GM-CSF at each concentration for 7 days was photographed and observed using an EVOS XL Core Imaging System (Thermo Fisher Scientific).

As a result, the morphology of the cells co-cultured with the CD131-CD116 bispecific antibody or the recombinant human GM-CSF was found to be similar. The size of the cells increased depending on the concentration of the CD131-CD116 bispecific antibody or the recombinant human GM-CSF, and the number of cells per well increased.

After co-culture, the cells attached to the bottom surface of the plate were peeled and collected. The collected cells were subjected to FcR blocking using an FcR Blocking Reagent, human (Miltenyi Biotec). Thereafter, each molecule on the cell surface was stained with a fluorescently labeled anti-human CD14 antibody (BioLegend) or anti-human CD206 antibody (BD Bioscience), and a fluorescence intensity was measured using FACSCanto II (BD Bioscience). The results are shown in FIG. 8.

Figure 8:
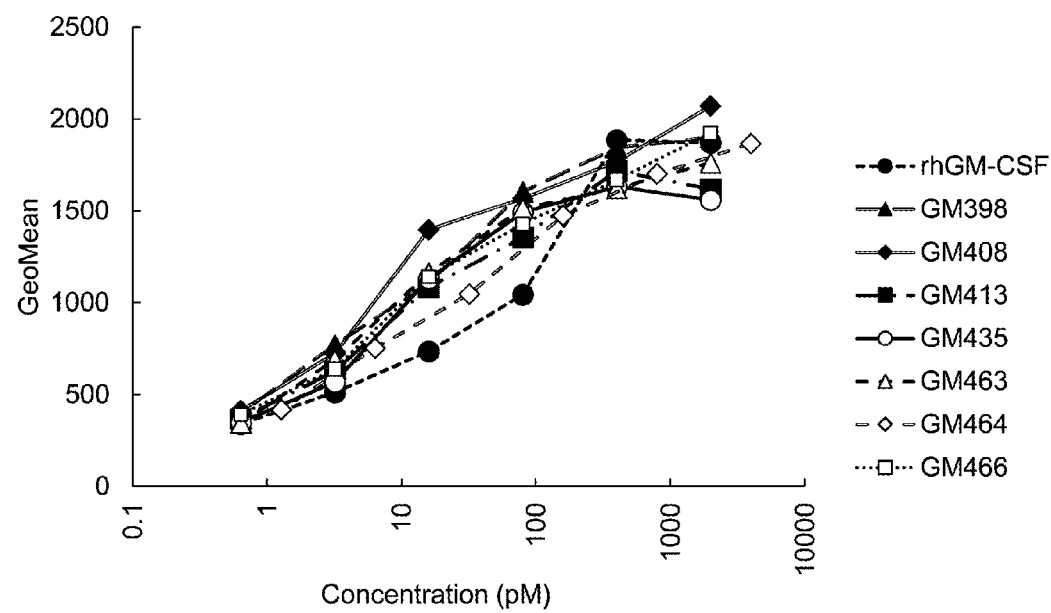
FIG. 8 shows an agonist activity of the CD131-CD116 bispecific antibody to human CD14-positive monocytes, and is a diagram showing changes in expression of CD206 on surfaces of the human CD14-positive monocytes when the CD131-CD116 bispecific antibody is added (average value of n=2), in which IgG4PE R409K is used for all constant regions, and a horizontal axis represents a concentration of the antibody.

As shown in FIG. 8, a concentration-dependent increase in expression of CD206 was observed in cells to which all CD131-CD116 bispecific antibodies and the recombinant human GM-CSF were added. The effectiveness of the CD131-CD116 bispecific antibody in increasing CD206 expression was comparable to that of the recombinant human GM-CSF.

From the above, it was confirmed that the bispecific antibody of the present invention exhibited an agonist activity equivalent to that of a GM-CSF on CD14-positive monocytes derived from human peripheral blood mononuclear cells, and induce differentiation into macrophages.

[Example 5] Analysis of Specificity of CD131-CD116 Bispecific Antibody to GM-CSF Receptor (1) Construction of Human GM-CSF Receptor Vector, IL-3 Receptor Vector, and IL-5 Receptor Expression Vector A GM-CSF receptor, an IL-3 receptor, and an IL-5 receptor have CD131 as constituent molecules of the receptor. Therefore, a specificity of the obtained CD131-CD116 bispecific antibody to the GM-CSF receptor was analyzed.

Human GM-CSF receptor, IL-3 receptor, and IL-5 receptor expression vectors were constructed by adding EcoRI and Kozak sequences at the 5' ends of nucleotide sequences encoding amino acid sequences of the following [1] to [3], adding a stop codon and a NotI sequence to the 3' ends, and inserting the nucleotide sequences into pEF6/Myc-HisC (Invitrogen) digested with EcoRI and NotI.

[1] Human GM-CSF receptor expression vector: the amino acid sequence (SEQ ID NO: 147) that connects an extracellular domain of CSF2RA (CD116, UniProt Entry. No. P15509), an extracellular domain of CSF2RB (CD131, UniProt Entry. No. P32927), and an Azami-Green sequence with a furin protein recognition sequence interposed therebetween

[2] Human IL-3 receptor expression vector: the amino acid sequence (SEQ ID NO: 148) that connects an extracellular domain of IL3RA (CD123, UniProt Entry. No. P26951), an extracellular domain of CSF2RB (CD131, UniProt Entry. No. P32927), and an Azami-Green sequence with a furin protein recognition sequence interposed therebetween

[3] Human IL-5 receptor expression vector: the amino acid sequence (SEQ ID NO: 149) that connects an extracellular domain of IL5RA (CD125, UniProt Entry. No. Q01344), an extracellular domain of CSF2RB (CD131, UniProt Entry. No. P32927), and an Azami-Green sequence with a furin protein recognition sequence interposed therebetween.

(2) Preparation of Ba/F3 Cells Expressing Human GM-CSF Receptor, IL-3 Receptor, and IL-5 Receptor The above vectors were introduced into Ba/F3 using Nucleofector 2b (Lonza) and a Cell Line Nucleofector kit V (Lonza), followed by culturing using a culture medium [5 ng/ml mouse IL-3 (Miltenyi Biotec), 10% FBS (GIBCO), 10 µg/mL Blasticidin (InvivoGen), and RPMI 1640 (nacalai tesque)].

After 4 days, in order to select cells into which a target gene was introduced, a medium exchange was performed with a drug selection medium [10% FBS (GIBCO), 50 µg/mL Gentamycin (Nacalai Tesque), 50 mg/mL G418 (nacalai tesque), RPMI1640 (nacalai tesque), hereinafter also referred to as selection medium] supplemented with a human GM-CSF (R&D Systems), human IL-3 (R&D Systems), or IL-5 (R&D Systems) at a final concentration of 10 ng/mL, followed by culturing for 2 weeks.

Next, after suspending in the selection medium, clones showing high sensitivity to each cytokine were selected by a limiting dilution method. The prepared Ba/F3 cells expressing the human GM-CSF receptor, human IL-3 receptor, or human IL-5 receptor are described as Ba/F3-hGM-CSFR, Ba/F3-hIL-3R, or Ba/F3-hIL-5R, respectively.

(3) Analysis of Specificity of CD131-CD116 Bispecific Antibody to GM-CSF Receptor The Ba/F3-hGM-CSFR, Ba/F3-hIL-3R, and Ba/F3-hIL-5R cultured using the selection medium were collected into centrifuge tubes, and after centrifugation at 1200 rpm for 3 minutes, a supernatant was removed by suction, followed by further washing 4 times with DPBS (nacalai tesque). The resultants were suspended in an assay medium [10% FBS (GIBCO), 50 µg/mL Blasticidin (InvivoGen), RPMI1640 (nacalai tesque)] at 5.0×10+ cells/mL, and seeded on a 96-well plate at 80 µL/well.

Thereafter, a CD131-CD116 bispecific antibody, a recombinant human GM-CSF (R & D Systems), a recombinant human IL-3 (R & D Systems), or a recombinant human IL-5 (R & D Systems) was prepared using a medium at 5 times the final concentration, and added at 20 µL/well, followed by allowing to stand for 3 days under conditions of 37° C. and 5% $CO_2$.

After 3 days, a luminescence reagent CellTiter-Glo2.0 (Promega) was added at 100 µL/well, and then a luminescence intensity due to an ATP luciferase reaction was measured using a microplate reader ARVO (PerkinElmer). A proliferation ratio by each CD131-CD116 bispecific antibody sample was calculated with an average value of luminescence of a group to which 1 nM of recombinant human GM-CSF, IL-3, or IL-5 was added as 100%. The results are shown in FIGS. 9A to 9C.

Figure 9A:
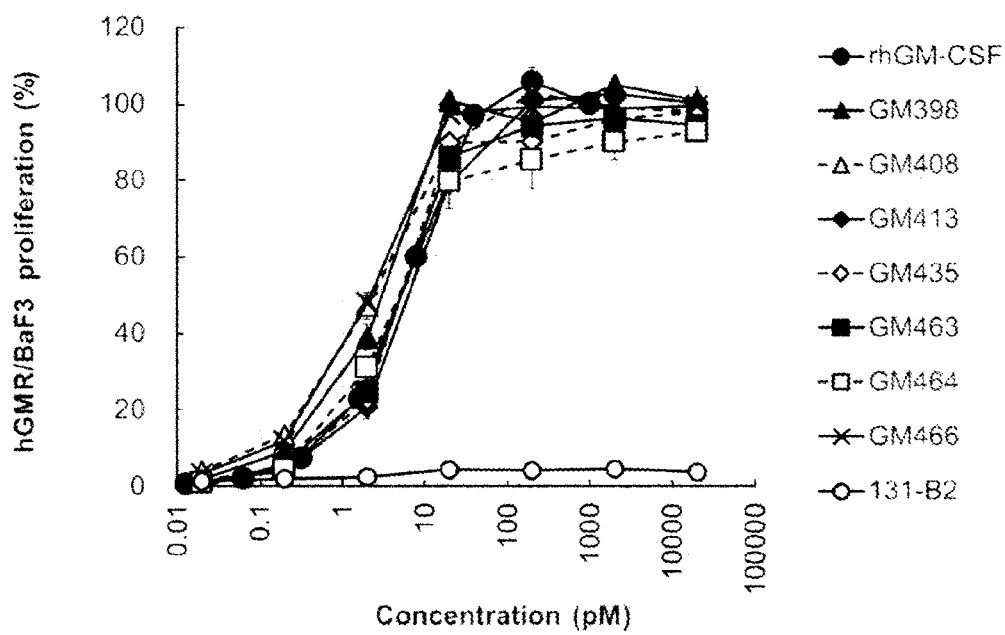
FIGS. 9A, 9B and 9C show specificity of the agonist activity exhibited by the CD131-CD116 bispecific antibody to GM-CSF receptors.
Figure 9B:
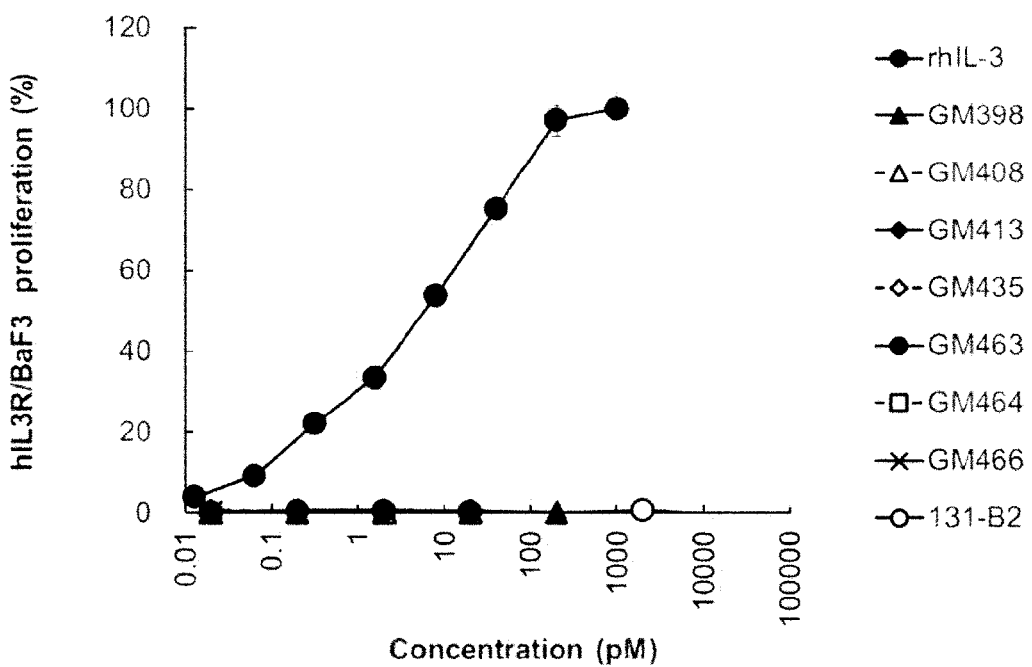
Figure 9C:
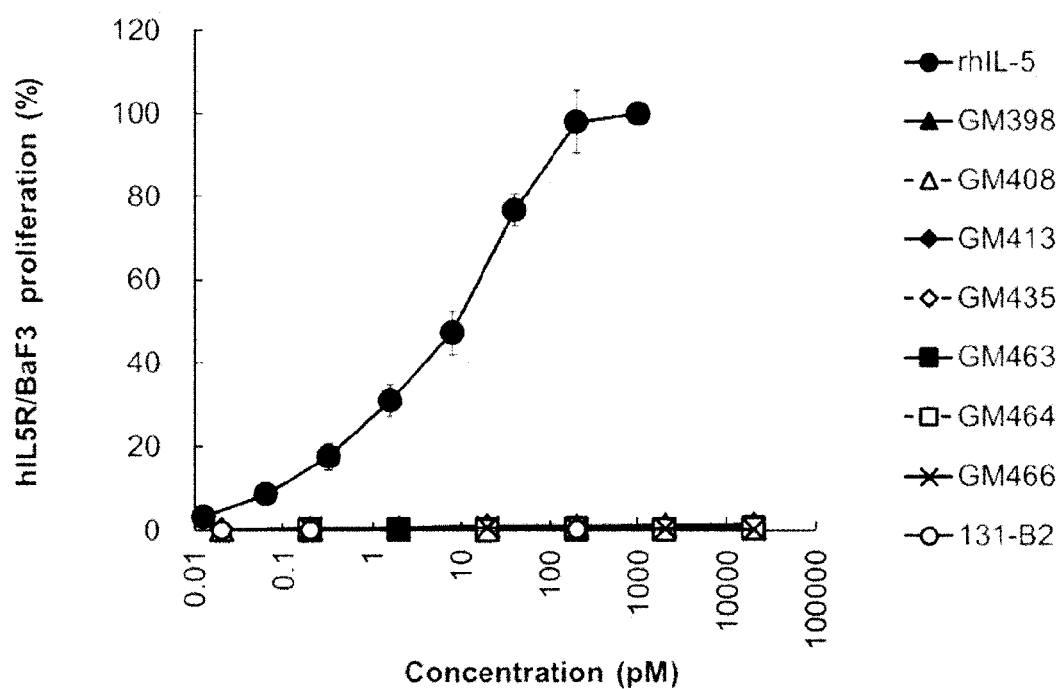

As shown in FIGS. 9A to 9C, the CD131-CD116 bispecific antibody showed a cell proliferation activity only to the Ba/F3 expressing a human GM-CSF receptor, and did not show the cell proliferation activity to the Ba/F3 expressing a human IL-3 receptor or a IL-5 receptor. Therefore, it was confirmed that the CD131-CD116 bispecific antibody exhibited an agonist activity specifically for the GM-CSF receptor.

[Example 6] Agonist Activity Analysis of CD131-CD116 Bispecific Antibody in Presence of Anti-GM-CSF Neutralizing Antibody Agonist activities of the three types of CD131-CD116 bispecific antibodies whose agonist activity was analyzed in Example 5 were analyzed in the presence of a GM-CSF neutralizing antibody. As the GM-CSF neutralizing antibody, a goat anti-human GM-CSF polyclonal antibody (R&D) whose GM-CSF neutralizing activity was reported in the literature [Protein Eng Des Sel., 28, 461 (2015)] was used.

In the same manner as in Example 3, TF-1 cells were washed, then suspended in a Macrophage-SFM medium (GIBCO) at 3.3×10⁵ cells/mL, and dispensed into a 96-well plate (Greiner) at 60 µL per well, 2.0×10+ cells/well.

The recombinant GM-CSF and the CD131-CD116 bispecific antibody were diluted to 100 pM in a Macrophage-SFM medium and added at 20 L/well. The GM-CSF neutralizing antibody was diluted to 1000 nM in a Macrophage-SFM medium, and a dilution series thereof was prepared by 10-fold dilution and added at 20 µL/well.

After allowing to stand for 3 days under conditions of 37° C. and 5% $CO_2$, a luminescence reagent CellTiter-Glo2.0 (Promega) was added at 100 µL/well, and a luminescence intensity due to an ATP luciferase reaction was measured using a microplate reader ARVO (PerkinElmer). A proliferation ratio was calculated when the GM-CSF neutralizing antibody was added at each concentration, with an average value of luminescence of a group to which the GM-CSF neutralizing antibody was not added as 100%. The results are shown in FIG. 10.

Figure 10:
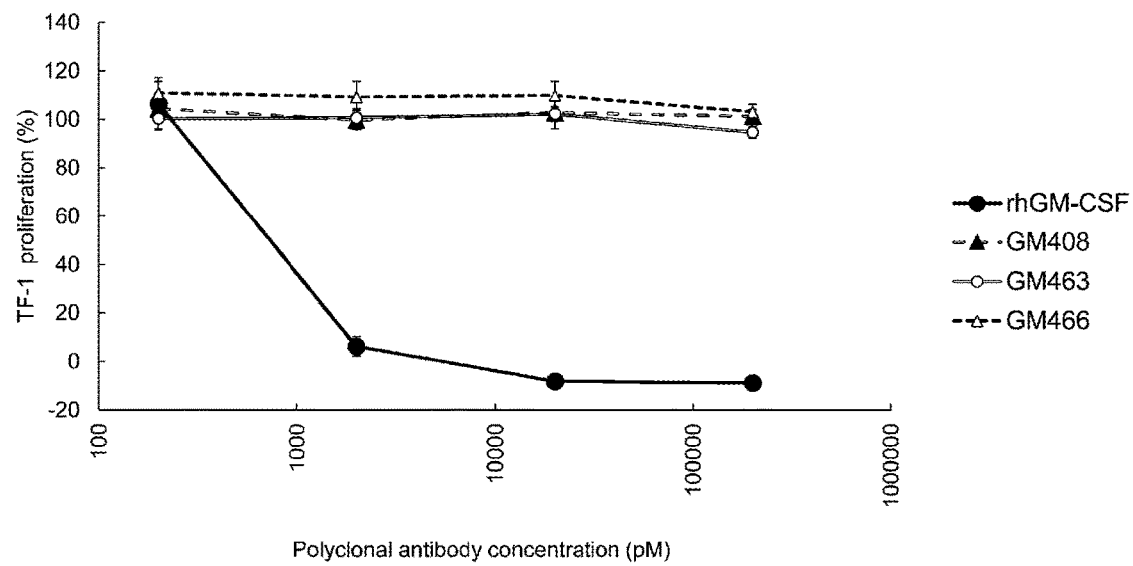
FIG. 10 shows the agonist activity of the CD131-CD116 bispecific antibody in the presence of a GM-CSF neutralizing antibody (mean value±standard deviation of n=3), in which IgG4PE R409K is used for all constant regions, and a horizontal axis represents a concentration of the antibody.

As a result of the analysis, cell proliferation induced by the recombinant GM-CSF was inhibited in an antibody concentration-dependent manner of the GM-CSF neutralizing antibody, and as shown in FIG. 10, cell proliferation induced by the CD131-CD116 bispecific antibody of the present invention was not inhibited in the presence of GM-CSF neutralizing antibody at any concentration. Therefore, it was confirmed that the CD131-CD116 bispecific antibody of the present invention has a GM-CSF receptor agonist activity even in the presence of a GM-CSF neutralizing antibody.

[Example 7] Preparation and Activity Evaluation of Bispecific Antibody Binding to CD131 and CD116

(1) Acquisition of Anti-CD116 Monoclonal Antibody Using Next Generation Sequencing System Sequence analysis was performed using a DNA prepared from *Escherichia coli* obtained by infecting TG1 with the concentrated phage in Example 2-(6) in an Ion S5 (trademark) system (manufactured by Thermo Fisher Scientific), and the amino acid sequences represented by SEQ ID NOs: 190 to 199 were selected as amino acid sequences of the concentrated antibody.

(2) Acquisition of Anti-CD116 Monoclonal Antibody by Affinity Maturation of Anti-CD116 Antibody An anti-CD116 antibody obtained by modifying amino acid sequences of CDRs 1 to 3 of an anti-CD116 clone VH of GM-408 was screened using a phage display method by Abwiz Bio Inc. Amino acid sequence information of the obtained antibody was analyzed, and the amino acid sequences represented by SEQ ID NOs: 200 to 209 were selected as amino acid sequences of the antibody.

(3) Preparation of Bispecific Antibody Binding to CD131 and CD116

A bispecific antibody expression vector having the anti-CD116 antibody sequence and anti-CD131 antibody sequence, which are obtained in Example 7-(1) and 7-(2), was prepared.

A structure of the bispecific antibody had an N-terminus type structure shown in FIG. 4A, and the bispecific antibody was a CD131-CD116 bispecific antibody in which the VH1 was a VH of anti-CD131 antibody (an amino acid sequence thereof is represented by SEQ ID NO: 29), the CH1 was a CH1 of a human IgG4 (an amino acid sequence thereof is represented by SEQ ID NO: 144), the VH2 was a VH of an anti-CD116 antibody, and a constant region contained a constant region sequence of a human antibody obtained by adding an amino acid residue substitution of H435F as represented by the EU index to human IgG4PE R409K (an amino acid sequence thereof is represented by SEQ ID NO: 155). The light chain was the same as that of the GM408.

As the L chain expression vector, a pCI-OtCMCMV_hK vector having a signal sequence and a human L chain (K-chain) constant region sequence was used. As the H chain expression vector, a pcDNA3.4 vector (manufactured by Thermo Fisher Scientific) having a signal sequence and human IgG4PE R409K and H435F mutations was used. The prepared L chain expression vector and H chain expression vector of the CD131-CD116 bispecific antibody were transfected in the same manner as in Example 4, followed by expressing and purifying to obtain each CD131-CD116 bispecific antibody.

(4) Analysis of Binding Activity of CD131-CD116 Bispecific Antibody to CD116

An affinity of the clone obtained in Example 7-(2) to CD116 was evaluated using a Biacore T200 system (Cytiva). As a Running buffer, an HBS-EP+ buffer (Cytiva) was used. An anti-human Fc antibody was immobilized on the surface of a CM5 Sensor chip (Cytiva) using an Anti-human antibody capture kit and an Amine Coupling Kit (Cytiva). At this time, each antibody was also immobilized on a control flow cell.

The binding of the CD131-CD116 bispecific antibody to a CD116 protein was evaluated using a chip immobilized with an Anti-human Fc. In the measurement, first, the CD131-CD116 bispecific antibody was captured on the chip by adding the CD131-CD116 bispecific antibody diluted to 10 nM for 90 seconds (flow rate: 10 µL/min). Next, the human CD116 soluble antigen (His-tag form) prepared in Example 1-(3) and diluted to 0.33 nM, 1 nM, 3 nM, 9 nM, or 27 nM was added for 120 seconds (flow rate: 30 µL/min), and measurement was performed with a dissociation time of 90 seconds (flow rate: 30 µL/min). In experiments using the monkey CD116 soluble antigen (His-tag form), the monkey CD116 soluble antigen was added at concentrations of 3 nM, 9 nM, 27 nM, 81 nM, and 243 nM.

In quantitative analysis, calculations were performed by a single cycle kinetics method using Biacore T200 Evaluation Software version 3.2 (Cytiva). The results are shown in Table 5.

TABLE 5

| | hCD116-His | | | cynoCD116-His | | |
|---|---|---|---|---|---|---|
| | ka (1/Ms) | kd (1/s) | KD (M) | ka (1/Ms) | kd (1/s) | KD (M) |
| GM408 | $2.62 \times 10^5$ | $8.99 \times 10^{-3}$ | $3.43 \times 10^{-8}$ | $2.98 \times 10^4$ | $3.22 \times 10^{-3}$ | $1.08 \times 10^{-7}$ |
| GM408_H101 | $1.51 \times 10^5$ | $8.77 \times 10^{-3}$ | $5.81 \times 10^{-8}$ | $1.29 \times 10^4$ | $2.27 \times 10^{-3}$ | $1.76 \times 10^{-7}$ |
| GM408_H102 | $1.34 \times 10^5$ | $6.52 \times 10^{-3}$ | $4.87 \times 10^{-8}$ | $1.20 \times 10^4$ | $1.60 \times 10^{-3}$ | $1.34 \times 10^{-7}$ |
| GM408_H103 | $1.16 \times 10^5$ | $6.18 \times 10^{-3}$ | $5.34 \times 10^{-8}$ | $6.46 \times 10^3$ | $4.82 \times 10^{-3}$ | $7.47 \times 10^{-7}$ |
| GM408_H104 | $2.77 \times 10^5$ | $6.52 \times 10^{-3}$ | $2.35 \times 10^{-8}$ | $3.24 \times 10^4$ | $1.85 \times 10^{-3}$ | $5.71 \times 10^{-8}$ |
| GM408_H105 | $1.63 \times 10^5$ | $6.28 \times 10^{-3}$ | $3.85 \times 10^{-8}$ | $1.51 \times 10^4$ | $1.64 \times 10^{-3}$ | $1.09 \times 10^{-7}$ |
| GM408_H301 | $9.87 \times 10^5$ | $9.14 \times 10^{-4}$ | $9.26 \times 10^{-10}$ | $7.49 \times 10^4$ | $5.10 \times 10^{-4}$ | $6.82 \times 10^{-9}$ |
| GM408_H302 | $8.53 \times 10^5$ | $1.41 \times 10^{-3}$ | $1.65 \times 10^{-9}$ | $8.09 \times 10^4$ | $3.93 \times 10^{-4}$ | $4.86 \times 10^{-9}$ |
| GM408_H303 | $6.44 \times 10^5$ | $1.31 \times 10^{-3}$ | $2.04 \times 10^{-9}$ | $4.44 \times 10^4$ | $6.19 \times 10^{-4}$ | $1.39 \times 10^{-8}$ |
| GM408_H106 | $1.91 \times 10^5$ | $7.59 \times 10^{-3}$ | $3.98 \times 10^{-8}$ | $1.32 \times 10^4$ | $2.51 \times 10^{-3}$ | $1.90 \times 10^{-7}$ |
| GM408_H107 | $9.22 \times 10^4$ | $8.68 \times 10^{-3}$ | $9.41 \times 10^{-8}$ | $6.49 \times 10^3$ | $2.36 \times 10^{-3}$ | $3.63 \times 10^{-7}$ |

As shown in Table 5, it was found that the binding activity of the GM408_H301, H302, and H303 to CD116 was better than that of the original GM408.

By using clones having high binding activity, it is expected to enhance specificity of agonist action to target cells.

(5) Agonist Activity Analysis of CD131-CD116 Bispecific Antibody

Agonist activities of the 20 types of CD131-CD116 bispecific antibodies (constant regions all used IgG4PE R409K H435F) prepared above were analyzed by static culture for 2 days in the same manner as in Example 3-(2). The results are shown in FIGS. 11 and 12.

Figure 11:
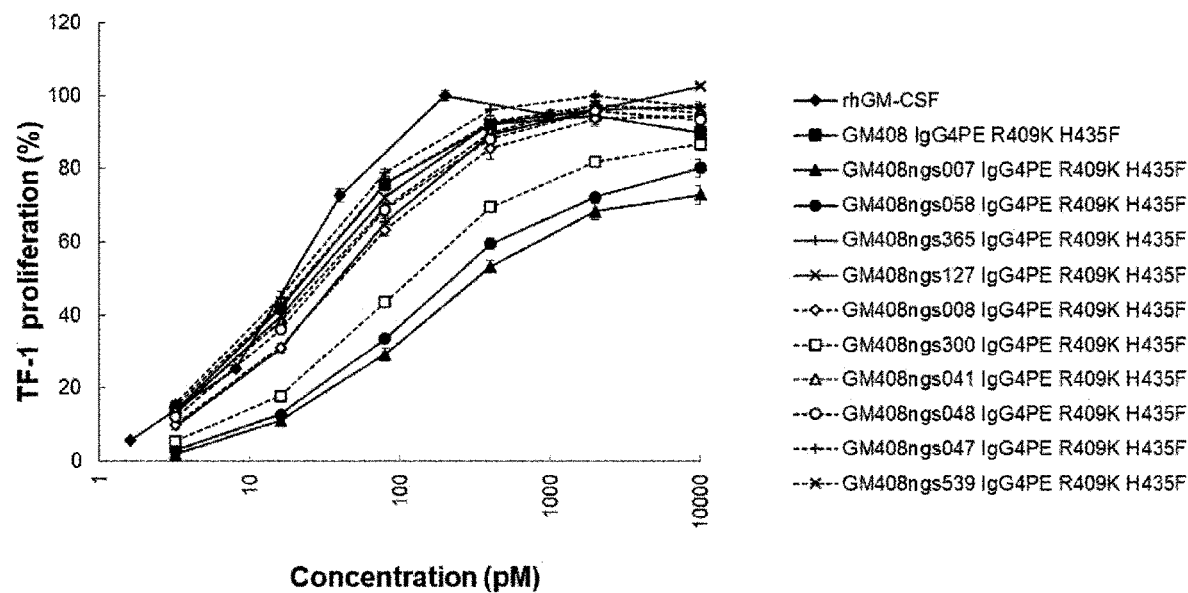
FIG. 11 shows a GM-CSF receptor agonist activity of a CD131-CD116 bispecific antibody, which is prepared from an anti-CD116 antibody obtained using a next-generation sequencing system, to TF-1 cells, in which the agonist activity is shown as a TF-1 cell proliferation ratio, where an activity when 200 pM of recombinant human GM-CSF (rhGM-CSF) is added is taken as 100% (mean value±standard deviation of n=3), and an IgG4PE R409K H435F mutant is used for all constant regions, and a horizontal axis represents a concentration of the antibody.
Figure 12:
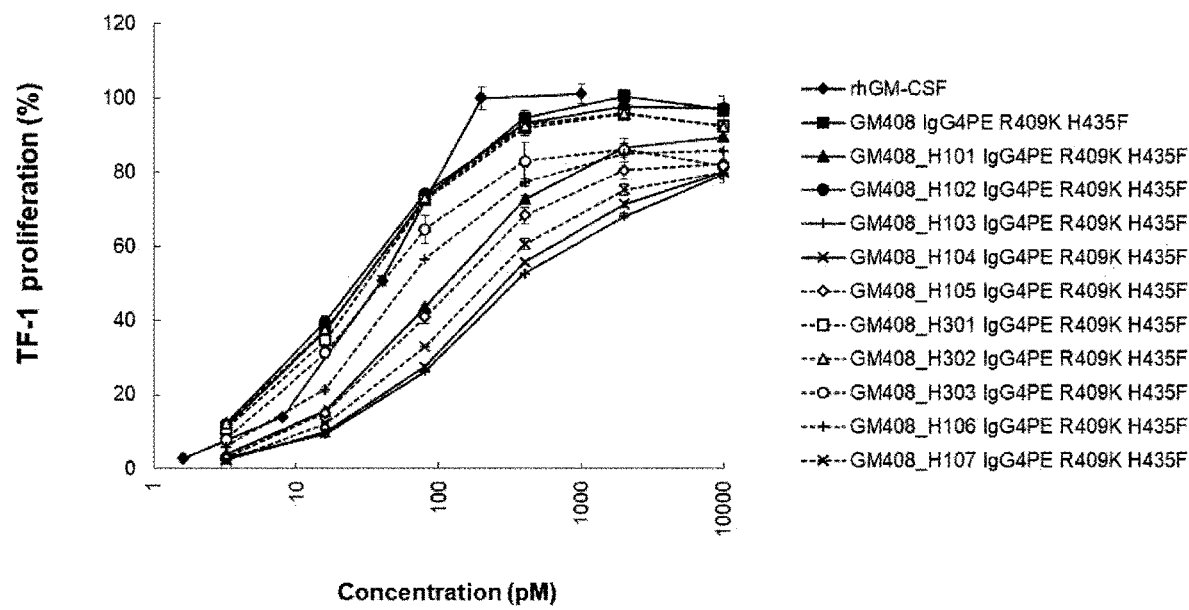
FIG. 12 shows a GM-CSF receptor agonist activity of a CD131-CD116 bispecific antibody, which is prepared from an anti-CD116 antibody obtained by affinity maturation, to TF-1 cells, in which the agonist activity is shown as a TF-1 cell proliferation ratio, where an activity when 200 pM of recombinant human GM-CSF (rhGM-CSF) is added is taken as 100% (mean value±standard deviation of n=3), and an IgG4PE R409K H435F mutant is used for all constant regions, and a horizontal axis represents a concentration of the antibody.

As shown in FIGS. 11 and 12, all CD131-CD116 bispecific antibodies exhibited agonist activity comparable to that of the recombinant human GM-CSF.

[Example 8] Preparation and Agonist Activity Analysis of CD116-CD131 Bispecific Antibody For the three types of N-terminus type CD131-CD116 bispecific antibodies (GM408, GM463, and GM466) shown in Example 4, the VH1 and the VH2 shown in FIG. 4A were replaced to prepare N-terminus type CD116-CD131 bispecific antibodies in the same manner as in Example 4 (1) (GM408 inverse, GM463 inverse, GM466 inverse, constant regions all using IgG4PE R409K). The agonist activities of the CD116-CD131 bispecific antibodies were analyzed in the same manner as in Example 3 (2). The results are shown in FIG. 13.

Figure 13:
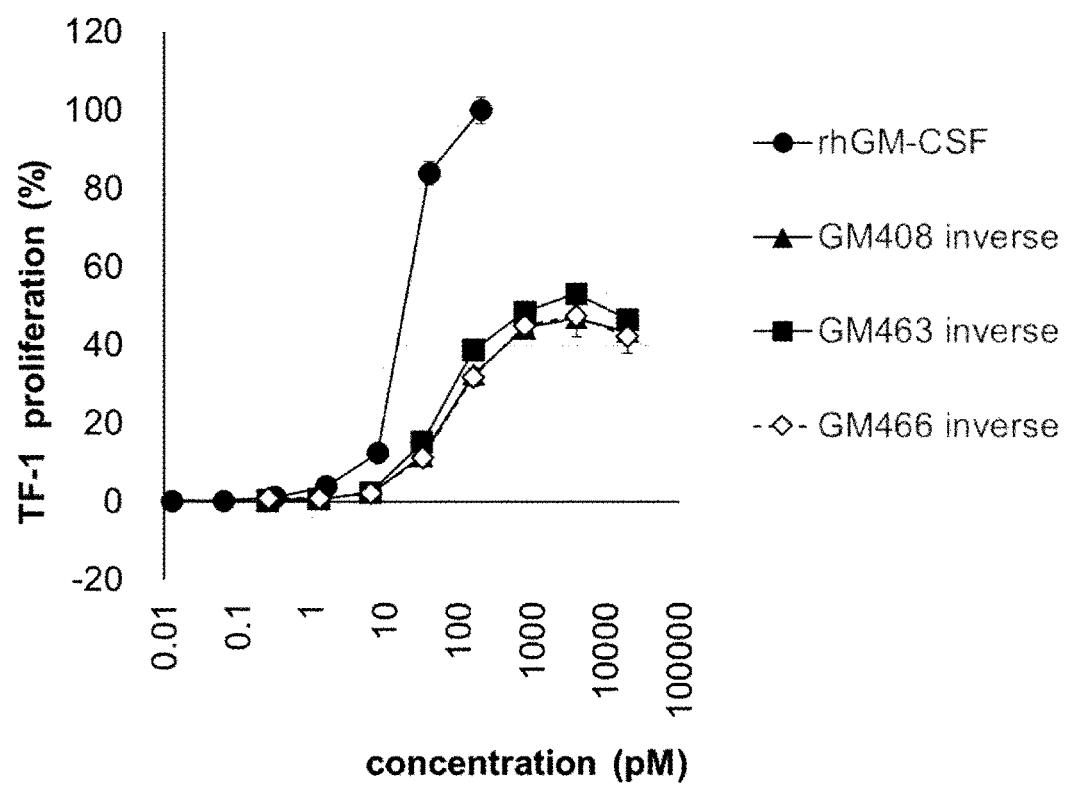
FIG. 13 shows a GM-CSF receptor agonist activity of a CD116-CD131 bispecific antibody to TF-1 cells, in which the agonist activity is shown as a TF-1 cell proliferation ratio, where an activity when 200 pM of recombinant human GM-CSF (rhGM-CSF) is added is taken as 100% (mean value±standard deviation of n=3), and IgG4PE R409K is used for all constant regions, and a horizontal axis represents a concentration of the antibody.

As shown in FIG. 13, all of the CD116-CD131 bispecific antibodies were confirmed to exhibit a GM-CSF receptor agonist activity.

[Example 9] Preparation and Agonist Activity Analysis of C-Terminus Type CD131-CD116 Bispecific Antibody and C-Terminus Type CD116-CD131 Bispecific Antibody Two types of C-terminus type bispecific antibodies were prepared based on the three types of N-terminus type CD131-CD116 bispecific antibodies (GM408, GM463, and GM466) shown in Example 4. As shown in FIG. 4B, C-terminus type CD131-CD116 bispecific antibodies each having a CD131-binding VH sequence in the VH1 and a CD116-binding VH sequence in the VH2 (Ct GM408, Ct GM463, Ct GM466, constant regions all using IgG4PE R409K), and C-terminus type CD116-CD131 bispecific antibodies each having a CD116-binding VH sequence in the VH1 and a CD131-binding VH sequence in the VH2 (Ct GM408 inverse, Ct GM463 inverse, Ct GM466 inverse, constant regions all using IgG4PE R409K) were prepared in the same manner as in Example 3 (2), and agonist activities thereof were analyzed. The results are shown in FIGS. 14A and 14B.

Figure 14A:
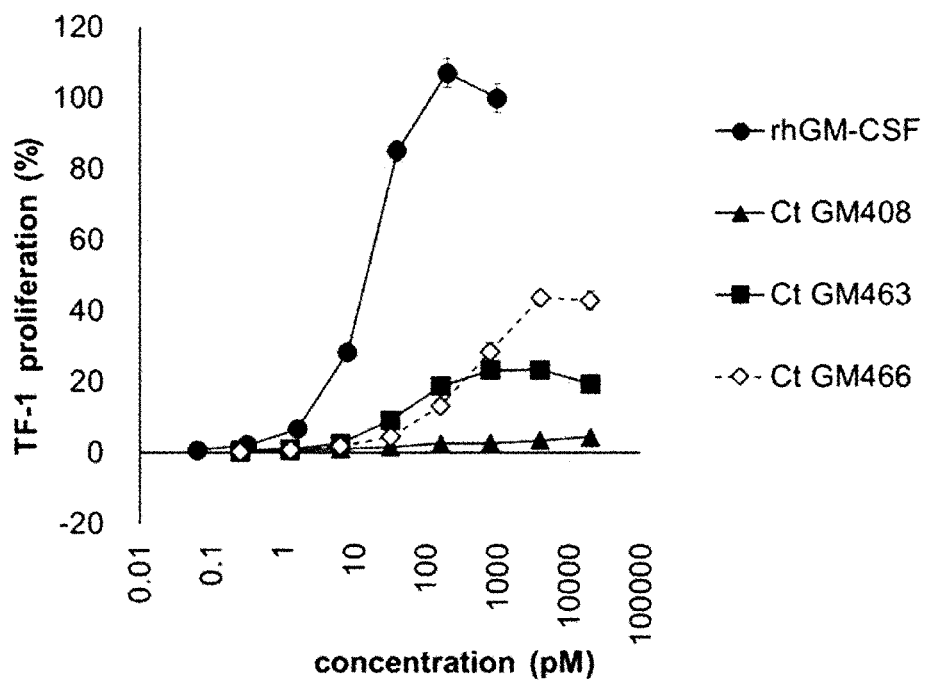
FIG. 14A shows a GM-CSF receptor agonist activity of a C-terminus type CD131-CD116 bispecific antibody to TF-1 cells.
Figure 14B:
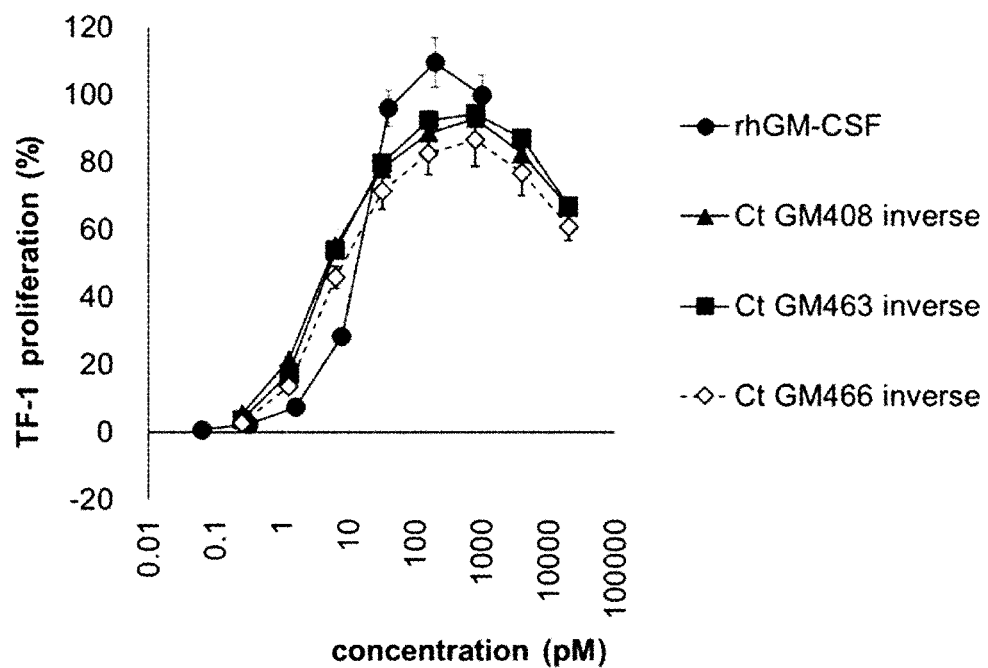
FIG. 14B shows a GM-CSF receptor agonist activity of a C-terminus type CD116-CD131 bispecific antibody to TF-1 cells, in which the agonist activity is shown as a TF-1 cell proliferation ratio, where an activity when 1000 pM of recombinant human GM-CSF (rhGM-CSF) is added is taken as 100% (mean value±standard deviation of n=3), IgG4PE R409K is used for all constant regions, and a horizontal axis represents a concentration of the antibody.

As a result, it was confirmed that the C-terminus type CD116-CD131 bispecific antibody shown in FIG. 14B exhibited a high GM-CSF receptor agonist activity as compared with the C-terminus type CD131-CD116 bispecific antibody shown in FIG. 14A.

Figure 15:
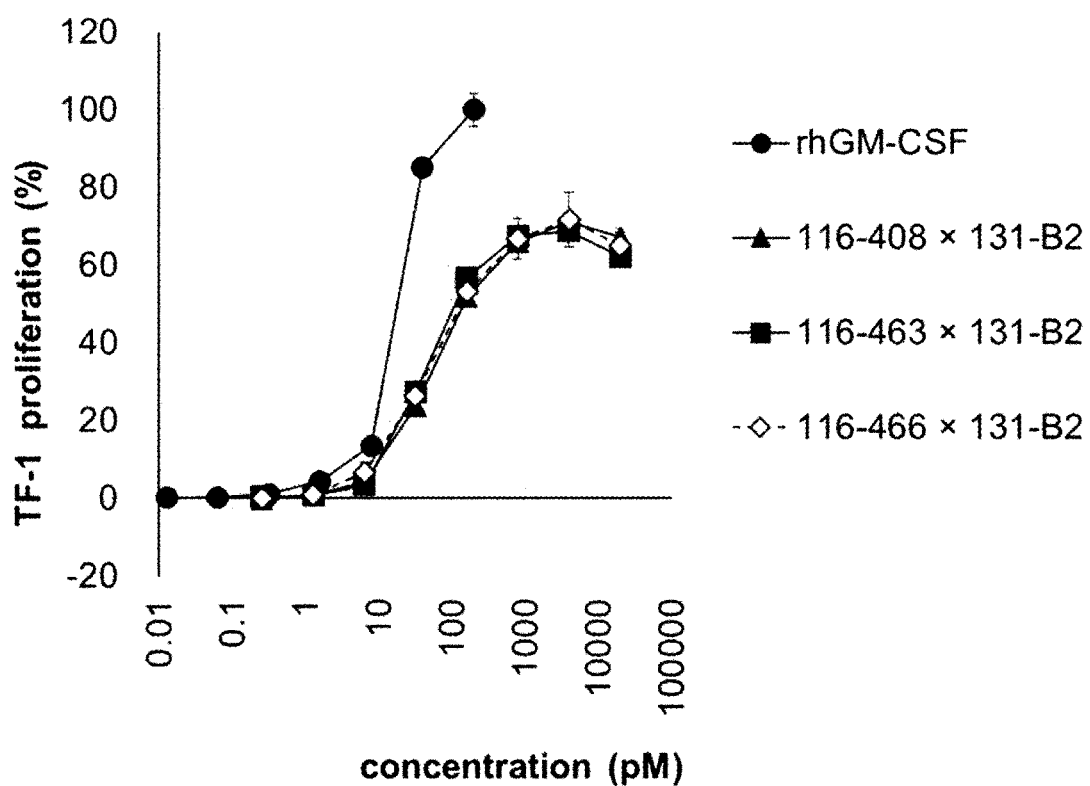
FIG. 15 shows a GM-CSF receptor agonist activity of a CD131-CD116 bispecific antibody converted to an IgG-type bispecific antibody to TF-1 cells, in which the agonist activity is shown as a TF-1 cell proliferation ratio, where an activity when 200 pM of recombinant human GM-CSF (rhGM-CSF) is added is taken as 100% (mean value±standard deviation of n=3)

[Example 10] Conversion of CD131-CD116 Bispecific Antibody to IgG-Type Bispecific Antibody and Agonist Activity Analysis The three types of N-terminus type CD131-CD116 bispecific antibodies (GM408, GM463, and GM466) shown in Example 4 were prepared in the same manner as in Example 3 (1) as the IgG-type CD131-CD116 bispecific antibody shown in FIG. 2. The agonist activity of the prepared IgG-type CD131-CD116 bispecific antibody was analyzed in the same manner as in Example 3 (2), and the results thereof were shown in FIG. 15. As a result of the analysis, it was confirmed that all of the IgG-type CD131-CD116 bispecific antibodies exhibited a GM-CSF receptor agonist activity.

[Example 11] Analysis of CD131-CD116 Bispecific Antibody Exhibiting High Activity For the CD131-CD116 bispecific antibody GM408 described in Example 4, a variant with controlled valence of anti-CD131 antibody and anti-CD116 antibody was prepared, and the influence on the GM-CSF receptor agonist activity was analyzed.

Figure 17A:
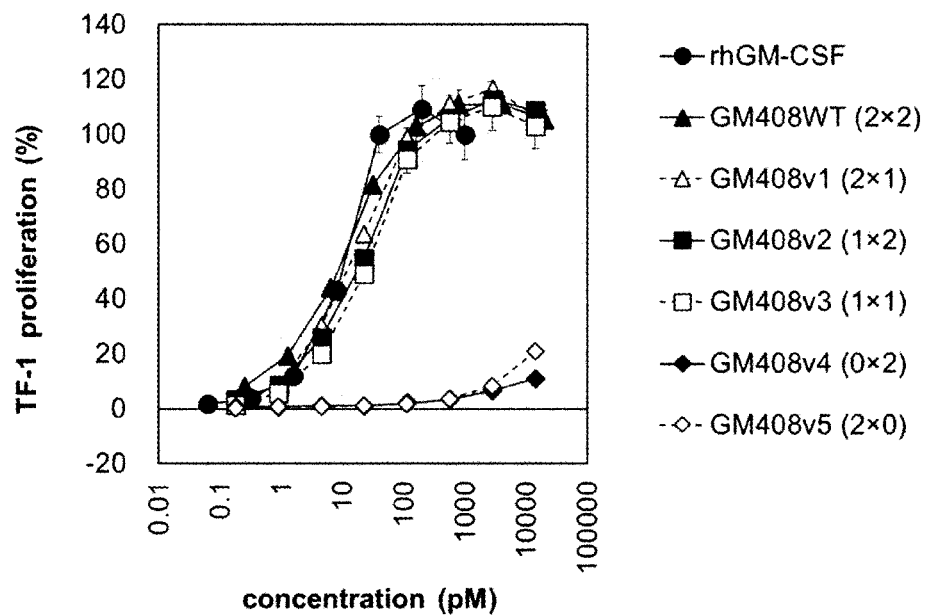
FIGS. 17A and 17B show a GM-CSF receptor agonist activity of the CD131-CD116 bispecific antibody with controlled valence shown in FIGS. 16 to TF-1 cells, in which the agonist activity is shown as a TF-1 cell proliferation ratio, where an activity when 1000 pM of recombinant human GM-CSF (rhGM-CSF) is added is taken as 100% (mean value±standard deviation of n=3)
Figure 17B:
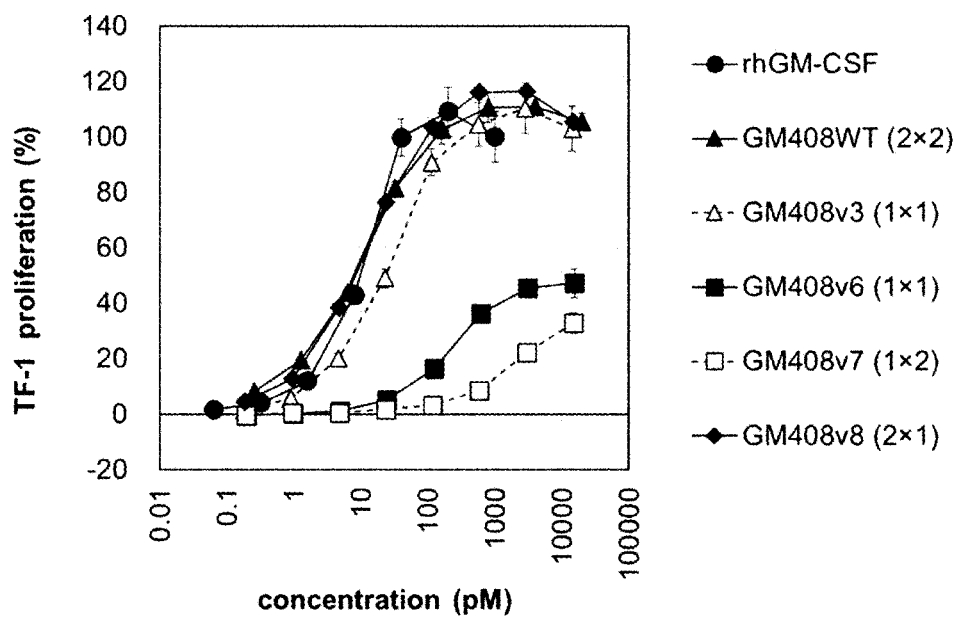

As shown in FIG. 16, each variant was prepared in the same manner as in Example 3 (1) and Example 4 (1) (constant regions all using IgG4PE R409K). For the purpose of controlling the valence of binding to CD131 and CD116, 2 amino acid mutations (D31A and Y98A, described as D31A_Y98A) were introduced into CDR1 and CDR3 of an anti-CD116 antibody 116-408 to prepare a VH whose binding activity to CD116 completely was lost. For GM408v1 (2×1), GM408v2 (1×2), GM408v3 (1×1), GM408v6 (1×1), GM408v7 (1×2), and GM408v8 (2×1), which combine two types of H chains, Knobs-into-Holes (S354C/T366W mutation in a first H chain, Y349C/T366S/L368A/Y407V/H435R/Y436F mutation in a second H chain) was used in the same manner as in Example 3 (1). At this time, since the light chain variable regions were all the same, unlike Example 3 (1), a wild-type sequence containing no mutations was used for the first H chain, the second H chain, and the L chain constant region. The agonist activity of each variant was analyzed in the same manner as in Example 3 (2). The results are shown in FIGS. 17A and 17B.

The numbers in parentheses represent (anti-CD116 antibody valence × anti-CD131 antibody valence). In addition to wild-type GM408WT (2× 2), GM408v1 (2× 1), GM408v2 (1×2) and GM408v3 (1×1), GM408v6 (1×1), GM408v7 (1×2), and GM408v8 (2×1) were confirmed to exhibit a GM-CSF receptor agonist activity. However, the GM-CSF receptor agonist activity could not be confirmed in GM408v4 (0×2) and GM408v5 (2× 0), confirming that binding to both CD116 and CD131 is important in exerting agonist activity.

[Example 12] Epitope Analysis of CD131-CD116 Bispecific Antibody

For an anti-CD116 antibody 116-408 and an anti-CD131 antibody 131-B2, which constitute the CD131-CD116 bispecific antibody described in Example 4, epitopes in the respective antigens human CD116 and human CD131 were analyzed by contracting with Integral Molecular.

By comprehensively introducing an amino acid substitution (Ala substitution) into human CD116 and CD131 and identifying an Ala substitution site where binding activities of the anti-CD116 antibody 116-408 and the anti-CD131 antibody 131-B2 were greatly reduced, epitope analysis was performed. First, expression vectors for expressing human CD116 and CD131 into which the Ala substitutions were comprehensively introduced were prepared using mammalian cell vectors.

For the human CD116, 289 amino acids of a full-length human CD116 extracellular domain were substituted, and for the human CD131, 100 amino acids corresponding to a human CD131 extracellular domain 3 were substituted (289 types of expression vectors were prepared for a human CD116 amino acid substitute and 100 types of expression vectors were prepared for a human 131 amino acid substitute).

These expression vectors were each introduced into HEK-293T cells to express mutant human CD116 or human CD131 into which the Ala substitution was introduced. Fab was prepared from the anti-CD116 antibody 116-408 and the anti-CD131 antibody 131-B2 by an enzyme treatment, prepared to 0.25 µg/mL using PBS, and allowed to react with mutant human CD116 or human CD131 expression HEK-293T at 25° C. for 30 minutes. After washing with PBS, a secondary antibody (AlexaFluor (registered trademark) 488 AffiniPure Goat Anti-Human IgG F(ab')$_2$ Fragment, manufactured by Jackson ImmunoResearch) prepared at 7.5 µg/mL with PBS was allowed to react at 25° C. for 30 minutes, and a Fab binding amount was analyzed by a flow cytometry method.

Each of the mutant human CD116 and the mutant human CD131 had an expression level of 70% or more of wild-type human CD116 and wild-type human CD131, and the Ala substitution site where the Fab binding amount was reduced to 40% or less was selected as an amino acid residue constituting the epitope. The results are shown in Table 6. As a result of the analysis, N156, K158, and T187 in the human CD116 were identified as epitopes for the anti-CD116 antibody 116-408, and W163 and R221 in the human CD131 were identified as epitopes for the anti-CD131 antibody 131-B2.

TABLE 6

| 116-408 epitope Binding Reactivity (% WT) | | 131-B2 epitope Binding Reactivity (% WT) | |
|---|---|---|---|
| Mutation | 116-408 | Mutation | 131-B2 |
| N156A | 5.8 | Mutation | 129 |
| K158A | 35.2 | D144A | 88.4 |
| T187A | 16.2 | D146A | 109.9 |
| K213A | 98.4 | H147A | −9 |
| Y248A | 78.2 | W163A | 193.5 |
| L249A | 92.4 | G198A | 96.8 |
| D250A | 95.8 | P199A | 38 |
| F251A | 99.3 | | |
| D300A | 84.8 | | |
| R302A | 93.8 | | |

[Example 13] Identification of Fc Mutation with Loss of Binding to FcRn

It has been suggested that binding between an antibody Fc region and a Neonatal Fc receptor (FcRn) is important for maintaining the half-life of antibodies in blood (Nat. Rev. Immunol., 7, 715 (2007)) and for transcytosis of antibodies from alveoli into blood (Proc Natl Acad Sci USA., 101, 9763 (2004)). Therefore, in the case of transpulmonary administration of the bispecific antibodies of the invention, the loss of binding between the CD131-CD116 bispecific antibody and FcRn improves the retention of the CD131-CD116 bispecific antibody in the alveoli, and a sustained therapeutic effect is expected. In addition, by shortening the half-life of the CD131-CD116 bispecific antibody in the blood, it is expected that the risk of unexpected side effects caused by the bispecific antibody leaking from the lungs into the systemic circulation can be reduced.

CD131-CD116 bispecific antibody mutants with various amino acid substitutions introduced into Ile253, His310, His435, and Tyr436, which are known as important residues for binding between an antibody Fc region and FcRn at pH 6.0 were prepared in the same manner as in Example 4 (1) (constant regions using IgG4PE R409K and IgG1 LALAGA and being represented by SEQ ID NOs: 147 to 159 and SEQ ID NOs: 160 to 172, respectively). The human FcRn binding activity of the prepared CD131-CD116 bispecific antibody mutant was analyzed by a surface plasmon resonance (SPR) method as described below.

Biacore T100 and T200 (manufactured by GE Healthcare) were used as measurement devices. Using an Amine Coupling Kit (Manufactured by GE Healthcare), an Anti-His Antibody (BSA-Free, manufactured by QIAGEN) diluted to 20 μg/mL with Acetate 4.5 (manufactured by GE Healthcare) was immobilized on a CM5 sensor chip according to the attached document. Human FcRn (in-house preparation) was diluted to 10 μg/mL with HBS-EP+ (pH 7.4, manufactured by GE Healthcare) and added for 120 seconds at a flow rate of 10 μL/min.

Next, a CD131-CD116 bispecific antibody mutant (diluted with an HBS-EP+ solution of pH 6.0) diluted 2 times in 5 serial dilutions from 1000 nM was added at a flow rate of 30 μL/min as an analyte, and a binding reaction with FcRn was measured for 60 seconds, and a dissociation reaction was measured for 150 seconds. The measurement was performed using an equilibrium value analysis method, and the obtained sensorgram was analyzed using Bia Evaluation Software (manufactured by GE Healthcare). The results are shown in FIGS. 18A to 18C, FIG. 19, and FIG. 20.

Figure 18A:
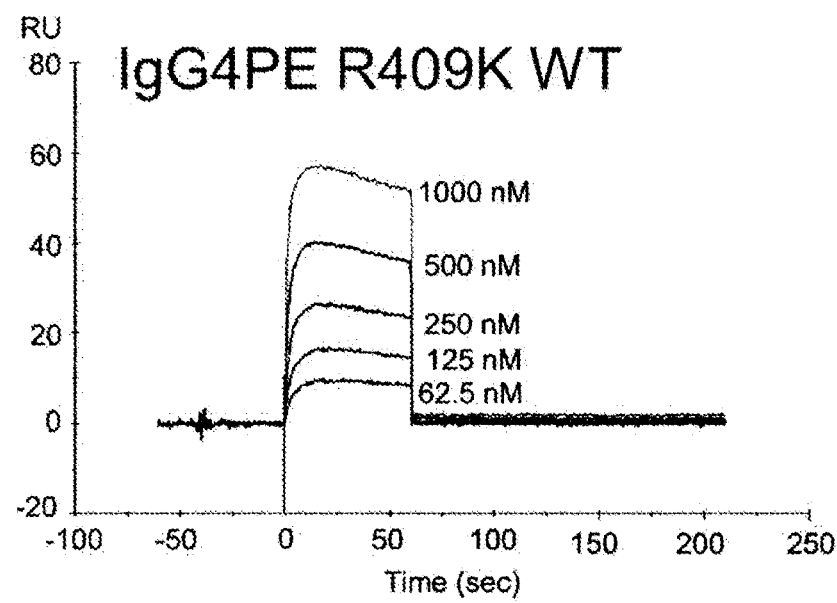
FIGS. 18A, 18B and 18C show results of analysis of binding activity, to human FcRn, of a CD131-CD116 bispecific antibody with an amino acid mutation inserted in an Fc region that loses binding to FcRn.
Figure 18B:
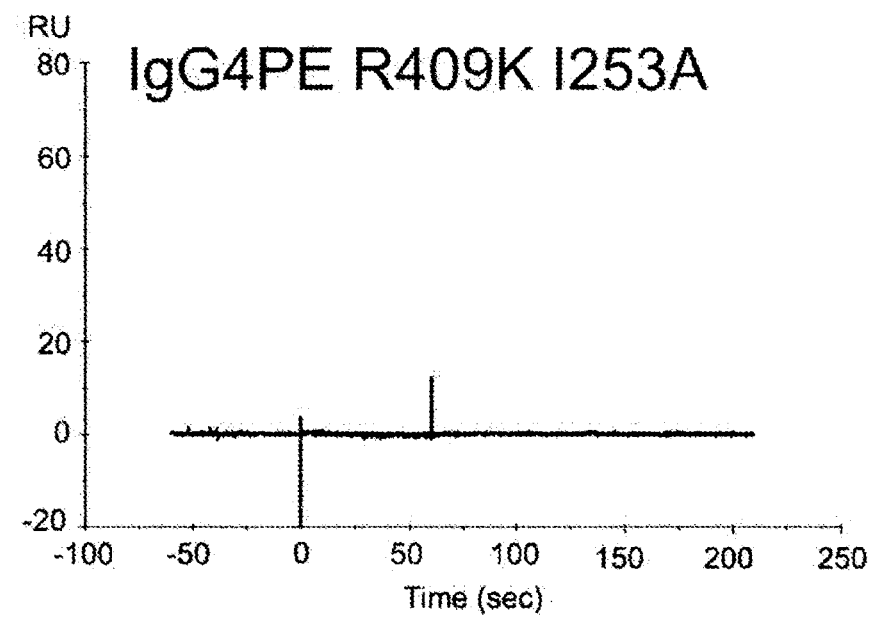
Figure 18C:
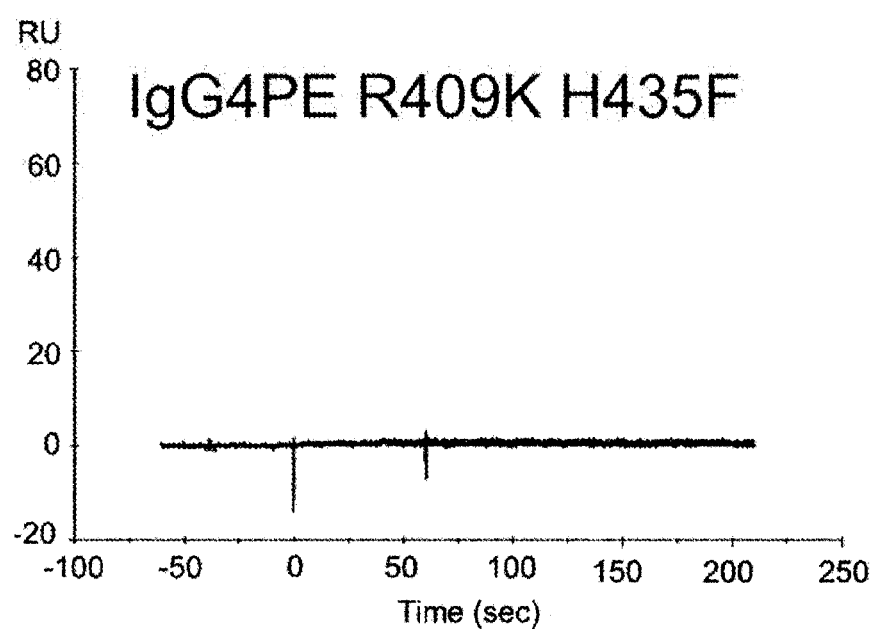

As shown in FIGS. 18A and 18B, it was confirmed that, under conditions where the CD131-CD116 bispecific antibody using wild-type IgG4PE R409K as a constant region clearly binds to human FcRn, an I253A mutant (Int Immunol., 18, 1759 (2006)), which is reported to lose binding to FcRn, did not exhibit a binding reaction.

Figure 19:
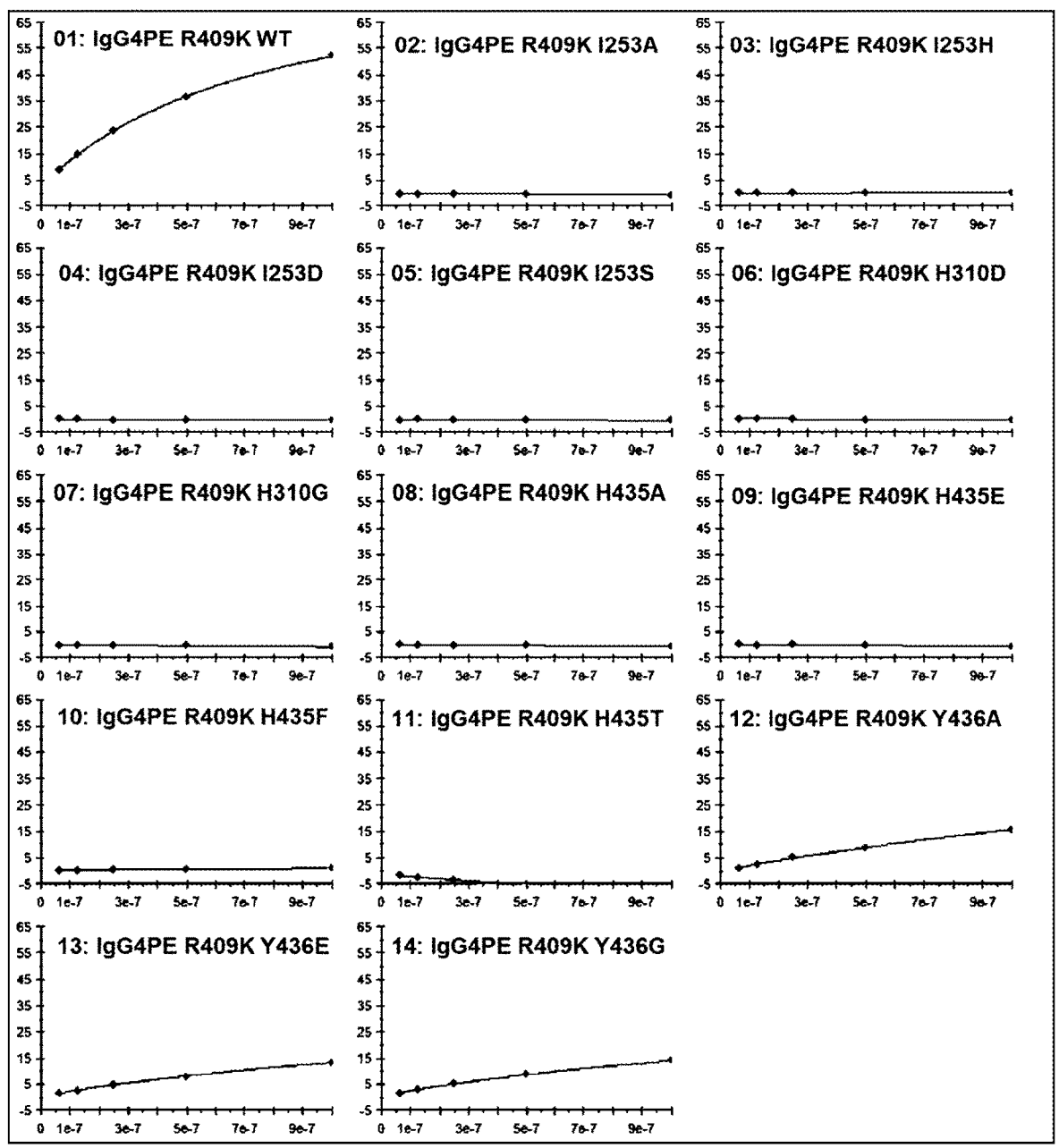
FIG. 19 shows an equilibrium plot related to binding of each CD131-CD116 bispecific antibody mutant to human FcRn using an IgG4PE R409K mutant in the Fc region, in which a vertical axis shows a resonant unit (RU), and a horizontal axis shows a bispecific antibody concentration (M, mol/L).

FIG. 19 shows a diagram in which an equilibrium RU value at each analyte concentration is plotted for a mutant using mutation-inserted IgG4PE R409K as a constant region. As shown in FIG. 19, a mutant with an amino acid mutation at Tyr436 remained weakly binding activity, while mutants with amino acid mutations at Ile253, His310 and His435 all showed loss of binding.

Figure 20:
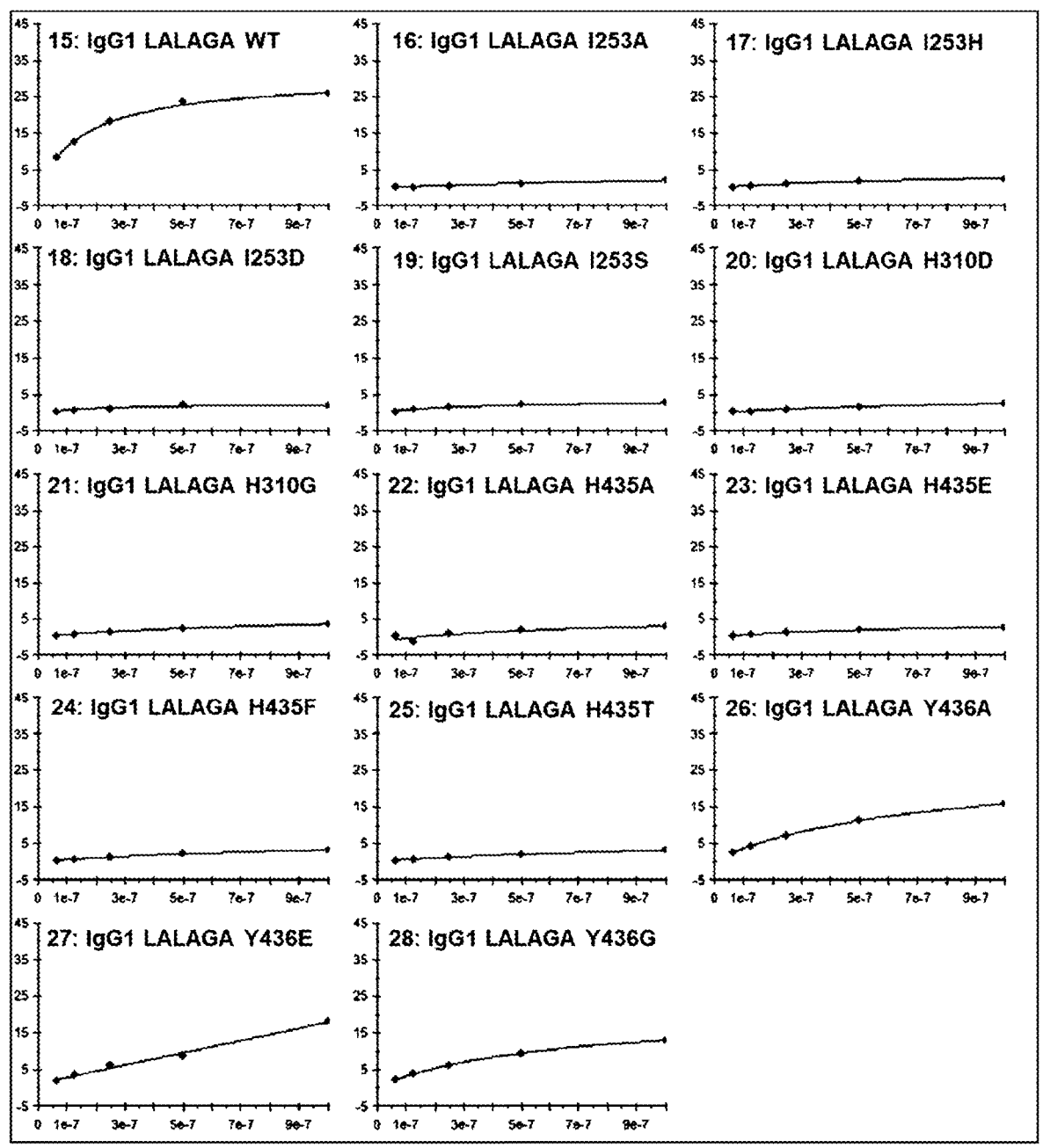
FIG. 20 shows an equilibrium plot related to binding of each CD131-CD116 bispecific antibody mutant to human FcRn using an IgG1LALAGA mutant in the Fc region, in which a vertical axis shows a resonant unit (RU), and a horizontal axis shows a bispecific antibody concentration (M, mol/L).

As shown in FIG. 20, the same results were obtained for a mutant using mutation-inserted IgG1 LALAGA as a constant region as in the case of using the mutation-inserted IgG4PE R409K.

[Example 14] Analysis of Protein A Binding Activity of Fc Mutant with Loss of Binding to FcRn For each mutant of the CD131-CD116 bispecific antibody prepared in Example 13, a binding activity to Protein A was determined in the same manner as in Example 13 using Biacore T100 and T200.

Using an Amine Coupling Kit, 75 RU of Protein A (derived from *Staphylococcus aureus*, manufactured by Nacalai) diluted to 1.0 μg/mL with Acetate 4.5 was immobilized on a CM5 sensor chip according to the attached document. Next, the above-described antibody samples (diluted with an HBS-EP+ solution of pH 7.4) diluted 4 times in 5 serial dilutions from 100 nM as analytes were added at a flow rate of 30 μL/min, and a binding reaction with Protein A was measured for 120 seconds, and a dissociation reaction was measured for 120 seconds.

The measurements were performed using a single cycle kinetics method. The obtained sensorgram was analyzed using Bia Evaluation Software (manufactured by GE Healthcare), and the kinetic constant of each antibody was calculated in a Bivalent analyte model. An association rate constant (ka), a dissociation rate constant (kd), and a binding affinity (KD) were determined. The results are shown in Table 7 and Table 8.

As shown in Table 7 and Table 8, under conditions where the CD131-CD116 bispecific antibody using wild-type IgG4PE R409K and IgG1 LALAGA shows an affinity of about 10 nM to Protein A, most of amino acid mutation insertions into Ile253, His310, and His435 that were confirmed to lose binding to FcRn in Example 13 also lost a Protein A binding affinity. However, in the IgG4PE R409K H435F mutant and the IgG1 LALAGA H435F mutant, the binding affinity to Protein A was maintained equivalent to that of the wild type.

Currently, most antibody drugs are purified using Protein A affinity chromatography. Therefore, mutants that lose FcRn binding while maintaining a Protein A binding activity are preferred from a production standpoint.

TABLE 7

| No. | sample | $K_D$ (nM) | Rmax (RU) |
|---|---|---|---|
| 01 | GM408_hIgG4PE(R409K)_WT | 11.3 | 359.6 |
| 02 | GM408_hIgG4PE(R409K)_I253A | ND | 35.0 |
| 03 | GM408_hIgG4PE(R409K)_I253H | ND | 0.4 |
| 04 | GM408_hIgG4PE(R409K)_I253D | ND | 0.2 |
| 05 | GM408_hIgG4PE(R409K)_I253S | ND | 0.2 |
| 06 | GM408_hIgG4PE(R409K)_H310D | ND | 15.3 |
| 07 | GM408_hIgG4PE(R409K)_H310G | ND | 29.8 |
| 08 | GM408_hIgG4PE(R409K)_H435A | ND | 149.2 |
| 08 | GM408_hIgG4PE(R409K)_H435E | ND | 5.8 |
| 10 | GM408_hIgG4PE(R409K)_H435F | 9.7 | 325.8 |
| 11 | GM408_hIgG4PE(R409K)_H435T | ND | 1.9 |
| 12 | GM408_hIgG4PE(R409K)_Y436A | 35.1 | 214.4 |
| 13 | GM408_hIgG4PE(R409K)_Y436E | 34.9 | 214.8 |
| 14 | GM408_hIgG4PE(R409K)_Y436G | 30.4 | 260.9 |

TABLE 8

| No. | sample | $K_D$ (nM) | Rmax (RU) |
|---|---|---|---|
| 15 | GM408_hIgG1_LALAGA_WT | 10.5 | 351.4 |
| 16 | GM408_hIgG1_LALAGA_I253A | ND | 33.3 |
| 17 | GM408_hIgG1_LALAGA_I253H | ND | 0.2 |
| 18 | GM408_hIgG1_LALAGA_I253D | ND | 0.0 |
| 19 | GM408_hIgG1_LALAGA_I253S | ND | 0.0 |
| 20 | GM408_hIgG1_LALAGA_H310D | ND | 6.8 |
| 21 | GM408_hIgG1_LALAGA_H310G | ND | 61.4 |
| 2 | GM408_hIgG1_LALAGA_H435A | ND | 162.3 |
| 23 | GM408_hIgG1_LALAGA_H435E | ND | 1.1 |
| 24 | GM408_hIgG1_LALAGA_H435F | 9.7 | 392.5 |
| 25 | GM408_hIgG1_LALAGA_H435T | ND | 1.6 |
| 26 | GM408_hIgG1_LALAGA_Y436A | 26.1 | 292.3 |
| 27 | GM408_hIgG1_LALAGA_Y436E | 28.3 | 271.8 |
| 28 | GM408_hIgG1_LALAGA_Y436G | 20.5 | 306.2 |

Although the present invention has been described in detail with reference to specific aspects, it is obvious to those skilled in the art that various changes and modifications can be made without departing from the spirit and scope of the present invention. The present application is based on a Japanese patent application (JP2021-138181) filed on Aug. 26, 2021, the disclosure of which is hereby incorporated by reference herein in its entirety. All references cited herein are incorporated in their entirety.

SEQUENCE LISTING FREE TEXT

SEQ ID NO: 1: full-length nucleotide sequence of human CD131
SEQ ID NO: 2: full-length nucleotide sequence of monkey CD131
SEQ ID NO: 3: nucleotide sequence of human CD131 extracellular region
SEQ ID NO: 4: nucleotide sequence of monkey CD131 extracellular region
SEQ ID NO: 5: nucleotide sequence of mouse CD131 extracellular region
SEQ ID NO: 6: full-length nucleotide sequence of human CD116
SEQ ID NO: 7: full-length nucleotide sequence of monkey CD116
SEQ ID NO: 8: nucleotide sequence of human CD116 extracellular region
SEQ ID NO: 9: nucleotide sequence of monkey CD116 extracellular region
SEQ ID NO: 10: nucleotide sequence of mouse CD116 extracellular region
SEQ ID NO: 11: amino acid sequence of 116-08 VH
SEQ ID NO: 12: amino acid sequence of 116-08 VL
SEQ ID NO: 13: amino acid sequence of 116-09 VH
SEQ ID NO: 14: amino acid sequence of 116-09 VL
SEQ ID NO: 15: amino acid sequence of 116-18 VH
SEQ ID NO: 16: amino acid sequence of 116-18 VL
SEQ ID NO: 17: amino acid sequence of 116-21 VH
SEQ ID NO: 18: amino acid sequence of 116-21 VL
SEQ ID NO: 19: amino acid sequence of 116-22 VH
SEQ ID NO: 20: amino acid sequence of 116-22 VL
SEQ ID NO: 21: amino acid sequence of 131-03 VH
SEQ ID NO: 22: amino acid sequence of 131-03 VL
SEQ ID NO: 23: amino acid sequence of 131-16 VH
SEQ ID NO: 24: amino acid sequence of 131-16 VL
SEQ ID NO: 25: amino acid sequence of 131-18 VH
SEQ ID NO: 26: amino acid sequence of 131-18 VL
SEQ ID NO: 27: amino acid sequence of 131-B1 VH
SEQ ID NO: 28: amino acid sequence of 131-B1 VL
SEQ ID NO: 29: amino acid sequence of 131-B2 VH
SEQ ID NO: 30: amino acid sequence of 131-B2 VL
SEQ ID NO: 31: amino acid sequence of 116-08 VH CDR1
SEQ ID NO: 32: amino acid sequence of 116-08 VH CDR2
SEQ ID NO: 33: amino acid sequence of 116-08 VH CDR3
SEQ ID NO: 34: amino acid sequence of 116-08 VL CDR1
SEQ ID NO: 35: amino acid sequence of 116-08 VL CDR2
SEQ ID NO: 36: amino acid sequence of 116-08 VL CDR3
SEQ ID NO: 37: amino acid sequence of 116-09 VH CDR1
SEQ ID NO: 38: amino acid sequence of 116-09 VH CDR2
SEQ ID NO: 39: amino acid sequence of 116-09 VH CDR3
SEQ ID NO: 40: amino acid sequence of 116-09 VL CDR1
SEQ ID NO: 41: amino acid sequence of 116-09 VL CDR2
SEQ ID NO: 42: amino acid sequence of 116-09 VL CDR3
SEQ ID NO: 43: amino acid sequence of 116-18 VH CDR1
SEQ ID NO: 44: amino acid sequence of 116-18 VH CDR2
SEQ ID NO: 45: amino acid sequence of 116-18 VH CDR3
SEQ ID NO: 46: amino acid sequence of 116-18 VL CDR1
SEQ ID NO: 47: amino acid sequence of 116-18 VL CDR2
SEQ ID NO: 48: amino acid sequence of 116-18 VL CDR3
SEQ ID NO: 49: amino acid sequence of 116-21 VH CDR1
SEQ ID NO: 50: amino acid sequence of 116-21 VH CDR2
SEQ ID NO: 51: amino acid sequence of 116-21 VH CDR3
SEQ ID NO: 52: amino acid sequence of 116-21 VL CDR1
SEQ ID NO: 53: amino acid sequence of 116-21 VL CDR2
SEQ ID NO: 54: amino acid sequence of 116-21 VL CDR3
SEQ ID NO: 55: amino acid sequence of 116-22 VH CDR1
SEQ ID NO: 56: amino acid sequence of 116-22 VH CDR2
SEQ ID NO: 57: amino acid sequence of 116-22 VH CDR3
SEQ ID NO: 58: amino acid sequence of 116-22 VL CDR1
SEQ ID NO: 59: amino acid sequence of 116-22 VL CDR2
SEQ ID NO: 60: amino acid sequence of 116-22 VL CDR3
SEQ ID NO: 61: amino acid sequence of 131-03 VH CDR1
SEQ ID NO: 62: amino acid sequence of 131-03 VH CDR2
SEQ ID NO: 63: amino acid sequence of 131-03 VH CDR3
SEQ ID NO: 64: amino acid sequence of 131-03 VL CDR1
SEQ ID NO: 65: amino acid sequence of 131-03 VL CDR2
SEQ ID NO: 66: amino acid sequence of 131-03 VL CDR3
SEQ ID NO: 67: amino acid sequence of 131-16 VH CDR1
SEQ ID NO: 68: amino acid sequence of 131-16 VH CDR2
SEQ ID NO: 69: amino acid sequence of 131-16 VH CDR3
SEQ ID NO: 70: amino acid sequence of 131-16 VL CDR1
SEQ ID NO: 71: amino acid sequence of 131-16 VL CDR2
SEQ ID NO: 72: amino acid sequence of 131-16 VL CDR3
SEQ ID NO: 73: amino acid sequence of 131-18 VH CDR1
SEQ ID NO: 74: amino acid sequence of 131-18 VH CDR2
SEQ ID NO: 75: amino acid sequence of 131-18 VH CDR3

SEQ ID NO: 76: amino acid sequence of 131-18 VL CDR1
SEQ ID NO: 77: amino acid sequence of 131-18 VL CDR2
SEQ ID NO: 78: amino acid sequence of 131-18 VL CDR3
SEQ ID NO: 79: amino acid sequence of 131-B1 VH CDR1
SEQ ID NO: 80: amino acid sequence of 131-B1 VH CDR2
SEQ ID NO: 81: amino acid sequence of 131-B1 VH CDR3
SEQ ID NO: 82: amino acid sequence of 131-B1 VL CDR1
SEQ ID NO: 83: amino acid sequence of 131-B1 VL CDR2
SEQ ID NO: 84: amino acid sequence of 131-B1 VL CDR3
SEQ ID NO: 85: amino acid sequence of 131-B2 VH CDR1
SEQ ID NO: 86: amino acid sequence of 131-B2 VH CDR2
SEQ ID NO: 87: amino acid sequence of 131-B2 VH CDR3
SEQ ID NO: 88: amino acid sequence of 131-B2 VL CDR1
SEQ ID NO: 89: amino acid sequence of 131-B2 VL CDR2
SEQ ID NO: 90: amino acid sequence of 131-B2 VL CDR3
SEQ ID NO: 91: amino acid sequence of 131-B2 VL
SEQ ID NO: 92: amino acid sequence of 116-398
SEQ ID NO: 93: amino acid sequence of 116-412
SEQ ID NO: 94: amino acid sequence of 116-413
SEQ ID NO: 95: amino acid sequence of 116-421
SEQ ID NO: 96: amino acid sequence of 116-433
SEQ ID NO: 97: amino acid sequence of 116-435
SEQ ID NO: 98: amino acid sequence of 116-439
SEQ ID NO: 99: amino acid sequence of 116-463
SEQ ID NO: 100: amino acid sequence of 116-464
SEQ ID NO: 101: amino acid sequence of 116-465
SEQ ID NO: 102: amino acid sequence of 116-466
SEQ ID NO: 103: amino acid sequence of 116-408
SEQ ID NO: 104: amino acid sequence of 116-398 VH CDR1
SEQ ID NO: 105: amino acid sequence of 116-398 VH CDR2
SEQ ID NO: 106: amino acid sequence of 116-398 VH CDR3
SEQ ID NO: 107: amino acid sequence of 116-412 VH CDR1
SEQ ID NO: 108: amino acid sequence of 116-412 VH CDR2
SEQ ID NO: 109: amino acid sequence of 116-412 VH CDR3
SEQ ID NO: 110: amino acid sequence of 116-413 VH CDR1
SEQ ID NO: 111: amino acid sequence of 116-413 VH CDR2
SEQ ID NO: 112: amino acid sequence of 116-413 VH CDR3
SEQ ID NO: 113: amino acid sequence of 116-421 VH CDR1
SEQ ID NO: 114: amino acid sequence of 116-421 VH CDR2
SEQ ID NO: 115: amino acid sequence of 116-421 VH CDR3
SEQ ID NO: 116: amino acid sequence of 116-433 VH CDR1
SEQ ID NO: 117: amino acid sequence of 116-433 VH CDR2
SEQ ID NO: 118: amino acid sequence of 116-433 VH CDR3
SEQ ID NO: 119: amino acid sequence of 116-435 VH CDR1
SEQ ID NO: 120: amino acid sequence of 116-435 VH CDR2
SEQ ID NO: 121: amino acid sequence of 116-435 VH CDR3
SEQ ID NO: 122: amino acid sequence of 116-439 VH CDR1
SEQ ID NO: 123: amino acid sequence of 116-439 VH CDR2
SEQ ID NO: 124: amino acid sequence of 116-439 VH CDR3
SEQ ID NO: 125: amino acid sequence of 116-463 VH CDR1
SEQ ID NO: 126: amino acid sequence of 116-463 VH CDR2
SEQ ID NO: 127: amino acid sequence of 116-463 VH CDR3
SEQ ID NO: 128: amino acid sequence of 116-464 VH CDR1
SEQ ID NO: 129: amino acid sequence of 116-464 VH CDR2
SEQ ID NO: 130: amino acid sequence of 116-464 VH CDR3
SEQ ID NO: 131: amino acid sequence of 116-465 VH CDR1
SEQ ID NO: 132: amino acid sequence of 116-465 VH CDR2
SEQ ID NO: 133: amino acid sequence of 116-465 VH CDR3
SEQ ID NO: 134: amino acid sequence of 116-466 VH CDR1
SEQ ID NO: 135: amino acid sequence of 116-466 VH CDR2
SEQ ID NO: 136: amino acid sequence of 116-466 VH CDR3
SEQ ID NO: 137: amino acid sequence of 116-408 VH CDR1
SEQ ID NO: 138: amino acid sequence of 116-408 VH CDR2
SEQ ID NO: 139: amino acid sequence of 116-408 VH CDR3
SEQ ID NO: 140: amino acid sequence of DuetMAb LALAPG CH1 to CH3 constant region 1
SEQ ID NO: 141: amino acid sequence of DuetMAb LALAPG CL constant region 1
SEQ ID NO: 142: amino acid sequence of DuetMAb LALAPG CH1 to CH3 constant region 2
SEQ ID NO: 143: amino acid sequence of DuetMAb LALAPG CL constant region 2
SEQ ID NO: 144: amino acid sequence of IgG4CH1 constant region
SEQ ID NO: 145: amino acid sequence of IgG4PE R409K CH1 to CH3 constant region
SEQ ID NO: 146: amino acid sequence of IgG1 LALAGA CH1 to CH3 constant region
SEQ ID NO: 147: amino acid sequence of IgG4PE R409K CH1 to CH3 constant region I253A mutant
SEQ ID NO: 148: amino acid sequence of IgG4PE R409K CH1 to CH3 constant region I253H mutant SEQ ID NO: 149: amino acid sequence of IgG4PE R409K CH1 to CH3 constant region I253D mutant
SEQ ID NO: 150: amino acid sequence of IgG4PE R409K CH1 to CH3 constant region I253S mutant
SEQ ID NO: 151: amino acid sequence of IgG4PE R409K CH1 to CH3 constant region H310D mutant
SEQ ID NO: 152: amino acid sequence of IgG4PE R409K CH1 to CH3 constant region H310G mutant
SEQ ID NO: 153: amino acid sequence of IgG4PE R409K CH1 to CH3 constant region H435A mutant
SEQ ID NO: 154: amino acid sequence of IgG4PE R409K CH1 to CH3 constant region H435E mutant
SEQ ID NO: 155: amino acid sequence of IgG4PE R409K CH1 to CH3 constant region H435F mutant
SEQ ID NO: 156: amino acid sequence of IgG4PE R409K CH1 to CH3 constant region H435T mutant
SEQ ID NO: 157: amino acid sequence of IgG4PE R409K CH1 to CH3 constant region Y436A mutant
SEQ ID NO: 158: amino acid sequence of IgG4PE R409K CH1 to CH3 constant region Y436E mutant
SEQ ID NO: 159: amino acid sequence of IgG4PE R409K CH1 to CH3 constant region Y436G mutant
SEQ ID NO: 160: amino acid sequence of IgG1 LALAGA CH1 to CH3 constant region I253A mutant
SEQ ID NO: 161: amino acid sequence of IgG1 LALAGA CH1 to CH3 constant region I253H mutant
SEQ ID NO: 162: amino acid sequence of IgG1 LALAGA CH1 to CH3 constant region I253D mutant
SEQ ID NO: 163: amino acid sequence of IgG1 LALAGA CH1 to CH3 constant region I253S mutant
SEQ ID NO: 164: amino acid sequence of IgG1 LALAGA CH1 to CH3 constant region H310D mutant
SEQ ID NO: 165: amino acid sequence of IgG1 LALAGA CH1 to CH3 constant region H310G mutant
SEQ ID NO: 166: amino acid sequence of IgG1 LALAGA CH1 to CH3 constant region H435A mutant
SEQ ID NO: 167: amino acid sequence of IgG1 LALAGA CH1 to CH3 constant region H435E mutant
SEQ ID NO: 168: amino acid sequence of IgG1 LALAGA CH1 to CH3 constant region H435F mutant
SEQ ID NO: 169: amino acid sequence of IgG1 LALAGA CH1 to CH3 constant region H435T mutant
SEQ ID NO: 170: amino acid sequence of IgG1 LALAGA CH1 to CH3 constant region Y436A mutant
SEQ ID NO: 171: amino acid sequence of IgG1 LALAGA CH1 to CH3 constant region Y436E mutant
SEQ ID NO: 172: amino acid sequence of IgG1 LALAGA CH1 to CH3 constant region Y436G mutant
SEQ ID NO: 173: nucleotide sequence of 131-B2 VH
SEQ ID NO: 174: nucleotide sequence of IgG4CH1 constant region
SEQ ID NO: 175: amino acid sequence of GM398 116 VH
SEQ ID NO: 176: amino acid sequence obtained by optimizing GM412 116 VH FR1 for bispecific antibody
SEQ ID NO: 177: amino acid sequence obtained by optimizing GM413 116 VH FR1 for bispecific antibody
SEQ ID NO: 178: amino acid sequence obtained by optimizing GM421 116 VH FR1 for bispecific antibody
SEQ ID NO: 179: amino acid sequence obtained by optimizing GM433 116 VH FR1 for bispecific antibody
SEQ ID NO: 180: amino acid sequence of GM435 116 VH SEQ ID NO: 181: amino acid sequence of GM439 116 VH
SEQ ID NO: 182: amino acid sequence obtained by optimizing GM463 116 VH FR1 for bispecific antibody
SEQ ID NO: 183: amino acid sequence obtained by optimizing GM464 116 VH FR1 for bispecific antibody
SEQ ID NO: 184: amino acid sequence obtained by optimizing GM465 116 VH FR1 for bispecific antibody
SEQ ID NO: 185: amino acid sequence obtained by optimizing GM466 116 VH FR1 for bispecific antibody
SEQ ID NO: 186: amino acid sequence of GM408 116 VH
SEQ ID NO: 187: amino acid sequence of human GM-CSF receptor expression vector
SEQ ID NO: 188: amino acid sequence of human IL-3 receptor expression vector
SEQ ID NO: 189: amino acid sequence of human IL-5 receptor expression vector
SEQ ID NO: 190: amino acid sequence of GM408ngs007 VH
SEQ ID NO: 191: amino acid sequence of GM408ngs058 VH
SEQ ID NO: 192: amino acid sequence of GM408ngs365 VH
SEQ ID NO: 193: amino acid sequence of GM408ngs127 VH
SEQ ID NO: 194: amino acid sequence of GM408ngs008 VH
SEQ ID NO: 195: amino acid sequence of GM408ngs300 VH
SEQ ID NO: 196: amino acid sequence of GM408ngs041 VH
SEQ ID NO: 197: amino acid sequence of GM408ngs048 VH
SEQ ID NO: 198: amino acid sequence of GM408ngs047 VH
SEQ ID NO: 199: amino acid sequence of GM408ngs539 VH
SEQ ID NO: 200: amino acid sequence of GM408_H101 VH
SEQ ID NO: 201: amino acid sequence of GM408_H102 VH
SEQ ID NO: 202: amino acid sequence of GM408_H103 VH
SEQ ID NO: 203: amino acid sequence of GM408_H104 VH
SEQ ID NO: 204: amino acid sequence of GM408_H105 VH
SEQ ID NO: 205: amino acid sequence of GM408_H301 VH
SEQ ID NO: 206: amino acid sequence of GM408_H302 VH
SEQ ID NO: 207: amino acid sequence of GM408_H303 VH
SEQ ID NO: 208: amino acid sequence of GM408_H106 VH
SEQ ID NO: 209: amino acid sequence of GM408_H107 VH
SEQ ID NO: 210: amino acid sequence of human_CD116 ECD (23-320)
SEQ ID NO: 211: amino acid sequence of human_CD131 ECD (17-443)

SEQUENCE LISTING

```
Sequence total quantity: 211
SEQ ID NO: 1              moltype = DNA   length = 2691
FEATURE                   Location/Qualifiers
source                    1..2691
                          mol_type = genomic DNA
                          organism = Homo sapiens
SEQUENCE: 1
atggtgctgg ctcaaggcct tttgagtatg gcacttctgg ccctttgttg ggaacggtct   60
ctcgccggcg cagaggagac gattccgctt caaacattga gatgctataa cgattataca  120
tctcacatta cctgtcggtg ggccgacact caagatgccc agcggcttgt gaacgtaacc  180
cttatcagac gggtgaatga agacctcttg gaaccggtat catgcgatct gtctgacgac  240
atgccgtgga gtgcgtgtcc tcatccgagg tgcgttccgc ggcgctgtgt gatcccgtgt  300
caaagtttcg tagtgactga tgttgactat ttcagtttcc agcctgacag gcccctcgga  360
actaggctga ccgtgacgtt gactcaacat gtccagcctc ctgaacctcg ggatttgcag  420
atcagtacag accaagatca tttccttctg acttggtcag ttgctctcgg cagtccgcaa  480
tcacactggt tgtcaccagg tgatctggag ttcgaagtag tgtacaagag gcttcaggat  540
tcatgggagg atgcagcgat cttgctcagt aatacaagtc aggctacgct cgggccagag  600
cacctcatgc catctagtac ttacgtcgca cgcgttcgaa ctcgcttggc accgggcagc  660
cgacttagcg gacggccttc caagtggtcc ccggaagtat gttgggattc tcagccaggg  720
gatgaggccc aaccacaaaa cttggaatgt ttctttgatg gtgcggctgt tttgagttgt  780
agctgggaag tgcgaaagga ggtggcatcc agtgtcagct tcggtctgtt ctataagccg  840
tctcctgatg cgggtgagga ggagtgtagt ccggtcctgc gcgaaggtct gggttccttg  900
cataccggc accactgtca aataccggtc cctgacccgg ctactcacgg ccagtacata  960
gtatctgtac agccaaggcg ggctgagaag catatcaaaa gctcagtgaa cattcagatg 1020
gctcctccca gtttgaatgt taccaaggat ggagattcct attcattgag gtgggagacc 1080
atgaagatga ggtacgaaca catcgaccat actttcgaaa tacaataccg aaaggacact 1140
gcgacgtgga aagatagtaa aacggagacg cttcagaacg ctcattccat ggcgttgcct 1200
gctttggagc cgtctacgag gtactgggca cgggtaaggg tgcggacatc tcgcactggc 1260
tataacggga tatggtcaga atggagtgaa gcaagatcat gggataccga gagtgttctt 1320
cctatgtggg tgctggccct catcgtcatt ttcctcacca tagccgtact tcttgcgctg 1380
cgattctgtg aatatacggg ttatcgcttg agacgcaagt ggggaggaaaa gattccgaac 1440
ccttctaagt ctcacttgtt ccagaatggc agtgccgaac tttggccgcc aggttctatg 1500
tcagcattca ctagcgggtc tccgccccat cagggacccc gggatccagg atttccagag 1560
ctcgaaggcg ttttcccggt gggttttggt gactccgagg tatcacctttt gacgattgaa 1620
gatccgaagc acgtttgcga tccacctagt ggtcctgaca ctacgccggc cgcatctgat 1680
cttccgacag aacaaccacc gtctccacaa ccgggaccgg cagcagcttc ccacaccct  1740
gaaaagcaag cttcctcttt cgactttaac ggtccatatc ttggtccacc acactctagg 1800
tctctgcccg atatactcgg acaacctgag ccgcctcaag aaggaggctc acaaaagagc 1860
ccgcctccag ggagtttgga atatctttgc ctcccagctg gaggtcaagt gcagttggtt 1920
cccctttgcc aggctatggg gccaggacag gcagttggag ttgagagacg cccttctcag 1980
ggtgcagccg ggagtccatc acttgagtct ggaggagggc cagcccctcc tgctctcggg 2040
ccaagagttg gtggtcaaga tcaaaaggat tctccggtag ctattccaat gagctctggc 2100
gatacagaag accctggagt cgccagtggt tacgtgtcct ctgcagacct ggtattcact 2160
cccaacagtg gcgccagttc tgtttctctg gtaccgagtc ttggccttcc aagtgatcaa 2220
actccgagcc tctgcccagg gcttgcctca ggtccgccag gagctccagg ccctgttaaa 2280
agtggcttcg agggttacgt tgagctgccg ccgatagagg gccgcagccc gagatcccct 2340
aggaataacc cagtacctcc cgaagcaaaa tcaccagtac tcaacccggg cgagcgacca 2400
gctgactct ccccgacaag tccccaacct gaaggcttgt tggttctgca acaagtggga 2460
gattactgct tcttgccggg gcttggcccg gggccattgt ctcttaggtc taaaccctcc 2520
agtcctgggc ctggccccga gattaagaat ctcgaccaag ccttccaagt aaagaagcct 2580
ccaggtcaag ctgttcctca ggtcccagtg atacaacttt tcaaggcctt gaaacagcaa 2640
gattacctct ccctcccgcc ttgggaagtc aataagccag gagaagtatg t          2691

SEQ ID NO: 2              moltype = DNA   length = 2694
FEATURE                   Location/Qualifiers
source                    1..2694
                          mol_type = genomic DNA
                          organism = Macaca fascicularis
SEQUENCE: 2
atggcattgg ctcaaaggct gttgtccatg gcattgttgg ccttgtgctg gggacactca   60
ctgcctggag ccgaagaaac aataccactg cgcacgctcc gatgctataa tgactataca  120
agtcacatta catgtcgctg ggcggacact caagacgccc aaaggttggt caatgttacc  180
ttgagcagac gcgtcaatga tagagaccct ccggaacctg tttcttgcga tctctccgaa  240
gacatgccgt ggtccgcatg cccgtacccg cgatgtgttc cacgccgctg tgtcatccct  300
tatcgagagct ttgtcgtgac cgatgtcgac tactactcta ttcagccaga ccggcccctt  360
ggtactcaat tgacggttac acttacgcaa catgtccaac cgcccgcacc taaggacctt  420
cagatcaata ctgatcagga tcacttcctt cttacgtgga gtgttgcacc aggttcacct  480
cagagccact ggctcagcct tggtgatctt gagagtaagt agtgtataa gagacttcaa  540
gactcttggg aggacgctgc tacacttctt tccaatgcat ctcaggccac cctgggcct  600
gagcatctca tgcccagctc tacatacgtt gccagagtga ggacccgact tcaagcggg  660
tctagactta gtggacggcc gagcgagtgg tctcccgaag taaggtggga ctctcagcct  720
ggggatgaag cacagccaca aaaccttcag tgtttcttcg acgggctgc tgtgctctcc  780
tgcagtggga aagttcggca ggaagtggca tccagtatct catttgggct cttttacaaa  840
ccatctccgg acgctggaga aggaagaatgc agcccagtgc ttagggaagg cctgggctct  900
ctttacacaa gaccaccactg ccagattccc gtacccgacc caggcaccca cggcagtat  960
attgtcagtg tgcaacctcg agagccgag aaacgcataa agtccagtga aaatataaca 1020
atggcccccc cttctctgtc cgttaccagg gacggagaca gttattctct tcgctgggag 1080
acgatgaaga tgcagtatga acacatcgat catacgttcg aaaatacaata acaaaggac 1140
```

```
actgctactt ggaaggatag caagacagag actcttcaga acgcacattc tatggccctc   1200
ccggcattgg aaccgtccac gcggtactgg gcgcgagtcc gcgtcagaac tagtagaacg   1260
ggctacaatg ggacatggtc tgattggagt gaggtctgtt catgggacac ggagagcgta   1320
cttccgatgt gggtccttgc cttggtcgtc atcttcctca ccatagctgt cctgctggcc   1380
ttgcggttct gcggtattta cggatacaga ctcaggcgaa agtggggaga gcggataccc   1440
aacccgtcta agtcacatct gttccagaat ggttccgccg agttgtggac tccaggttcc   1500
atgatggctt ttacctcagg atcaccactt caccagggac catgggacag tagatttccc   1560
gagctcgaag gcgtattccc ggttgggttt ggcgactctg aagtgtcccc attgactatt   1620
gaggatctgc gccacgtctg tgaccctcca tccggacccg ataccacacc agcggcatcc   1680
gatctcccta cagaacaacc tccgtcccca cagccgggac ctccagcctc cagtcatacg   1740
cccgagaagc aagtttcaag cttttgatttc aacgggccct acttgggccc tccgcactcc   1800
cggtcactgc cagacatcct gggtcagcca gaaccgcctc aagcttgcgg gtcccagaag   1860
agcccgcctc cgggtagtct cgaatacctc tgcctgcccg caggcggcca agttcaattg   1920
gtccctctgg ctcaggctat gggacacggt caagcgatgg acgttgaacg gcggccgtcc   1980
caaggagccg caggatcctc cagtcttgaa tctgagggcg acccggcgcc accggccttg   2040
ggaccacgcg ttggcggaca agacccgaag gacagtcctg tagcaattcc ggcctccagc   2100
ggggtcccgg aggaccaagg ggtcgcatca ggttacgtat cctctgctga cttggtactg   2160
ccaccccact caggcacgtc tgctctttca ctcgtgccat ccccgggaat ccctttcagat   2220
caaacaccct ctttctgccc gggttttggca agtggaccac caggcgctcc aggtcctgtt   2280
aagtccgaat tgaggggata tgtggaactg ccgccgacag aaggacagag tcctaagtct   2340
cctgtgaaca acttggtgcc accggaagta cggtcccctg ttcttaaccc cggcgagaga   2400
cgggccgacg tgagtcctac cagcccgcaa cccgaaggtg tcttggtgct ccaacaagtt   2460
ggggattact gcttccttcc ggggctcggt cctggccctc tgagtcccccg gtcaaaaccg   2520
tctagtcctg gcccgtgccc tgaaatcaga gacctcgacc aggcctgtca ggtgaagaaa   2580
ccgccgggc aggcggtccc tcaggtgccg gtcattcaac tgttcaaggt actcaaacaa   2640
caggattacc tgtcccttcc tccgtgggag gttaacaagc caggcgaagt gtgt           2694

SEQ ID NO: 3              moltype = DNA  length = 1281
FEATURE                   Location/Qualifiers
source                    1..1281
                          mol_type = genomic DNA
                          organism = Homo sapiens
SEQUENCE: 3
tgggaacgga gtctggccgg agctgaggag acaattccac tgcagacatt gcgctgctac     60
aatgactata cctcccacat cacatgtcgg tgggctgaca gcaagacgc ccagagactg     120
gtgaatgtga ctctgattcg gcgagtgaat gaggatctct tggagcccgt ttccttgcgt     180
ctgagcgacg acatgccttg gagcgcatgt ccccatccta ggtgcgtgcc caggaggtgc     240
gtaataccct gtcagagctt tgtggtgaca gactgtggact acttctcctt ccagccggat     300
aggcctctgg gcactagatt gaccgttact ctcactcagc acgtacaacc gccggaaccc     360
agggacctcc aaatctcccac agaccaggat cacttcctcc tgacctggtc agtagctctg     420
ggcagtccac agtctcactg gcttagccct ggggatttga agtttgaagt cgtgtacaaa     480
cgtctgcagg atagctggga ggatgccgcg attctgctga gcaacacttc ccaagcaaca     540
cttggcccag agcacctgat gccttccagc acctatgtcg ctagagtccg cactaggctt     600
gcaccaggaa gccggttgtc aggtcgcccc tctaaatggt ccccagaggt ctgttgggac     660
tcacaacctg ggacgaagc ccagccgcag aaccttgagt gcttctttga tggtgccgca     720
gtgctctcat gtagttggga agtcagaaaa gaggttgcca gcagcgtgtc ctttggcctg     780
ttctataagc catcacccga tgccggggaa gaagagtgct ctcctgtact gagggaagga     840
ctcggatctc tccataccg acaccattgc cagataccag tgcctgatcc agccactcat     900
ggccagtaca tcgttagtgt gcaacccgc agagctgaga agcacatcaa gagcagtgtc     960
aacattcaga tggcacctcc ctctctgaac gtgaccaaag atggtgacag ctactccctt   1020
cggtgggaaa cgatgaagat gcgtttatgaa cacatcgatc acacctttga gatccagtac   1080
cgcaaggata cggccacatg gaaggacagc aaaaccgaaa cactgcagaa tgcgcactca   1140
atggcactgc cagctctgga accctccacc cggtatttggg cccgagttcg tgtgcgcacc   1200
tccgaaacag gctacaacgg gatttggagt gagtggtcag aggcgagatc ttgggacacc   1260
gagtctgtcc tgcccatgtg g                                             1281

SEQ ID NO: 4              moltype = DNA  length = 873
FEATURE                   Location/Qualifiers
source                    1..873
                          mol_type = genomic DNA
                          organism = Macaca fascicularis
SEQUENCE: 4
gagaaaccag caagctctct gaatgtccgg tttgatgcga ggaccatgaa tctcacatgg     60
gattgccagg aaaacaccac ctttacccgc tgttttctga ctgacaagaa gaatagagtt    120
gtagagccca gagtgactaa gaaagaatgc tcctgtacgt tccacgaggt ttgcctgcac    180
ggaggtgtga cattcgaggt tcacgtgaat actagtcaaa gggcatttca gcagaagctg    240
ctgtatccca attctgggag agaagggaca gccgctcaga acttctcctg cttcatctac    300
aacgtggatt tcatgaactg tacctggct agaggtccaa ctgctcctcg ggatgtgcag    360
tacttcctgt acatacagaa cagcaaacgt cgcaggagga tccaatgccc ctactacatc    420
gaggactcag gcacacatgt gggatgtcac ctcggcaatc ttagcggcct tactagccga    480
aactactttc tggtcaatgg gacctctcag gagattggga ttcagttctt tgattccctc    540
ctggacacga agaagataga gaggttcaat cctcctgaca atgtccaggt acggtgcaac    600
acaacccact gttttggttcg gtggaaacaa ccgaggacct atcagaaact ctcatatctg    660
gacttccagt atcagcttga cgtgcatcgg aagaatacccc aaccaggcac agaaaatctg    720
cctatcaacg tgtctggaga cttggagaac cgctataact ttcccagcag tgaaccacga    780
gccaagcatg ccgtcaaaat tagagctgcc gatgtgcgta tcctgaactg gtccagctgg    840
tcagaagcag ccgaatttgg aagtgatgac cgc                                 873
```

```
SEQ ID NO: 5            moltype = DNA  length = 1257
FEATURE                 Location/Qualifiers
source                  1..1257
                        mol_type = genomic DNA
                        organism = Mus musculus
SEQUENCE: 5
catgggtga ctgaggctga agaaaccgtt ccctgaaaa cgctgcaatg ctacaacgat    60
tataccaacc acatcatttg cagctgggca gataccgagg acgcccaagg attgatcaac   120
atgacgctgt accatcagct ggagaagaaa cagcctgtct cctgtgagct ctccgaagaa   180
ctgatgtggt cagaatgtcc cagtagccat aggtgtgttc ccggcgttg cgtgattccc    240
tacacaaggt tcagtatcac caatgaggac tactacagct ttagaccaga ctcagatctc   300
ggcatacaac tgatggtacc tctggctcag aatgtgcagc cacccttgcc taagaatgtc   360
agcatttcca gcagcgaaga tcgcttcctc ttggaatggt cctgtgtcact tggtgatgcc   420
caagtgtctt ggttgagttc caaggacatc gagtttgagg tcgcctataa gcggctgcag   480
gatagctggg aggacgcgta tagccttcac acatctaagt ttcaggtgaa cttcgagcca   540
aagctgttcc tgcccaattc catctatgca gcacgcgttc ggacacgact gtctccagga   600
tcatccctct ccgggcgacc ttctagatgg tcaccggaag tgcactggga ctcacagcct   660
ggagataaag cacagccaca gaaccttcag tgcttctttg acgggatcca atcccttcac   720
tgctcatggg aggtgtggac tcaaaccacc ggcagtgtga gctttggcct cttttacagg   780
ccctctcctg tggctccgga agagaaatgt ctccccgtag taaaagagcc tccgggagct   840
agcgtctata cccgttatca ctgcagtctg cctgttcctg aaccctccgc tcactctcag   900
tacacagtga gtgtcaaaca cctgaacag ggtaagttca tcatgagcta taaccacatt    960
cagatggaac caccaacact caacctcact aagaatcgcg actccatatc cctgcattgg  1020
gagactcaga aaatggccta cagtttcatt gagcacactt tccaggtcca gtacaagaag  1080
aagagcgact catgggagga ctctaaaact gagaatctgc atagagccca tagtatggat  1140
ctgagccagc tggaaccaga taccagctat tgtgccaggg ttagagtgaa gccaatcagc  1200
aactacgacg gcatatggtc taagtggtct gaggagtaca catggaaaac agactgg     1257

SEQ ID NO: 6            moltype = DNA  length = 1200
FEATURE                 Location/Qualifiers
source                  1..1200
                        mol_type = genomic DNA
                        organism = Homo sapiens
SEQUENCE: 6
atgctgcttc ttgtgacctc tcttctgctg tgcgaactgc cccatcctgc ctttctgctg    60
attcccgaga aatccgactt gaggacagta gccccagcat ctagtctgaa cgtgagattc   120
gatagtcgac ctatgaacct gtcatgggac tgtcaggaga acactacctt cagcaagtgc   180
tttctgactg acaagaagaa cagggttgtg aaccagtga tgagcaataa cgaatgctct    240
tgtacattcc gggagatttg cctgcatgag ggagttacct tcgaagtgca cgtgaacacg   300
agccaacgcg gttccagca gaaactgctg tacccccaact cagggagaga aggaacagca   360
gcccagaact ttagctgctt catctacaat gccgatctca tgaactgtac ctgggctaga   420
ggcctacag ctccacgcga cgttcagtac ttcctctaca ttcgaaatag caaacgtcgt   480
cgcgagatac gatgtcccta ttacatccag gattctggca cacatgtggg ttgccatttg   540
gacaatctgt caggcttgac atccggaac tatttcctgg tgaacggcac tagccgcgaa    600
attggcatcc agttcttcga cagccttctt gataccaaga aaattgagcg atttaaccct   660
ccctccaatg tgacagtacg ctgtaatacc actcactgtc tgtcgcgtg gaagcagccc    720
agaacctatc agaagctctc ttatctggac tttcagtatc aactggatgt ccacagaaag   780
aacacccaac tggcactga atttgctgct atcaatgtca gtggtgattt ggagaatcgg    840
tacaactttc catcctcaga accaagggcg aaacactccg tgaagatcag ggctgcagat   900
gttaggatcc tgaattggag cagttggtct gaagccatag agtttgggtc cgatgacggg   960
aatctgggaa gcgtctacat ctacgtgctc tcattgtcg ggaccttggt atgcggaatt  1020
gtcctcggat tcctcttaa acggttcctg agaatacaaa ggctgtttcc acctgtgccg   1080
cagatcaagg ataagctcaa tgacaatcac gaagtggagg acgagattat ctgggaggag  1140
tttactcctg aggaagggaa aggctatcgg gaggaagtcc ttacgttaa agagatcacg    1200

SEQ ID NO: 7            moltype = DNA  length = 1179
FEATURE                 Location/Qualifiers
source                  1..1179
                        mol_type = genomic DNA
                        organism = Macaca fascicularis
SEQUENCE: 7
atgtttctgc tggtgacctc tcttgtactg tttgaactgc tgcaaccagc gtttctgctg    60
atacccgaga aaccagcctc tagcctgaat gtgcgctttg acgctagaac gatgaatctc   120
acatgggact gccaggaaaa caccacattt agccgatgtt tcctcactga caagaaaggc   180
cgtgttgtcg agccaaggt aaccaacaag gagtgttcct gcacctttag ggaaatttgc   240
ttgcatggag gcgtcacgtt cgaagtcac gtgaatactt cccaaagaac ctttcaggag    300
aagctgctgt atcccaactc tggaagggaa gggacagcag cccagaactt tagctgcttc   360
atctacaatg tggactttat gaactgtact tgggcgcagtg gtcctactgc tcctcgcgat   420
gtgcagtatt tcctgtatat ccagaacagc aaacgggagc gagagattca gtgcccatac   480
tacattgagg attcagggac acacgttggc tgtcacctgg gtaatcttag cggtctgacc   540
tcacgaaact acttcctcgt taacggcaca tctcaagaga taggcattca gttcttcgat   600
tccttgctcg acaccaagaa aatcgagcgc ttcaatcctc cagggaatgt cacagtgcgc   660
tgcaatacta ccccactgtct ggtgagatgg aaacaactctca gaaactgc ctagaactgc   720
tacctggatt tccagtatca gcttgacgta caccggaaga atatgcaacc cggaacggaa   780
aaccttccca tcaacgtgag tggagatctg gagaatcggt acaactttcc cagttccgaa   840
ccgagagcga agcatgccgt caagatcaga gctgccgatg tgcggatact gaactggagt   900
tcctggtctg aagcagccga gtttgggtca gatgacagga ccccagttc agtgcatatc    960
tatgtgctcc tgatactggg tacactggtc tgtgttctct tgttcggctt tctctttaag  1020
```

```
cgtttctttc gaatccagag gcttttcccg ccagttcccc agatcaaaga caaactgaat   1080
gacaaccacg aggttgagga cgaaatcatt tgggaggagt tcatgccaga agagggcaag   1140
ggctatcgcg aagaagtcct gactgtcaaa gaaatcacg                          1179

SEQ ID NO: 8              moltype = DNA  length = 894
FEATURE                   Location/Qualifiers
source                    1..894
                          mol_type = genomic DNA
                          organism = Homo sapiens
SEQUENCE: 8
gagaaatccg acttgcgaac tgtcgcacca gccagctctc tgaatgtccg atttgactct    60
cggacaatga acctgagttg ggactgtcag gagaatacca ccttcagcaa atgcttcctg   120
actgataaga agaatcgggt ggttgaacct agactctcca acaatgagtg ctcatgtacc   180
tttagggaga tatgcctgca tgaaggtgtg acgttcgaa tgcacgtgaa cacctcccaa   240
aggggctttc agcagaagct gctgtatccc aatagcggga gagagggcac tgctgcgcag   300
aatttcagct gcttcatcta caacgctgat ctgatgaact gcacatgggc aagaggccct   360
acagccccga gagatgtgca gtacttcctc tacataagga actccaaaag acgcagggaa   420
attcggtgtc cctattacat ccaggatagc ggaactcacg tgggatgtca ccttgacaat   480
ctgtcagggc ttacaagtcg caactatttt ctcgtcaatg ggacatctcg cgagattggc   540
atccaattct ttgactcact gctggacacc aagaaaatcg agcgtttcaa tccacccagt   600
aacgtgacgg tacgctgcaa caccacacac tgtttggtca ggtggaaaca gcctcgtacc   660
taccagaaac tctcctattt ggacttccag tatcagcttg atgtacaccg aaagaacact   720
caaccaggta ccgagaatct gctgatcaac gtttccggag atctggaaaa ccggtacaac   780
tttccctcat ctgaacctag agccaagcat agcgtgaaga ttcgcgcagc tgacgttcgg   840
attctcaatt ggagctcttg gagcgaagcc atcgagtttg gcagtgatga cgga          894

SEQ ID NO: 9              moltype = DNA  length = 891
FEATURE                   Location/Qualifiers
source                    1..891
                          mol_type = genomic DNA
                          organism = Macaca fascicularis
SEQUENCE: 9
gagaaaccag cctctagcct gaatgtgcgc tttgacgcta gaacgatgaa tctcacatgg    60
gactgccagg aaaacaccac atttagccga tgtttcctca ctgacaagaa aggccgtgtt   120
gtcgagccaa gggtaaccaa caaggagtgt tcctgcacct ttagggaaat ttgcttgcat   180
ggaggcgtca cgttcgaagt gcacgtgaat acttcccaaa gaacctttca ggagaagctg   240
ctgtatccca actctggaag ggaagggaca gcagcccaga actttagctg cttcatctac   300
aatgtggact ttatgaactg tacttgggca cgtggtccta ctgctcctcg cgatgtgcag   360
tattcctgt atatccagaa cagcaaacgg aggcgagaga ttcagtgcc atactacatt   420
gaggattcag ggacacacgt tggctgtcac ctgggtaatc ttagcggtct gacctcacga   480
aactacttcc tcgttaacgg cacatctcaa gagataggca ttcagttctt cgattccttg   540
ctcgacacca gaaaaatcga gcgcttcaat cctccaggga atgtcacagt gcgctgcaat   600
actcccact gtctggtgag atggaaacaa cctcggacct atcagaaact gagctacctg   660
gatttccagt atcagcttga cgtacaccgg aagaatatgc aacccggaac ggaaaacctt   720
cccatcaacg tgagtggaga tctggagaat cggtacaact ttcccagttc gaaccgagag   780
gcgaagcatg ccgtcaagat cagagctgcc gatgtgcgga tactgaactg gagttcctgg   840
tctgaagcag ccgagtttgg gtcagatgac aggcatcacc accatcatca c             891

SEQ ID NO: 10             moltype = DNA  length = 894
FEATURE                   Location/Qualifiers
source                    1..894
                          mol_type = genomic DNA
                          organism = Mus musculus
SEQUENCE: 10
cttttggccc ctaccacacc tgatgccggc tcagccctca acctgacatt cgatccttgg    60
acaaggaccc tcacatgggg ctgtgataca gcagctggga atgtgacggt aaccagctgc   120
accgtgacta gtcgggaagc aggaatccat cgaagggtta gtccctttgg tgtcggtgc   180
tggttcagac ggatgatggc cttgcatcac ggtgtgactc tggatgtgaa tggcaccgta   240
ggaggagcag ctgcccattg gcggttgagc ttcgtcaacg aaggggcagc tggttctggc   300
gcagagaatc tgacgtcga gataagggca gcacggtttc tgtcctgtgc ctggcgagga   360
ggacccgctg ccccagccga tgttcgctac tcccctcaggg ttctcaactc tacaggtcac   420
gacgtcgcca gatgtatggc tgatccaggg gatgacgtca ttacgcagtg catcgcgaac   480
gaccttagcc ttctgggcag tgaggcctat ctggtggtga ctggccgttc aggagcagga   540
cccgtcagat ttctggacga cgttgtggcc actaaagcgc tgaacgact cggccctcca   600
cgcgacgtga ctgcttcctg caactcctct cactgtaccg tgagcggggc tccaccctca   660
acctgggcta gcctgactgc gcgtgacttc cagttcgagg tgcagtggca atccgctgag   720
ccggggagca caccccgcaa ggtactggtc gttgaggaaa ccagactggc cttccctctc   780
cctgcaccgc atggtggcca aaggtcaaa gtgagggctg gggacacacg catgaagcac   840
tggggcgaat ggagtccagc tcatcctctg gaagccgagg acaccagagt gcca           894

SEQ ID NO: 11             moltype = AA   length = 123
FEATURE                   Location/Qualifiers
source                    1..123
                          mol_type = protein
                          organism = Homo sapiens
SEQUENCE: 11
EVQLVESGGG LVKPGGSLRL SCVASELTFS NVWMTWVRQA PGKGLEWVGR IKSKADGGTT    60
DYAAPVKGRF TISRDDSKNT LYLQMNSLKT EDTAVYYCTT GGYSYGDNWF DPWGQGTLVT   120
VSS                                                                 123
```

```
SEQ ID NO: 12            moltype = AA   length = 107
FEATURE                  Location/Qualifiers
source                   1..107
                         mol_type = protein
                         organism = Homo sapiens
SEQUENCE: 12
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPWTFGQ GTKVEIK                 107

SEQ ID NO: 13            moltype = AA   length = 126
FEATURE                  Location/Qualifiers
source                   1..126
                         mol_type = protein
                         organism = Homo sapiens
SEQUENCE: 13
EVQLVESGGG LVQPGRSLRL SCAASGFTFD DYAMHWVRQA PGKGLEWVSG ISWNSGIIGY    60
ADSVKGRFTI SRDNAKNSLY LQMNSLRAED TALYYCAKDT GSSGWYDYNY YGMDVWGQGT   120
TVTVSS                                                             126

SEQ ID NO: 14            moltype = AA   length = 107
FEATURE                  Location/Qualifiers
source                   1..107
                         mol_type = protein
                         organism = Homo sapiens
SEQUENCE: 14
AIQLTQSPSS LSASVGDRVT ITCRASQGIS SVLAWYQQKP GKAPKLLIYD ASSLESGVPS    60
RFSGSGSGTD FTLTISSLQP EDFATYYCQQ FNSYPRTFGQ GTKVEIK                 107

SEQ ID NO: 15            moltype = AA   length = 126
FEATURE                  Location/Qualifiers
source                   1..126
                         mol_type = protein
                         organism = Homo sapiens
SEQUENCE: 15
EVQLVESGGG LVQPGRSLRL SCAASGFTFG DYAMHWVRQA PGKGLEWVSG ISWNSGIIGY    60
ADSVKGRFTI SRDNAKNSLY LQMNSLRAED TALYYCVKDE GSSGWYDFNY FGMDVWGQGT   120
TVTVSS                                                             126

SEQ ID NO: 16            moltype = AA   length = 107
FEATURE                  Location/Qualifiers
source                   1..107
                         mol_type = protein
                         organism = Homo sapiens
SEQUENCE: 16
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPITFGQ GTRLEIK                 107

SEQ ID NO: 17            moltype = AA   length = 126
FEATURE                  Location/Qualifiers
source                   1..126
                         mol_type = protein
                         organism = Homo sapiens
SEQUENCE: 17
EVQLVESGGG LVQPGRSLRL SCAASGFTFD DYAMHWVRQA PGKGLEWVSG ISWNSGIIGY    60
ADSVKGRFTI SRDNAKNSLY LQMNSLRAED TALYYCAKDM GSSGWYDYNY FGMDVWGQGT   120
TVTVSS                                                             126

SEQ ID NO: 18            moltype = AA   length = 107
FEATURE                  Location/Qualifiers
source                   1..107
                         mol_type = protein
                         organism = Homo sapiens
SEQUENCE: 18
AIQLTQSPSS LSASVGDRVT ITCRASQGIS SVLAWYQQKP GKAPKLLIYD ASSLESGVPS    60
RFSGSGSGTD FTLTISSLQP EDFATYYCQQ FNSYPRTFGQ GTKVEIK                 107

SEQ ID NO: 19            moltype = AA   length = 114
FEATURE                  Location/Qualifiers
source                   1..114
                         mol_type = protein
                         organism = Homo sapiens
SEQUENCE: 19
QVQLVQSGAE VKKPGASVKV SCKVSGYTLT EFSIHWVRQA PGKGLEWMGG FDPEDDETIY    60
AQKFQGRVTM TEDTSTDTAY MELSSLRSED TAVYYCATSQ MLLWGQGTMV TVSS         114
```

```
SEQ ID NO: 20           moltype = AA  length = 107
FEATURE                 Location/Qualifiers
source                  1..107
                        mol_type = protein
                        organism = Homo sapiens
SEQUENCE: 20
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNSYPHTFGQ GTKLEIK                 107

SEQ ID NO: 21           moltype = AA  length = 122
FEATURE                 Location/Qualifiers
source                  1..122
                        mol_type = protein
                        organism = Homo sapiens
SEQUENCE: 21
EVQLVESGGG LVKPGGSLRL SCEASGFTLS SYTMNWVRQA PGKGLEWVSS IRSSSSFIYY    60
ADSVKGRFTI SRDIAKNSLY LQINSLRAED TAVYYCARDY YGSGSYWYFD LWGRGTLVTV   120
SS                                                                  122

SEQ ID NO: 22           moltype = AA  length = 107
FEATURE                 Location/Qualifiers
source                  1..107
                        mol_type = protein
                        organism = Homo sapiens
SEQUENCE: 22
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPLTFGG GTKVEIK                 107

SEQ ID NO: 23           moltype = AA  length = 124
FEATURE                 Location/Qualifiers
source                  1..124
                        mol_type = protein
                        organism = Homo sapiens
SEQUENCE: 23
QVQLVESGGG LVKPGGSLRL SCAASGFTFS DYYMSWIRQA PGKGLEWVSF ISSSGIIIYY    60
ADSVKGRFTI SRDNAKNSLY LQMNSLRAED TAVYYCARRG YSGYDYYYYG LDVWGQGTTV   120
TVSS                                                                124

SEQ ID NO: 24           moltype = AA  length = 105
FEATURE                 Location/Qualifiers
source                  1..105
                        mol_type = protein
                        organism = Homo sapiens
SEQUENCE: 24
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSTFGGGT KVEIK                   105

SEQ ID NO: 25           moltype = AA  length = 118
FEATURE                 Location/Qualifiers
source                  1..118
                        mol_type = protein
                        organism = Homo sapiens
SEQUENCE: 25
QVQLVESGGG LVKPGGSLRL SCAASGFTFS DYYMNWIRQA PGKGLEWVSY ISTSGSIIYY    60
ADSVKGRFTI SRDNAKNSLY LQMNSLRAED TAVYYCARRR YYYGMDVWGQ GTTVTVSS     118

SEQ ID NO: 26           moltype = AA  length = 105
FEATURE                 Location/Qualifiers
source                  1..105
                        mol_type = protein
                        organism = Homo sapiens
SEQUENCE: 26
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGRTFGQGT KVEIK                   105

SEQ ID NO: 27           moltype = AA  length = 128
FEATURE                 Location/Qualifiers
source                  1..128
                        mol_type = protein
                        organism = Homo sapiens
SEQUENCE: 27
QVQLVQSGAE VKKPGASVKV SCKASGYTFT SDYMHWVRQA PGQGLEWMGI INPSGGATSY    60
VQKFQGRVTM TRDTSTSTVY MELSSLRSED TAVYYCARER YYGSGTYFNI GLWYFDLWGR   120
GTLVTVSS                                                            128

SEQ ID NO: 28           moltype = AA  length = 108
FEATURE                 Location/Qualifiers
```

```
source                  1..108
                        mol_type = protein
                        organism = Homo sapiens
SEQUENCE: 28
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPLTFG GGTKVEIK                108

SEQ ID NO: 29           moltype = AA  length = 128
FEATURE                 Location/Qualifiers
source                  1..128
                        mol_type = protein
                        organism = Homo sapiens
SEQUENCE: 29
QVQLVQSGAE VKEPGASVKI SCKASGYTFT NDYMHWVRQA PGQGLEWMGI INPTGGGTSY    60
AQKFRGRVTM TRDTSTSTVY MELSSLRSED TAVFYCARER YYGSGTYFNI GLWYFDLWGR   120
GTLVTVSS                                                           128

SEQ ID NO: 30           moltype = AA  length = 108
FEATURE                 Location/Qualifiers
source                  1..108
                        mol_type = protein
                        organism = Homo sapiens
SEQUENCE: 30
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPLTFG GGTKVEIK                108

SEQ ID NO: 31           moltype = AA  length = 5
FEATURE                 Location/Qualifiers
source                  1..5
                        mol_type = protein
                        organism = Homo sapiens
SEQUENCE: 31
NVWMT                                                                5

SEQ ID NO: 32           moltype = AA  length = 19
FEATURE                 Location/Qualifiers
source                  1..19
                        mol_type = protein
                        organism = Homo sapiens
SEQUENCE: 32
RIKSKADGGT TDYAAPVKG                                                19

SEQ ID NO: 33           moltype = AA  length = 12
FEATURE                 Location/Qualifiers
source                  1..12
                        mol_type = protein
                        organism = Homo sapiens
SEQUENCE: 33
GGYSYGDNWF DP                                                       12

SEQ ID NO: 34           moltype = AA  length = 11
FEATURE                 Location/Qualifiers
source                  1..11
                        mol_type = protein
                        organism = Homo sapiens
SEQUENCE: 34
RASQSVSSYL A                                                        11

SEQ ID NO: 35           moltype = AA  length = 7
FEATURE                 Location/Qualifiers
source                  1..7
                        mol_type = protein
                        organism = Homo sapiens
SEQUENCE: 35
DASNRAT                                                              7

SEQ ID NO: 36           moltype = AA  length = 9
FEATURE                 Location/Qualifiers
source                  1..9
                        mol_type = protein
                        organism = Homo sapiens
SEQUENCE: 36
QQRSNWPWT                                                            9

SEQ ID NO: 37           moltype = AA  length = 5
FEATURE                 Location/Qualifiers
source                  1..5
                        mol_type = protein
                        organism = Homo sapiens
```

```
SEQUENCE: 37
DYAMH                                                                    5

SEQ ID NO: 38          moltype = AA  length = 17
FEATURE                Location/Qualifiers
source                 1..17
                       mol_type = protein
                       organism = Homo sapiens
SEQUENCE: 38
GISWNSGIIG YADSVKG                                                      17

SEQ ID NO: 39          moltype = AA  length = 17
FEATURE                Location/Qualifiers
source                 1..17
                       mol_type = protein
                       organism = Homo sapiens
SEQUENCE: 39
DTGSSGWYDY NYYGMDV                                                      17

SEQ ID NO: 40          moltype = AA  length = 11
FEATURE                Location/Qualifiers
source                 1..11
                       mol_type = protein
                       organism = Homo sapiens
SEQUENCE: 40
RASQGISSVL A                                                            11

SEQ ID NO: 41          moltype = AA  length = 7
FEATURE                Location/Qualifiers
source                 1..7
                       mol_type = protein
                       organism = Homo sapiens
SEQUENCE: 41
DASSLES                                                                  7

SEQ ID NO: 42          moltype = AA  length = 9
FEATURE                Location/Qualifiers
source                 1..9
                       mol_type = protein
                       organism = Homo sapiens
SEQUENCE: 42
QQFNSYPRT                                                                9

SEQ ID NO: 43          moltype = AA  length = 5
FEATURE                Location/Qualifiers
source                 1..5
                       mol_type = protein
                       organism = Homo sapiens
SEQUENCE: 43
DYAMH                                                                    5

SEQ ID NO: 44          moltype = AA  length = 17
FEATURE                Location/Qualifiers
source                 1..17
                       mol_type = protein
                       organism = Homo sapiens
SEQUENCE: 44
GISWNSGIIG YADSVKG                                                      17

SEQ ID NO: 45          moltype = AA  length = 17
FEATURE                Location/Qualifiers
source                 1..17
                       mol_type = protein
                       organism = Homo sapiens
SEQUENCE: 45
DEGSSGWYDF NYFGMDV                                                      17

SEQ ID NO: 46          moltype = AA  length = 11
FEATURE                Location/Qualifiers
source                 1..11
                       mol_type = protein
                       organism = Homo sapiens
SEQUENCE: 46
RASQGISSAL A                                                            11

SEQ ID NO: 47          moltype = AA  length = 7
FEATURE                Location/Qualifiers
```

```
source                          1..7
                                mol_type = protein
                                organism = Homo sapiens
SEQUENCE: 47
DASSLES                                                                     7

SEQ ID NO: 48                   moltype = AA   length = 9
FEATURE                         Location/Qualifiers
source                          1..9
                                mol_type = protein
                                organism = Homo sapiens
SEQUENCE: 48
QQFNSYPIT                                                                   9

SEQ ID NO: 49                   moltype = AA   length = 5
FEATURE                         Location/Qualifiers
source                          1..5
                                mol_type = protein
                                organism = Homo sapiens
SEQUENCE: 49
DYAMH                                                                       5

SEQ ID NO: 50                   moltype = AA   length = 17
FEATURE                         Location/Qualifiers
source                          1..17
                                mol_type = protein
                                organism = Homo sapiens
SEQUENCE: 50
GISWNSGIIG YADSVKG                                                         17

SEQ ID NO: 51                   moltype = AA   length = 17
FEATURE                         Location/Qualifiers
source                          1..17
                                mol_type = protein
                                organism = Homo sapiens
SEQUENCE: 51
DMGSSGWYDY NYFGMDV                                                         17

SEQ ID NO: 52                   moltype = AA   length = 11
FEATURE                         Location/Qualifiers
source                          1..11
                                mol_type = protein
                                organism = Homo sapiens
SEQUENCE: 52
RASQGISSVL A                                                               11

SEQ ID NO: 53                   moltype = AA   length = 7
FEATURE                         Location/Qualifiers
source                          1..7
                                mol_type = protein
                                organism = Homo sapiens
SEQUENCE: 53
DASSLES                                                                     7

SEQ ID NO: 54                   moltype = AA   length = 9
FEATURE                         Location/Qualifiers
source                          1..9
                                mol_type = protein
                                organism = Homo sapiens
SEQUENCE: 54
QQFNSYPRT                                                                   9

SEQ ID NO: 55                   moltype = AA   length = 5
FEATURE                         Location/Qualifiers
source                          1..5
                                mol_type = protein
                                organism = Homo sapiens
SEQUENCE: 55
EFSIH                                                                       5

SEQ ID NO: 56                   moltype = AA   length = 17
FEATURE                         Location/Qualifiers
source                          1..17
                                mol_type = protein
                                organism = Homo sapiens
SEQUENCE: 56
GFDPEDDETI YAQKFQG                                                         17

SEQ ID NO: 57                   moltype = AA   length = 5
```

```
FEATURE                 Location/Qualifiers
source                  1..5
                        mol_type = protein
                        organism = Homo sapiens
SEQUENCE: 57
SQMLL                                                                         5

SEQ ID NO: 58           moltype = AA  length = 11
FEATURE                 Location/Qualifiers
source                  1..11
                        mol_type = protein
                        organism = Homo sapiens
SEQUENCE: 58
RASQGISSWL A                                                                  11

SEQ ID NO: 59           moltype = AA  length = 7
FEATURE                 Location/Qualifiers
source                  1..7
                        mol_type = protein
                        organism = Homo sapiens
SEQUENCE: 59
AASSLQS                                                                       7

SEQ ID NO: 60           moltype = AA  length = 9
FEATURE                 Location/Qualifiers
source                  1..9
                        mol_type = protein
                        organism = Homo sapiens
SEQUENCE: 60
QQYNSYPHT                                                                     9

SEQ ID NO: 61           moltype = AA  length = 5
FEATURE                 Location/Qualifiers
source                  1..5
                        mol_type = protein
                        organism = Homo sapiens
SEQUENCE: 61
SYTMN                                                                         5

SEQ ID NO: 62           moltype = AA  length = 17
FEATURE                 Location/Qualifiers
source                  1..17
                        mol_type = protein
                        organism = Homo sapiens
SEQUENCE: 62
SIRSSSSFIY YADSVKG                                                            17

SEQ ID NO: 63           moltype = AA  length = 13
FEATURE                 Location/Qualifiers
source                  1..13
                        mol_type = protein
                        organism = Homo sapiens
SEQUENCE: 63
DYYGSGSYWY FDL                                                                13

SEQ ID NO: 64           moltype = AA  length = 11
FEATURE                 Location/Qualifiers
source                  1..11
                        mol_type = protein
                        organism = Homo sapiens
SEQUENCE: 64
RASQSVSSYL A                                                                  11

SEQ ID NO: 65           moltype = AA  length = 7
FEATURE                 Location/Qualifiers
source                  1..7
                        mol_type = protein
                        organism = Homo sapiens
SEQUENCE: 65
DASNRAT                                                                       7

SEQ ID NO: 66           moltype = AA  length = 9
FEATURE                 Location/Qualifiers
source                  1..9
                        mol_type = protein
                        organism = Homo sapiens
SEQUENCE: 66
QQRSNWPLT                                                                     9
```

-continued

| | | |
|---|---|---|
| SEQ ID NO: 67<br>FEATURE<br>source<br><br>SEQUENCE: 67<br>DYYMS | moltype = AA  length = 5<br>Location/Qualifiers<br>1..5<br>mol_type = protein<br>organism = Homo sapiens | <br><br><br><br><br>5 |
| SEQ ID NO: 68<br>FEATURE<br>source<br><br>SEQUENCE: 68<br>FISSSGIIIY YADSVKG | moltype = AA  length = 17<br>Location/Qualifiers<br>1..17<br>mol_type = protein<br>organism = Homo sapiens | <br><br><br><br><br>17 |
| SEQ ID NO: 69<br>FEATURE<br>source<br><br>SEQUENCE: 69<br>RGYSGYDYYY YGLDV | moltype = AA  length = 15<br>Location/Qualifiers<br>1..15<br>mol_type = protein<br>organism = Homo sapiens | <br><br><br><br><br>15 |
| SEQ ID NO: 70<br>FEATURE<br>source<br><br>SEQUENCE: 70<br>RASQSVSSSY LA | moltype = AA  length = 12<br>Location/Qualifiers<br>1..12<br>mol_type = protein<br>organism = Homo sapiens | <br><br><br><br><br>12 |
| SEQ ID NO: 71<br>FEATURE<br>source<br><br>SEQUENCE: 71<br>GASSRAT | moltype = AA  length = 7<br>Location/Qualifiers<br>1..7<br>mol_type = protein<br>organism = Homo sapiens | <br><br><br><br><br>7 |
| SEQ ID NO: 72<br>FEATURE<br>source<br><br>SEQUENCE: 72<br>QQYGST | moltype = AA  length = 6<br>Location/Qualifiers<br>1..6<br>mol_type = protein<br>organism = Homo sapiens | <br><br><br><br><br>6 |
| SEQ ID NO: 73<br>FEATURE<br>source<br><br>SEQUENCE: 73<br>DYYMN | moltype = AA  length = 5<br>Location/Qualifiers<br>1..5<br>mol_type = protein<br>organism = Homo sapiens | <br><br><br><br><br>5 |
| SEQ ID NO: 74<br>FEATURE<br>source<br><br>SEQUENCE: 74<br>YISTSGSIIY YADSVKG | moltype = AA  length = 17<br>Location/Qualifiers<br>1..17<br>mol_type = protein<br>organism = Homo sapiens | <br><br><br><br><br>17 |
| SEQ ID NO: 75<br>FEATURE<br>source<br><br>SEQUENCE: 75<br>RRYYYGMDV | moltype = AA  length = 9<br>Location/Qualifiers<br>1..9<br>mol_type = protein<br>organism = Homo sapiens | <br><br><br><br><br>9 |
| SEQ ID NO: 76<br>FEATURE<br>source<br><br>SEQUENCE: 76<br>RASQSVSSSY LA | moltype = AA  length = 12<br>Location/Qualifiers<br>1..12<br>mol_type = protein<br>organism = Homo sapiens | <br><br><br><br><br>12 |

```
SEQ ID NO: 77              moltype = AA   length = 7
FEATURE                    Location/Qualifiers
source                     1..7
                           mol_type = protein
                           organism = Homo sapiens
SEQUENCE: 77
GASSRAT                                                                   7

SEQ ID NO: 78              moltype = AA   length = 6
FEATURE                    Location/Qualifiers
source                     1..6
                           mol_type = protein
                           organism = Homo sapiens
SEQUENCE: 78
QQYGRT                                                                    6

SEQ ID NO: 79              moltype = AA   length = 5
FEATURE                    Location/Qualifiers
source                     1..5
                           mol_type = protein
                           organism = Homo sapiens
SEQUENCE: 79
SDYMH                                                                     5

SEQ ID NO: 80              moltype = AA   length = 17
FEATURE                    Location/Qualifiers
source                     1..17
                           mol_type = protein
                           organism = Homo sapiens
SEQUENCE: 80
IINPSGGATS YVQKFQG                                                       17

SEQ ID NO: 81              moltype = AA   length = 19
FEATURE                    Location/Qualifiers
source                     1..19
                           mol_type = protein
                           organism = Homo sapiens
SEQUENCE: 81
ERYYGSGTYF NIGLWYFDL                                                     19

SEQ ID NO: 82              moltype = AA   length = 12
FEATURE                    Location/Qualifiers
source                     1..12
                           mol_type = protein
                           organism = Homo sapiens
SEQUENCE: 82
RASQSVSSSY LA                                                            12

SEQ ID NO: 83              moltype = AA   length = 7
FEATURE                    Location/Qualifiers
source                     1..7
                           mol_type = protein
                           organism = Homo sapiens
SEQUENCE: 83
GASSRAT                                                                   7

SEQ ID NO: 84              moltype = AA   length = 9
FEATURE                    Location/Qualifiers
source                     1..9
                           mol_type = protein
                           organism = Homo sapiens
SEQUENCE: 84
QQYGSSPLT                                                                 9

SEQ ID NO: 85              moltype = AA   length = 5
FEATURE                    Location/Qualifiers
source                     1..5
                           mol_type = protein
                           organism = Homo sapiens
SEQUENCE: 85
NDYMH                                                                     5

SEQ ID NO: 86              moltype = AA   length = 17
FEATURE                    Location/Qualifiers
source                     1..17
                           mol_type = protein
                           organism = Homo sapiens
```

```
SEQUENCE: 86
IINPTGGGTS YAQKFRG                                                       17

SEQ ID NO: 87            moltype = AA  length = 19
FEATURE                  Location/Qualifiers
source                   1..19
                         mol_type = protein
                         organism = Homo sapiens
SEQUENCE: 87
ERYYGSGTYF NIGLWYFDL                                                     19

SEQ ID NO: 88            moltype = AA  length = 12
FEATURE                  Location/Qualifiers
source                   1..12
                         mol_type = protein
                         organism = Homo sapiens
SEQUENCE: 88
RASQSVSSSY LA                                                            12

SEQ ID NO: 89            moltype = AA  length = 7
FEATURE                  Location/Qualifiers
source                   1..7
                         mol_type = protein
                         organism = Homo sapiens
SEQUENCE: 89
GASSRAT                                                                   7

SEQ ID NO: 90            moltype = AA  length = 9
FEATURE                  Location/Qualifiers
source                   1..9
                         mol_type = protein
                         organism = Homo sapiens
SEQUENCE: 90
QQYGSSPLT                                                                 9

SEQ ID NO: 91            moltype = AA  length = 324
FEATURE                  Location/Qualifiers
source                   1..324
                         mol_type = protein
                         organism = Homo sapiens
SEQUENCE: 91
GAAATTGTGT TGACGCAGTC TCCAGGCACC CTGTCTTTGT CTCCAGGGGA AAGAGCCACC         60
CTCTCCTGCA GGGCCAGTCA GAGTGTTAGC AGCAGCTACT TAGCCTGGTA CCAGCAGAAA        120
CCTGGCCAGG CTCCCAGGCT CCTCATCTAT GGTGCATCCA GCAGGGCCAC TGGCATCCCA        180
GACAGGTTCA GTGGCAGTGG GTCTGGGACA GACTTCACTC TCACCATCAG CAGACTGGAG        240
CCTGAAGATT TTGCAGTGTA TTACTGTCAG CAGTATGGTA GCTCACCGCT CACTTTCGGC        300
GGAGGGACCA AGGTGGAGAT CAAA                                              324

SEQ ID NO: 92            moltype = AA  length = 120
FEATURE                  Location/Qualifiers
source                   1..120
                         mol_type = protein
                         organism = Homo sapiens
SEQUENCE: 92
EVQLVQSGAE VKKPGASVKV SCKVSGYTLA ELSMHWVRQA PGKGLEWMGG FDPEDGERIY         60
AQKFQGRVTM TEDTSKDTAY MELSSLRSED TAVYYCTTGL FYYQYGMDVW GQGTMVTVSS        120

SEQ ID NO: 93            moltype = AA  length = 120
FEATURE                  Location/Qualifiers
source                   1..120
                         mol_type = protein
                         organism = Homo sapiens
SEQUENCE: 93
EVQLVQSGAE VKKPGASVKV SCKVSGYTLT DLSMHWVRQA PGKGLEWMGG LDPEDGETIY         60
AQKFQGRVTM TEDTSTDTAY MELSSLRSED TAVYYCATGL FYYQYGMDVW GQGTLVTVSS        120

SEQ ID NO: 94            moltype = AA  length = 120
FEATURE                  Location/Qualifiers
source                   1..120
                         mol_type = protein
                         organism = Homo sapiens
SEQUENCE: 94
QVQLVQSGAE VKKPGASVKV SCKVSGYTLT DLSMHWVRQA PGKGLEWMGG FDPEDGETIY         60
AQKFQGRVTM TEDTSTDTAY MELSSLRSED TAVYYCATGL FYYQYGMDVW GQGTTVTVSS        120

SEQ ID NO: 95            moltype = AA  length = 120
FEATURE                  Location/Qualifiers
```

```
                        source          1..120
                                        mol_type = protein
                                        organism = Homo sapiens
SEQUENCE: 95
QVQLQQSGAE VKKPGASVKV SCKVSGYTLT DLSMHWVRQA PGKGLEWMGG FDPEDGERIY   60
AQKFQGRVTM TEDTATDTAY MELSSLRSED TAVYHCATGL FYYQYGMDVW GQGTTVTVSS  120

SEQ ID NO: 96           moltype = AA   length = 120
FEATURE                 Location/Qualifiers
source                  1..120
                        mol_type = protein
                        organism = Homo sapiens
SEQUENCE: 96
QVQLVQSGAE VKKPGASVKV SCKVSGYTLT DFAIHWVRQA PGKGLEWMGG FDPEDGERIY   60
AQKFQGRVTM TEDTSTDTAY MELSSLRSED TAVYYCTTGL FYYQYGMDVW GQGTLVTVSS  120

SEQ ID NO: 97           moltype = AA   length = 120
FEATURE                 Location/Qualifiers
source                  1..120
                        mol_type = protein
                        organism = Homo sapiens
SEQUENCE: 97
EVQLVQSGAE VKKPGASVKV SCKVSGYTLT ELSMHWVRQA PGKGLEWMGG FDPEDGERIY   60
AQKFQGRVTM TEDTSTDTAY MELSSLRSED TAVYYCATGL FYYQYGMDVW GQGTTVTVSS  120

SEQ ID NO: 98           moltype = AA   length = 120
FEATURE                 Location/Qualifiers
source                  1..120
                        mol_type = protein
                        organism = Homo sapiens
SEQUENCE: 98
QVQLQQSGAE VKKPGASVKV SCKVSGYTLT DLSMHWVRQA PGKGLEWMGG FDPEDGERIY   60
AQKFQGRVTM TEDTSTDTAY MELSSLRSED TAVYYCATGL FYYQYGMDVW GQGTLVTVSS  120

SEQ ID NO: 99           moltype = AA   length = 120
FEATURE                 Location/Qualifiers
source                  1..120
                        mol_type = protein
                        organism = Homo sapiens
SEQUENCE: 99
QVQLVQSGAE VKKPGASVKV SCKVSGYTLT DFAIHWVRQA PGKGLEWMGG FDPEDGERIY   60
AQKFQGRVTM TEDTSTDTAY MELSSLRSED TAVYYCATGL FYYQYGMDVW GQGTTVTVSS  120

SEQ ID NO: 100          moltype = AA   length = 120
FEATURE                 Location/Qualifiers
source                  1..120
                        mol_type = protein
                        organism = Homo sapiens
SEQUENCE: 100
QVQLVQSGAE VKKPGASVKV SCKVSGYTLT DLSMHWVRQA PGKGLEWMGG FDPEDGERIY   60
AQKFQGRVTM TEDTSTDTAY MELSSLRSED TAMYYCATGL FYYQYGMDVW GQGTTVTVSS  120

SEQ ID NO: 101          moltype = AA   length = 120
FEATURE                 Location/Qualifiers
source                  1..120
                        mol_type = protein
                        organism = Homo sapiens
SEQUENCE: 101
QVQLVQSGAE VKKPGASVKV SCKVSGYPLT DLSMHWVRQA PGEGLEWMGG SDPEDGETIY   60
AQKFQGRVTV TEDTSTDTAY MELSNLRSED TAVYYCATGL FYYQYGMDVW GQGTTVTVSS  120

SEQ ID NO: 102          moltype = AA   length = 120
FEATURE                 Location/Qualifiers
source                  1..120
                        mol_type = protein
                        organism = Homo sapiens
SEQUENCE: 102
QVQLVQSGAE VKKPGASVKV SCKVSGYTLT DLSMHWVRQA PGKGLEWMGG FDPEDGERIY   60
AQKFQDRVTM TEDTSTDTAY MELSSLRSED TAVYYCATGL FYYQYGMDVW GQGTLVTVSS  120

SEQ ID NO: 103          moltype = AA   length = 120
FEATURE                 Location/Qualifiers
source                  1..120
                        mol_type = protein
                        organism = Homo sapiens
SEQUENCE: 103
EVQLVQSGAE VKKPGASVKV SCKVSGYTLT DLSMHWVRQA PGKGLEWMGG FDPEDGERIY   60
AQKFQGRVTM TEDTSTDTAY MELSSLRSED TAVYYCATGL FYYYYGMDVW GQGTMVTVSS  120
```

```
SEQ ID NO: 104            moltype = AA   length = 5
FEATURE                   Location/Qualifiers
source                    1..5
                          mol_type = protein
                          organism = Homo sapiens
SEQUENCE: 104
ELSMH                                                                    5

SEQ ID NO: 105            moltype = AA   length = 17
FEATURE                   Location/Qualifiers
source                    1..17
                          mol_type = protein
                          organism = Homo sapiens
SEQUENCE: 105
GFDPEDGERI YAQKFQG                                                      17

SEQ ID NO: 106            moltype = AA   length = 11
FEATURE                   Location/Qualifiers
source                    1..11
                          mol_type = protein
                          organism = Homo sapiens
SEQUENCE: 106
GLFYYQYGMD V                                                            11

SEQ ID NO: 107            moltype = AA   length = 5
FEATURE                   Location/Qualifiers
source                    1..5
                          mol_type = protein
                          organism = Homo sapiens
SEQUENCE: 107
DLSMH                                                                    5

SEQ ID NO: 108            moltype = AA   length = 17
FEATURE                   Location/Qualifiers
source                    1..17
                          mol_type = protein
                          organism = Homo sapiens
SEQUENCE: 108
GLDPEDGETI YAQKFQG                                                      17

SEQ ID NO: 109            moltype = AA   length = 11
FEATURE                   Location/Qualifiers
source                    1..11
                          mol_type = protein
                          organism = Homo sapiens
SEQUENCE: 109
GLFYYQYGMD V                                                            11

SEQ ID NO: 110            moltype = AA   length = 5
FEATURE                   Location/Qualifiers
source                    1..5
                          mol_type = protein
                          organism = Homo sapiens
SEQUENCE: 110
DLSMH                                                                    5

SEQ ID NO: 111            moltype = AA   length = 17
FEATURE                   Location/Qualifiers
source                    1..17
                          mol_type = protein
                          organism = Homo sapiens
SEQUENCE: 111
GFDPEDGETI YAQKFQG                                                      17

SEQ ID NO: 112            moltype = AA   length = 11
FEATURE                   Location/Qualifiers
source                    1..11
                          mol_type = protein
                          organism = Homo sapiens
SEQUENCE: 112
GLFYYQYGMD V                                                            11

SEQ ID NO: 113            moltype = AA   length = 5
FEATURE                   Location/Qualifiers
source                    1..5
                          mol_type = protein
                          organism = Homo sapiens
SEQUENCE: 113
DLSMH                                                                    5
```

```
SEQ ID NO: 114            moltype = AA   length = 17
FEATURE                   Location/Qualifiers
source                    1..17
                          mol_type = protein
                          organism = Homo sapiens
SEQUENCE: 114
GFDPEDGERI YAQKFQG                                                    17

SEQ ID NO: 115            moltype = AA   length = 11
FEATURE                   Location/Qualifiers
source                    1..11
                          mol_type = protein
                          organism = Homo sapiens
SEQUENCE: 115
GLFYYQYGMD V                                                          11

SEQ ID NO: 116            moltype = AA   length = 5
FEATURE                   Location/Qualifiers
source                    1..5
                          mol_type = protein
                          organism = Homo sapiens
SEQUENCE: 116
DFAIH                                                                 5

SEQ ID NO: 117            moltype = AA   length = 17
FEATURE                   Location/Qualifiers
source                    1..17
                          mol_type = protein
                          organism = Homo sapiens
SEQUENCE: 117
GFDPEDGERI YAQKFQG                                                    17

SEQ ID NO: 118            moltype = AA   length = 11
FEATURE                   Location/Qualifiers
source                    1..11
                          mol_type = protein
                          organism = Homo sapiens
SEQUENCE: 118
GLFYYQYGMD V                                                          11

SEQ ID NO: 119            moltype = AA   length = 5
FEATURE                   Location/Qualifiers
source                    1..5
                          mol_type = protein
                          organism = Homo sapiens
SEQUENCE: 119
ELSMH                                                                 5

SEQ ID NO: 120            moltype = AA   length = 17
FEATURE                   Location/Qualifiers
source                    1..17
                          mol_type = protein
                          organism = Homo sapiens
SEQUENCE: 120
GFDPEDGERI YAQKFQG                                                    17

SEQ ID NO: 121            moltype = AA   length = 11
FEATURE                   Location/Qualifiers
source                    1..11
                          mol_type = protein
                          organism = Homo sapiens
SEQUENCE: 121
GLFYYQYGMD V                                                          11

SEQ ID NO: 122            moltype = AA   length = 5
FEATURE                   Location/Qualifiers
source                    1..5
                          mol_type = protein
                          organism = Homo sapiens
SEQUENCE: 122
DLSMH                                                                 5

SEQ ID NO: 123            moltype = AA   length = 17
FEATURE                   Location/Qualifiers
source                    1..17
                          mol_type = protein
                          organism = Homo sapiens
```

-continued

```
SEQUENCE: 123
GFDPEDGERI YAQKFQG                                                      17

SEQ ID NO: 124          moltype = AA  length = 11
FEATURE                 Location/Qualifiers
source                  1..11
                        mol_type = protein
                        organism = Homo sapiens
SEQUENCE: 124
GLFYYQYGMD V                                                            11

SEQ ID NO: 125          moltype = AA  length = 5
FEATURE                 Location/Qualifiers
source                  1..5
                        mol_type = protein
                        organism = Homo sapiens
SEQUENCE: 125
DFAIH                                                                   5

SEQ ID NO: 126          moltype = AA  length = 17
FEATURE                 Location/Qualifiers
source                  1..17
                        mol_type = protein
                        organism = Homo sapiens
SEQUENCE: 126
GFDPEDGERI YAQKFQG                                                      17

SEQ ID NO: 127          moltype = AA  length = 11
FEATURE                 Location/Qualifiers
source                  1..11
                        mol_type = protein
                        organism = Homo sapiens
SEQUENCE: 127
GLFYYQYGMD V                                                            11

SEQ ID NO: 128          moltype = AA  length = 5
FEATURE                 Location/Qualifiers
source                  1..5
                        mol_type = protein
                        organism = Homo sapiens
SEQUENCE: 128
DLSMH                                                                   5

SEQ ID NO: 129          moltype = AA  length = 17
FEATURE                 Location/Qualifiers
source                  1..17
                        mol_type = protein
                        organism = Homo sapiens
SEQUENCE: 129
GFDPEDGERI YAQKFQG                                                      17

SEQ ID NO: 130          moltype = AA  length = 11
FEATURE                 Location/Qualifiers
source                  1..11
                        mol_type = protein
                        organism = Homo sapiens
SEQUENCE: 130
GLFYYQYGMD V                                                            11

SEQ ID NO: 131          moltype = AA  length = 5
FEATURE                 Location/Qualifiers
source                  1..5
                        mol_type = protein
                        organism = Homo sapiens
SEQUENCE: 131
DLSMH                                                                   5

SEQ ID NO: 132          moltype = AA  length = 17
FEATURE                 Location/Qualifiers
source                  1..17
                        mol_type = protein
                        organism = Homo sapiens
SEQUENCE: 132
GSDPEDGETI YAQKFQG                                                      17

SEQ ID NO: 133          moltype = AA  length = 11
FEATURE                 Location/Qualifiers
```

```
source                        1..11
                              mol_type = protein
                              organism = Homo sapiens
SEQUENCE: 133
GLFYYQYGMD V                                                             11

SEQ ID NO: 134                moltype = AA   length = 5
FEATURE                       Location/Qualifiers
source                        1..5
                              mol_type = protein
                              organism = Homo sapiens
SEQUENCE: 134
DLSMH                                                                     5

SEQ ID NO: 135                moltype = AA   length = 17
FEATURE                       Location/Qualifiers
source                        1..17
                              mol_type = protein
                              organism = Homo sapiens
SEQUENCE: 135
GFDPEDGERI YAQKFQD                                                       17

SEQ ID NO: 136                moltype = AA   length = 11
FEATURE                       Location/Qualifiers
source                        1..11
                              mol_type = protein
                              organism = Homo sapiens
SEQUENCE: 136
GLFYYQYGMD V                                                             11

SEQ ID NO: 137                moltype = AA   length = 5
FEATURE                       Location/Qualifiers
source                        1..5
                              mol_type = protein
                              organism = Homo sapiens
SEQUENCE: 137
DLSMH                                                                     5

SEQ ID NO: 138                moltype = AA   length = 17
FEATURE                       Location/Qualifiers
source                        1..17
                              mol_type = protein
                              organism = Homo sapiens
SEQUENCE: 138
GFDPEDGERI YAQKFQG                                                       17

SEQ ID NO: 139                moltype = AA   length = 11
FEATURE                       Location/Qualifiers
source                        1..11
                              mol_type = protein
                              organism = Homo sapiens
SEQUENCE: 139
GLFYYYYGMD V                                                             11

SEQ ID NO: 140                moltype = AA   length = 330
FEATURE                       Location/Qualifiers
source                        1..330
                              mol_type = protein
                              organism = Homo sapiens
SEQUENCE: 140
ASTKGPSVCP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSADKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPCRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 141                moltype = AA   length = 107
FEATURE                       Location/Qualifiers
source                        1..107
                              mol_type = protein
                              organism = Homo sapiens
SEQUENCE: 141
RTVAAPSVFI FPPCDEQLKS GTASVVCLLN NFYPREAKVQ WKVDNALQSG NSQESVTEQD   60
SKDSTYSLSS TLTLSKADYE KHKVYACEVT HQGLSSPVTK SFNRGES                107

SEQ ID NO: 142                moltype = AA   length = 330
FEATURE                       Location/Qualifiers
```

```
source                        1..330
                              mol_type = protein
                              organism = Homo sapiens
SEQUENCE: 142
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VCTLPPSRDE   240
LTKNQVSLSC AVKGFYPSDI AVEWESNGQP ENNYKTTPPV LDSDGSFFLV SKLTVDKSRW   300
QQGNVFSCSV MHEALHNRFT QKSLSLSPGK                                   330

SEQ ID NO: 143                moltype = AA   length = 107
FEATURE                       Location/Qualifiers
source                        1..107
                              mol_type = protein
                              organism = Homo sapiens
SEQUENCE: 143
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 144                moltype = AA   length = 98
FEATURE                       Location/Qualifiers
source                        1..98
                              mol_type = protein
                              organism = Homo sapiens
SEQUENCE: 144
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRV                            98

SEQ ID NO: 145                moltype = AA   length = 327
FEATURE                       Location/Qualifiers
source                        1..327
                              mol_type = protein
                              organism = Homo sapiens
SEQUENCE: 145
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVMHE ALHNHYTQKS LSLSLGK                                      327

SEQ ID NO: 146                moltype = AA   length = 330
FEATURE                       Location/Qualifiers
source                        1..330
                              mol_type = protein
                              organism = Homo sapiens
SEQUENCE: 146
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 147                moltype = AA   length = 327
FEATURE                       Location/Qualifiers
source                        1..327
                              mol_type = protein
                              organism = Homo sapiens
SEQUENCE: 147
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMASRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVMHE ALHNHYTQKS LSLSLGK                                      327

SEQ ID NO: 148                moltype = AA   length = 327
FEATURE                       Location/Qualifiers
source                        1..327
                              mol_type = protein
                              organism = Homo sapiens
SEQUENCE: 148
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMHSRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
```

```
NVFSCSVMHE ALHNHYTQKS LSLSLGK                                          327

SEQ ID NO: 149              moltype = AA  length = 327
FEATURE                     Location/Qualifiers
source                      1..327
                            mol_type = protein
                            organism = Homo sapiens
SEQUENCE: 149
ASTKGPSVFP LAPCSRSTSE STAALGCLVK DYFPEPVTVS WNSGALTSGV HTFPAVLQSS       60
GLYSLSSVVT VPSSSLGTKT YTCNVDHKPS NTKVDKRVES KYGPPCPPCP APEFEGGPSV      120
FLFPPKPKDT LMDSRTPEVT CVVVDVSQED PEVQFNWYVD GVEVHNAKTK PREEQFNSTY      180
RVVSVLTVLH QDWLNGKEYK CKVSNKGLPS SIEKTISKAK GQPREPQVYT LPPSQEEMTK      240
NQVSLTCLVK GFYPSDIAVE WESNGQPENN YKTTPPVLDS DGSFFLYSKL TVDKSRWQEG      300
NVFSCSVMHE ALHNHYTQKS LSLSLGK                                          327

SEQ ID NO: 150              moltype = AA  length = 327
FEATURE                     Location/Qualifiers
source                      1..327
                            mol_type = protein
                            organism = Homo sapiens
SEQUENCE: 150
ASTKGPSVFP LAPCSRSTSE STAALGCLVK DYFPEPVTVS WNSGALTSGV HTFPAVLQSS       60
GLYSLSSVVT VPSSSLGTKT YTCNVDHKPS NTKVDKRVES KYGPPCPPCP APEFEGGPSV      120
FLFPPKPKDT LMSSRTPEVT CVVVDVSQED PEVQFNWYVD GVEVHNAKTK PREEQFNSTY      180
RVVSVLTVLH QDWLNGKEYK CKVSNKGLPS SIEKTISKAK GQPREPQVYT LPPSQEEMTK      240
NQVSLTCLVK GFYPSDIAVE WESNGQPENN YKTTPPVLDS DGSFFLYSKL TVDKSRWQEG      300
NVFSCSVMHE ALHNHYTQKS LSLSLGK                                          327

SEQ ID NO: 151              moltype = AA  length = 327
FEATURE                     Location/Qualifiers
source                      1..327
                            mol_type = protein
                            organism = Homo sapiens
SEQUENCE: 151
ASTKGPSVFP LAPCSRSTSE STAALGCLVK DYFPEPVTVS WNSGALTSGV HTFPAVLQSS       60
GLYSLSSVVT VPSSSLGTKT YTCNVDHKPS NTKVDKRVES KYGPPCPPCP APEFEGGPSV      120
FLFPPKPKDT LMISRTPEVT CVVVDVSQED PEVQFNWYVD GVEVHNAKTK PREEQFNSTY      180
RVVSVLTVLD QDWLNGKEYK CKVSNKGLPS SIEKTISKAK GQPREPQVYT LPPSQEEMTK      240
NQVSLTCLVK GFYPSDIAVE WESNGQPENN YKTTPPVLDS DGSFFLYSKL TVDKSRWQEG      300
NVFSCSVMHE ALHNHYTQKS LSLSLGK                                          327

SEQ ID NO: 152              moltype = AA  length = 327
FEATURE                     Location/Qualifiers
source                      1..327
                            mol_type = protein
                            organism = Homo sapiens
SEQUENCE: 152
ASTKGPSVFP LAPCSRSTSE STAALGCLVK DYFPEPVTVS WNSGALTSGV HTFPAVLQSS       60
GLYSLSSVVT VPSSSLGTKT YTCNVDHKPS NTKVDKRVES KYGPPCPPCP APEFEGGPSV      120
FLFPPKPKDT LMISRTPEVT CVVVDVSQED PEVQFNWYVD GVEVHNAKTK PREEQFNSTY      180
RVVSVLTVLG QDWLNGKEYK CKVSNKGLPS SIEKTISKAK GQPREPQVYT LPPSQEEMTK      240
NQVSLTCLVK GFYPSDIAVE WESNGQPENN YKTTPPVLDS DGSFFLYSKL TVDKSRWQEG      300
NVFSCSVMHE ALHNHYTQKS LSLSLGK                                          327

SEQ ID NO: 153              moltype = AA  length = 327
FEATURE                     Location/Qualifiers
source                      1..327
                            mol_type = protein
                            organism = Homo sapiens
SEQUENCE: 153
ASTKGPSVFP LAPCSRSTSE STAALGCLVK DYFPEPVTVS WNSGALTSGV HTFPAVLQSS       60
GLYSLSSVVT VPSSSLGTKT YTCNVDHKPS NTKVDKRVES KYGPPCPPCP APEFEGGPSV      120
FLFPPKPKDT LMISRTPEVT CVVVDVSQED PEVQFNWYVD GVEVHNAKTK PREEQFNSTY      180
RVVSVLTVLH QDWLNGKEYK CKVSNKGLPS SIEKTISKAK GQPREPQVYT LPPSQEEMTK      240
NQVSLTCLVK GFYPSDIAVE WESNGQPENN YKTTPPVLDS DGSFFLYSKL TVDKSRWQEG      300
NVFSCSVMHE ALHNAYTQKS LSLSLGK                                          327

SEQ ID NO: 154              moltype = AA  length = 327
FEATURE                     Location/Qualifiers
source                      1..327
                            mol_type = protein
                            organism = Homo sapiens
SEQUENCE: 154
ASTKGPSVFP LAPCSRSTSE STAALGCLVK DYFPEPVTVS WNSGALTSGV HTFPAVLQSS       60
GLYSLSSVVT VPSSSLGTKT YTCNVDHKPS NTKVDKRVES KYGPPCPPCP APEFEGGPSV      120
FLFPPKPKDT LMISRTPEVT CVVVDVSQED PEVQFNWYVD GVEVHNAKTK PREEQFNSTY      180
RVVSVLTVLH QDWLNGKEYK CKVSNKGLPS SIEKTISKAK GQPREPQVYT LPPSQEEMTK      240
NQVSLTCLVK GFYPSDIAVE WESNGQPENN YKTTPPVLDS DGSFFLYSKL TVDKSRWQEG      300
NVFSCSVMHE ALHNEYTQKS LSLSLGK                                          327
```

```
SEQ ID NO: 155           moltype = AA  length = 327
FEATURE                  Location/Qualifiers
source                   1..327
                         mol_type = protein
                         organism = Homo sapiens
SEQUENCE: 155
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVMHE ALHNFYTQKS LSLSLGK                                       327

SEQ ID NO: 156           moltype = AA  length = 327
FEATURE                  Location/Qualifiers
source                   1..327
                         mol_type = protein
                         organism = Homo sapiens
SEQUENCE: 156
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVMHE ALHNTYTQKS LSLSLGK                                       327

SEQ ID NO: 157           moltype = AA  length = 327
FEATURE                  Location/Qualifiers
source                   1..327
                         mol_type = protein
                         organism = Homo sapiens
SEQUENCE: 157
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVMHE ALHNHATQKS LSLSLGK                                       327

SEQ ID NO: 158           moltype = AA  length = 327
FEATURE                  Location/Qualifiers
source                   1..327
                         mol_type = protein
                         organism = Homo sapiens
SEQUENCE: 158
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVMHE ALHNHETQKS LSLSLGK                                       327

SEQ ID NO: 159           moltype = AA  length = 327
FEATURE                  Location/Qualifiers
source                   1..327
                         mol_type = protein
                         organism = Homo sapiens
SEQUENCE: 159
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSKL TVDKSRWQEG   300
NVFSCSVMHE ALHNHGTQKS LSLSLGK                                       327

SEQ ID NO: 160           moltype = AA  length = 330
FEATURE                  Location/Qualifiers
source                   1..330
                         mol_type = protein
                         organism = Homo sapiens
SEQUENCE: 160
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMASRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330
```

```
SEQ ID NO: 161          moltype = AA  length = 330
FEATURE                 Location/Qualifiers
source                  1..330
                        mol_type = protein
                        organism = Homo sapiens
SEQUENCE: 161
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMHSRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 162          moltype = AA  length = 330
FEATURE                 Location/Qualifiers
source                  1..330
                        mol_type = protein
                        organism = Homo sapiens
SEQUENCE: 162
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMDSRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 163          moltype = AA  length = 330
FEATURE                 Location/Qualifiers
source                  1..330
                        mol_type = protein
                        organism = Homo sapiens
SEQUENCE: 163
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMSSRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 164          moltype = AA  length = 330
FEATURE                 Location/Qualifiers
source                  1..330
                        mol_type = protein
                        organism = Homo sapiens
SEQUENCE: 164
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLDQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 165          moltype = AA  length = 330
FEATURE                 Location/Qualifiers
source                  1..330
                        mol_type = protein
                        organism = Homo sapiens
SEQUENCE: 165
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLGQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 166          moltype = AA  length = 330
FEATURE                 Location/Qualifiers
source                  1..330
                        mol_type = protein
                        organism = Homo sapiens
SEQUENCE: 166
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNAYT QKSLSLSPGK                                    330

SEQ ID NO: 167          moltype = AA  length = 330
```

```
FEATURE              Location/Qualifiers
source               1..330
                     mol_type = protein
                     organism = Homo sapiens
SEQUENCE: 167
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNEYT QKSLSLSPGK                                   330

SEQ ID NO: 168       moltype = AA   length = 330
FEATURE              Location/Qualifiers
source               1..330
                     mol_type = protein
                     organism = Homo sapiens
SEQUENCE: 168
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNFYT QKSLSLSPGK                                   330

SEQ ID NO: 169       moltype = AA   length = 330
FEATURE              Location/Qualifiers
source               1..330
                     mol_type = protein
                     organism = Homo sapiens
SEQUENCE: 169
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNTYT QKSLSLSPGK                                   330

SEQ ID NO: 170       moltype = AA   length = 330
FEATURE              Location/Qualifiers
source               1..330
                     mol_type = protein
                     organism = Homo sapiens
SEQUENCE: 170
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHAT QKSLSLSPGK                                   330

SEQ ID NO: 171       moltype = AA   length = 330
FEATURE              Location/Qualifiers
source               1..330
                     mol_type = protein
                     organism = Homo sapiens
SEQUENCE: 171
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHET QKSLSLSPGK                                   330

SEQ ID NO: 172       moltype = AA   length = 330
FEATURE              Location/Qualifiers
source               1..330
                     mol_type = protein
                     organism = Homo sapiens
SEQUENCE: 172
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHGT QKSLSLSPGK                                   330

SEQ ID NO: 173       moltype = DNA   length = 384
FEATURE              Location/Qualifiers
```

```
source                  1..384
                        mol_type = genomic DNA
                        organism = Homo sapiens
SEQUENCE: 173
caggtgcagc tcgtgcagtc cggagccgaa gtgaaggagc caggagcctc cgtgaagatc    60
tcctgcaagg cctccggcta caccttcacc aacgactaca tgcactgggt gaggcaggcc   120
ccaggacagg gactgagtg gatggggatc atcaacccca caggaggagg acatcctat    180
gcccagaagt tccgcggacg cgtgacaatg acacgcgaca catccacatc cacagtgtac   240
atggagctgt cctccctgcg ctccgaggac acagccgtgt tctactgtgc ccgcgaacgc   300
tactatggct ccgggaccta cttcaacatc gggctgtggg acttcgacct gtggggacgc   360
ggaacactcg tgacagtgtc ctcc                                           384

SEQ ID NO: 174          moltype = DNA  length = 294
FEATURE                 Location/Qualifiers
source                  1..294
                        mol_type = genomic DNA
                        organism = Homo sapiens
SEQUENCE: 174
gcgtccacaa aggggccctc cgtgttcccg ctggccccat gttcccgctc acatccgag     60
tccacagctg ccctgggatg tctcgtgaag gattactttc ccgagccgt gacagtgtcc    120
tggaactccg ggccctgac atccggcgtc cacacattcc cagccgtgct gcagtcctcc    180
gggctgtact ccctgtcctc cgtcgtgaca gtgccatcct cctccctggg gaccaagaca   240
tacacatgca acgtggacca caagccctcc aacacaaaag tggacaagcg cgtg         294

SEQ ID NO: 175          moltype = AA  length = 120
FEATURE                 Location/Qualifiers
source                  1..120
                        mol_type = protein
                        organism = Homo sapiens
SEQUENCE: 175
EVQLVQSGAE VKKPGASVKV SCKVSGYTLA ELSMHWVRQA PGKGLEWMGG FDPEDGERIY    60
AQKFQGRVTM TEDTSKDTAY MELSSLRSED TAVYYCTTGL FYYQYGMDVW GQGTMVTVSS   120

SEQ ID NO: 176          moltype = AA  length = 120
FEATURE                 Location/Qualifiers
source                  1..120
                        mol_type = protein
                        organism = Homo sapiens
SEQUENCE: 176
EVQLQESGAE VKKPGASVKV SCKVSGYTLT DLSMHWVRQA PGKGLEWMGG LDPEDGETIY    60
AQKFQGRVTM TEDTSTDTAY MELSSLRSED TAVYYCATGL FYYQYGMDVW GQGTLVTVSS   120

SEQ ID NO: 177          moltype = AA  length = 120
FEATURE                 Location/Qualifiers
source                  1..120
                        mol_type = protein
                        organism = Homo sapiens
SEQUENCE: 177
EVQLEQSGAE VKKPGASVKV SCKVSGYTLT DLSMHWVRQA PGKGLEWMGG FDPEDGETIY    60
AQKFQGRVTM TEDTSTDTAY MELSSLRSED TAVYYCATGL FYYQYGMDVW GQGTTVTVSS   120

SEQ ID NO: 178          moltype = AA  length = 120
FEATURE                 Location/Qualifiers
source                  1..120
                        mol_type = protein
                        organism = Homo sapiens
SEQUENCE: 178
EVQLVESGAE VKKPGASVKV SCKVSGYTLT DLSMHWVRQA PGKGLEWMGG FDPEDGERIY    60
AQKFQGRVTM TEDTATDTAY MELSSLRSED TAVYHCATGL FYYQYGMDVW GQGTTVTVSS   120

SEQ ID NO: 179          moltype = AA  length = 120
FEATURE                 Location/Qualifiers
source                  1..120
                        mol_type = protein
                        organism = Homo sapiens
SEQUENCE: 179
QVQLVESGAE VKKPGASVKV SCKVSGYTLT DFAIHWVRQA PGKGLEWMGG FDPEDGERIY    60
AQKFQGRVTM TEDTSTDTAY MELSSLRSED TAVYYCTTGL FYYQYGMDVW GQGTLVTVSS   120

SEQ ID NO: 180          moltype = AA  length = 120
FEATURE                 Location/Qualifiers
source                  1..120
                        mol_type = protein
                        organism = Homo sapiens
SEQUENCE: 180
EVQLVQSGAE VKKPGASVKV SCKVSGYTLT ELSMHWVRQA PGKGLEWMGG FDPEDGERIY    60
AQKFQGRVTM TEDTSTDTAY MELSSLRSED TAVYYCATGL FYYQYGMDVW GQGTTVTVSS   120

SEQ ID NO: 181          moltype = AA  length = 120
```

```
FEATURE                 Location/Qualifiers
source                  1..120
                        mol_type = protein
                        organism = Homo sapiens
SEQUENCE: 181
QVQLQQSGAE VKKPGASVKV SCKVSGYTLT DLSMHWVRQA PGKGLEWMGG FDPEDGERIY        60
AQKFQGRVTM TEDTSTDTAY MELSSLRSED TAVYYCATGL FYYQYGMDVW GQGTLVTVSS       120

SEQ ID NO: 182          moltype = AA  length = 120
FEATURE                 Location/Qualifiers
source                  1..120
                        mol_type = protein
                        organism = Homo sapiens
SEQUENCE: 182
EVQLVQSGAE VKKPGASVKV SCKVSGYTLT DFAIHWVRQA PGKGLEWMGG FDPEDGERIY        60
AQKFQGRVTM TEDTSTDTAY MELSSLRSED TAVYYCATGL FYYQYGMDVW GQGTTVTVSS       120

SEQ ID NO: 183          moltype = AA  length = 120
FEATURE                 Location/Qualifiers
source                  1..120
                        mol_type = protein
                        organism = Homo sapiens
SEQUENCE: 183
EVQLLQSGAE VKKPGASVKV SCKVSGYTLT DLSMHWVRQA PGKGLEWMGG FDPEDGERIY        60
AQKFQGRVTM TEDTSTDTAY MELSSLRSED TAMYYCATGL FYYQYGMDVW GQGTTVTVSS       120

SEQ ID NO: 184          moltype = AA  length = 120
FEATURE                 Location/Qualifiers
source                  1..120
                        mol_type = protein
                        organism = Homo sapiens
SEQUENCE: 184
QVQLQESGAE VKKPGASVKV SCKVSGYPLT DLSMHWVRQA PGEGLEWMGG SDPEDGETIY        60
AQKFQGRVTV TEDTSTDTAY MELSNLRSED TAVYYCATGL FYYQYGMDVW GQGTTVTVSS       120

SEQ ID NO: 185          moltype = AA  length = 120
FEATURE                 Location/Qualifiers
source                  1..120
                        mol_type = protein
                        organism = Homo sapiens
SEQUENCE: 185
EVQLVQSGAE VKKPGASVKV SCKVSGYTLT DLSMHWVRQA PGKGLEWMGG FDPEDGERIY        60
AQKFQDRVTM TEDTSTDTAY MELSSLRSED TAVYYCATGL FYYQYGMDVW GQGTLVTVSS       120

SEQ ID NO: 186          moltype = AA  length = 120
FEATURE                 Location/Qualifiers
source                  1..120
                        mol_type = protein
                        organism = Homo sapiens
SEQUENCE: 186
EVQLVQSGAE VKKPGASVKV SCKVSGYTLT DLSMHWVRQA PGKGLEWMGG FDPEDGERIY        60
AQKFQGRVTM TEDTSTDTAY MELSSLRSED TAVYYCATGL FYYYYGMDVW GQGTMVTVSS       120

SEQ ID NO: 187          moltype = AA  length = 1579
FEATURE                 Location/Qualifiers
source                  1..1579
                        mol_type = protein
                        organism = Homo sapiens
SEQUENCE: 187
MLLLVTSLLL CELPHPAFLL IPEKSDLRTV APASSLNVRF DSRTMNLSWD CQENTTFSKC        60
FLTDKKNRVV EPRLSNNECS CTFREICLHE GVTFEVHVNT SQRGFQQKLL YPNSGREGTA       120
AQNFSCFIYN ADLMNCTWAR GPTAPRDVQY FLYIRNSKRR REIRCPYYIQ DSGTHVGCHL       180
DNLSGLTSRN YFLVNGTSRE IGIQFFDSLL DTKKIERFNP PSNVTVRCNT THCLVRWKQP       240
RTYQKLSYLD FQYQLDVHRK NTQPGTENLL INVSGDLENR YNFPSSEPRA KHSVKIRAAD       300
VRILNWSSWS EAIEFGSDDG NLGSVYIYVL LIVGTLVCGI VLGFLFKRFL RIQRLFPPVP       360
QIKDKLNDNH EVEDEIIWEE FTPEEGKGYR EEVLTVKEIT RAKRAPVKQT LNFDLLKLAG       420
DVESNPGPMV LAQGLLSMAL LALCWERSLA GAEETIPLQT LRCYNDYTSH ITCRWADTQD       480
AQRLVNVTLI RRVNEDLLEP VSCDLSDDMP WSACPHPRCV PRRCVIPCQS FVVTDVDYFS       540
FQPDRPLGTR LTVTLTQHVQ PPEPRDLQIS TDQDHFLLTW SVALGSPQSH WLSPGDLEFE       600
VVYKRLQDSW EDAAILLSNT SQATLGPEHL MPSSTYVARV RTRLAPGSRL SGRPSKWSPE       660
VCWDSQPGDE AQPQNLECFF DGAAVLSCSW EVRKEVASSV SFGLFYKPSP DAGEEECSPV       720
LREGLGSLHT RHHCQIPVPD PATHGQYIVS VQPRRAEKHI KSSVNIQMAP PSLNVTKDGD       780
SYSLRWETMK MRYEHIDHTF EIQYRKDTAT WKDSKTETLQ NAHSMALPAL EPSTRYWARV       840
RVRTSRTGYN GIWSEWSEAR SWDTESVLPM WVLALIVIFL TIAVLLALRF CGIYGYRLRR       900
KWEEKIPNPS KSHLFQNGSA ELWPPGSMSA FTSGSPPHQG PWGSRFPELE GVFPVGFGDS       960
EVSPLTIEDP KHVCDPPSGP DTTPAASDLP TEQPPSPQPG PPAASHTPEK QASSFDFNGP      1020
YLGPPHSRSL PDILGQPEPP QEGGSQKSPP PGSLEYLCLP AGGQVQLVPL AQAMGPGQAV      1080
EVERRPSQGA AGSPSLESGG GPAPPALGPR VGGQDQKDSP VAIPMSSGDT EDPGVASGYV      1140
SSADLVFTPN SGASSVSLVP SLGLPSDQTP SLCPGLASGP PGAPGPVKSG FEGYVELPPI      1200
```

```
EGRSPRSPRN NPVPPEAKSP VLNPGERPAD VSPTSPQPEG LLVLQQVGDY CFLPGLGPGP    1260
LSLRSKPSSP GPGPEIKNLD QAFQVKKPPG QAVPQVPVIQ LFKALKQQDY LSLPPWEVNK    1320
PGEVCRAKRA PVKQTLNFDL LKLAGDVESN PGPMVSVIKP EMKIKLCMRG TVNGHNFVIE    1380
GEGKGNPYEG TQILDLNVTE GAPLPFAYDI LTTVFQYGNR AFTKYPADIQ DYFKQTFPEG    1440
YHWERSMTYE DQGICTATSN ISMRGDCFFY DIRFDGTNFP PNGPVMQKKT LKWEPSTEKM    1500
YVEDGVLKGD VNMRLLLEGG GHYRCDFKTT YKAKKEVRLP DAHKIDHRIE ILKHDKDYNK    1560
VKLYENAVAR YSMLPSQAK                                                1579

SEQ ID NO: 188          moltype = AA  length = 1557
FEATURE                 Location/Qualifiers
source                  1..1557
                        mol_type = protein
                        organism = Homo sapiens
SEQUENCE: 188
MVLLWLTLLL IALPCLLQTK EDPNPPITNL RMKAKAQQLT WDLNRNVTDI ECVKDADYSM    60
PAVNNSYCQF GAISLCEVTN YTVRVANPPF STWILFPENS GKPWAGAENL TCWIHDVDFL    120
SCSWAVGPGA PADVQYDLYL NVANRRQQYE CLHYKTDAQG TRIGCRFDDI SRLSSSGSQSS    180
HILVRGRSAA FGIPCTDKFV VFSQIEILTP PNMTAKCNKT HSFMHWKMRS HFNRKFRYEL    240
QIQKRMPPVI TEQVRDRTSF QLLNPGTYTV QIRARERVYE FLSAWSTPQR FECDQEEGAN    300
TRAWRTSLLI ALGTLLALVC VFVICRRYLV MQRLFPRIPH MKDPIGDSFQ NDKLVVWEAG    360
KAGLEECLVT EVQVVQKTRA KRAPVKQTLN FDLLKLAGDV ESNPGPMVLA QGLLSMALLA    420
LCWERSLAGA EETIPLQTLR CYNDYTSHIT CRWADTQDAQ RLVNVTLIRR VNEDLLEPVS    480
CDLSDDMPWS ACPHPRCVPR RCVIPCQSFV VTDVDYFSFQ PDRPLGTRLT VTLTQHVQPP    540
EPRDLQISTD QDHFLLTWSV ALGSPQSHWL SPGDLEFEVV YKRLQDSWED AAILLSNTSQ    600
ATLGPEHLMP SSTYVARVRT RLAPGSRLSG RPSKWSPEVC WDSQPGDEAQ PQNLECFFDG    660
AAVLSCSWEV RKEVASSVSF GLFYKPSPDA GEEECSPVLR EGLGSLHTRH HCQIPVPDPA    720
THGQYIVSVQ PRRAEKHIKS SVNIQMAPPS LNVTKDGDSY SLRWETMKMR YEHIDHTFEI    780
QYRKDTATWK DSKTETLQNA HSMALPALEP STRYWARVRV RTSRTGYNGI WSEWSEARSW    840
DTESVLPMWV LALIVIFLTI AVLLALRFCG IYGYRLRRKW EEKIPNPSKS HLFQNGSAEL    900
WPPGSMSAFT SGSPPHQGPW GSRFPELEGV FPVGFGDSEV SPLTIEDPKH VCDPPSGPDT    960
TPAASDLPTE QPPSPQPGPP AASHTPEKQA SSFDFNGPYL GPPHSRSLPD ILGQPEPPQE    1020
GGSQKSPPPG SLEYLCLPAG GQVQLVPLAQ AMGPGQAVEV ERRPSQGAAG SPSLESGGGP    1080
APPALGPRVG GQDQKDSPVA IPMSSGDTED PGVASGYVSS ADLVFTPNSG ASSVSLVPSL    1140
GLPSDQTPSL CPGLASGPPG APGPVKSGFE GYVELPPIEG RSPRSPRNNP VPPEAKSPVL    1200
NPGERPADVS PTSQPEGLL VLQQVGDYCF LPGLGPGPLS LRSKPSSPGP GPEIKNLDQA    1260
FQVKKPPGQA VPQVPVIQLF KALKQQDYLS LPPWEVNKPG EVCRAKRAPV KQTLNFDLLK    1320
LAGDVESNPG PMVSVIKPEM KIKLCMRGTV NGHNFVIEGE GKGNPYEGTQ ILDLNVTEGA    1380
PLPFAYDILT TVFQYGNRAF TKYPADIQDY FKQTFPEGYH WERSMTYEDQ GICTATSNIS    1440
MRGDCFFYDI RFDGTNFPPN GPVMQKKTLK WEPSTEKMYV EDGVLKGDVN MRLLEGGGH    1500
YRCDFKTTYK AKKEVRLPDA HKIDHRIEIL KHDKDYNKVK LYENAVARYS MLPSQAK      1557

SEQ ID NO: 189          moltype = AA  length = 1599
FEATURE                 Location/Qualifiers
source                  1..1599
                        mol_type = protein
                        organism = Homo sapiens
SEQUENCE: 189
MIIVAHVLLI LLGATEILQA DLLPDEKISL LPPVNFTIKV TGLAQVLLQW KPNPDQEQRN    60
VNLEYQVKIN APKEDDYETR ITESKCVTIL HKGFSASVRT ILQNDHSLLA SSWASAELHA    120
PPGSPGTSIV NLTCTTNTTE DNYSRLRSYQ VSLHCTWLVG TDAPEDTQYF LYYRYGSWTE    180
ECQEYSKDTL GRNIACWFPR TFILSKGRDW LAVLVNGSSK HSAIRPFDQL FALHAIDQIN    240
PPLNVTAEIE GTRLSIQWEK PVSAFPIHCF DYEVKIHNTR NGYLQIEKLM TNAFISIIDD    300
LSKYDVQVRA AVSSMCREAG LWSEWSQPIY VGNDEHKPLR EWFVIVIMAT ICFILLILSL    360
ICKICHLWIK LFPPIPAPKS NIKDLFVTTN YEKAGSSETE IEVICYIEKP GVETLEDSVF    420
RAKRAPVKQT LNFDLLKLAG DVESNPGPMV LAQGLLSMAL LALCWERSLA GAEETIPLQT    480
LRCYNDYTSH ITCRWADTQD AQRLVNVTLI RRVNEDLLEP VSCDLSDDMP WSACPHPRCV    540
PRRCVIPCQS FVVTDVDYFS FQPDRPLGTR LTVTLTQHVQ PPEPRDLQIS TDQDHFLLTW    600
SVALGSPQSH WLSPGDLEFE VVYKRLQDSW EDAAILLSNT SQATLGPEHL MPSSTYVARV    660
RTRLAPGSRL SGRPSKWSPE VCWDSQPGDE AQPQNLECFF DGAAVLSCSW EVRKEVASSV    720
SFGLFYKPSP DAGEEECSPV LREGLGSLHT RHHCQIPVPD PATHGQYIVS VQPRRAEKHI    780
KSSVNIQMAP PSLNVTKDGD SYSLRWETMK MRYEHIDHTF EIQYRKDTAT WKDSKTETLQ    840
NAHSMALPAL EPSTRYWARV RVRTSRTGYN GIWSEWSEAR SWDTESVLPM WVLALIVIFL    900
TIAVLLALRF CGIYGYRLRR KWEEKIPNPS KSHLFQNGSA ELWPPGSMSA FTSGSPPHQG    960
PWGSRFPELE GVFPVGFGDS EVSPLTIEDP KHVCDPPSGP DTTPAASDLP TEQPPSPQPG    1020
PPAASHTPEK QASSFDFNGP YLGPPHSRSL PDILGQPEPP QEGGSQKSPP PGSLEYLCLP    1080
AGGQVQLVPL AQAMGPGQAV EVERRPSQGA AGSPSLESGG GPAPPALGPR VGGQDQKDSP    1140
VAIPMSSGDT EDPGVASGYV SSADLVFTPN SGASSVSLVP SLGLPSDQTP SLCPGLASGP    1200
PGAPGPVKSG FEGYVELPPI EGRSPRSPRN NPVPPEAKSP VLNPGERPAD VSPTSPQPEG    1260
LLVLQQVGDY CFLPGLGPGP LSLRSKPSSP GPGPEIKNLD QAFQVKKPPG QAVPQVPVIQ    1320
LFKALKQQDY LSLPPWEVNK PGEVCRAKRA PVKQTLNFDL LKLAGDVESN PGPMVSVIKP    1380
EMKIKLCMRG TVNGHNFVIE GEGKGNPYEG TQILDLNVTE GAPLPFAYDI LTTVFQYGNR    1440
AFTKYPADIQ DYFKQTFPEG YHWERSMTYE DQGICTATSN ISMRGDCFFY DIRFDGTNFP    1500
PNGPVMQKKT LKWEPSTEKM YVEDGVLKGD VNMRLLLEGG GHYRCDFKTT YKAKKEVRLP    1560
DAHKIDHRIE ILKHDKDYNK VKLYENAVAR YSMLPSQAK                          1599

SEQ ID NO: 190          moltype = AA  length = 120
FEATURE                 Location/Qualifiers
```

```
source                  1..120
                        mol_type = protein
                        organism = Homo sapiens
SEQUENCE: 190
EVQLVQSGAE VKKPGASVKV SCKVSGNTLT DLSMHWVRQA PGKGLEWMGG FDPEDGEKIY    60
AQKFQGRVTM TEDTSTDTAY MELSSLRSED TAVYYCATGL FYYYYGMDVW GQGTLVTVSS   120

SEQ ID NO: 191          moltype = AA   length = 120
FEATURE                 Location/Qualifiers
source                  1..120
                        mol_type = protein
                        organism = Homo sapiens
SEQUENCE: 191
EVQLVQSGAE VKKPGASVKV SCKVSGNTLT DLSMHWVRQA PGKGLEWMGG FDPEDGEKIY    60
AQKFQGRVTM TEDTSTDTAY MELSSLRSED TAVYYCATGL FYYYYGMDVW GQGTMVTVSS   120

SEQ ID NO: 192          moltype = AA   length = 120
FEATURE                 Location/Qualifiers
source                  1..120
                        mol_type = protein
                        organism = Homo sapiens
SEQUENCE: 192
EVQLVQSGAE VKKPGASVKV SCKVSGYTLT DLSMHWVRQA PGKGLEWMGG FDPEDGEKIY    60
AQKFQGRVTM TEDTSTDTAY MELSSLRSED TAVYYCATGL FYYYYGMDVW GQGTTVTVSS   120

SEQ ID NO: 193          moltype = AA   length = 120
FEATURE                 Location/Qualifiers
source                  1..120
                        mol_type = protein
                        organism = Homo sapiens
SEQUENCE: 193
EVQLVQSGAE VKKPGASVKV SCKVSGYTLT DLSMHWVRQA PGKGLEWMGG FDPEDGERIY    60
AQKFQDRVTM TEDTSTDTAY MELSSLRSED TAVYYCATGL FYYYYGMDVW GQGTTVTVSS   120

SEQ ID NO: 194          moltype = AA   length = 120
FEATURE                 Location/Qualifiers
source                  1..120
                        mol_type = protein
                        organism = Homo sapiens
SEQUENCE: 194
EVQLVQSGAE VKKPGASVKV SCKVSGYTLT DLSMHWVRQA PGKGLEWMGG FDPEDGETIY    60
AQKFQGRVTV TEDTSTDTAY MELSSLRSED TAVYYCATGL FYYYYGMDVW GQGTTVTVSS   120

SEQ ID NO: 195          moltype = AA   length = 120
FEATURE                 Location/Qualifiers
source                  1..120
                        mol_type = protein
                        organism = Homo sapiens
SEQUENCE: 195
EVQLQQSGAE VKKPGASVKV SCKVSGYTLT DLSMHWVRQA PGKGLEWMGG FDPEDGETIY    60
AQKFQGRVTM TEDTSTDTAY MELSSLRSED TAVYYCATGL FYYYYGMDVW GQGTLVTVSS   120

SEQ ID NO: 196          moltype = AA   length = 120
FEATURE                 Location/Qualifiers
source                  1..120
                        mol_type = protein
                        organism = Homo sapiens
SEQUENCE: 196
EVQLVQSGAE VKKPGASVKV SCKVSGYTLT DLSMHWVRQA PGKGLEWMGG LDPEDGETIY    60
AQKFQGRVTM TEDTSTDTAY MELSSLRSED TAVYYCATGL FYYYYGMDVW GQGTTVTVSS   120

SEQ ID NO: 197          moltype = AA   length = 120
FEATURE                 Location/Qualifiers
source                  1..120
                        mol_type = protein
                        organism = Homo sapiens
SEQUENCE: 197
EVQLVQSGAE VKKPGASVKV SCKVSGYTLT DLSMHWVRQA PGKGLEWMGG LDPEDGETIY    60
AQKFQGRVTM TEDTSTDTAY MELSSLRSED TAVYYCATGL FYYYYGMDVW GQGTLVTVSS   120

SEQ ID NO: 198          moltype = AA   length = 120
FEATURE                 Location/Qualifiers
source                  1..120
                        mol_type = protein
                        organism = Homo sapiens
SEQUENCE: 198
EVQLVQSGAE VKKPGASVKV SCKVSGYTLT DLSMHWVRQA PGKGLEWMGG SDPEDGETIY    60
AQKFQGRVTM TEDTSTDTAY MELSSLRSED TAVYYCATGL FYYYYGMDVW GQGTTVTVSS   120
```

```
SEQ ID NO: 199          moltype = AA   length = 120
FEATURE                 Location/Qualifiers
source                  1..120
                        mol_type = protein
                        organism = Homo sapiens
SEQUENCE: 199
EVQLVQSGAE VKKPGASVKV SCKVSGYTLT DLSMHWVRQA PGKGLEWMGG SDPEDGETIY    60
AQKFQGRVTM TEDISTDTAY MELSSLRSED TAVYYCATGL FYYYYGMDVW GQGTTVTVSS   120

SEQ ID NO: 200          moltype = AA   length = 120
FEATURE                 Location/Qualifiers
source                  1..120
                        mol_type = protein
                        organism = Homo sapiens
SEQUENCE: 200
EVQLVQSGAE VKKPGASVKV SCKASGYPLS DVALHWVRQA PGKGLEWMGG FDPEDGERIY    60
AQKFQGRVTM TEDTSTDTAY MELSSLRSED TAVYYCATGL FYYYYGMDVW GQGTMVTVSS   120

SEQ ID NO: 201          moltype = AA   length = 120
FEATURE                 Location/Qualifiers
source                  1..120
                        mol_type = protein
                        organism = Homo sapiens
SEQUENCE: 201
EVQLVQSGAE VKKPGASVKV SCKVSGYPLS DFAMHWVRQA PGKGLEWMGG FDPEDGERIY    60
AQKFQGRVTM TEDTSTDTAY MELSSLRSED TAVYYCATGL FYYYYGMDVW GQGTMVTVSS   120

SEQ ID NO: 202          moltype = AA   length = 120
FEATURE                 Location/Qualifiers
source                  1..120
                        mol_type = protein
                        organism = Homo sapiens
SEQUENCE: 202
EVQLVQSGAE VKKPGASVKV SCAVSGFGLN DLALHWVRQA PGKGLEWMGG FDPEDGERIY    60
AQKFQGRVTM TEDTSTDTAY MELSSLRSED TAVYYCATGL FYYYYGMDVW GQGTMVTVSS   120

SEQ ID NO: 203          moltype = AA   length = 120
FEATURE                 Location/Qualifiers
source                  1..120
                        mol_type = protein
                        organism = Homo sapiens
SEQUENCE: 203
EVQLVQSGAE VKKPGASVKV SCEVSGYPLS DYAMHWVRQA PGKGLEWMGG FDPEDGERIY    60
AQKFQGRVTM TEDTSTDTAY MELSSLRSED TAVYYCATGL FYYYYGMDVW GQGTMVTVSS   120

SEQ ID NO: 204          moltype = AA   length = 120
FEATURE                 Location/Qualifiers
source                  1..120
                        mol_type = protein
                        organism = Homo sapiens
SEQUENCE: 204
EVQLVQSGAE VKKPGASVKV SCEVSGYPLS DFAMHWVRQA PGKGLEWMGG FDPEDGERIY    60
AQKFQGRVTM TEDTSTDTAY MELSSLRSED TAVYYCATGL FYYYYGMDVW GQGTMVTVSS   120

SEQ ID NO: 205          moltype = AA   length = 120
FEATURE                 Location/Qualifiers
source                  1..120
                        mol_type = protein
                        organism = Homo sapiens
SEQUENCE: 205
EVQLVQSGAE VKKPGASVKV SCKVSGYTLT DLSMHWVRQA PGKGLEWMGG FDPEDGERIY    60
AQKFQGRVTM TEDTSTDTAY MELSSLRSED TAVYYCATGE FYYYYGMDVW GQGTMVTVSS   120

SEQ ID NO: 206          moltype = AA   length = 120
FEATURE                 Location/Qualifiers
source                  1..120
                        mol_type = protein
                        organism = Homo sapiens
SEQUENCE: 206
EVQLVQSGAE VKKPGASVKV SCKVSGYTLT DLSMHWVRQA PGKGLEWMGG FDPEDGERIY    60
AQKFQGRVTM TEDTSTDTAY MELSSLRSED TAVYYCATGE FYWMYGMDVW GQGTMVTVSS   120

SEQ ID NO: 207          moltype = AA   length = 120
FEATURE                 Location/Qualifiers
source                  1..120
                        mol_type = protein
                        organism = Homo sapiens
```

```
SEQUENCE: 207
EVQLVQSGAE VKKPGASVKV SCKVSGYTLT DLSMHWVRQA PGKGLEWMGG FDPEDGERIY    60
AQKFQGRVTM TEDTSTDTAY MELSSLRSED TAVYYCASGE FYYYYGMDVW GQGTMVTVSS   120

SEQ ID NO: 208          moltype = AA  length = 120
FEATURE                 Location/Qualifiers
source                  1..120
                        mol_type = protein
                        organism = Homo sapiens
SEQUENCE: 208
EVQLVQSGAE VKKPGASVKV SCTVSGFPIS DFAMHWVRQA PGKGLEWMGG FDPEDGERIY    60
AQKFQGRVTM TEDTSTDTAY MELSSLRSED TAVYYCATGL FYYYYGMDVW GQGTMVTVSS   120

SEQ ID NO: 209          moltype = AA  length = 120
FEATURE                 Location/Qualifiers
source                  1..120
                        mol_type = protein
                        organism = Homo sapiens
SEQUENCE: 209
EVQLVQSGAE VKKPGASVKV SCAVSGFPLT DFALHWVRQA PGKGLEWMGG FDPEDGERIY    60
AQKFQGRVTM TEDTSTDTAY MELSSLRSED TAVYYCATGL FYYYYGMDVW GQGTMVTVSS   120

SEQ ID NO: 210          moltype = AA  length = 298
FEATURE                 Location/Qualifiers
source                  1..298
                        mol_type = protein
                        organism = Homo sapiens
SEQUENCE: 210
EKSDLRTVAP ASSLNVRFDS RTMNLSWDCQ ENTTFSKCFL TDKKNRVVEP RLSNNECSCT    60
FREICLHEGV TFEVHVNTSQ RGFQQKLLYP NSGREGTAAQ NFSCFIYNAD LMNCTWARGP   120
TAPRDVQYFL YIRNSKRRRE IRCPYYIQDS GTHVGCHLDN LSGLTSRNYF LVNGTSREIG   180
IQFFDSLLDT KKIERFNPPS NVTVRCNTTH CLVRWKQPRT YQKLSYLDFQ YQLDVHRKNT   240
QPGTENLLIN VSGDLENRYN FPSSEPRAKH SVKIRAADVR ILNWSSWSEA IEFGSDDG     298

SEQ ID NO: 211          moltype = AA  length = 427
FEATURE                 Location/Qualifiers
source                  1..427
                        mol_type = protein
                        organism = Homo sapiens
SEQUENCE: 211
WERSLAGAEE TIPLQTLRCY NDYTSHITCR WADTQDAQRL VNVTLIRRVN EDLLEPVSCD    60
LSDDMPWSAC PHPRCVPRRC VIPCQSFVVT DVDYFSFQPD RPLGTRLTVT LTQHVQPPEP   120
RDLQISTDQD HFLLTWSVAL GSPQSHWLSP GDLEFEVVYK RLQDSWEDAA ILLSNTSQAT   180
LGPEHLMPSS TYVARVRTRL APGSRLSGRP SKWSPEVCWD SQPGDEAQPQ NLECFFDGAA   240
VLSCSWEVRK EVASSVSFGL FYKPSPDAGE EECSPVLREG LGSLHTRHHC QIPVPDPATH   300
GQYIVSVQPR RAEKHIKSSV NIQMAPPSLN VTKDGDSYSL RWETMKMRYE HIDHTFEIQY   360
RKDTATWKDS KTETLQNAHS MALPALEPST RYWARVRVRT SRTGYNGIWS EWSEARSWDT   420
ESVLPMW                                                             427
```

The invention claimed is:

1. A bispecific antibody or a bispecific antibody fragment thereof comprising:

a first antigen-binding domain; and a second antigen-binding domain, wherein the first antigen-binding domain is an antigen-binding domain binding to CD131, and the second antigen-binding domain is an antigen-binding domain binding to CD116, and the first antigen-binding domain comprises a heavy chain variable region (VH) comprising CDRs 1 to 3 comprising the amino acid sequences represented by SEQ ID NOs: 85 to 87, respectively, and a light chain variable region (VL) comprising CDRs 1 to 3 comprising the amino acid sequences represented by SEQ ID NOs: 88 to 90, respectively, and the second antigen-binding domain comprises a VH comprising CDRs 1 to 3 comprising the amino acid sequences represented by SEQ ID NOs: 137 to 139, respectively, and a VL comprising CDRs 1 to 3 comprising the amino acid sequences represented by SEQ ID NOs: 88 to 90, respectively.

2. The bispecific antibody or the bispecific antibody fragment thereof according to claim 1, which has an agonist activity to a granulocyte macrophage-colony stimulating factor (GM-CSF) receptor.

3. The bispecific antibody or the bispecific antibody fragment thereof according to claim 1, comprising one or two first antigen-binding domains and one or two second antigen-binding domains.

4. The bispecific antibody or the bispecific antibody fragment thereof according to claim 1, wherein the first antigen-binding domain is a Fab (first Fab) and the second antigen-binding domain is a Fab (second Fab), the first Fab comprises a heavy chain (VH$_1$-CH1) comprising a VH and CH1 domain, and a light chain (VL-CL), and the second Fab comprises a heavy chain (VH$_2$-CH1') comprising a VH and CH1 domain, and a light chain (VL-CL).

5. The bispecific antibody or the bispecific antibody fragment thereof according to claim 4, comprising:

one first Fab and a hinge region;

one second Fab and a hinge region; and wherein
a C-terminus of the heavy chain in the first Fab is bound to an N-terminus of the hinge region and a C-terminus of the heavy chain in the second Fab is bound to an N-terminus of the hinge region.

6. The bispecific antibody or the bispecific antibody fragment thereof according to claim 4, comprising:
a first polypeptide and a hinge region;
a second polypeptide and a hinge region; and
wherein
a C-terminus of the first polypeptide is bound to an N-terminus of the hinge region and a C-terminus of the second polypeptide is bound to an N-terminus of the hinge region,
the first polypeptide comprises at least the first Fab (VH$_1$-CH1, VL-CL) and optionally the second Fab (VH$_2$-CH1', VL-CL) positioned at the N- or C-terminus of the first Fab, and
the second polypeptide comprises at least the second Fab (VH$_2$-CH1', VL-CL) and optionally the first Fab (VH$_1$-CH1, VL-CL) positioned at the N- or C-terminus of the second Fab.

7. The bispecific antibody or the bispecific antibody fragment thereof according to claim 4, comprising:
(a) two polypeptide chains each comprising (i) a heavy chain from the first Fab and a heavy chain from the second Fab (VH$_1$-CH1-VH$_2$-CH1') in which the C-terminus of the heavy chain in the first Fab and the N-terminus of the heavy chain in the second Fab bind to each other directly or via a linker, and (ii) a hinge region; and
wherein
a C-terminus of the (VH$_1$-CH1-VH$_2$-CH1') is bound to an N-terminus of the hinge region in each polypeptide chain, and
(b) four light chains (VL-CL).

8. The bispecific antibody or the bispecific antibody fragment thereof according to claim 7, wherein each polypeptide chain further comprises:
a Fc region, wherein a N-terminus of each Fc region is bound to a C-terminus of the hinge region of each polypeptide chain.

9. The bispecific antibody or the bispecific antibody fragment thereof according to claim 8, wherein the VH$_1$ comprises the amino acid sequence represented by SEQ ID NO: 29, the CH1 comprises the amino acid sequence represented by SEQ ID NO: 144, and the VH$_2$ comprises the amino acid sequence represented by SEQ ID NO: 186,
the CH1', the hinge region and the Fc region (CH2-CH3) comprise the amino acid sequence represented by SEQ ID NO: 155, and
each light chain comprises a VL comprising the amino acid sequence represented by SEQ ID NO: 30.

10. The bispecific antibody or the bispecific antibody fragment thereof according to claim 8, wherein the first antigen-binding domain comprises a VH comprising the amino acid sequence represented by SEQ ID NO: 29, and a VL comprising the amino acid sequence represented by SEQ ID NO: 30, and the second antigen-binding domain comprises a VH comprising the amino acid sequence represented by SEQ ID NO: 186, and a VL comprising the amino acid sequence represented by SEQ ID NO: 30.

11. The bispecific antibody or the bispecific antibody fragment thereof according to claim 1, wherein the first antigen-binding domain comprises a VH comprising the amino acid sequence represented by SEQ ID NO: 29, and a VL comprising the amino acid sequence represented by SEQ ID NO: 30, and the second antigen-binding domain comprises a VH comprising the amino acid sequence represented by SEQ ID NO: 186, and a VL comprising the amino acid sequence represented by SEQ ID NO: 30.

12. A DNA encoding the bispecific antibody or the bispecific antibody fragment thereof according to claim 1.

13. A recombinant vector comprising the DNA according to claim 12.

14. A host cell comprising transformant obtained by introducing the recombinant vector according to claim 13.

* * * * *